(12) United States Patent
Aicher et al.

(10) Patent No.: US 8,212,045 B2
(45) Date of Patent: Jul. 3, 2012

(54) PYRIDIN-2-YL-AMINO-1, 2, 4-THIADIAZOLE DERIVATIVES AS GLUCOKINASE ACTIVATORS FOR THE TREATMENT OF DIABETES MELLITUS

(75) Inventors: Thomas Daniel Aicher, Superior, CO (US); Steven Armen Boyd, Longmont, CO (US); Mark Joseph Chicarelli, Longmont, CO (US); Kevin Ronald Condroski, Lafayette, CO (US); Jay Bradford Fell, Longmont, CO (US); John P. Fischer, Longmont, CO (US); Indrani W. Gunawardana, Longmont, CO (US); Ronald Jay Hinklin, Longmont, CO (US); Ajay Singh, Longmont, CO (US); Timothy M. Turner, Longmont, CO (US); Eli M. Wallace, Lyons, CO (US)

(73) Assignee: Array BioPharma, Inc., Boulder, CO (US)

( * ) Notice: Subject to any disclaimer, the term of this patent is extended or adjusted under 35 U.S.C. 154(b) by 0 days.

(21) Appl. No.: 12/678,995

(22) PCT Filed: Sep. 15, 2008

(86) PCT No.: PCT/US2008/076401
§ 371 (c)(1),
(2), (4) Date: Mar. 18, 2010

(87) PCT Pub. No.: WO2009/042435
PCT Pub. Date: Apr. 2, 2009

(65) Prior Publication Data
US 2010/0204240 A1    Aug. 12, 2010

Related U.S. Application Data

(60) Provisional application No. 60/974,225, filed on Sep. 21, 2007.

(51) Int. Cl.
*A61K 31/44* (2006.01)
*C07D 417/00* (2006.01)
(52) U.S. Cl. .................. 546/268.7; 546/269.7; 514/342
(58) Field of Classification Search ........................ None
See application file for complete search history.

(56) References Cited

U.S. PATENT DOCUMENTS

| | | | |
|---|---|---|---|
| 5,326,776 A | 7/1994 | Winn | |
| 6,465,467 B1 | 10/2002 | Nilsson | |
| 6,586,423 B2 | 7/2003 | Bilodeau | |
| 6,586,424 B2 | 7/2003 | Bilodeau | |
| 6,596,746 B1 | 7/2003 | Das | |
| 6,846,928 B2 | 1/2005 | Bebbington | |
| 6,875,767 B2 * | 4/2005 | Bilodeau et al. | 514/253.1 |
| 6,906,067 B2 | 6/2005 | Moriarty | |
| 6,979,694 B2 | 12/2005 | Das | |
| 7,015,227 B2 | 3/2006 | Darrow | |
| 7,071,216 B2 | 7/2006 | Renhowe | |
| 7,091,223 B2 | 8/2006 | Das | |
| 7,091,343 B2 | 8/2006 | Bebbington | |
| 7,115,746 B2 | 10/2006 | Snoonian | |
| 7,125,875 B2 | 10/2006 | Das | |
| 7,144,903 B2 | 12/2006 | Collins | |
| 7,179,826 B2 | 2/2007 | Bebbington | |
| 7,244,763 B2 | 7/2007 | Bratton | |
| 7,262,204 B2 | 8/2007 | Collins | |
| 7,276,502 B2 | 10/2007 | Brenchley | |
| 7,345,051 B2 | 3/2008 | Zhou | |
| 7,375,222 B2 | 5/2008 | Kubota | |
| 7,470,712 B2 | 12/2008 | Herpin | |
| 7,479,495 B2 | 1/2009 | Moriarty | |
| 7,534,794 B2 | 5/2009 | Nilsson | |
| 7,601,836 B2 | 10/2009 | Pitts | |
| 7,642,354 B2 | 1/2010 | Wang | |
| 7,648,986 B2 | 1/2010 | Nagarathnam | |
| 2002/0147203 A1 | 10/2002 | Bilodeau | |
| 2003/0064996 A1 | 4/2003 | Bilodeau | |
| 2003/0092694 A1 | 5/2003 | Nilsson | |
| 2003/0130264 A1 | 7/2003 | Jaen | |
| 2004/0009981 A1 | 1/2004 | Bebbington | |
| 2004/0014755 A1 | 1/2004 | Nagarathnam | |
| 2004/0024208 A1 | 2/2004 | Das | |
| 2004/0054186 A1 | 3/2004 | Das | |
| 2004/0073026 A1 | 4/2004 | Das | |
| 2004/0087626 A1 | 5/2004 | Renhowe | |
| 2004/0122237 A1 | 6/2004 | Amiri et al. | |

(Continued)

FOREIGN PATENT DOCUMENTS

DE    2949913 A  *  6/1981

(Continued)

OTHER PUBLICATIONS

Silverman, R. "The Organic Chemistry of Drug Design and Drug Action," 2004, Elsevier, pp. 17-20 and 29-32.*

(Continued)

*Primary Examiner* — Janet Andres
*Assistant Examiner* — Heidi Reese
(74) *Attorney, Agent, or Firm* — Banner & Witcoff, Ltd.

(57) ABSTRACT

Provided are compounds of Formula (I): wherein $R^2$, $R^3$, $R^{13}$, L and $D^2$ are as defined in the specification, which are useful in the treatment and/or prevention of diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed herein.

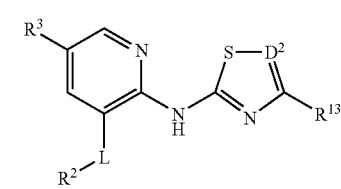

(I)

9 Claims, No Drawings

U.S. PATENT DOCUMENTS

| | | |
|---|---|---|
| 2004/0132726 A1 | 7/2004 | Arora |
| 2004/0132730 A1 | 7/2004 | Axon |
| 2004/0248850 A1 | 12/2004 | Ernst |
| 2005/0209297 A1 | 9/2005 | Sanner |
| 2006/0194803 A1 | 8/2006 | Kubota |
| 2006/0258701 A1 | 11/2006 | Mitsuya et al. |
| 2007/0027321 A1 | 2/2007 | Kamenecka |
| 2007/0173516 A1 | 7/2007 | Mortimore |
| 2007/0179125 A1 | 8/2007 | Fraysse |
| 2007/0238741 A1 | 10/2007 | Nagarathnam |
| 2007/0265297 A1 | 11/2007 | Bebernitz et al. |
| 2007/0299039 A1 | 12/2007 | Amiri et al. |
| 2008/0076800 A1 | 3/2008 | Huang |
| 2008/0108600 A1 | 5/2008 | Wang |
| 2008/0227785 A1 | 9/2008 | Kubota |
| 2009/0012091 A1 | 1/2009 | Yu |
| 2009/0048269 A1 | 2/2009 | Finlay |
| 2009/0069297 A1 | 3/2009 | Cee |
| 2009/0156603 A1 | 6/2009 | Aicher |
| 2009/0181938 A1 | 7/2009 | Binch |
| 2009/0192317 A1 | 7/2009 | Benjahad |
| 2009/0247526 A1 | 10/2009 | Aicher |
| 2010/0056530 A1 | 3/2010 | Aicher |
| 2010/0093689 A1 | 4/2010 | Sutton |
| 2010/0099713 A1 | 4/2010 | Aicher |
| 2010/0105659 A1 | 4/2010 | Aicher |

FOREIGN PATENT DOCUMENTS

| | | |
|---|---|---|
| DE | 102005025161 | 12/2006 |
| EP | 0300688 A1 | 1/1989 |
| EP | 1921074 A1 * | 5/2008 |
| WO | WO/93/17681 | 9/1993 |
| WO | WO/93/24442 | 12/1993 |
| WO | 0117995 | 3/2001 |
| WO | WO/01/47897 | 7/2001 |
| WO | WO/02/18346 | 3/2002 |
| WO | WO/02/30357 | 4/2002 |
| WO | WO/2004/041164 | 5/2004 |
| WO | 2004050645 | 6/2004 |
| WO | WO/2005/077373 | 8/2005 |
| WO | 2005095417 | 10/2005 |
| WO | WO 2005/092896 | 10/2005 |
| WO | WO 2006/071095 | 7/2006 |
| WO | WO/2007/038387 | 4/2007 |
| WO | WO 2007117381 A2 * | 10/2007 |
| WO | 2008050117 | 5/2008 |
| WO | 2008073687 | 6/2008 |
| WO | WO/2009/046784 | 4/2009 |

OTHER PUBLICATIONS

Tomita, M. et al., "Synthesis of thiazole derivatives containing diphenyl ether nucleus", Yakugaku Zasshi, vol. 75, pp. 1077-1081 (1955) (English abstract).

Office Action dated (mailed) Dec. 27, 2010 in U.S. Appl. No. 12/282,600.

* cited by examiner

PYRIDIN-2-YL-AMINO-1, 2, 4-THIADIAZOLE DERIVATIVES AS GLUCOKINASE ACTIVATORS FOR THE TREATMENT OF DIABETES MELLITUS

This application claims priority to U.S. Provisional Application No. 60/974,225, filed on Sep. 21, 2007.

The present invention relates to novel compounds, to pharmaceutical compositions comprising the compounds, to a process for making the compounds and to the use of the compounds in therapy. More particularly, it relates to certain glucokinase activators useful in the treatment of diseases and disorders that would benefit from activation of glucokinase.

Glucokinase (hexokinase IV or D) is a glycolytic enzyme that plays an important role in blood sugar regulation related to the glucose utilization and metabolism in the liver and pancreatic beta cells. Serving as a glucose sensor, glucokinase controls plasma glucose levels. Glucokinase plays a dual role in reducing plasma glucose levels: glucose-mediated activation of the enzyme in hepatocytes facilitates hepatic glucose update and glycogen synthesis, while that in pancreatic beta cells ultimately induces insulin secretion. Both of these effects in turn reduce plasma glucose levels.

Clinical evidence has shown that glucokinase variants with decreased and increased activities are associated with diabetes of the young type (MODY2) and persistent hyperinsulinemic hypoglycemia of infancy (PHHI), respectively. Also, non-insulin dependent diabetes mellitus (NIDDM) patients have been reported to have inappropriately low glucokinase activity. Furthermore, overexpression of glucokinase in dietary or genetic animal models of diabetes either prevents, ameliorates, or reverses the progress of pathological symptoms in the disease. For these reasons, compounds that activate glucokinase have been sought by the pharmaceutical industry.

International patent application, Publication No. WO 2007/053345, which was published on May 10, 2007, discloses as glucokinase activators certain 2-aminopyridine derivatives bearing at the 3-position a methyleneoxy-linked aromatic group and on the amino group a heteroaryl ring, such as thiazolyl or 1,2,4-thiadiazolyl.

It has now been found that 2-aminopyridine derivatives bearing at the 3-position an oxy- or thio-linked aromatic group and on the amino group a thiazolyl or 1,2,4-thiadiazolyl substituted by a polyhydroxyalkyl or polyhydroxycloalkyl group at the 4 or 3 position of the thiazole or thiadiazole ring, respectively are glucokinase activators. Certain of these compounds have been found to have an outstanding combination of properties that especially adapts them for oral use with controlled plasma glucose levels.

According to one aspect, the present invention provides a compound of general Formula I

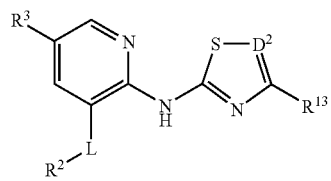

or a salt thereof, wherein:

$R^{13}$ is a polyhydroxy-(2-6C) alkyl, methoxy(polyhydroxy-(3-6C) alkyl) or polyhydroxy-(5-6C)cycloalkyl;

L is O or S;

$D^2$ is N or CH;

$R^2$ is $Ar^1$, $hetAr^1$, $hetAr^2$, or $hetAr^3$;

$Ar^1$ is phenyl or naphthyl, each of which is optionally substituted with one or more groups independently selected from (1-6C)alkyl, F, Br, $CF_3$, OH, CN, $SO_2Me$, C(=O)NH(1-3C alkyl)N(alkyl)$_2$ and C(=C)NH(1-3C alkyl)hetCyc$^1$;

$hetAr^1$ is a 5-6 membered heteroaryl group having 1-3 ring nitrogen atoms and optionally substituted with one or more groups independently selected from (1-6C alkyl), Cl, $CF_3$ and (1-6C alkyl)OH;

$hetAr^2$ is a partially unsaturated 5,6 or 6,6 bicyclic heteroaryl ring system having 1-2 ring nitrogen atoms and optionally having a ring oxygen atom;

$hetAr^3$ is a 9-10 membered bicyclic heteroaryl ring having 1-3 ring nitrogen atoms;

$R^3$ is Cl, Br, $CF_3$, aryl, $hetAr^a$, $SR^6$ or $OR^6$;

$hetAr^a$ is a 6-membered heteroaryl having 1-2 ring nitrogen atoms;

$R^6$ is $Ar^2$, $hetAr^4$, (1-6C alkyl), -(1-6C alkyl)OH, polyhydroxy(1-6C alkyl), —CH($R^9$)—$Ar^3$, —CH($R^{10}$)-$hetAr^5$, $hetAr^6$, (5-6C)cycloalkyl substituted with 1 to 4 OH, (1-3 C alkoxy)(1-6C alkyl), or cyclopropyl(1-6C alkyl);

$Ar^2$ is phenyl optionally substituted with one or more groups independently selected from (1-6C)alkyl, F, Br, Cl, $CF_3$, CN, OH, O-(1-6C alkyl), C(=O)OH, C(=O)O(1-6C alkyl), C(=O)NH(1-3C alkyl)N(1-3Calkyl)$_2$ and C(=O)NH(1-3C alkyl)hetCyc$^2$;

$hetAr^4$ is a 5-6-membered heteroaryl ring having 1-3 nitrogen atoms and optionally substituted with one or more groups independently selections from (1-6C)alkyl, F, Br, Cl, $CF_3$, CN, OH, O-(1-6C alkyl), C(=O)OH, C(=O)O(1-6C alkyl), C(=O)NH(1-3C alkyl)N(1-3Calkyl)$_2$ and C(=O)NH(1-3C alkyl)hetCyc$^2$;

$Ar^3$ is phenyl optionally substituted with one or more groups independently selected from F, Cl, Br, and (1-6C) alkyl;

$hetAr^5$ is a 5-6-membered heteroaryl having 1-2 ring nitrogen atoms;

$hetAr^6$ is a 9-10 membered bicyclic heteroaromatic ring having 2-3 heteroatoms independently selected from N, S, O (provided the ring does not contain an O—O bond) which is optionally substituted with one or more groups independently selected from (1-6C)alkyl, F, Br, Cl, $CF_3$, CN, OH, —O-(1-6C alkyl), C(=O)OH, C(=O)O(1-6C alkyl) and C(=O)NH(1-3C alkyl)N(1-3Calkyl)$_2$;

$R^9$ and $R^{10}$ are independently hydrogen, (1-6C)alkyl, (1-6C)alkylOH, or $CF_3$; and $hetCyc^1$ and $hetCyc^2$ are independently a 5-7 membered heterocyclic ring having 1-2 ring heteroatoms independently selected from N and O.

Compounds of Formula I include compounds, including salts thereof, wherein:

$R^{13}$ is a polyhydroxy-(2-6C) alkyl or polyhydroxy-(5-6C) cycloalkyl;

L is O or S;

$D^2$ is N or CH;

$R^2$ is $Ar^1$, $hetAr^1$, $hetAr^2$, or $hetAr^3$;

$Ar^1$ is phenyl or naphthyl, each of which is optionally substituted with one or more groups independently selected from (1-6C)alkyl, F, Br, $CF_3$, OH, CN, $SO_2Me$, C(=O)NH(1-3C alkyl)N(alkyl)$_2$ and C(=O)NH(1-3C alkyl)hetCyc$^1$;

$hetAr^1$ is a 5-6 membered heteroaryl group having 1-3 ring nitrogen atoms and optionally substituted with one or more groups independently selected from (1-6C alkyl), Cl, $CF_3$ and (1-6C alkyl)OH;

hetAr² is a partially unsaturated 5,6 or 6,6 bicyclic heteroaryl ring system having 1-2 ring nitrogen atoms and optionally having a ring oxygen atom;

hetAr³ is 9-10 membered bicyclic heteroaryl ring having 1-3 ring nitrogen atoms;

R³ is Cl, Br, CF₃, aryl, hetAr$^a$, SR⁶ or OR⁶;

hetAr$^a$ is a 6-membered heteroaryl having 1-2 ring nitrogen atoms,

R⁶ is Ar², hetAr⁴, (1-6C alkyl), -(1-6C alkyl)OH, polyhydroxy(1-6C alkyl), —CH(R⁹)—Ar³, —CH(R¹⁰)-hetAr⁵, hetAr⁶ or (5-6C)cycloalkyl substituted with 1 to 4 OH;

Ar² is phenyl optionally substituted with one or more groups independently selected from (1-6C)alkyl, F, Br, Cl, CF₃, CN, OH, O-(1-6C alkyl), C(=O)OH, C(=O)O(1-6C alkyl), C(=O)NH(1-3C alkyl)N(1-3Calkyl)₂ and C(=C alkyl)hetCyc²;

hetAr⁴ is a 5-6 membered heteroaryl ring having 1-3 nitrogen atoms and optionally substituted with one or more groups independently selected from (1-6C)alkyl, F, Br, Cl, CF₃, CN, OH, O-(1-6C alkyl), C(=O)OH, C(=O)O(1-6C alkyl), C(=O)NH(1-3C alkyl)N(1-3Calkyl)₂ and C(=O)NH(1-3C alkyl)hetCyc²;

Ar³ is phenyl optionally substituted with one or more groups independently selected from F, Cl, Br, and (1-6C) alkyl;

hetAr⁵ is a 5-6-membered heteroaryl having 1-2 ring nitrogen atoms;

hetAr⁶ is a 9-10 membered bicyclic heteroaromatic ring having 2-3 heteroatoms independently selected from N, S and O (provided the ring does not contain an O—O bond) which is optionally substituted with one or more groups independently selected from (1-6C)alkyl, F, Br, Cl, CF₃, CN, OH, —O-(1-6C alkyl), C(=O)OH, C(=O)O(1-6C alkyl) and C(=O)NH(1-3C alkyl)N(1-3Calkyl)₂;

R⁹ and R¹⁰ are independently hydrogen, (1-6C)alkyl, (1-6C)alkylOH, or CF₃; and hetCyc¹ and hetCyc² are independently a 5-7 membered heterocyclic ring having 1-2 ring heteroatoms independently selected from N and O.

The terms "(1-6C)alkyl," "(1-3C)alkyl," and "(2-6C)alkyl" as used herein refer to a saturated linear or branched-chain monovalent hydrocarbon radical of one to six, one to three, or two to six carbon atoms, respectively. Examples include but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

In one embodiment of Formula I, R¹³ is a polyhydroxy-(2-6C) alkyl. For example, in one embodiment R¹³ is a (2-6C) alkyl group substituted with two to three hydroxy groups, for example two hydroxy groups. Examples include ethyl, propyl, isopropyl, butyl, isobutyl, sec-butyl, 1,2-dimethylbutyl, 2,3-dimethylbutyl, tert-butyl, pentyl, neopentyl and isopentyl groups substituted with 2-3 hydroxy groups, for example 2 hydroxy groups.

Particular values for R¹³ include the structures:

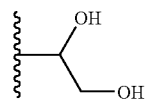 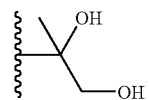 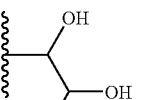

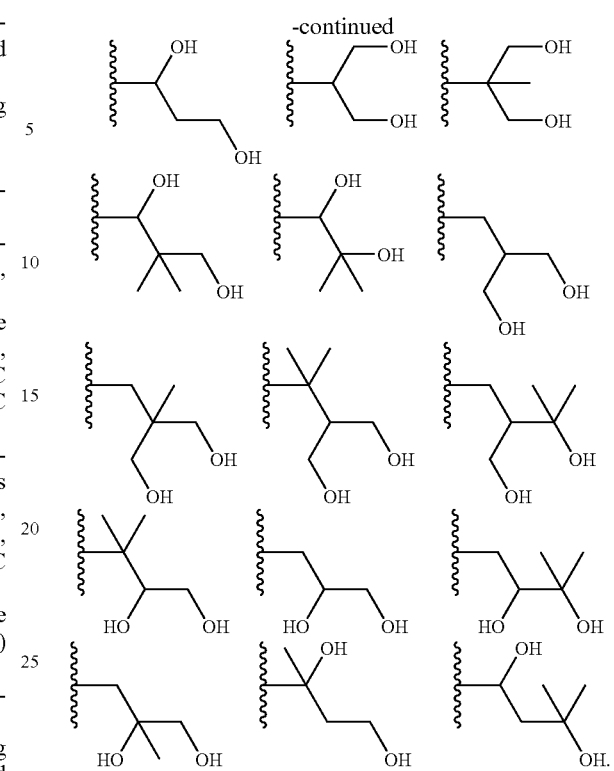

In certain embodiments, R¹³ is a methoxy(polyhydroxy-(3-6C)alkyl). In certain embodiments, R¹³ is a methoxy(dihydroxy(3-6C)alkyl). An example of a particular value for R¹³ is the structure

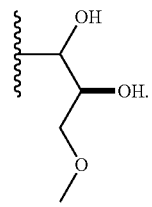

In certain embodiments of Formula I, the alpha carbon is in the S configuration. In other embodiments, the alpha carbon is in the R configuration.

In certain embodiments of Formula I, R¹³ is selected from the structures:

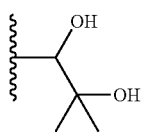 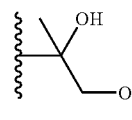 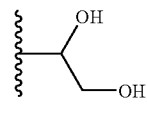

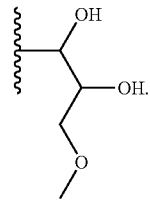

In particular embodiments, R¹³ is 1,2-dihydroxyethyl.

In certain embodiments, $R^{13}$ is a polyhydroxy-(2-6C) alkyl group in which one of the hydroxy groups is on the alpha carbon. In one embodiment, the alpha carbon is in the S configuration. In other embodiments, the alpha carbon is in the R configuration. A particular value of $R^{13}$ is (S)-1,2-dihydroxyethyl or (R)-1,2-dihydroxyethyl, which can be represented, respectively, by the structures:

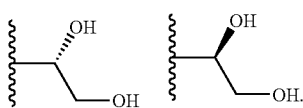

In one embodiment of Formula I, $R^{13}$ is a polyhydroxy-(5-6C)cycloalkyl group. For example, in certain embodiments, $R^{13}$ is cyclopentyl or cyclohexyl substituted with 2-3 hydroxyl groups, for example 2 hydroxyl groups. Particular values for $R^{13}$ include the structures:

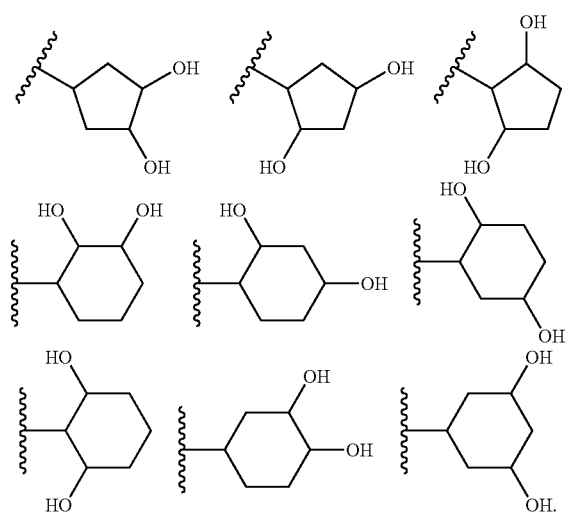

In certain embodiments, $R^2$ is $Ar^1$. In certain embodiments, $Ar^1$ is optionally substituted with one or more groups independently selected from (1-6C)alkyl, F, Br, Cl, $CF_3$, CN, OH, —O-(1-6C alkyl), C(=O)OH, C(=O)O(1-6C alkyl), C(=O)NH(1-3C alkyl)N(1-3Calkyl)$_2$ and C(=O)NH(1-3C alkyl)hetCyc$^1$. In certain embodiments, $Ar^1$ is optionally substituted with one or more groups independently selected from $C_1$-$C_6$ alkyl, F, Br and $CF_3$.

In certain embodiments, $Ar^1$ is phenyl. In other embodiments, $Ar^1$ is naphthyl. In certain embodiments, $Ar^1$ is optionally substituted with one or more groups independently selected from (1-6C)alkyl, F, Br, $CF_3$, CN, $SO_2Me$ and $C(=O)NHCH_2CH_2NMe_2$.

Exemplary embodiments of $R^2$ when represented by $Ar^1$ include the structures:

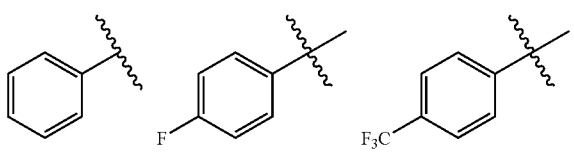

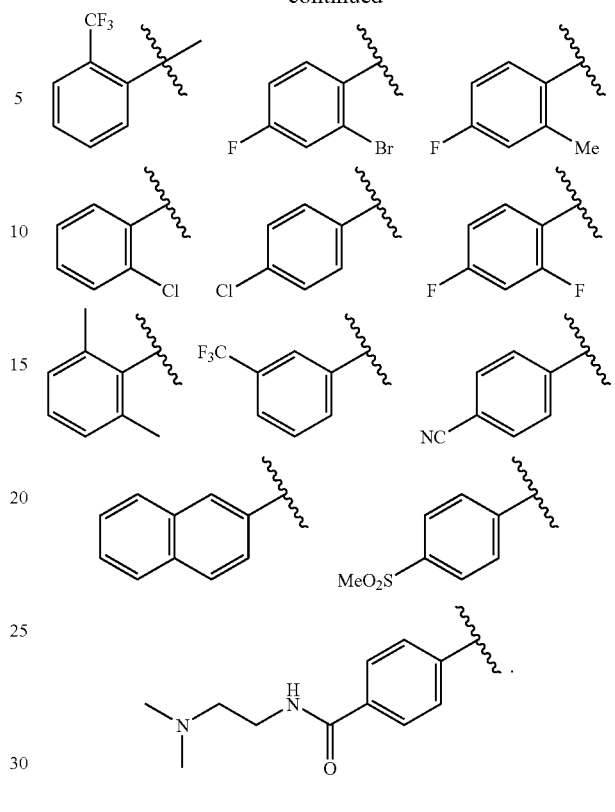

In one embodiment, $R^2$ is hetAr$^1$.

In one embodiment, hetAr$^1$ is unsubstituted. In another embodiment, hetAr$^1$ is substituted with one or more groups independently selected from (1-6C alkyl), Cl, $CF_3$ and (1-5C alkyl)OH.

In one embodiment, hetAr$^1$ is an optionally substituted 6-membered heteroaryl group having 1-2 ring nitrogen atoms. Examples of hetAr$^1$ include unsubstituted or substituted pyridyl, pyrazinyl and pyridazinyl groups. In certain embodiment, the 6-membered hetAr$^1$ is unsubstituted or substituted with one or more groups independently selected from methyl, ethyl, isopropyl, chloro, $CF_3$, $CH_2OH$, and $CH_2CH_2OH$. Examples include pyridyl, methylpyridyl, dimethylpyridyl, ethylpyridyl, isopropylpyridyl, chloropyridyl, trifluoromethylpyridyl, hydroxymethylpyridyl, hydroxyethylpyridyl, methylpyrazinyl and methylpyridazinyl.

In another embodiment, hetAr$^1$ is an optionally substituted 5-membered heteroaryl group having 1-3 ring nitrogen atoms. Examples include pyrazolyl, imidazolyl and triazolyl groups. In certain embodiments, the 5-membered hetAr$^1$ is unsubstituted or substituted with one or more groups independently selected from (1-6C alkyl), $CF_3$, Cl, or (1-3C alkyl)OH, for example one or more groups independently selected from methyl, ethyl, isopropyl, $CF_3$, $CH_2OH$ and $CH_2CH_2OH$. Examples include pyrazolyl, methylpyrazolyl, dimethylpyrazolyl, imidazolyl, methylimidazolyl, dimethylimidazolyl, hydroxyethylpyrazolyl, and dimethylhydroxyethylpyrazolyl groups.

Further examples of hetAr$^1$ include ethylpyrazolyl and trimethylpyrazolyl groups.

Particular values for R² when represented by hetAr¹ include the structures:

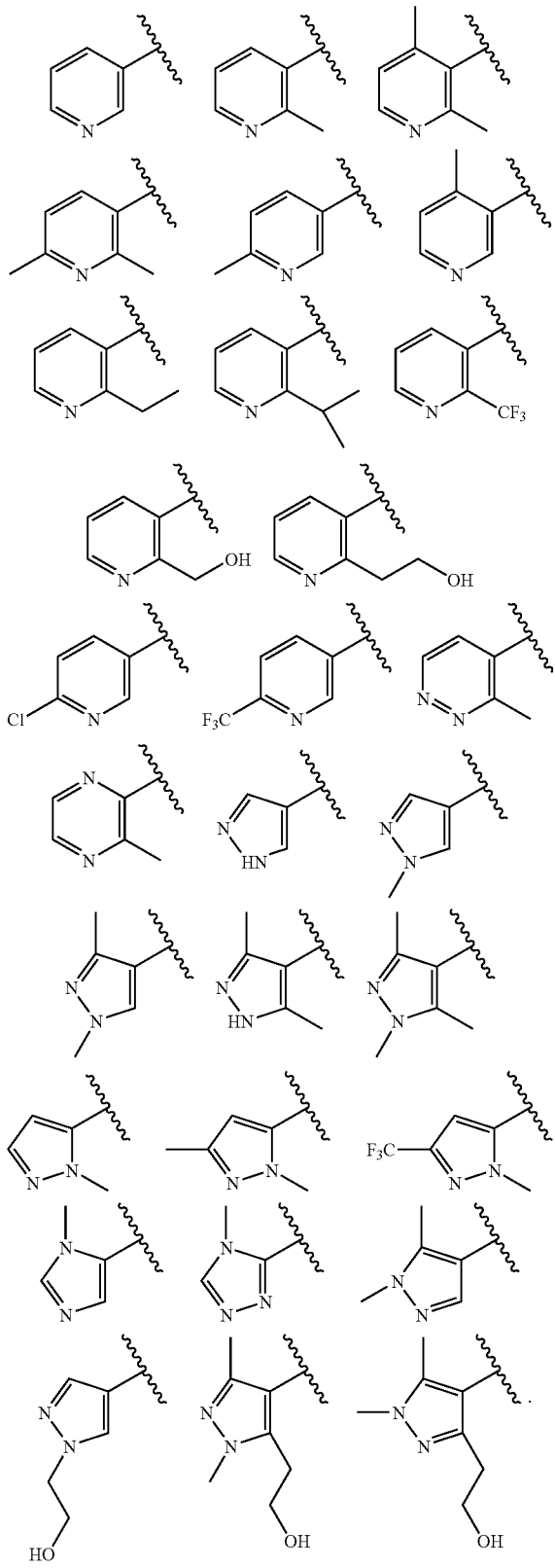

Additional values for R² when represented by hetAr¹ include the structures:

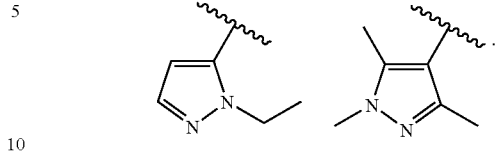

In certain embodiments of Formula I, R² is a pryidyl or pyrazolyl ring substituted with one or more groups independently selected from (1-6C)alkyl. In certain embodiments, R² is pyrid-3-yl, pyrazol-4-yl or pyrazol-5-yl substituted with one or more groups independently selected from methyl and ethyl. Particular values for R² include the structures:

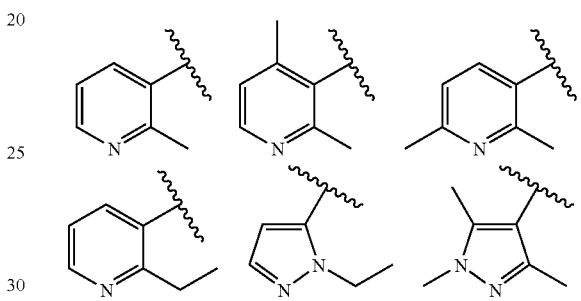

In certain embodiments, R² is hetAr² wherein herAr² is a partially unsaturated 5,5, 5,6 or 6,6 bicyclic ring system having 1-2 ring nitrogen atoms and optionally having a ring oxygen atom. Examples of such ring systems include 5,6,7,8-tetrahydroquinolinyl, 5,6,7,8-tetrahydroisoquinolinyl, 5,6,7,8-tetrahydroquinazolinyl, 6,7-dihydro-5H-cyclopenta[d]pyrimidinyl, 6,7-dihydro-5H-cyclopenta[b]pyridinyl, 6,7-dihydro-5H-cyclopenta[c]pyridinyl, 2,3-dihydrofuro[2,3-b]pyridinyl, 2,3-dihydrofuro[2,3-c]pyridinyl, 2,3-dihydrofuro[3,2-b]pyridinyl, 2,3-dihydrofuro[3,2-c]pyridinyl, 3,4-dihydro-2H-pyrano[2,3-b]pyridinyl, 3,4-dihydro-2H-pyrano[2,3-c]pyridinyl, 3,4-dihydro-2H-pyrano[3,2-c]pyridinyl, and 3,4-dihydro-2H-pyrano[3,2-b]pyridinyl.

Particular examples of R² when represented by hetAr² include the structures:

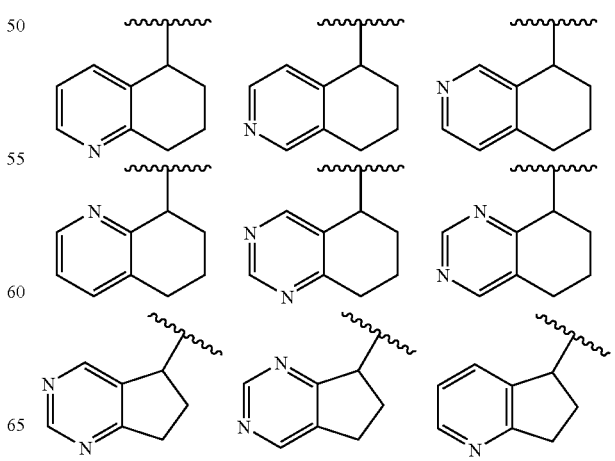

-continued

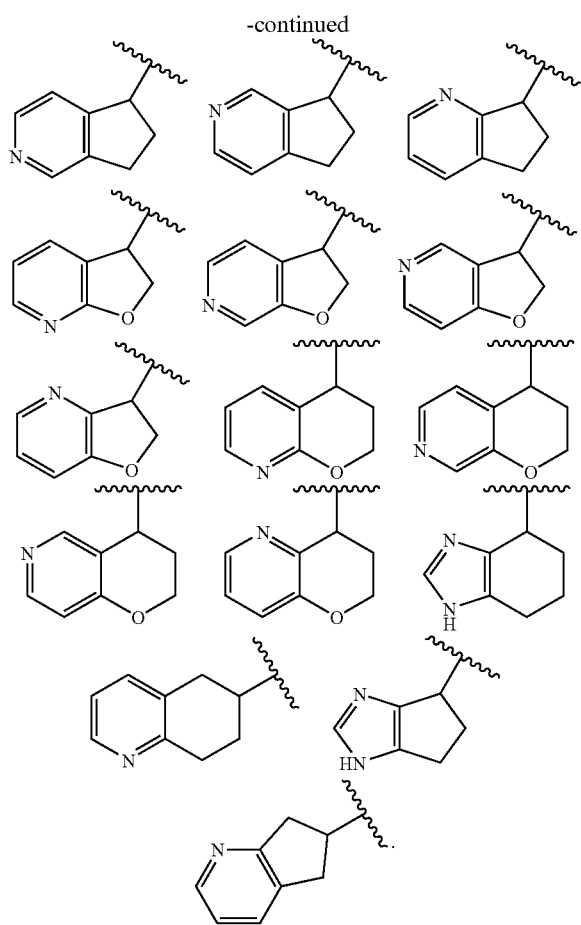

In certain embodiments, R² is hetAr³ wherein hetAr³ is a 9-10 membered bicyclic heteroaryl ring having 1-3 ring nitrogen atoms. Examples of such ring systems include [1,2,4]triazolo[4,3-a]pyridinyl and [1,2,4]triazolo[1,5-a]pyridinyl rings.

Particular values for R² when represented by hetAr³ include the structures:

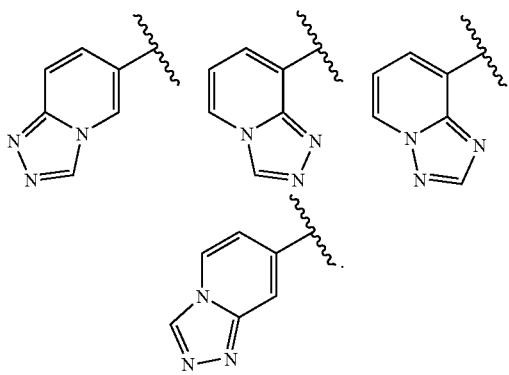

Referring to the R³ group of Formula I, in certain embodiments R³ is SR⁶.

In certain embodiment, R³ is SR⁶ and R⁶ is Ar². In certain embodiments, Ar² is unsubstituted. In other embodiments, Ar² is substituted with one or more groups independently selected from (1-6C)alkyl, F, Br, Cl, CF₃, CN, OH, —O-(1-6C alkyl), C(=O)OH, C(=O)O(1-6C alkyl), C(=O)NH(1-3C alkyl)N(1-3Calkyl)₂ and C(=O)NH(1-3C alkyl)hetCyc². In certain embodiments, Ar² is substituted with one or two groups independently selected from Cl, (1-6C)alkyl, CN, CF₃, and —O($C_1$-$C_6$ alkyl).

In a certain embodiment, Ar² is an optionally substituted phenyl.

Exemplary embodiment of R³ when represented by —S—Ar² include phenylthio, (chlorophenyl)thio, (fluorophenyl)thio, (methylphenyl)thio, (trifluromethylphenyl)thio, (dimethylphenyl)thio, (cyanotrifluoromethylphenyl)thio, (cyanophenyl)thio, and (methoxyphenyl)thio.

Particular values of R³ when represented by —S—Ar² include the structures:

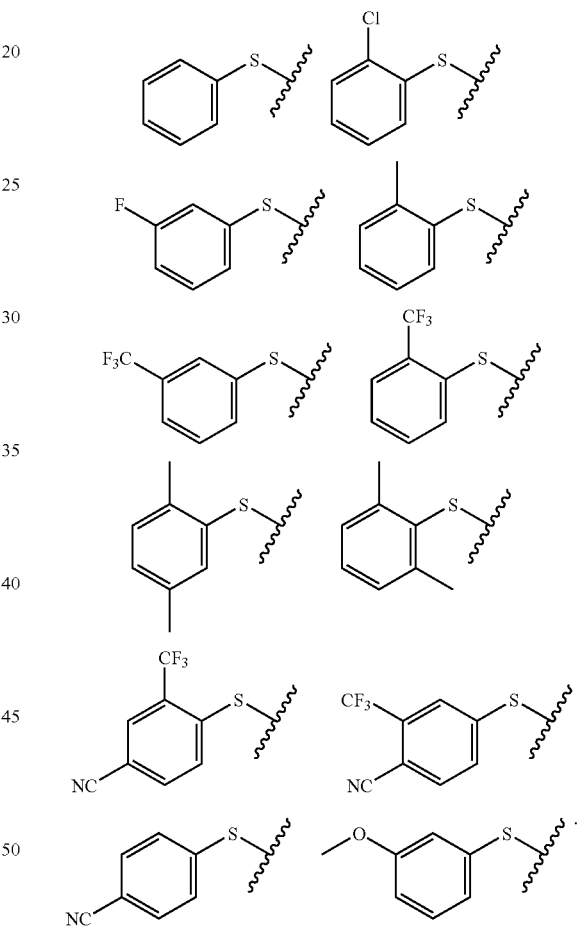

In another embodiment of Formula I, R³ is SR⁶ wherein R⁶ is hetAr⁴, and hetAr⁴ is an optionally substituted 5-6 membered heteroaryl ring having 1-3 ring nitrogen atoms. Examples include optionally substituted pyridyl, pyrimidyl, pyrrolyl, imidazolyl and triazolyl rings. In certain embodiments, hetAr⁴ is unsubstituted or substituted with one or more groups independently selected from (1-6C)alkyl, F, Br, Cl, CF₃, CN, OH, —O-(1-6C alkyl), C(=O)OH, C(=O)O(1-6C alkyl), C(=O)NH(1-3C alkyl)N(1-3Calkyl)₂ and C(=O)NH (1-3C alkyl)hetCyc². In particular embodiments, herAr⁴ is substituted with one or more (1-6C) alkyl groups, for example one or more methyl groups.

Particular values for $R^3$ when represented by —S-hetAr$^4$ include the structures:

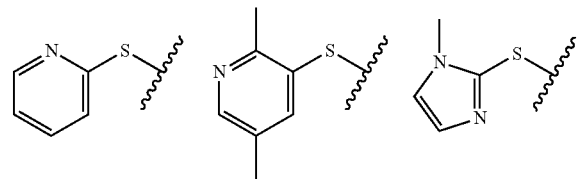
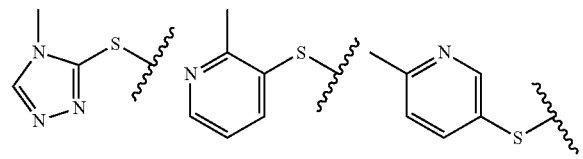
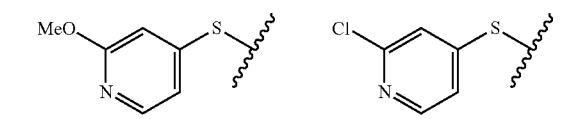
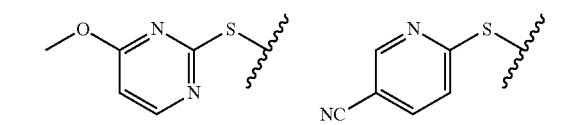
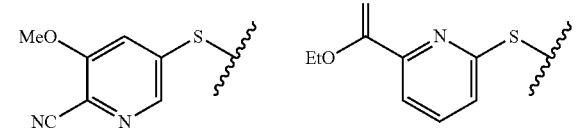
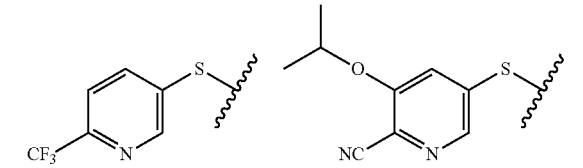
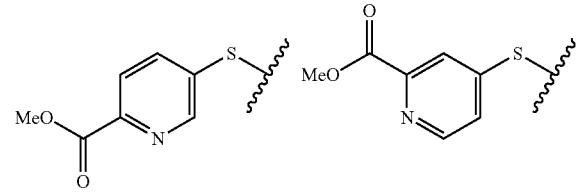
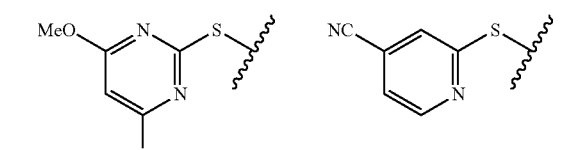
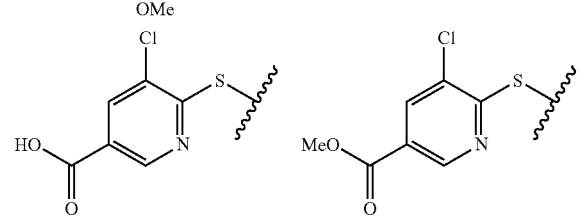
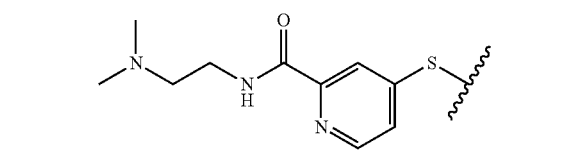

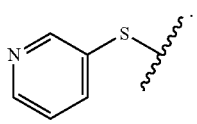

An additional value of —S-hetAr$^4$ includes the structure:

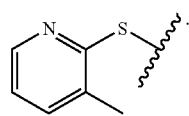

Particular mention is made of —S-hetAr$^4$ groups selected from —S-(methylpyridyl), —S-(dimethylpyridyl), —S-(methylimidazolyl), and —S-(methyltriazolyl).

In another embodiment of Formula I, $R^3$ is $SR^6$ wherein $R^6$ is (1-6C alkyl)OH or polyhydroxy(1-6C alkyl). Examples of polyhydroxy(1-6C alkyl) groups include 1-6C alkyl groups substituted with 2 to 3 hydroxy groups. Particular values include the structures:

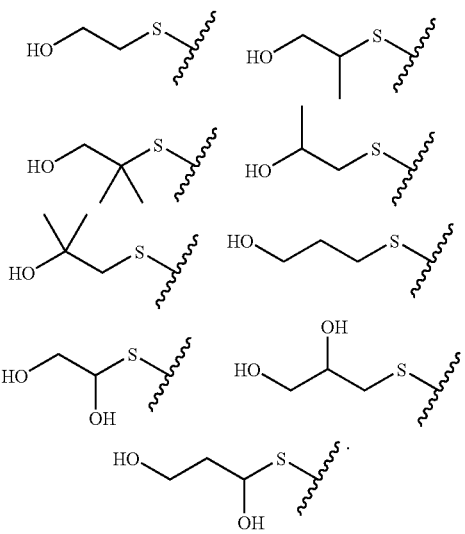

In certain embodiments, $R^3$ is $SR^6$ where $R^6$ is (5-6C) cycloalkyl substituted with 1-4 OH groups, for example 1-2 OH groups.

In another embodiment of Formula I, $R^3$ is $SR^6$ wherein $R^6$ is CH($R^9$)—Ar$^3$. In certain embodiments, $R^9$ is H. In certain embodiments, $R^9$ is (1-6C)alkyl, for example (1-3C alkyl), for example methyl. In certain embodiments, $R^9$ is CH$_2$OH. In certain embodiments, Ar$^3$ is an unsubstituted phenyl. In other embodiments, Ar$^3$ is phenyl which is substituted with one or more groups independently selected from F, Cl, Br, and (1-6C)alkyl. Particular values for $R^3$ when represented by S—(CH($R^9$)—Ar$^3$ include the structures:

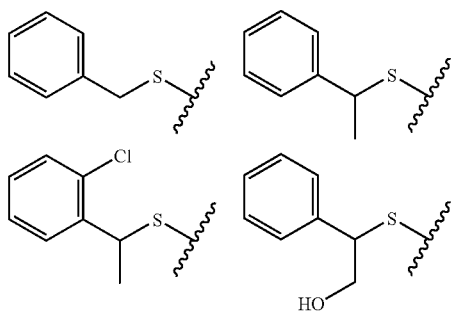

In another embodiment of Formula I, $R^3$ is $SR^6$ wherein $R^6$ is $CH(R^{10})$-hetAr$^5$. In certain embodiments, $R^{10}$ is H. In certain embodiments, $R^{10}$ is (1-6C)alkyl, for example (1-3C alkyl), for example methyl. In certain embodiments, $R^{10}$ is $CH_2OH$. In certain embodiments, hetAr$^5$ is pyridyl. In other embodiments, hetAr$^5$ is pyrimidyl.

Particular values for $R^3$ when represented by S—$CH(R^{10})$-hetAr$^5$ include the structures:

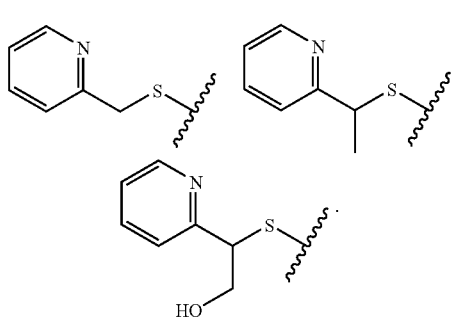

In certain embodiments of Formula I, $R^3$ is $SR^6$ wherein $R^6$ is hetAr$^6$ and hetAr$^6$ is a 9-10 membered bicyclic heteroaromatic ring having 2-3 heteroatoms independently selected from N, S and O (provided the ring does not contain an O—O bond). Examples include 5,5 and 5,6 fused ring systems. Particular examples include thienopyridyl, thienopyrimidyl, isoxazolopyridyl, pyrazolopyrimidyl and imidazopyridine rings.

In certain embodiments, hetAr$^6$ is unsubstituted. In certain embodiments, hetAr$^6$ is substituted with one or more groups independently selected from (1-6C)alkyl, F, Br, Cl, $CF_3$, CN, OH, —O-(1-6C alkyl), C(=O)OH, C(=O)O(1-6C alkyl) and C(=O)NH(1-3C alkyl)N(1-3Calkyl)$_2$.

In particular embodiments, herAr$^6$ is optionally substituted with one or two groups independently selected from Br, Cl, $C_1$-$C_6$ alkyl, and O(1-6 alkyl). Particular substituents include Br, Cl, Me, and OMe.

Particular values of $R^3$ when represented by S-hetAr$^6$ include the structures:

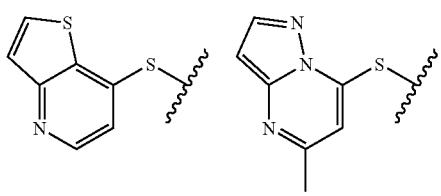

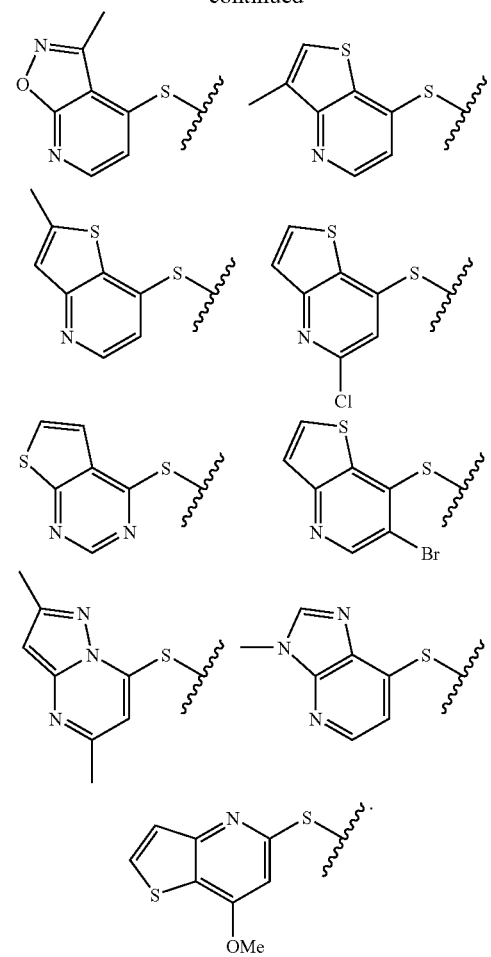

In certain embodiments, $R^3$ is $SR^6$ wherein $R^6$ is (1-6C) alkyl. A particular value for $R^3$ when represented by —S(1-6C alkyl) is SMe.

In certain embodiments, $R^3$ is $SR^6$ wherein $R^6$ is (1-3C alkoxy)(1-6C alkyl). Examples of $R^6$ include methoxy(1-6C alkyl) groups. Particular values for $SR^6$ include —S(CH$_2$CH$_2$)OMe and —S(CH$_2$CH$_2$CH$_2$)OMe.

In certain embodiments, $R^3$ is $SR^6$ wherein $R^6$ is cyclopropyl(1-6C alkyl). A particular value for $SR^6$ is —SCH$_2$(cyclopropyl).

In certain embodiments, $R^3$ is $SR^6$ wherein $R^6$ is selected from (1-3C alkoxy)(1-6C alkyl), cyclopropyl(1-6C alkyl), and pyridyl optionally substituted with one or more groups independently selected from (1-6C alkyl).

In certain embodiments, $R^3$ is $SR^6$ wherein $R^6$ is selected from methoxy(2-3C alkyl), cyclopropylmethyl, or pyridyl-2-yl optionally substituted with (1-6C alkyl).

Particular values for $R^6$ of Formula I include the structures:

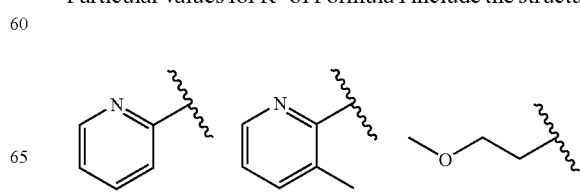

-continued

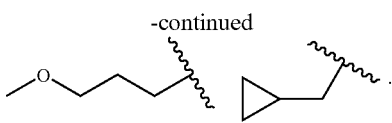

In certain embodiments, $R^3$ is aryl. In a particular embodiment, $R^3$ is phenyl.

In certain embodiments, $R^3$ is $hetAr^a$. In certain embodiments, $R^3$ is pyridyl or pyrimidyl. In a particular embodiment, $R^3$ is 2-pyridyl.

In certain embodiments, $R^3$ is Cl.

In certain embodiments, $R^3$ is Br.

In certain embodiments, $R^3$ is $CF_3$.

In certain embodiments, $R^3$ is $OR^6$. In one embodiment, $R^6$ is an optionally substituted $Ar^2$. In other embodiments, $R^6$ is an optionally substituted $hetAr^4$. In certain embodiments, $hetAr^4$ is a 6-membered heteroaryl having 1-2 ring nitrogens, for example pyridyl. Examples of $R^6$ groups include phenyl, chlorophenyl, pyridyl and methylpyridyl. Particular values of $R^3$ when represented by $OR^6$ include the structures:

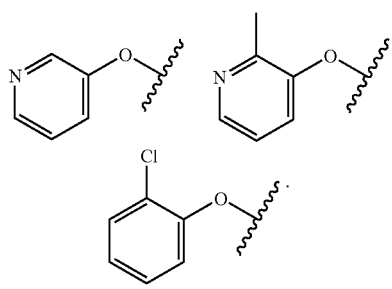

In certain embodiments, $R^3$ is $OR^6$ where $R^6$ is $hetAr^4$.

In certain embodiments, $R^3$ is $OR^6$ where $R^6$ is (1-6C alkyl).

In certain embodiments, $R^3$ is $OR^6$ where $R^6$ is -(1-6C alkyl)OH.

In certain embodiments, $R^3$ is $OR^6$ where $R^6$ is polyhydroxy(1-6C alkyl).

In certain embodiments, $R^3$ is $OR^6$ where $R^6$ is —CH($R^9$)—$Ar^3$.

In certain embodiments, $R^3$ is $OR^6$ where $R^6$ is —CH($R^{10}$)-$hetAr^5$.

In certain embodiments, $R^3$ is $OR^6$ where $R^6$ is $hetAr^6$.

In certain embodiments, $R^3$ is $OR^6$ where $R^6$ is (5-6C) cycloalkyl substituted with 1-4 OH.

In one embodiment of Formula I, $D^2$ is CH.
In one embodiment of Formula I, $D^2$ is N.
In one embodiment of Formula I, L is O.
In one embodiment of Formula I, L is S.

The compounds of Formula I also include compounds of Formula Ia

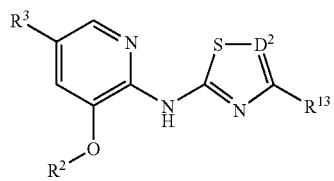

and salts thereof, wherein:

$R^{13}$ is a dihydroxy-(2-6C) alkyl or dihydroxy-(5-6C)cycloalkyl;

$D^2$ is N or CH;

$R^2$ is $hetAr^1$, $hetAr^2$, or $hetAr^3$;

$hetAr^1$ is a 5-6 membered heteroaryl group having 1-3 ring nitrogen atoms and optionally substituted with one or more groups independently selected from (1-6C alkyl), Cl, $CF_3$ and (1-6C alkyl)OH;

$hetAr^2$ is a partially unsaturated 5,5, 5,6 or 6,6 bicyclic ring system having 1-2 ring nitrogen atoms and optionally having a ring oxygen atom;

$hetAr^3$ is a 9-10 membered bicyclic heteroaryl ring having 1-3 ring nitrogen atoms;

$R^3$ is Cl, Br, $CF_3$, aryl, $hetAr^a$, $SR^6$ or $OR^6$;

$hetAr^a$ is a 6-membered heteroaryl having 1-2 ring nitrogen atoms;

$R^6$ is $Ar^2$, $hetAr^4$, (1-6C alkyl)OH, CH($R^9$)—$Ar^3$, or CH($R^{10}$)-$hetAr^5$;

$Ar^2$ is phenyl optionally substituted with one or more groups independently selected from (1-6C)alkyl, F, Br, Cl, $CF_3$, CN, OH, O-(1-6C alkyl), C(=O)OH, C(=O)O(1-6C alkyl), C(=O)NH(1-3C alkyl)N(1-3Calkyl)$_2$ and C(=O)NH(1-3C alkyl)$hetCyc^2$;

$hetAr^4$ is a 5-6 membered heteroaryl ring having 1-3 nitrogen atoms and optionally substituted with one or more groups independently selected from (1-6C)alkyl, F, Br, Cl, $CF_3$, CN, OH, O-(1-6C alkyl), C(=O)OH, C(=O)O(1-6C alkyl), C(=O)NH(1-3C alkyl)N(1-3Calkyl)$_2$ and C(=O)NH(1-3C alkyl)$hetCyc^2$;

$Ar^3$ is phenyl optionally substituted with one or more groups independently selected from F, Cl, Br, and (1-6C) alkyl;

$hetAr^5$ is a 6-membered heteroaryl having 1-2 ring nitrogen atoms; and $R^9$ and $R^{10}$ are independently hydrogen, (1-6C)alkyl, or $CH_2OH$.

In certain embodiments of Formula Ia, $R^2$ is $hetAr^1$.
In certain embodiments of Formula Ia, $R^2$ is $hetAr^2$.
In certain embodiments of Formula Ia, $R^2$ is $hetAr^3$.
In certain embodiments of Formula Ia, $R^3$ is Cl.
In certain embodiments of Formula Ia, $R^3$ is Br.
In certain embodiments of Formula Ia, $R^3$ is $CF_3$.
In certain embodiments of Formula Ia, $R^3$ is aryl.
In certain embodiments of Formula Ia, $R^3$ is $hetAr^a$.
In certain embodiments of Formula Ia, $R^3$ is $SR^6$.
In certain embodiments of Formula Ia, $R^3$ is $OR^6$.

The compounds of Formula I also include compounds of Formula Ib

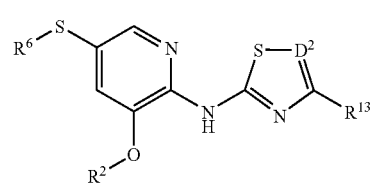

and salts thereof wherein:

$R^{13}$ is 1,2-dihydroxyethyl;

$D^2$ is N or CH;

$R^2$ is phenyl, pyridyl or pyrazolyl, each of which is optionally substituted with one or more (1-6C)alkyl groups; and $R^6$ is phenyl, pyridyl or (1-6C alkyl)OH, wherein said phenyl and pyridyl are optionally substituted with one or more (1-6C)alkyl groups.

It has been found that compounds of Formula Ib have improved pharmacokinetic properties. For example, certain compounds of Formula Ib have been found to have increased oral bioavailability, increased exposure (i.e., increased blood levels over time), and/or lower clearance. In addition, certain compounds of Formula Ib have been found to have increased aqueous solubility.

In certain embodiments of Formula Ib, $R^{13}$ is (S)-1,2-dihydroxyethyl.

In certain embodiments of Formula Ib, $R^{13}$ is (R)-1,2-dihydroxyethyl.

In certain embodiments of Formula Ib, $D^2$ is N.

In certain embodiments of Formula Ib, $D^2$ is CH.

In certain embodiments of Formula Ib, $R^2$ is phenyl.

In certain embodiments of Formula Ib, $R^2$ is pyridyl. In certain embodiments, the pyridyl group is substituted with one or more (1-6C)alkyl groups, for example one or more methyl groups, for example one methyl group. In particular embodiments of Formula Ib, $R^2$ is selected from the structures:

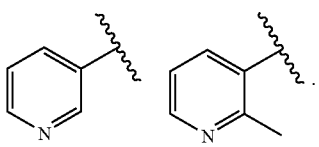

In certain embodiments of Formula Ib, $R^2$ is pyrazolyl which is optionally substituted with one or more (1-6C)alkyl groups. In certain embodiments, $R^2$ is 1H-pyrazolyl. In particular embodiments, $R^2$ is 1H-pyrazol-4-yl. In certain embodiments, the pyrazolyl group is substituted with one or more (1-3C)alkyl groups, for example one or more methyl groups. In particular embodiments of Formula Ib, $R^2$ is selected from the structures:

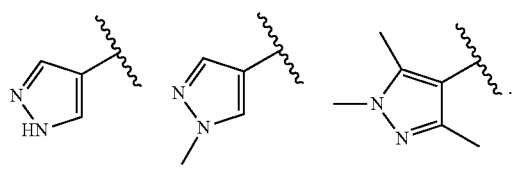

In certain embodiments of Formula Ib, $R^6$ is phenyl.

In certain embodiments of Formula Ib, $R^6$ is pyridyl. In certain embodiments, $R^6$ is 3-pyridyl. In certain embodiments, the pyridyl is substituted with a (1-6C)alkyl group, for example a methyl group. Particular values for $R^6$ include pyrid-3-yl and 2-methylpyrid-3-yl.

In certain embodiments of Formula Ib, $R^6$ is (1-3C alkyl)OH. A particular value is —CH$_2$CH$_2$OH.

In a particular embodiment of Formula Ib:

$D^2$ is N;

$R^2$ is pyridyl or pyrazolyl, each of which is optionally substituted with one or more methyl groups; and $R^3$ is pyridyl optionally substituted with one or more methyl groups.

Formula I also includes a compound of the general Formula Ic:

or a pharmaceutically acceptable salt thereof, wherein:

$R^{13}$ is dihydroxy(2-6C)alkyl or methoxy(dihydroxy(3-6C)alkyl);

$R^2$ is a pyridyl or pyrazolyl ring, each of which is optionally substituted with one or more groups independently selected from (1-6C)alkyl; and $R^6$ is (1-3C alkoxy)(1-6C alkyl)-, cyclopropyl(1-6 C alkyl)-, or pyridyl optionally substituted with one or more groups independently selected from (1-6C alkyl).

In one embodiment of Formula Ic, $R^{13}$ is dihydroxy(2-4C)alkyl or methoxy(dihydroxy(3-4C)alkyl).

In one embodiment of Formula Ic, $R^{13}$ is a 1,2-dihydroxy (2-4C alkyl) or a methoxy(1,2-dihydroxy(3-4C)alkyl), such as 3-methoxy-1,2-dihydroxy(3-4C alkyl). In one embodiment of Formula Ic, the alpha carbon of the $R^{13}$ group is in the S configuration. In another embodiment, the alpha carbon of the $R^{13}$ group is in the R configuration.

In one embodiment of Formula Ic, $R^{13}$ is selected from the structures:

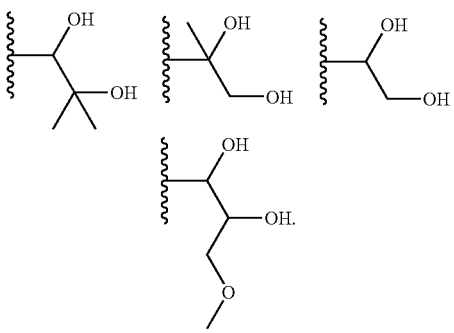

Particular values of $R^{13}$ for Formula Ic can be represented by the structures:

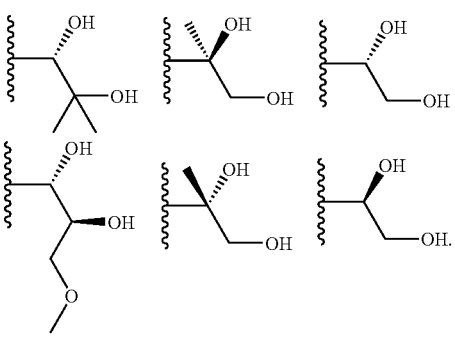

In certain embodiments of Formula Ic, $R^2$ is pyrid-3-yl, pyrazol-4-yl or pyrazol-5-yl, each of which is optionally substituted with one or more groups independently selected from (1-6C alkyl), for example one or more groups independently selected from methyl and ethyl. Particular values for $R^2$ include the structures:

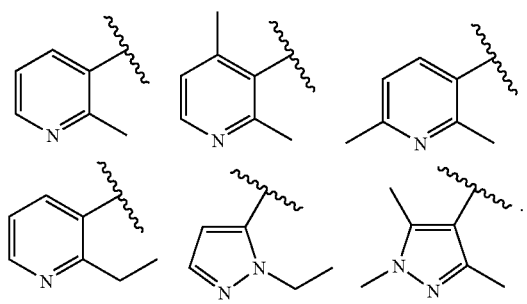

In one embodiment of Formula Ic, $R^6$ is (1-3C alkoxy)(1-6C alkyl). In one embodiment, $R^6$ is $CH_3O$-(2-3C alkyl)-. Particular values of $R^6$ for Formula Ic include the structures:

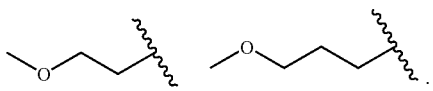

In one embodiment of Formula Ic, $R^6$ is cyclopropyl(1-6 C alkyl)-. In a particular embodiment, $R^6$ is cyclopropylmethyl.

In one embodiment of Formula Ic, $R^6$ is pyridyl optionally substituted with one or more groups independently selected from (1-6C alkyl). In one embodiment, $R^6$ is pyridyl-2-yl optionally substituted with one or more groups independently selected from (1-6C alkyl), for example one or more groups independently selected from methyl or ethyl. Particular values for $R^6$ of Formula Ic include the structures:

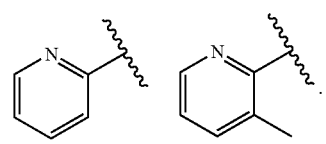

Formula I also includes a compound of the general Formula Id:

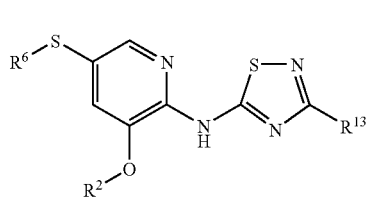

or a pharmaceutically acceptable salt thereof, wherein:
$R^{13}$ is a 1,2-dihydroxy(2-6C)alkyl or a methoxy(1,2-dihydroxy(3-6C)alkyl);
$R^2$ is pyrid-3-yl, pyrazol-4-yl or pyrazol-5-yl, each of which is optionally substituted with one or more groups independently selected from (1-6C)alkyl; and
$R^6$ is methoxy(2-3C alkyl), cyclopropylmethyl, or pyridyl-2-yl optionally substituted with (1-6C alkyl).

In one embodiment of Formula Id, the alpha carbon of the $R^{13}$ group is in the S configuration. In another embodiment, the alpha carbon of the $R^{13}$ group is in the R configuration.

In one embodiment of Formula Id, $R^{13}$ is a 1,2-dihydroxy(2-4C)alkyl or a methoxy(1,2-dihydroxy(3-4C)alkyl), such as 3-methoxy-1,2-dihydroxy(3-4C alkyl).

In one embodiment of Formula Id, $R^{13}$ is selected from the structures:

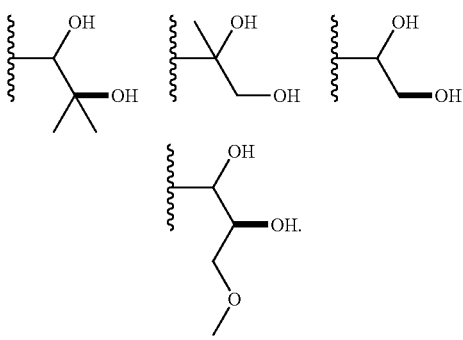

Particular values of $R^{13}$ for Formula Id can be represented by the structures:

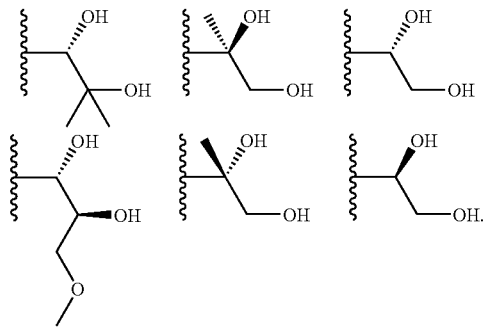

In certain embodiments of Formula Id, $R^2$ is optionally substituted with one to three groups independently selected from (1-6C alkyl), for example one to three groups independently selected from methyl and ethyl. Particular values for $R^2$ include the structures:

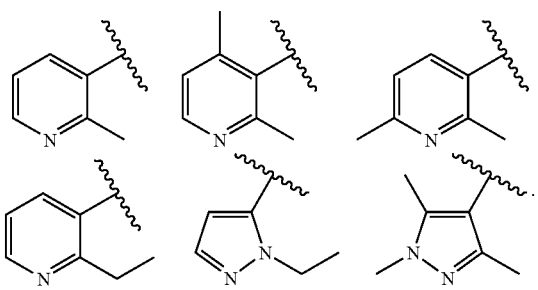

In certain embodiment of Formula Id, $R^6$ is methoxy(2-3C alkyl). Particular values include the structures:

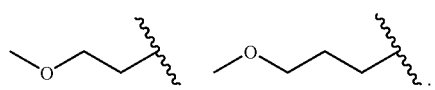

In certain embodiments of Formula Id, $R^6$ is cyclopropylmethyl.

In certain embodiments of Formula Id, $R^6$ is pyridyl-2-yl optionally substituted with (1-6C alkyl), for example methyl or ethyl. Particular values for $R^6$ of Formula Id include the structures:

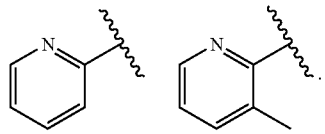

It has been found that compounds of Formulas Ic and Id have particularly unexpected and desirable properties. For example, the compounds have sufficient solubility, including at low pH, to have dose proportional PK. Compounds of Formulas Ic and Id also have superior activity in the presence of plasma proteins (i.e., in the presence of 4% HSA) when tested in the assay described in Example A.

The compounds of Formulas Ic and Id also unexpectedly have low clearance via conjugation reactions. The main course of clearance of compounds of Formulas Ic and Id is via hepatic oxidation of the 5-$SR^6$ moiety and not conjugation to and/or oxidation of the diol moiety. This property diminishes the likelihood of saturation of a clearance mechanism; allowing good predictability of blood levels of the active compound and contributing to dose proportional PK.

In addition, the compounds of Formulas Ic and Id unexpectedly achieve a high oral AUC (area under the plasma drug concentration-time curve after a low oral dose), which results in a greater amount of the compound which is available for binding to the glucokinase enzyme. Together with the linear and dose proportional PK, this allows the therapeutic concentrations of the compound to be reached in a predictable manner.

The dose proportionality and high exposure of compounds of Formulas Ic and Id afford pharmacokinetic parameters that won't change when different doses are administered or when the drug is given through different routes of administration or as single or multiple doses. As a result, patients are less likely to be overdosed when doses are slightly increased. In addition, lower doses will be needed to achieve the therapeutic efficacy.

In contrast, drugs with nonlinearity may have decreased oral bioavailability due to several possible reasons, including drug concentration approaching the drug's solubility limit in the GI tract, or saturatable transport system for absorption or increased oral bioavailability due to saturatable metabolism at high concentrations.

Particular examples of compounds of Formulas Ic and Id are provided in Table 1, which also includes relative values for the oral AUC (at 10 mg/kg) when tested in the assay described in Example B. The compounds in Table 1 were found to have an $EC_{50}$ value less than 1 μM when tested in 4% HSA according to the assay described in Example A.

Particular examples of compounds of Formulas Ic and Id are provided in Table 1, which also provides relative values for the oral AUC (at 10 mg/kg) when tested in the assay described in Example B. The compounds in Table 1 were found to have an $EC_{50}$ value less than 1 μM when tested in 4% HSA according to the assay described in Example A.

TABLE 1

| Example # | Structure | AUC indicator* |
|---|---|---|
| 134 | 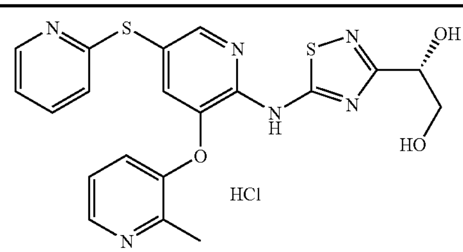 | +++ |
| 135 | 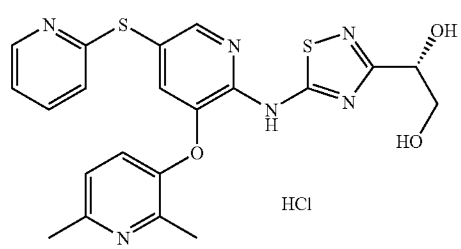 | ++ |
| 136 | 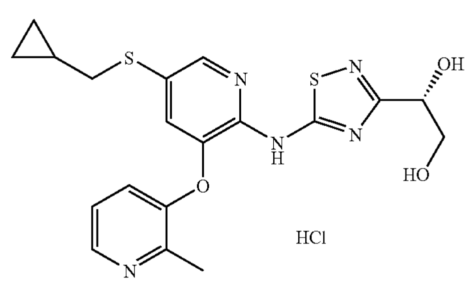 | +++ |

TABLE 1-continued

| Example # | Structure | AUC indicator* |
|---|---|---|
| 137 | 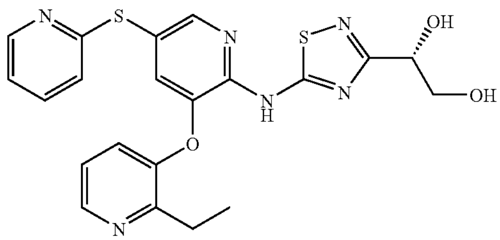 | ++ |
| 138 | HCl | + |
| 139 | HCl | ++++ |
| 140 | 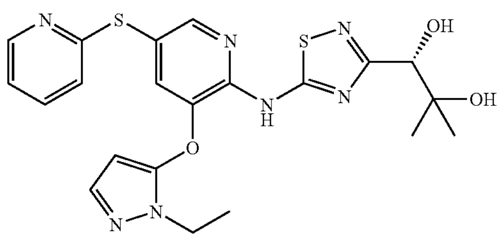 | ++++ |
| 141 | HCl | + |
| 142 | HCl | + |

TABLE 1-continued
| Example # | Structure | AUC indicator* |
|---|---|---|
| 143 | 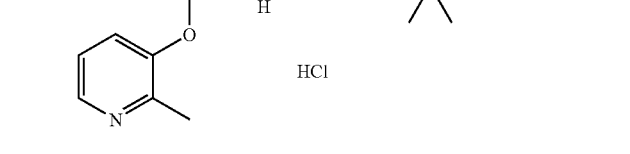 HCl | ++++ |
| 144 | 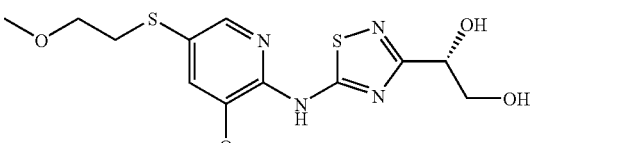 HCl | ++ |
| 145 |  HCl | ++ |
| 146 | 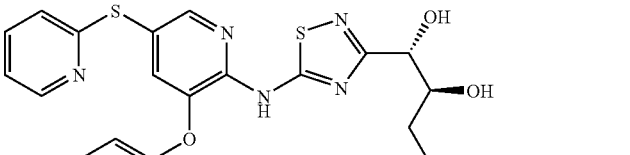 HCl | +++ |
| 147 |  HCl | + |
| 148 | 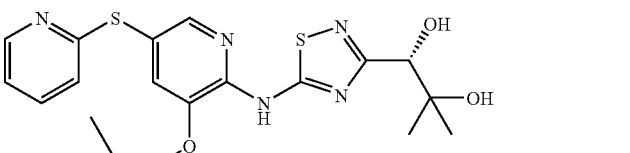 HCl | + |

TABLE 1-continued

| Example # | Structure | AUC indicator* |
|---|---|---|
| 149 | [structure: pyridine-S-pyridine linked to thiadiazole with CH(OH)CH2OH, with pyridinyloxy substituent] | ++ |
| 150 | [structure: similar to 149 with C(CH3)(OH)CH2OH, HCl salt] | +++ |
| 151 | [structure: similar to 150, HCl salt, stereochemistry indicated] | ++++ |

*Indicator:
+ AUC = 1-5 μg*hr/mL
++ AUC = 5-10 μg*hr/mL
+++ AUC = 10-20 μg*hr/mL
++++ AUC = >20 μg*hr/mL It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

For illustrative purposes, Schemes A-S show general methods for preparing the compounds of the present invention as well as key intermediates. For a more detailed description of the individual reaction steps, see the Examples section below.

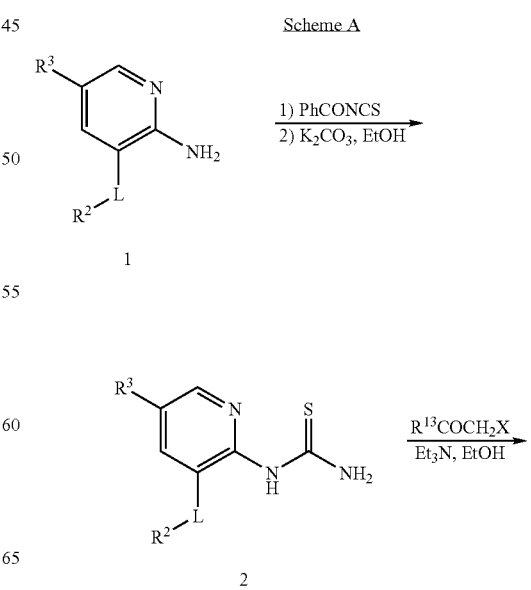

Scheme A

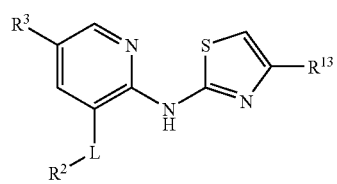

3A

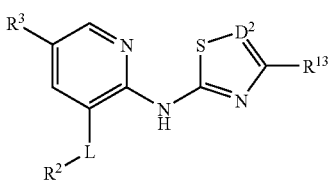

3

Scheme A shows a method of preparing compounds (3A) of Formula I. To prepare compound (3A), a 2-aminoheterocycle (1) is reacted with benzoylisothiocyanate to afford a benzoylthiourea intermediate, which is hydrolyzed to the thiourea (2) with a base such as, but not limited to, potassium carbonate in a suitable solvent such as, but not limited to, ethanol. Alternatively, the aminoheterocycle (1) can be treated with an inorganic or ammonium isothiocyanate, e.g., Meckler's procedure, in the presence of an acid to afford the thiourea (2) in one step. Treatment of the thiourea (2) with an α-haloketone $R^{13}COCH_2X$, wherein X=OTs, Cl, Br, I, or $NR_3$ (wherein $R=C_1$-$C_6$ alkyl), in a suitable base such as triethylamine, Hunig's base, DBU, alkali carbonate, sodium hydroxide, etc. and a suitable solvent such as ethanol affords the thiazole (3A). If the desired α-halo ketone $R^{13}COCH_2X$ is not commercially available, it can be prepared by various methods known to those skilled in the art. Examples include, but are not limited to, bromination of commercially or readily synthesized methyl ketones (*Tetrahedron* (1970) 5611-5615; *Organic Synthesis* (1946) 13-15; *Tetrahedron* (1990) 2943-2964), diazomethane treatment of carbonyl chlorides, oxidation of 1-chloro-2-alkanols, bromination of silyl enol ethers, or halogenation of β-keto esters followed by decarboxylation. After formation of the thiazole (3A), protecting groups, if present, can be removed.

Scheme B shows an alternative method of preparing a compound of Formula I. According to Scheme B, hydroxylated heteroaryl halide (5) (if not commercially available) can be prepared from heteroaryl halide (4) by: 1) ortho metalation with LDA or another suitable base; 2) conversion of the anion to the boronate via reaction with $B(OR)_3$; and 3) oxidation of the boronate with a suitable oxidant such as N-methylmorpholine oxide or hydrogen peroxide. The ortho metalated species can also be quenched with $(TMSO)_2$ to obtain the hydroxylated material (5) directly upon acidic workup. The hydroxylated heteroaromatic compound (5) can be alkylated with $R^2X$ in the presence of a base such as, but not limited to, cesium carbonate or sodium hydride and in a suitable solvent such as, but not limited to, DMF to afford compound (6). Compound (6) can be converted to compound (7) by the method of Hartwig et al. (for an example of this transformation via analogy see: *Organic Letters* (2001) 2729-2732), or by treatment with a Pd catalyst and benzophenone imine, or by heating in the presence of ammonia (or $NH_2PG$ where PG is a protecting group).

Compound (7) can be converted to compound (3) of Formula I upon reaction with a halo-substituted thiazole or halo-substituted thiadiazole in the presence of a base catalyst or metal (e.g., copper or palladium) catalyst. Alternatively, compound (6) can be converted directly to a compound (3) of Formula I upon treatment with an amino-substituted thiazole or amino-substituted thiadiazole via base catalysis or via copper or palladium catalysis; i.e., the Buchwald reaction. After formation of compound (3), protecting groups, if present, can be removed.

Scheme B

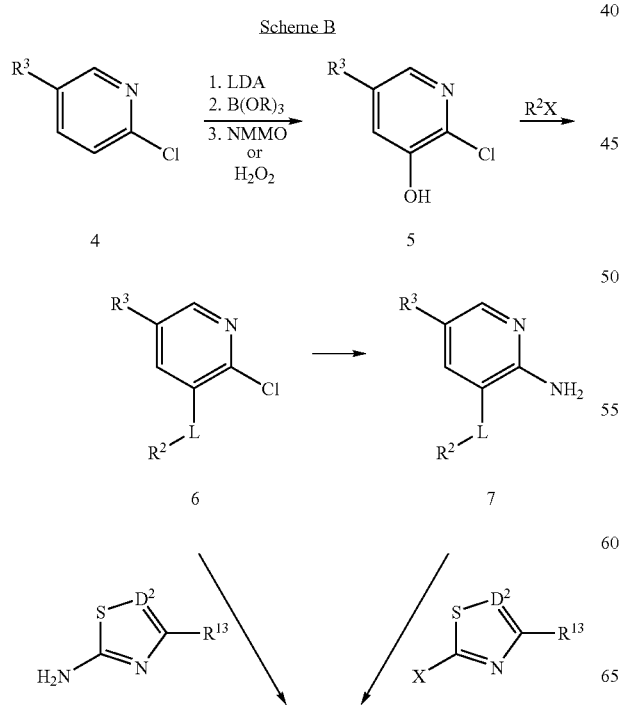

Scheme C

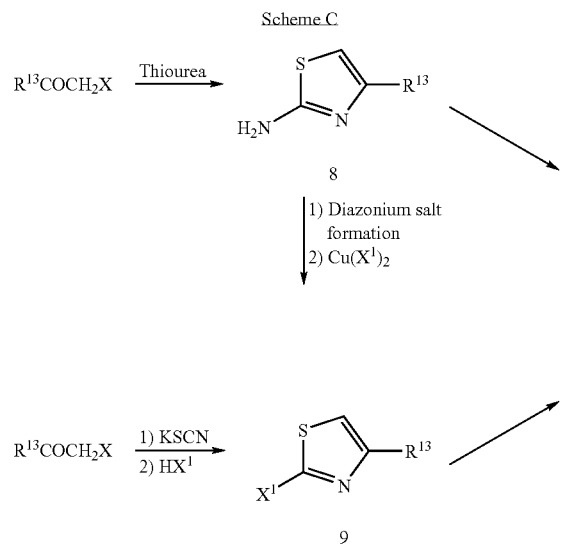

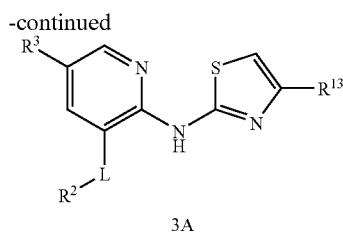

3A

Scheme C shows a method of preparing 2-aminothiazole and 2-halothiazole intermediates (8) and (9), respectively, which are suitable for use in preparing compounds of Formula I as shown in Scheme B. According to Scheme C, α-haloketone $R^{13}COCH_2X$ can be treated with thiourea in the presence of a suitable base such as potassium carbonate or triethylamine in an appropriate solvent such as DMF or ethanol to afford aminothiazole (8). The aminothiazole (8) can be converted to a diazonium salt intermediate by numerous methods including, but not limited to, treatment with sodium nitrite in acid or isobutylnitrite. Treatment of the in situ diazonium salt with $Cu(X^1)_2$ ($X^1$=Cl or Br) or HBr affords the corresponding 2-halothiazole (9). Alternatively, using the Hantzsch synthetic method, the α-haloketone $R^{13}COCH_2X$ can be treated first with KSCN, then with HX wherein X is Cl or Br, to provide the 2-halothiazole (9). The 2-halothiazole compounds (8) and (9) can be converted into compound (3A) by the methods shown in Scheme B.

and (16), respectively, which are suitable for use in preparing compounds of Formula I as shown in Scheme B. According to Scheme D, primary amide (14) can be converted into 5-amino-1,2,4 thiadiazole (15) by heating with KSCN in an appropriate solvent such as methanol or ethanol (*Adv. Heterocycl. Chem.*, (1982) 32, 285). Formation of the diazonium salt of compound (15), followed by treatment of the in situ diazonium salt with $CuCl_2$ affords the corresponding 5-chloro-1,2,4-thiadiazole (16). The corresponding bromo derivative can also be synthesized through the use of $CuBr_2$. Alternatively, reaction of amidine (17) with perchloromethyl mercaptan affords 5-chloro-1,2,4-thiadiazole (16) (*Bioorg. Med. Chem.*, (2003) 11, 5529-5537). Intermediates (15) and (16) can be converted into compound (3C) of Formula I by the methods shown in Scheme B.

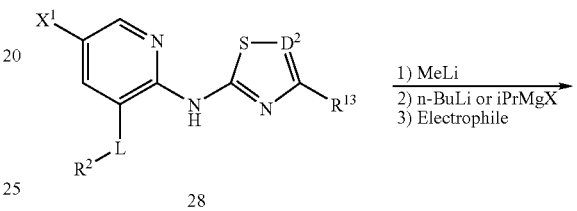

Scheme E

28

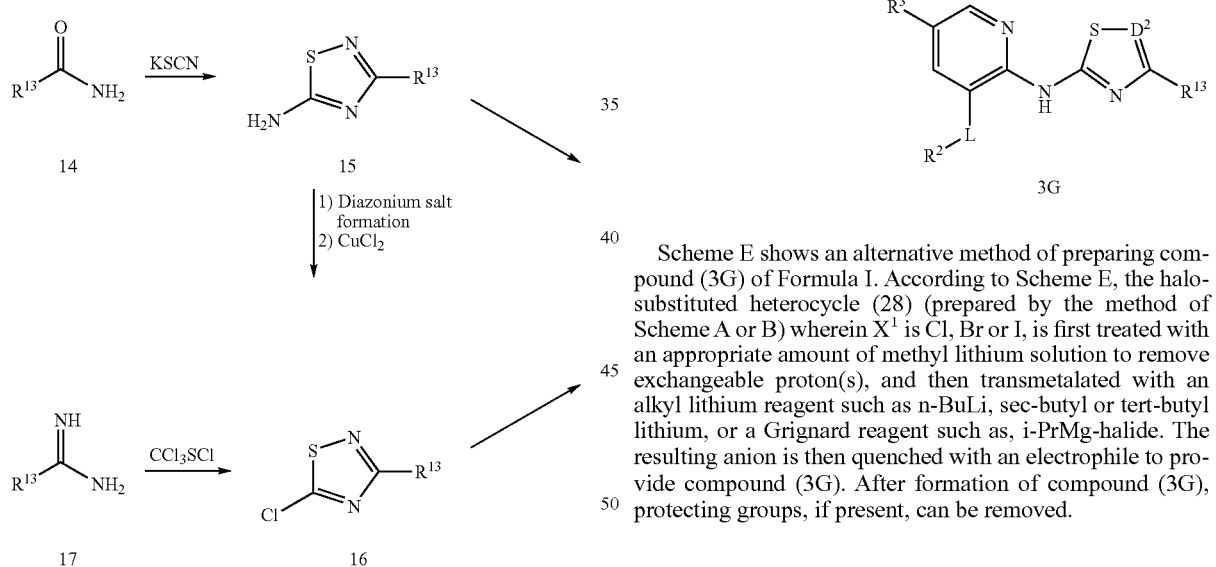

Scheme D

14

15

1) Diazonium salt formation
2) $CuCl_2$

17

16

3C

3G

Scheme E shows an alternative method of preparing compound (3G) of Formula I. According to Scheme E, the halo-substituted heterocycle (28) (prepared by the method of Scheme A or B) wherein $X^1$ is Cl, Br or I, is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with an electrophile to provide compound (3G). After formation of compound (3G), protecting groups, if present, can be removed.

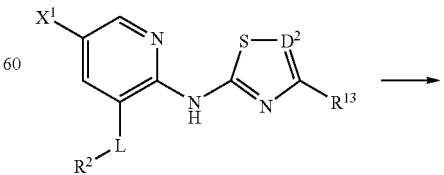

Scheme F

28

Scheme D shows a method of preparing 5-amino-1,2,4-thiadiazole and 5-chloro-1,2,4-thiadiazole intermediates (15)

-continued

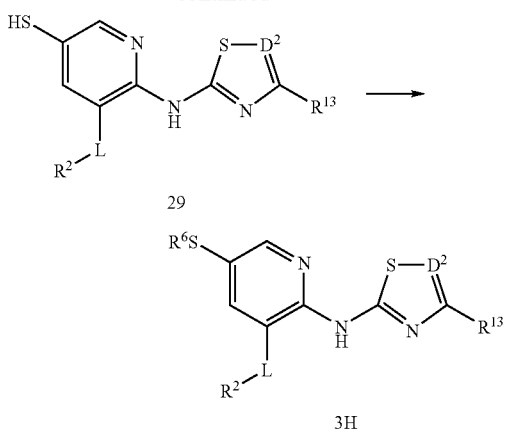

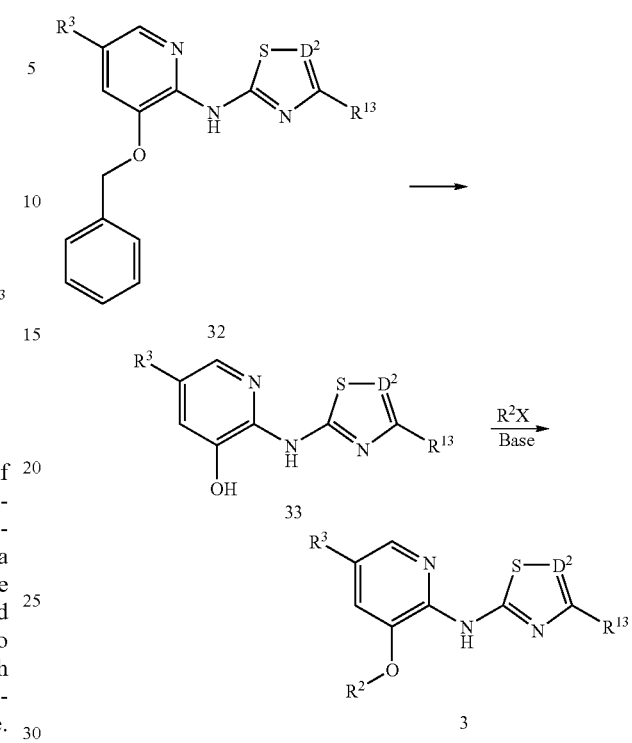

Scheme F shows a method of preparing compounds (3H) of Formula I from a halo substituted heterocycle (28). According to Scheme F, the halo-substituted heterocycle (28), prepared by the method of Scheme A or B, can be converted to a thiol (29) via one of several procedures. According to one method, the halo-substituted heterocycle (28) is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is quenched with either elemental sulfur or bis(trimethylsilyl) peroxide to form the corresponding mercapto-substituted compound (29). Alternatively, the halide (28) can be converted under Pd-mediated conditions to thiol (29) utilizing potassium triisopropylsilanethiolate (*Tetrahedron Letters* (1994) 3225-3226). The thiol can be reacted with a variety of electrophiles using standard reaction conditions to provide the corresponding ether (3H) of Formula I. Suitable electrophiles include, but are not limited to, activated heteroaryl halides such as, but not limited to, 2-fluorocyanobenzene, 4-fluorocyanobenzene, 2-fluoronitrobenzene, 4-fluoronitrobenzene, 2-chloro-4-nitropyridine, 2-halopyridine, 2-halopyrimidine, 4-halopyrimidine, aryl halides and heteroaryl halides. After formation of compound (3H), protecting groups, if present, can be removed.

Scheme G shows an alternate method of adding the linker $OR^2$ to a core heterocycle to provide a compound (3) of Formula I. According to Scheme G, a benzyl ether (32), prepared by the method of Scheme A or B, can be converted to the hydroxyl substituted heterocycle (33), for example by hydrolysis with a strong acid (e.g., 6N HCl) or by hydrogenation (e.g., $H_2$ or ammonium formate in the presence of a metal catalyst). Alkylation of the hydroxylated heterocycle (33) with $R^2X$, wherein X=F, Cl, Br, I, or $NR_3$ (where R is $C_1$-$C_6$ alkyl) in the presence of a base such as, but not limited to, cesium carbonate, in a suitable solvent such as, but not limited to, DMF, or via copper or palladium catalysis (i.e., the Ullman reaction) affords compound (3) of Formula I. After formation of compound (3), protecting groups, if present, can be removed.

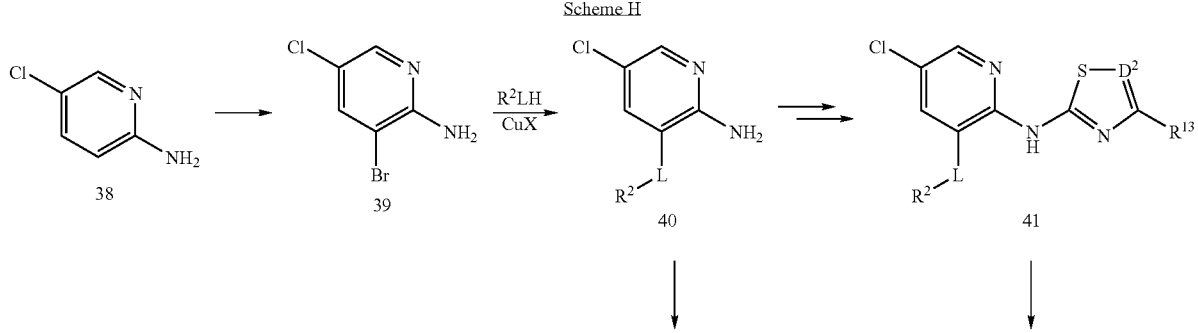

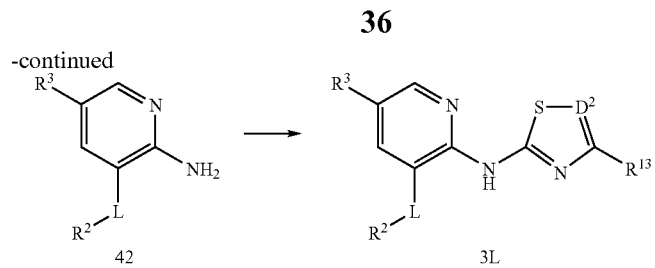

Scheme H shows an alternative method of preparing a compound (3 L) of Formula I. According to Scheme H, the 2-aminopyridine (38) is regioselectively brominated with a suitable brominating agent such as NBS or bromine to provide compound (39). The brominated compound can be converted to compound (40) upon reaction with $R^2LH$ (wherein L is O) in the presence of a suitable base such as cesium carbonate, sodium hydride or triethylamine in the presence of a metal catalyst (i.e.; CuI or $Pd_2dba_3$) in a suitable solvent such as DMSO or DMF. The chlorinated product (40) can be converted to compound (41) by the method of Scheme A, B or L. Compound (41) can be converted to a 5-substituted compound (3 L) of Formula I by the method of Scheme E or F. Alternatively, the chlorinated 2-aminopyridine (40) can be converted to a 5-substituted compound (42) by the method of Scheme E or F, and then the thiazolyl or thiadiazolyl group can be added to compound (42) by the method of Scheme A, B or L to provide compound (3 L). After formation of compound (3 L), protecting groups, if present, can be removed.

Scheme I shows an alternative method of preparing a compound (3 L) of Formula I. According to Scheme I, reaction of compound (43) with $R^2LH$ (where L is O) in the presence of a suitable base such cesium carbonate or sodium hydride either with or without a metal catalyst (i.e.; $Pd_2dba_3$ or CuI) in DMSO or DMF affords compound (44) wherein L is O.

The 2-aminopyridine (44) is then regioselectively brominated with a suitable brominating agent such as NBS or bromine to provide compound (45). The brominated product (45) can be converted to compound (46) by the method of Scheme A, B or L. Compound (46) can be converted to 5-substituted compounds (3 L) of Formula I by the method of Scheme E or F. Alternatively, the brominated 2-aminopyridine (45) can be converted to a 5-substituted compound (47) by the method of Scheme E or F, and then the thiazolyl or thiadiazolyl group can be added to compound (47) by the method of Scheme A, B or L to provide compound (3 L). After formation of compound (3 L), protecting groups, if present, can be removed.

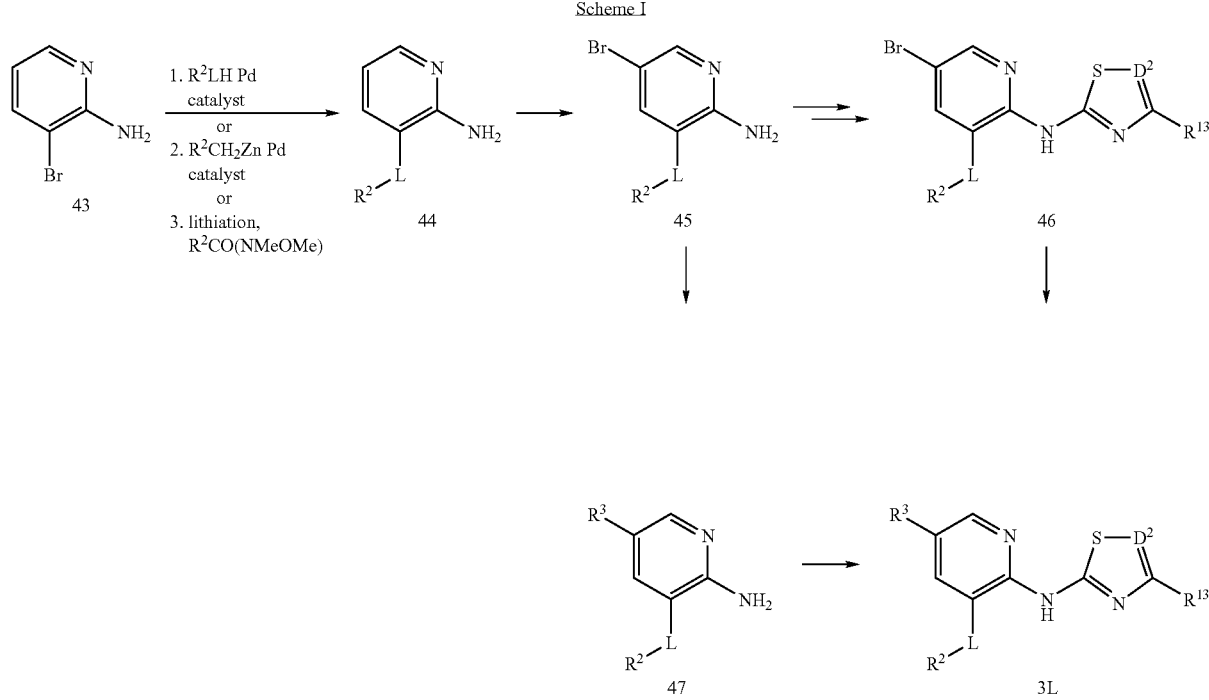

Scheme J

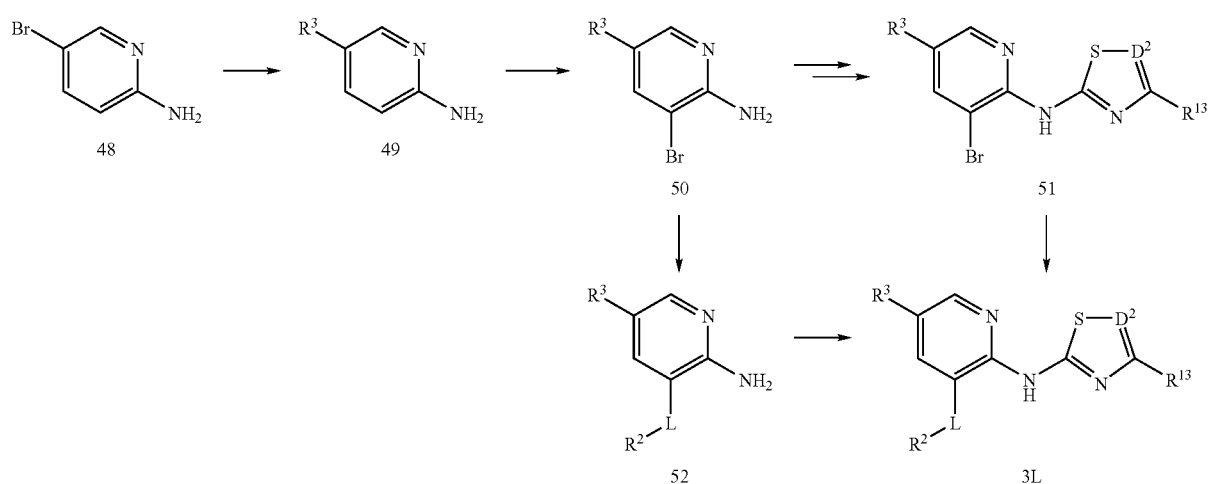

Scheme J shows an alternative method of preparing a compound (3L) of Formula I. According to Scheme J, reaction of compound (48) (which if not commercially available can be made from commercial aminopyridines via regioselective bromination) in the presence of a suitable base such cesium carbonate or sodium hydride and with or without a metal catalyst (e.g., $Pd_2\ dba_3$ or CuI) in DMSO or DMF affords compound (49) by a method such as: ipso replacement using $R^6SH$; Buchwald thioether formation with $R^6SH$, etc., according to procedures well known in the literature. The 2-aminopyridine (49) is then regioselectively brominated with a suitable brominating agent such as NBS or bromine to provide compound (50). The brominated product (50) can be converted to compound (51) by the method of Scheme A, B or L. Compound (51) can be converted to 5-substituted compounds (3L) of Formula I by Buchwald ether formation with $R^2OH$. Alternatively, the brominated 2-aminopyridine (50) can first be converted to compound (52) by the Buchwald chemistry, and compound (52) can be converted to compound (3L) by the method of Scheme A, B or L. After formation of compound (3L), protecting groups, if present, can be removed.

Scheme K

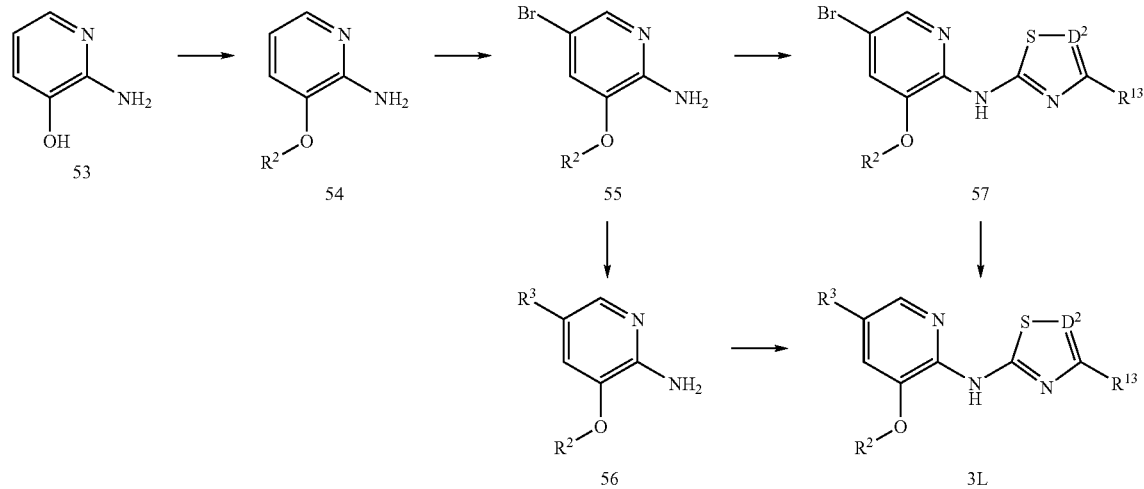

Scheme K shows an alternative method of preparing a compound (3L) of Formula I. Treatment of compound (53) with $R^2X$ in the presence of a suitable base such as cesium carbonate or sodium hydride, with or without a metal catalyst, affords compound 54. Subsequently, compound (54) can be regioselectively brominated to afford compound (55). This compound can be converted to compound (56) via the methods described in Schemes E or F. Compound (56) is then converted to compound (3L) via the procedures found in Schemes A, B or L. Alternatively, compound (55) can be converted to compound (57) via the procedures found in Schemes A, B or L, and then converted to compound (3L) via the procedures found in Schemes E or F. After formation of compound (3L), protecting groups, if present, can be removed.

Scheme L

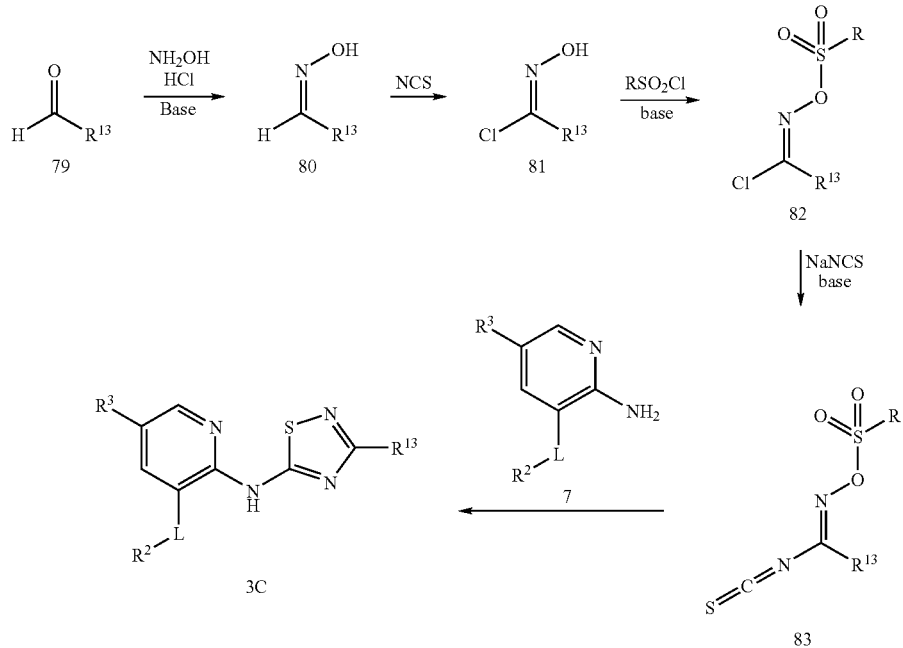

Scheme L shows an alternative method for producing compounds of the formula 3C wherein $D^2$ is N. Formation of oxime (80) from aldehyde (79) allows for the chlorination with N-chlorosuccinimide in a suitable solvent, such as DMF, to produce compound (81). Compound (81) is sulfonylated with a sulfonyl chloride having the formula R'SO$_2$Cl wherein R' is, C$_1$-C$_6$ alkyl (for example, methyl) or aryl optionally substituted with C$_1$-C$_6$ alkyl (for example, tolyl) in the presence of a base, such as but not limited to triethylamine, to afford compound (82) with a thiocyanate salt, such as NaNCS, in a suitable solvent, such as acetonitrile, and in the presence of a base, such as but not limited to pyridine, affords the activated intermediate (83) (see, for example, Takeuchi, K., JP 2001081084). Intermediate (83) can be reacted in situ with an appropriate amino heterocycle (7) to afford compound (3C) of Formula I. After formation of compound (3C), protecting groups, if present, can be removed.

Scheme M

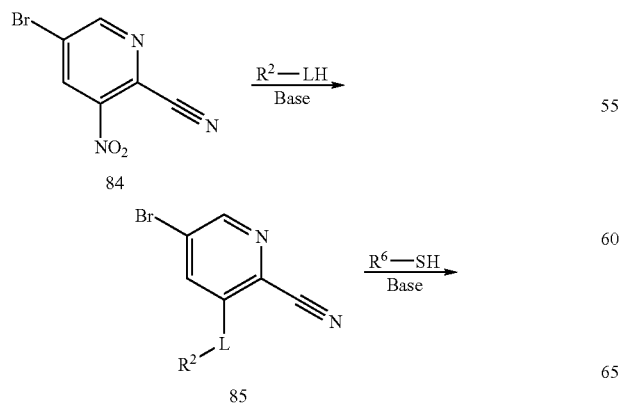

-continued

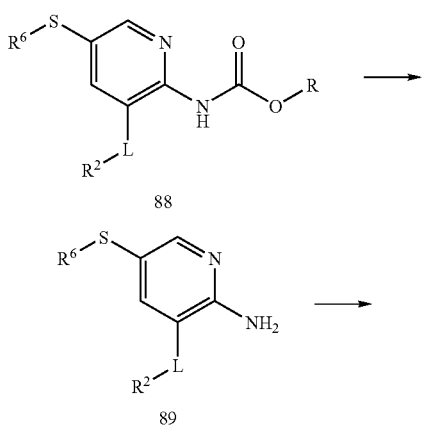

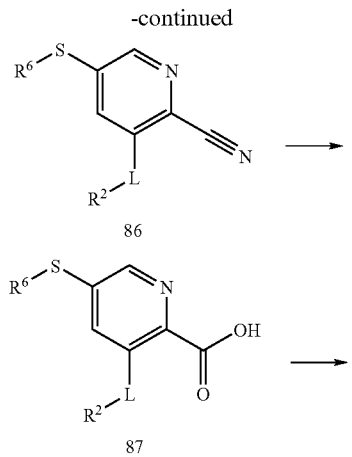

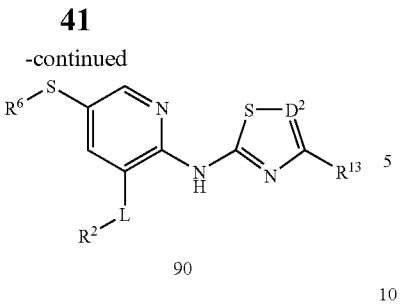

90

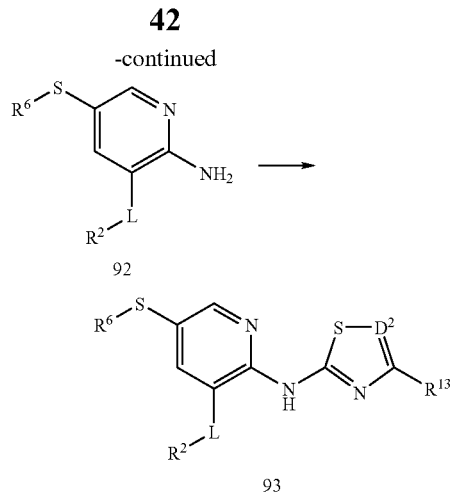

Scheme M shows an alternative method for the construction of compounds of Formula I. Starting from the commercially available 2-cyanopyridine (84), selective nucleophilic displacement can be achieved with compounds of the formula R²LH and an appropriate base, such as sodium hydride, in a suitable solvent, such as DMF to provide compound (85). Addition of a second nucleophile having the formula R⁶SH, under similar conditions, affords the functionalized 2-cyanopyridine (86). Hydrolysis of the nitrile can occur under many conditions, with NaOH in aqueous ethanol being preferred, to afford the picolinate (87). Curtius rearrangement in the presence of an appropriate alcohol affords the carbamate (88). The carbamate can be removed using various conditions, depending on the alcohol used in the previous step, to provide the 2-aminopyridine (89). Using procedures outlined in Schemes A, B or L, compound (90) of the Formula I can be synthesized from compound (89). After formation of compound (90), protecting groups, if present, can be removed.

Scheme N shows another alternative method for the construction of compounds of Formula I. Starting from the commercially available 5-bromo-3-nitropicolinonitrile (84), selective nucleophilic displacement can be achieved with compounds of the formula R²LH and an appropriate base, such as sodium hydride, in a suitable solvent, such as DMF to provide compound (85). Addition of a second nucleophile having the formula R⁶SH, under similar conditions, affords the functionalized 2-cyanopyridine (86). Hydrolysis of the nitrile to the amide (91) can occur under standard conditions, such as with concentrated $H_2SO_4$. A Hofmann reaction to convert (91) to the aminopyridine (92) can occur under standard conditions, such as with NaOBr. Using procedures outlined in Schemes A, B or L, compound (93) of the Formula I can be synthesized from compound (92). After formation of compound (93), protecting groups, if present, can be removed.

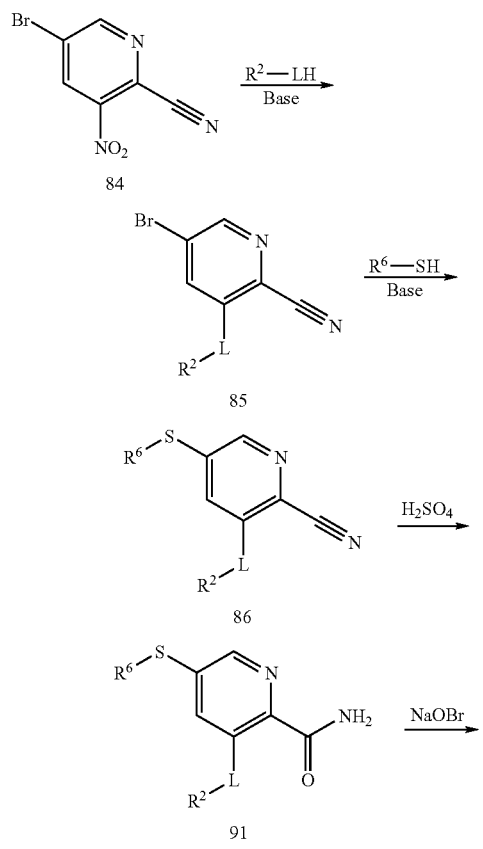

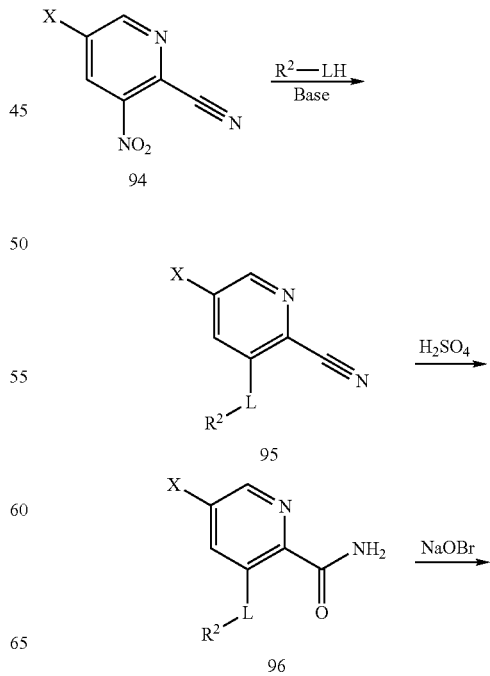

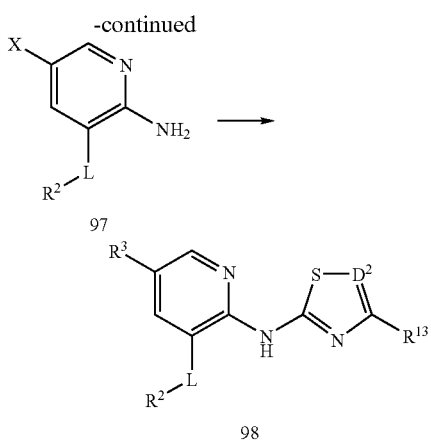

Scheme O shows an alternative method for the construction of compounds of Formula I. Starting from the commercially available substituted pyridine (94) in which X is Br or Cl, selective nucleophilic displacement can be achieved with compounds of the formula $R^2LH$ and an appropriate base, such as sodium hydride, in a suitable solvent, such as DMF to provide compound (95). Hydrolysis of the nitrile to the amide (96) can occur under standard conditions, such as with concentrated $H_2SO_4$. A Hofmann reaction to convert (96) to the aminopyridine (97) can occur under standard conditions, such as with NaOBr. Using procedures outlined in Schemes A, B, E, F or L, compound (98) of the Formula I can be synthesized from compound (97). After formation of compound (98), protecting groups, if present, can be removed.

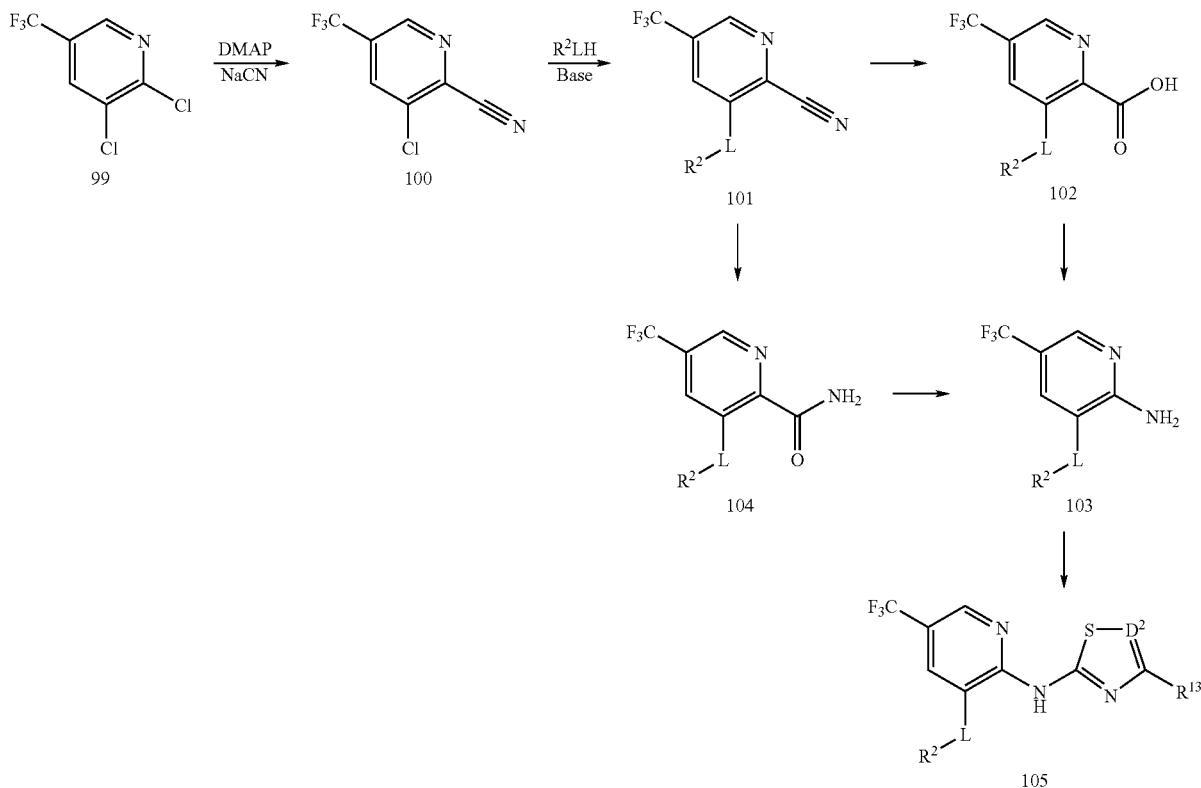

Scheme P shows a method of synthesizing compounds of Formula I where $R^3$ is $CF_3$ (105). The 2,3-dichloro-5-(trifluoromethyl)pyridine (99) is reacted with DMAP, followed by a cyanide source, such as NaCN, to provide the cyanopyridine (100). Nucleophilic displacement of the chlorine with compounds of the formula $R^2LH$ and an appropriate base, such as sodium hydride, in a suitable solvent, such as DMF provides compound (101). Utilizing the routes in Schemes M or N the cyanopyridine (101) can be converted into the aminopyridine (103). Using procedures outlined in Schemes A, B, or L, compounds (105) of the Formula I can be synthesized from compound (103). After formation of compound (105), protecting groups, if present, can be removed.

Scheme Q

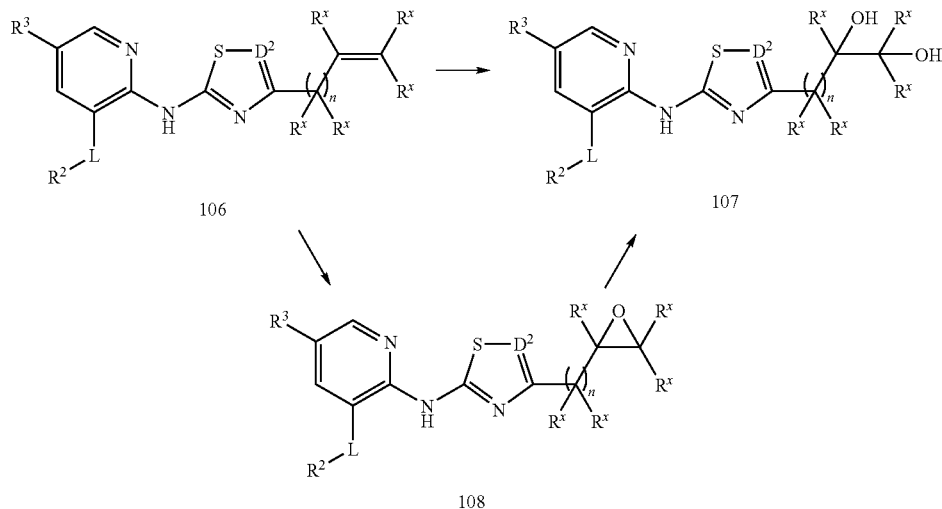

Scheme Q shows a method of synthesizing compounds of Formula I where n=0-2 and each $R^x$ is independently selected from hydrogen or a (1-2C)alkyl group. The pendant alkene in compound (106), which can be synthesized from the methods in schemes A, B or L, can be dihydroxylated by a variety of conditions, such as but not limited to, treating compound (106) with an oxidizing agent such as $OsO_4$ to provide the diol (107). Alternatively, compound (107) can be prepared in a chiral manner through the use of reagents or kits such as, but not limited to, AD-mix-α ($K_2OsO_2(OH)_4$, $(DHQ)_2$-PHAL (a chiral quinine ligand) and either potassium ferricyanide or N-methylmorpholine N-oxide) and AD-mix-β ($K_2OsO_2(OH)_4$, $(DHQD)_2$-PHAL (a chiral quinine ligand) and either potassium ferricyanide or N-methylmorpholine N-oxide). Additionally, the alkene (106) can be oxidized to the epoxide (108), which can be hydrolyzed to provide the diol (107).

Scheme R shows an alternative method of synthesizing compounds of Formula I where n=0-2 and each $R^x$ is independently selected from hydrogen or a (1-2C)alkyl group. According to the Scheme R, epoxide (108) can be opened with a cyanide source, such as NaCN, to afford compound (109). Compound (109) can be reacted with one or two equivalents of an alkali metal hydride reagent (for example $LiAlH_4$, DIBAL-H or $BH_3$) or an organometallic reagent $R^xM$ or $(R^x)_2M$ where M is a metal (for example $R^xLi$, $(R^x)_2Zn$ or $(R^x)_2CuLi$) to afford compound (110) or (111), respectively. Alternatively, compound (110) can be further reduced with an alkali metal hydride reagent (for example $LiAlH_4$, DIBAL-H or $BH_3$) or an organometallic reagent $R^xM$ or $(R^x)_2M$ where M is a metal (for example, $R^xLi$, $(R^x)_2Zn$ or $(R^x)_2CuLi$) to afford compound (111).

Scheme R

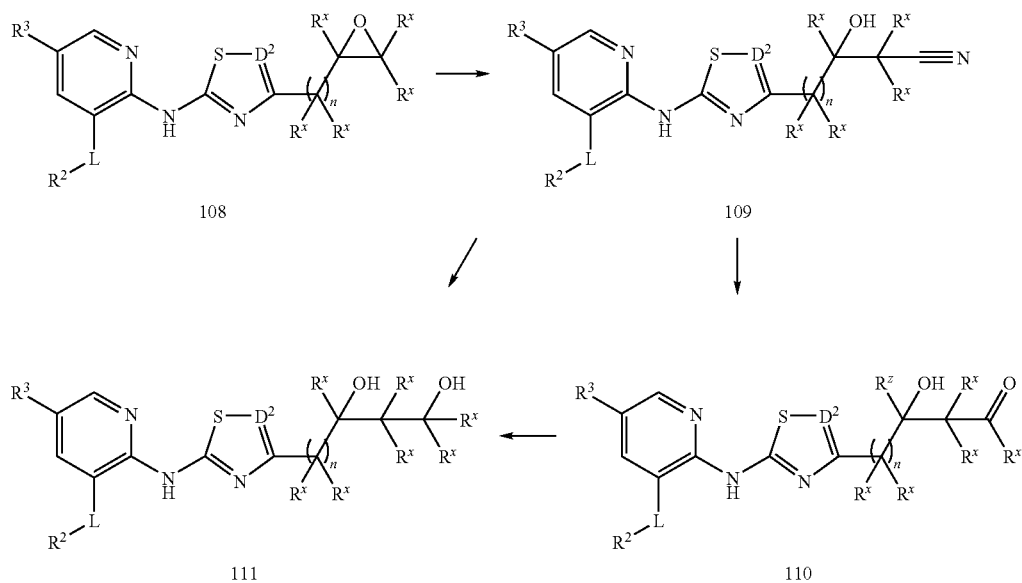

Scheme S

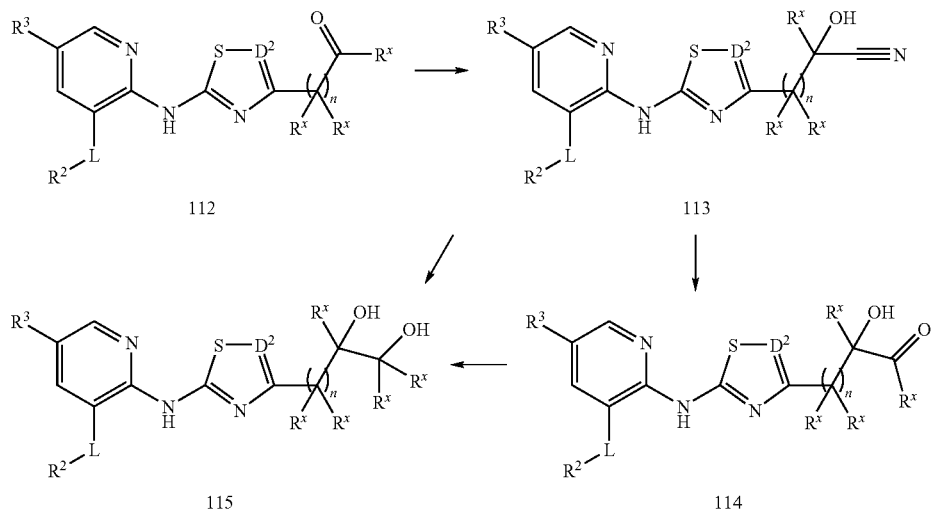

Scheme S shows the synthesis of compounds of Formula I where n=0-2 and each $R^x$ is independently selected from H or a (1-2C)alkyl group. Carbonyl compound (112), which can be synthesized by methods in Schemes A, B or L, can be converted to the cyanohydrin (113). The cyanohydrin (113) can be treated with 1 or 2 equivalents of an alkali metal hydride reagent (for example $LiAlH_4$, DIBAL-H or $BH_3$) or an organometallic reagent $R^xM$ or $(R^x)_2M$ where M is a metal (for example, $R^xLi$, $(R^x)_2Zn$ or $(R^x)_2CuLi$) to provide compound (114) or (115), respectively. Alternatively, compound (114) can be further reacted with an alkali metal hydride reagent $R^xM$ or $(R^x)_2M$ where M is a metal (for example $LiAlH_4$, DIBAL-H or $BH_3$) or an organometallic reagent (for example, $R^xLi$, $(R^x)_2Zn$ or $(R^x)_2CuLi$) to afford compound (115).

Accordingly, another embodiment of the invention provides a method for preparing a compound of Formula I or a salt thereof, comprising:

(a) reacting a corresponding compound of the formula (II)

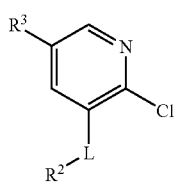

(II)

with a compound of the formula (III)

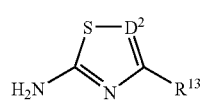

(III)

in the presence of a base catalyst or metal catalyst; or (b) reacting a corresponding compound of the formula (IV)

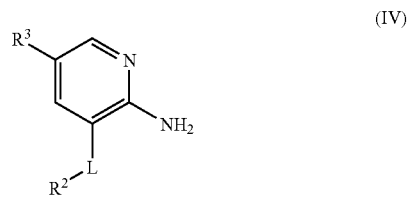

(IV)

with a compound of the formula (V)

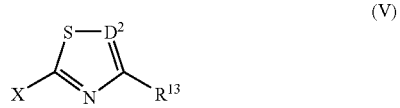

(V)

wherein X is a leaving atom or group in the presence of a base catalyst or metal catalyst; or (c) for a compound of Formula I wherein $D^2$ is CH, reacting a corresponding compound of the formula (VI)

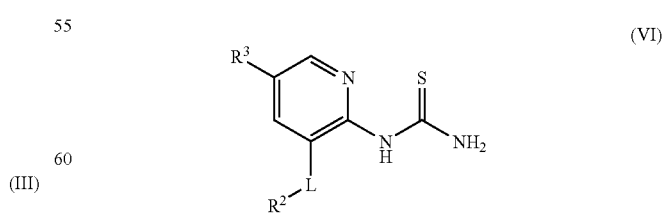

(VI)

with a compound of the formula $R^{13}COCH_2X$, wherein X is a leaving group or atom in the presence of a base; or (d) for a compound of Formula I wherein $D^2$ is N, reacting a corresponding compound of the formula (VII)

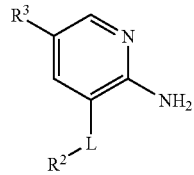
(VII)

with a compound having the formula (VIII)

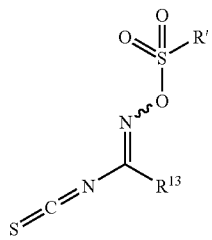
(VIII)

where R' is C1-C6 alkyl or aryl optionally substituted with C1-C6 alkyl, in the presence of a base; or (e) for compounds of Formula I where $R^3$ is $SR^6$, reacting a corresponding compound having the formula (IX)

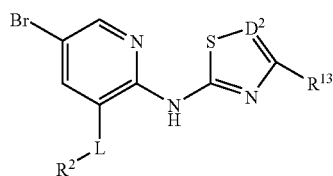
(IX)

with a compound having the formula $R^6SH$ in the presence of a suitable base; or (f) reacting a corresponding compound having the formula (XI)

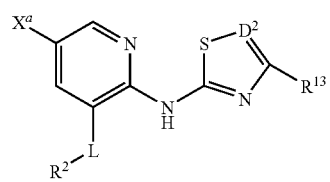
(XI)

wherein $X^a$ is a leaving atom or group, with a compound having the formula $R^3$—$X^b$ where $X^b$ is a leaving atom or a leaving group, in the presence of a suitable base; or (g) for compounds of Formula I where $R^3$ is $SR^6$, reacting a corresponding compound having the formula (XII)

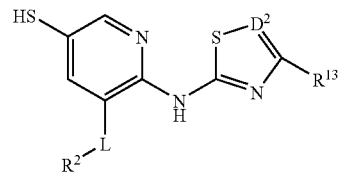
(XII)

with a compound having the formula $R^6$—$X^c$ wherein $X^c$ is a leaving atom or group in the presence of a suitable base; or (h) for compounds of Formula I where L is O, reacting a corresponding compound having the formula (XIII)

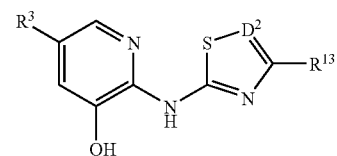
(XII)

with a compound having the formula $R^2$—$X^d$, wherein $X^d$ is a leaving atom or group in the presence of a base or in the presence of a copper or palladium catalyst; or (i) reacting a corresponding compound having the formula (XIV)

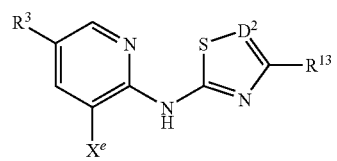
(XIV)

wherein $X^e$ is a leaving group or atom, with a compound having the formula $R^2LH$ wherein L is O or S, in the presence of a palladium catalyst and a suitable base; or (j) for a compound of Formula I where $R^{13}$ has the formula

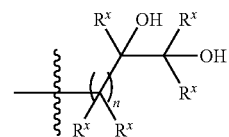

wherein each $R^x$ is independently selected from hydrogen and a (1-2C alkyl) group and n is 0-2, reacting a corresponding compound having the formula (XV)

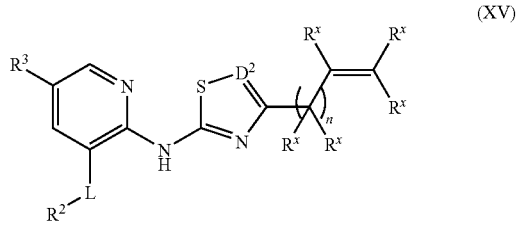
(XV)

with an oxidizing agent; or (k) for a compound of Formula I where $R^{13}$ has the formula

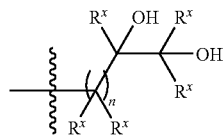

hydrolyzing a corresponding compound having the formula (XVI)

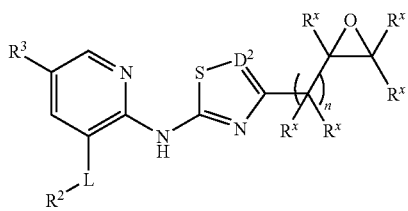
(XVI)

wherein each $R^x$ is independently selected from hydrogen and a (1-2C alkyl) group and n is 0-2; or (l) for a compound of Formula I wherein $R^{13}$ has the formula

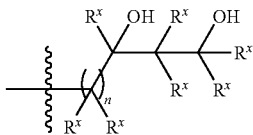

wherein each $R^x$ is independently selected from hydrogen and a (1-2C alkyl) group and n is 0-2, reacting a corresponding compound having the formula (XVII)

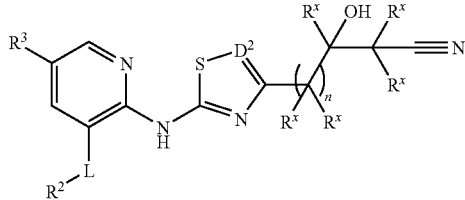
(XVII)

with two equivalents of a metal hydride reagent or an organometallic reagent having the formula $R^xM$ or $(R^x)_2M$ where each $R^x$ is independently selected from hydrogen and a (1-2C alkyl) group and M is a metal anion; or (m) for a compound of Formula I wherein $R^{13}$ has the formula

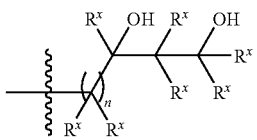

wherein each $R^x$ is independently selected from hydrogen and a (1-2C alkyl) group and n is 0-2, reacting a corresponding compound having the formula (XVIII)

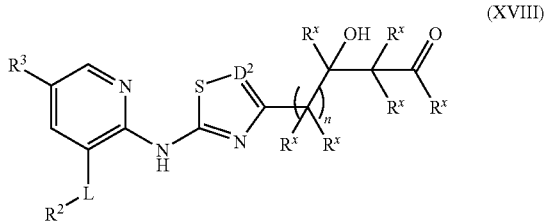
(XVIII)

with a metal hydride reagent or an organometallic reagent having the formula $R^xM$ or $(R^x)_2M$ where each $R^x$ is independently selected from hydrogen and a (1-2C alkyl) group and M is a metal anion; or (n) for a compound of Formula I wherein $R^{13}$ has the formula

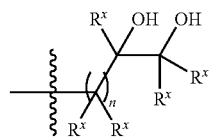

wherein each $R^x$ is independently selected from hydrogen and a (1-2C alkyl) group and n is 0-2, reacting a corresponding compound having the formula (XIX)

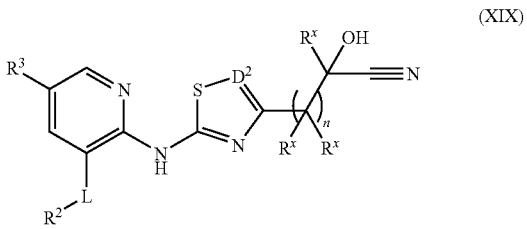
(XIX)

with two equivalents of a metal hydride reagent or an organometallic reagent having the formula $R^xM$ or $(R^x)_2M$ where each $R^x$ is independently selected from hydrogen and a (1-2C alkyl) group and M is a metal anion; or (o) for a compound of Formula I wherein $R^{13}$ has the formula

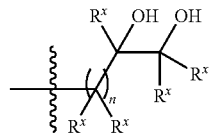

wherein each $R^x$ is independently selected from hydrogen and a (1-2C alkyl) group and n is 0-2, reacting a corresponding compound having the formula (XX)

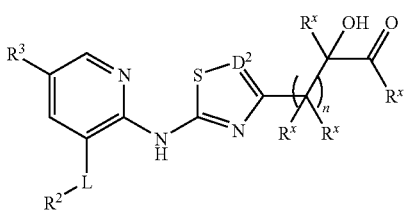

(XX)

with a metal hydride reagent or an organometallic reagent having the formula $R^xM$ or $(R^x)_2M$ where each $R^x$ is independently selected from hydrogen and a (1-2C alkyl) group and M is a metal anion; and removing any protecting group or groups and, if desired, forming a salt.

Referring to method (b), X can be a leaving atom (for example, Cl, Br) or a leaving group (e.g., OTs or OTf).

Referring to method (c), X can be a leaving group (such as OTs or $NR_3$ wherein R is $C_1C_6$ alkyl) or a leaving atom (for example Cl, Br, or I).

Referring to method (e), a suitable base may be, for example, an alkyl lithium base such as methyl lithium, butyl lithium, or a mixture thereof.

Referring to method (f), $X^a$ can be a leaving atom such as a halogen (e.g., F, Cl or Br) or a leaving group such as a sulfonate (e.g., OMs or OTs). $X^b$ may be a leaving atom such as a halogen (e.g., F, Cl or Br) or a leaving group such as a sulfonate (e.g., OMs or OTs). A suitable base may be, for example, an alkali metal alkoxide such as potassium t-butoxide.

Referring to method (g), $X^c$ may be a leaving atom such as a halogen, such as Br, Cl or I. A suitable base may be, for example, an alkyl lithium such as methyl lithium, butyl lithium, or a combination thereof.

Referring to method (h), $X^d$ may be a leaving atom such as a halogen (e.g., F, Cl or Br) or a leaving group such as a sulfonate (e.g., OMs or OTs).

Referring to method (i), $X^e$ may be a leaving group or atom e.g., a halogen such as Cl or Br; or a triflate or tosylate group. Suitable bases include alkali metal carbonates such as $CsCO_3$.

Referring to method (j), suitable oxidizing agents include $OsO_4$, $KMnO_4$, AD-mix-α, AD-mix-β and the like.

Referring to method (k), the hydrolysis of the epoxide can take place under either acidic or basic conditions.

Referring to methods (l), (m), (n) and (o), suitable metal hydride reagents include $LiAlH_4$, DIBAL-H and $BH_3$.

Referring to methods (l), (m), (n) and (o), suitable organometallic reagents include alkyl lithium, alkyl zinc, and alkyl cuprate reagents.

The compounds of Formulas (IX), (XI), (XII), (XIII), (XIV), (XV), (XVI), (XVII), (XVIII), (XIX), and (XX) are also believed to be novel and are provided as further aspects of this invention.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

The compounds of the present invention can be used as prophylactics or therapeutic agents for treating diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed below. Furthermore, the compounds of the present invention can be also used to prevent the progression of the borderline type, impaired glucose tolerance, IFG (impaired fasting glucose) or IFG (impaired fasting glycemia) to diabetes mellitus.

Accordingly, another aspect of the invention provides methods of treating or preventing diseases or conditions described herein by administering to a mammal, such as a human, a therapeutically effective amount of a compound of Formula I.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

The terms "treat" and "treatment" refer to both therapeutic treatment and prophylactic or preventative measures, wherein the object is to prevent or slow down (lessen) an undesired physiological change or disorder. For purposes of this invention, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "mammal" refers to a warm-blooded animal that has or is at risk of developing a disease described herein and includes, but is not limited to, guinea pigs, dogs, cats, rats, mice, hamsters, and primates, including humans.

In certain embodiments, the methods of this invention are useful for treating diabetes mellitus. Diabetes mellitus is a condition where the fasting plasma glucose level (glucose concentration in venous plasma) is greater than or equal to 126 mg/dL (tested on two occasions) and the 2-hour plasma glucose level of a 75 g oral glucose tolerance test (OGTT) is greater than or equal to 200 mg/dL. Additional classic symptoms include polydipsia, polyphagia and polyuria.

In certain embodiments, the methods of this invention are useful for treating the syndrome of impaired tolerance (IGT). IGT is diagnosed by the presentation of a fasting plasma glucose level of less than 126 mg/dL and a 2-hour post-oral glucose challenge lever greater than 140 mg/dL.

The compounds of the present invention can be also used as prophylactics or therapeutic agents of diabetic complications such as, but not limited to, neuropathy, nephropathy, retinopathy, cataract, macroangiopathy, osteopenia, diabetic hyperosmolar coma), infection, dermal soft tissue infection, lower limb infection etc.), diabetic gangrene, xerostomia, decreased sense of hearing, cerebrovascular disease, peripheral circulatory disturbance, etc.

The compounds of the present invention can be also used as prophylactics or therapeutic agents in the treatment of diseases and disorders such as, but not limited to, obesity, metabolic syndrome (syndrome X), hyperinsulinemia, hyperinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomerulosclerosis, nephrotic syndrome, hypertensive nephrosclerosis, terminal renal disorder etc.), myocardial infarction, angina pectoris, and cerebrovascular disease (e.g., cerebral infarction, cerebral apoplexy).

The compounds of the present invention can be also used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, SIDS, and the like.

The compounds of the present invention can be used in combination with one or more additional drugs, for example a compound that works by the same or a different mechanism or action, such as insulin preparations, agents for improving insulin resistance, alpha-glucosidase inhibitors, biguanides, insulin secretagogues, dipeptidylpeptidase IV (DPP IV) inhibitors, beta-3 agonists, amylin agonists, phosphotyrosine phosphatase inhibitors, gluconeogenesis inhibitors, sodium-glucose cotransporter inhibitors, known therapeutic agents for diabetic complications, antihyperlipidemic agents, hypotensive agents, and antiobesity agents. An example of an agent for improving insulin resistance is an agonist for peroxisome proliferator-activated receptor-gamma (PPAR gamma).

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

According to another aspect, the present invention provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

This invention also provides the use of a compound of Formula I in the treatment of diseases or disorders mediated by deficient levels of glucokinase activity or which can be treated by activating glucokinase.

An additional aspect of the invention is the use of a compound of Formula I in the preparation of a medicament for the treatment or prevention of diseases or disorders mediated by deficient levels of glucokinase activity or which can be treated by activating glucokinase.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane ($CH_2Cl_2$, methylene chloride), toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$HNMR spectra were obtained as $CDCl_3$, $CD_3OD$, $D_2O$ or d6-DMSO solutions (reported in ppm), using tetramethylsilane (0.00 ppm) or residual solvent ($CDCl_3$: 7.25 ppm; $CD_3OD$: 3.31 ppm; $D_2O$: 4.79 ppm; d6-DMSO: 2.50 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

(S)-1-(5-(5-bromo-3-(2-methylpyridin-3-yloxy)pyridin-2-ylamino)-1,2,4-thiadiazol-3-yl)ethane-1,2-diol

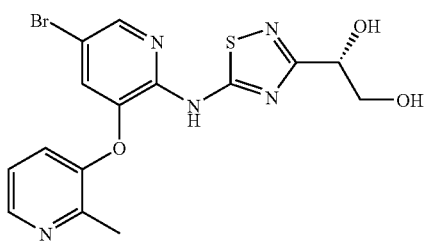

Step A: To a solution of (R)-1,4-dioxaspiro[4.5]decane-2-carbaldehyde (9.0 g, 52.9 mmol) in THF (120 mL and 60 mL of water) was added hydroxyl amine hydrochloride (3.73 g, 52.9 mmol) and the reaction stirred until clear (10 minutes). Sodium carbonate (2.75 g, 25.9 mmol) was added and the reaction stirred overnight at ambient temperature. The reaction was poured into ethyl acetate (500 mL) and the layers were separated. The organics were washed with water (200 mL), brine (200 mL), dried over magnesium sulfate and concentrated in vacuo to yield (S)-1,4-dioxaspiro[4.5]decane-2-carbaldehyde oxime (9.08 g, 49 mmol, 92.7%).

Step B: To a solution of (S)-1,4-dioxaspiro[4.5]decane-2-carbaldehyde oxime (9.08 g, 49 mmol) in DMF (50 mL) was added 1-chloropyrrolidine-2,5-dione (7.20 g, 53.9 mmol) and the reaction stirred overnight at ambient temperature. The reaction was poured into water (500 mL) extracted with ether. The organics were washed with brine and dried over magnesium sulfate. The material was concentrated in vacuo to yield (R)-N-hydroxy-1,4-dioxaspiro[4.5]decane-2-carbimidoyl chloride (10.4 g, 47 mmol, 96.6%).

Step C: To a solution of (R)-N-hydroxy-1,4-dioxaspiro[4.5]decane-2-carbimidoyl chloride (10.4 g, 47.3 mmol) cooled to 0° C. in THF (150 mL) was added methanesulfonyl chloride (5.97 g, 52.1 mmol) followed by N-ethyl-N-isopropylpropan-2-amine (6.75 g, 52.1 mmol) and the reaction stirred for 1 hr at ambient temperature. The reaction was concentrated in vacuo. The material was dissolved in dichloromethane and chromatographed using 8:1 Hexane/EtOAc to 4:1 Hexane/EtOAc (2 columns) to give the (R)-N-(methylsulfonyloxy)-1,4-dioxaspiro[4.5]decane-2-carbimidoyl chloride as a viscous oil that solidified on standing (12 g, 40 mmol, 85% yield).

Step D: A flask was charged with 2-methylpyridin-3-ol (3.0 g, 27.5 mmol) and DMF (100 mL). Sodium hydride (0.760 g, 30.2 mmol) was added and stirred for 5 minutes. 5-Bromo-3-nitropicolinonitrile (6.26 g, 27.5 mmol) was added and stirred for 10 minutes. The reaction was poured into a flask containing 300 mL saturated NH₄Cl and 300 mL water with vigorous stirring. The solids were filtered and dried under high vacuum to afford 5-bromo-3-(2-methylpyridin-3-yloxy)picolinonitrile (7.78 g, 97.6% yield) as light tan solid.

Step E: A flask was charged with 5-bromo-3-(2-methylpyridin-3-yloxy)picolinonitrile (60 g, 207 mmol) and sulfuric acid (203 g, 2068 mmol). The reaction was stirred at ambient temperature overnight. Water (500 mL) was added carefully and neutralized using 50% sodium hydroxide to pH 5.0. The mixture was extracted with dichloromethane and ethyl acetate, dried and concentrated to afford 5-bromo-3-(2-methylpyridin-3-yloxy)picolinamide (63.0 g, 204 mmol, 98.9% yield) as yellow solid.

Step F: A flask was charged with 2M sodium hydroxide (256 ml, 511 mmol) and cooled to 0° C. Bromine (7.85 ml, 153 mmol) was added and stirred for 15 minutes. 5-bromo-3-(2-methylpyridin-3-yloxy)picolinamide (31.5 g, 102 mmol) in dioxane (650 mL) was added and stirred at ambient temperature overnight. The aqueous layer was extracted with ethyl acetate and CH₂Cl₂. The organic layers were washed with water, brine, dried, concentrated and purified over silica gel (25-50-75-100% ethyl acetate in hexanes) to afford 5-bromo-3-(2-methylpyridin-3-yloxy)pyridin-2-amine (12 g, 43 mmol, 41.9% yield) as a yellow solid.

Step G: (R)-N-(methylsulfonyloxy)-1,4-dioxaspiro[4.5]decane-2-carbimidoyl chloride (1.86 g, 6.25 mmol), pyridine (1.13 g, 14.3 mmol) and sodium thiocyanate (0.58 g, 7.14 mmol) were dissolved in acetonitrile (45 mL). The solution was heated to 40° C. for 40 minutes. 5-bromo-3-(2-methylpyridin-3-yloxy)pyridin-2-amine (1.0 g, 3.57 mmol) was added and the reaction was heated at 60° C. overnight. The solution was cooled to 0° C., filtered and the solid was dried to give (S)-N-(5-bromo-3-(2-methylpyridin-3-yloxy)pyridin-2-yl)-3-(1,4-dioxaspiro[4.5]decan-2-yl)-1,2,4-thiadiazol-5-amine (0.90 g, 1.78 mmol, 50% yield) as a white solid.

Step H: To a solution of (S)-N-(5-bromo-3-(2-methylpyridin-3-yloxy)pyridin-2-yl)-3-(1,4-dioxaspiro[4.5]decan-2-yl)-1,2,4-thiadiazol-5-amine (0.072 g, 0.20 mmol) in methanol (10 mL) was added concentrated HCl (3 drops) and the reaction heated to 80° C. for 3 hr. The reaction was concentrated in vacuo. The material was triturated with ethyl acetate/methanol 1/1 (10 mL) to give (S)-1-(5-(5-bromo-3-(2-methylpyridin-3-yloxy)pyridine-2-ylamino)-1,2,4-thiadiazol-3-yl)ethane-1,2-diol (0.070 g, 0.16 mmol, 83%) as a white solid (APCI POS 424,426 M+H).

Example 2

(S)-1-(5-(5-trifluoromethyl-3-(2-methylpyridin-3-yloxy)pyridin-2-ylamino)-1,2,4-thiadiazol-3-yl)ethane-1,2-diol

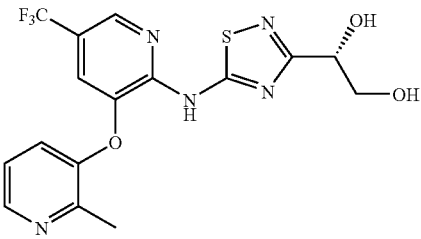

(S)-1-(5-(5-trifluoromethyl-3-(2-methylpyridin-3-yloxy)pyridin-2-ylamino)-1,2,4-thiadiazol-3-yl)ethane-1,2-diol (APCI POS 414 M'H) was synthesized following the procedure in example 1 substituting 5-trifluoromethyl-3-chloropicolinonitrile for 5-bromo-3-nitropicolinonitrile in step D.

Example 3

(S)-1-(5-(5-phenylthio-3-(2-methylpyridin-3-yloxy)pyridin-2-ylamino)-1,2,4-thiadiazol-3-yl)ethane-1,2-diol

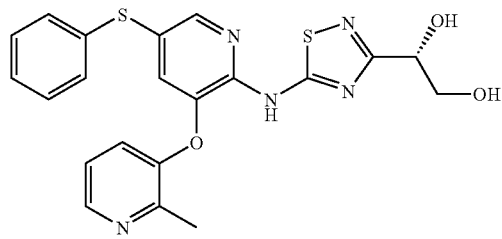

Step A: To a solution of 2-methylpyridin-3-ol (0.96 g, 8.8 mmol) in DMF (10 mL) cooled to 0° C. was added NaH (0.35 g, 8.8 mmol) in portions and the reaction warmed to ambient temperature. To this mixture was added 5-bromo-3-nitropicolinonitrile (2.0 g, 8.8 mmol) and the reaction stirred overnight at ambient temperature. To the reaction was added thiophenol (0.96 g, 8.8 mmol) and the reaction cooled to 0° C. NaH (0.35 g, 8.8 mmol) was added and the reaction warmed to ambient temperature and the reaction stirred at ambient temperature overnight. The reaction was poured into water (1000 mL) and the aqueous layer was extracted with ether (3×100 mL). The organics were washed with 1N NaOH (100 mL), water (2×100 mL) brine (100 mL), dried over MgSO₄ and concentrated in vacuo to give 5-phenylthio-3-(2-methylpyridin-3-yloxy)picolinonitrile (2.8 g, 8.8 mmol, 100%) as a solid.

Step B: (S)-1-(5-(5-phenylthio-3-(2-methylpyridin-3-yloxy)pyridin-2-ylamino)-1,2,4-thiadiazol-3-yl) ethane-1,2-diol (APCI POS 454 M+H) was synthesized following the procedure in Example 1 substituting 5-phenylthio-3-(2-methylpyridin-3-yloxy)picolinonitrile for 5-bromo-3-(2-methylpyridin-3-yloxy)picolinonitrile in step E.

Example 4

(S)-1-(5-(5-phenylthio-3-(pyridin-3-yloxy)pyridin-2-ylamino)-1,2,4-thiadiazol-3-yl)piperidin-1-yl)ethane-1,2-diol

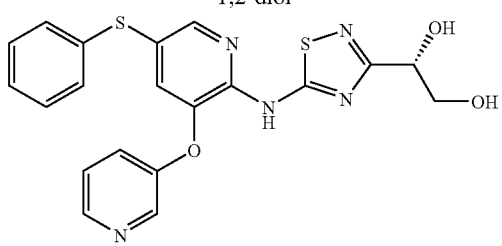

(S)-1-(5-(5-phenylthio-3-(pyridin-3-yloxy)pyridin-2-ylamino)-1,2,4-thiadiazol-3-yl)piperidin-1-yl)ethane-1,2-diol (APCI POS 440 M+H) was synthesized following the procedure in example 3 substituting pyridin-3-ol for 2-methylpyridin-3-ol in step A.

Example 5

(S)-1-(5-(3-(2-methylpyridin-3-yloxy)-5-(pyridin-2-ylthio)pyridin-2-ylamino)-1,2,4-thiadiazol-3-yl)ethane-1,2-diol

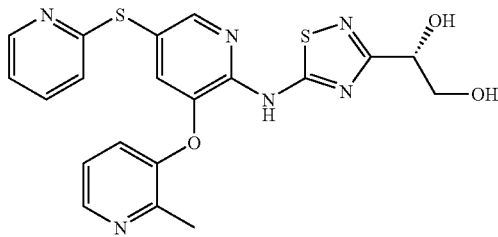

(S)-1-(5-(3-(2-methylpyridin-3-yloxy)-5-(pyridin-2-ylthio)pyridin-2-ylamino)-1,2,4-thiadiazol-3-yl)ethane-1,2-diol (APCI POS 455 M+H) was synthesized following the procedure in example 3 substituting 2-thiopyridine for thiophenol in step A.

Example 6

(S)-1-(5-(5-(2-hydroxyethylthio)-3-(2-methylpyridin-3-yloxy)pyridin-2-ylamino)-1,2,4-thiadiazol-3-yl)ethane-1,2-diol

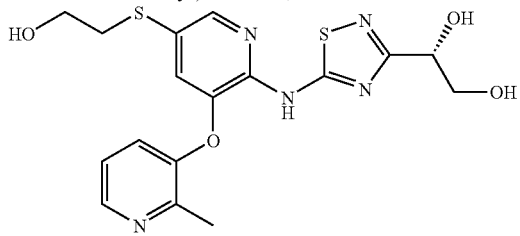

Step A: To dioxanes (50 mL) bubbled continuously with $N_2$ was added in this order $Pd_2dba_3$ (0.041 g, 0.046 mmol), Xanphos (0.055 g, 0.091 mmol), (S)-N-(5-bromo-3-(2-methylpyridin-3-yloxy)pyridin-2-yl)-3-(1,4-dioxaspiro[4.5]decan-2-yl)-1,2,4-thiadiazol-5-amine (0.46 g, 0.091 mmol), ethyl 2-mercaptoacetate (0.11 g, 0.091 mmol) and Hunig's base (0.12 g, 0.091 mmol) and the reaction was heated to 80° C. for 6 hr. The reaction was concentrated in vacuo and the material chromatographed using 40% EtOAc as eluent to give (S)-ethyl-2-(6-(3-(1,4-dioxaspiro[4.5]decan-2-yl)1,2,4-thiadiazo-5-ylamino)-5-(2-methylpyridin-3-yloxy)pyridin-3-ylthio)acetate (0.30 g, 0.55 mmol).

Step B: To a solution of (S)-ethyl-2-(6-(3-(1,4-dioxaspiro[4.5]decan-2-yl)1,2,4-thiadiazo-5-ylamino)-5-(2-methylpyridin-3-yloxy)pyridin-3-ylthio)acetate (0.30 g, 0.55 mmol) in THF (20 mL) cooled to 0° C. was added $LiAlH_4$ (1 M solution in THF) (0.55 mL, 0.55 mmol) and the reaction stirred for 3 hours while warming to ambient temperature. The reaction was quenched by the addition of water and poured into ethyl acetate (100 mL) and the layers were separated. The organics were washed with brine, dried over $MgSO_4$ and concentrated in vacuo to give (S) 2-(6-(3-(1,4-dioxaspiro[4.5]decan-2-yl)1,2,4-thiadiazo-5-ylamino)-5-(2-methylpyridin-3-yloxy)pyridine-3-ylthio)ethanol (0.28 g, 0.55 mmol).

Step C: (S)-1-(5-(5-(2-hydroxyethylthio)-3-(2-methylpyridin-3-yloxy)pyridine-2-ylamino)-1,2,4-thiadiazol-3-yl)ethane-1,2-diol (APCI POS 422 M+H) was synthesized following the procedure in example 1 substituting (S)-2-(6-(3-(1,4-dioxaspiro[4.5]decan-2-yl)1,2,4-thiadiazo-5-ylamino)-5-(2-methylpyridin-3-yloxy)pyridine-3-ylthio)ethanol for (S)-N-(5-bromo-3-(2-methylpyridin-3-yloxy)pyridin-2-yl)-3-(1,4-dioxaspiro[4.5]decan-2-yl)-1,2,4-thiadiazol-5-amine in step H.

Example 7

(S)-1-(5-(3-(4-fluorophenoxy)-5-(pyridin-2-ylthio)pyridin-2-ylamino)-1,2,4-thiadiazol-3-yl)ethane-1,2-diol

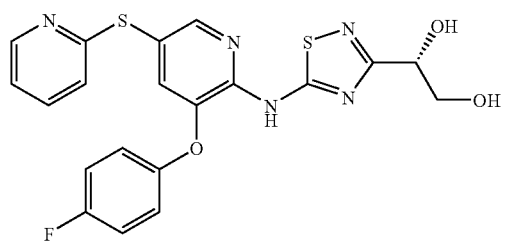

Step A: A flask was charged with 4-fluorophenol (44 g, 365 mmol) and DMF (500 mL). The reaction was cooled to 0° C. Sodium hydride (16.6 g, 414 mmol) was added and stirred for 10 minutes. 5-Bromo-3-nitropicolinonitrile (90 g, 395 mmol) was added and the mixture stirred at ambient temperature for 30 minutes. The reaction was poured into a flask containing water (5000 mL) and stirred for 10 minutes. The pH was adjusted to 10 to give 5-bromo-3-(4-fluorophenoxy)picolinonitrile (121 g, 413 mmol, 105% yield) as a solid.

Step B: To a solution of pyridine-2-thiol (2.5 g, 23 mmol) in DMA (25 mL) cooled to 0° C. was added NaH (0.90 g, 23 mmol) and the reaction stirred at ambient temperature for 20 min, followed by addition of the 5-bromo-3-(4-fluorophenoxy)picolinonitrile (6.6 g, 23 mmol) and stirring over night at ambient temperature. The reaction was poured into water (250 mL) and a solid formed. The solid was collected, washed with water, and dried in vacuo to yield 3-(4-fluorophenoxy)-5-(pyridin-2-ylthio)picolinonitrile (5 g, 16 mmol, 70%).

Step C: (S)-1-(5-(3-(4-fluorophenoxy)-5-(pyridin-2-ylthio)pyridin-2-ylamino)-1,2,4-thiadiazol-3-yl)ethane-1,2-diol (APCI POS 458 M+H) was synthesized following the procedure in example 1 substituting 3-(4-fluorophenoxy)-5-(pyridin-2-ylthio)picolinonitrile for 5-bromo-3-(2-methylpyridin-3-yloxy)picolinonitrile in step E.

Example 8

(R)-1-(2-(5-bromo-3-(4-fluorophenoxy)pyridin-2-ylamino)thiazol-4-yl)ethane-1,2-diol

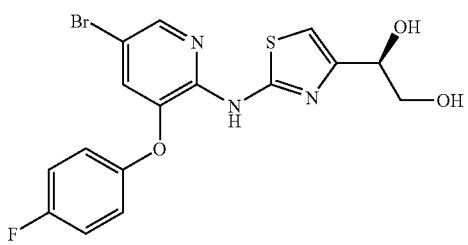

Step A: A flask was charged with 5-bromo-3-(4-fluorophenoxy)picolinonitrile (10 g, 34 mmol) and sulfuric acid (50 mL). The reaction was stirred at ambient temperature overnight. Water (500 mL) was added carefully and the mixture was adjusted to pH 5.0 using 50% sodium hydroxide. The mixture was extracted with dichloromethane and ethyl acetate, dried and concentrated to afford 5-bromo-3-(4-fluorophenoxy)picolinamide (10.6 g, 34 mmol, 100% yield) as yellow solid.

Step B: A flask was charged with 2M sodium hydroxide (115 ml, 230 mmol) and cooled to 0° C. Bromine (9.3 g, 58 mmol) was added and the mixture stirred for 15 minutes. 5-bromo-3-(4-fluorophenoxy)picolinamide (15.8 g, 51 mmol) in dioxane (200 mL) was added and the mixture stirred at ambient temperature overnight. The aqueous layer was extracted with ethyl acetate and $CH_2Cl_2$. The organic layers were washed with water, brine, dried over $MgSO_4$, concentrated and purified by chromatography (25-50-75-100% ethyl acetate in hexanes) to afford 5-bromo-3-(2-fluorophenoxy)pyridin-2-amine (12 g, 42 mmol, 82% yield) as a yellow solid.

Step C: To a solution of the 5-bromo-3-(2-fluorophenoxy)pyridin-2-amine (17 g, 60 mmol, in THF (500 mL) was added benzoyl isothiocyante (9.8 g, 60 mmol) and the reaction stirred at ambient temperature overnight. The reaction was poured into hexanes (2 L), the solid was collected and dried in vacuo to give N-(5-bromo-3-(4-fluorophenoxy)pyridin-2-ylcarbamothioyl)benzamide (25 g, 56 mmol, 93% yield).

Step D: To a solution of N-(5-bromo-3-(4-fluorophenoxy)pyridin-2-ylcarbamothioly)benzamide (25 g, 56 mmol) in ethanol (150 mL) was added NaOH (2 M) (56 mL, 112 mmol) and the reaction stirred ON at 80° C. The mixture was poured into water and the slurry filtered. The collected solid was dried in vacuo to yield 1-(5-bromo-3-(4-fluorophenoxy)pyridin-2-yl)thiourea (15.4 g, 45 mmol).

Step E: To a solution of (S)-methyl 2,2-dimethyl-1,3-dioxolane-4-carboxylate (1.3 g, 8.1 mmol) and chloroiodomethane (4.3 g, 24 mmol) in THF (50 mL) at −78° C. was added a solution of LDA (16.2 mL, 24 mmol) in portions over 10 minutes. The reaction was stirred at −78° C. After addition, the slurry was warmed to ambient temperature. The reaction was poured into EtOAc (200 mL) and the aqueous layer basified using 1 N NaOH. The organics were separated and washed with brine, dried over $MgSO_4$ and concentrated in vacuo. The material was purified by chromatography using DCM as eluent to give (S)-2-chloro-1-(2,2-dimethyl-1,3-dioxolane-4-yl)ethanone (0.60 g, 3.4 mmol, 42% yield) as an oil.

Step F: To 1-(5-bromo-3-(4-fluorophenoxy)pyridin-2-yl)thiourea (0.5 g, 1.5 mmol) in ethanol (50 mL) was added (S)-2-chloro-1-(2,2-dimethyl-1,3-dioxolane-4-yl)ethanone (0.34 g, 1.9 mmol) and the reaction stirred at 80° C. for 1 hr. The reaction was poured into water (250 mL) and the filtered. The solid was triturated with ethyl acetate and methanol. The solid was suspended in ethyl acetate (500 mL) and washed with 1 N NaOH (500 mL). The organics were concentrated and the crude material was purified by chromatography using 3 to 10% $MeOH/CH_2Cl_2$ as eluent to give (R)-1-(2-(5-bromo-3-(4-fluorophenoxy)pyridin-2-ylamino)thiazol-4-yl)ethane-1,2-diol (0.043 g, 0.10 mmol, 7%) (APCI POS 426, 428 M+H).

Example 9

(S)-1-(2-(5-bromo-3-(4-fluorophenoxy)pyridin-2-ylamino)thiazol-4-yl)ethane-1,2-diol

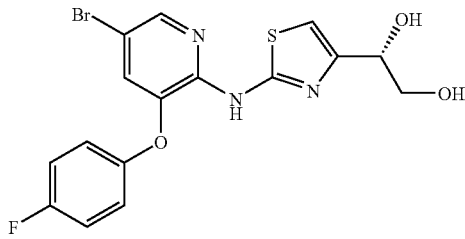

(S)-1-(2-(5-bromo-3-(4-fluorophenoxy)pyridin-2-ylamino)thiazol-4-yl)ethane-1,2-diol (APCI POS 426, 428 M+H) was synthesized following the procedure in example 8 substituting (R)-methyl 2,2-dimethyl-1,3-dioxolane-4-carboxylate for (S)-methyl 2,2-dimethyl-1,3-dioxolane-4-carboxylate in step E.

Example 10

(R)-1-(2-(3-(4-fluorophenoxy)-5-(pyridin-2-ylthio)pyridin-2-ylamino)thiazol-4-yl)ethane-1,2-diol

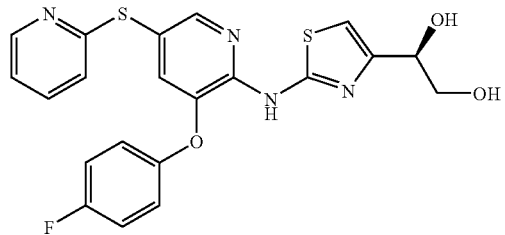

(R)-1-(2-(3-(4-fluorophenoxy)-5-(pyridin-2-ylthio)pyridin-2-ylamino)thiazol-4-yl)ethane-1,2-diol (APCI POS 457 M+H) was synthesized following the procedure in example 8 substituting 3-(4-fluorophenoxy)-5-pyridin-2-ylthio)pyridin-2-amine for 5-bromo-3-(2-fluorophenoxy)pyridin-2-amine in step C.

Example 11

(1S)-1-(5-(5-bromo-3-(5,6,7,8-tetrahydroquinolin-5-yloxy)pyridin-2-ylamino)-1,2,4-thiazol-3-yl)ethane-1,2-diol

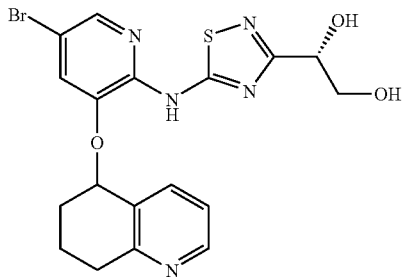

(1S)-1-(5-(5-bromo-3-(5,6,7,8-tetrahydroquinolin-5-yloxy)pyridin-2-ylamino)-1,2,4-thiadiazol-3-yl)ethane-1,2-diol was synthesized following the procedure in example 1 substituting 5,6,7,8-tetrahydroquinolin-5-ol for 2-methylpyridin-3-ol in step D. M+H (apci)=464, 466.

Example 12

(S)-1-(5-(5-bromo-3-(1-(2-hydroxyethyl)-1H-pyrazol-4-yloxy)pyridin-2-ylamino)-1,2,4-thiadiazol-3-yl)ethane-1,2-diol

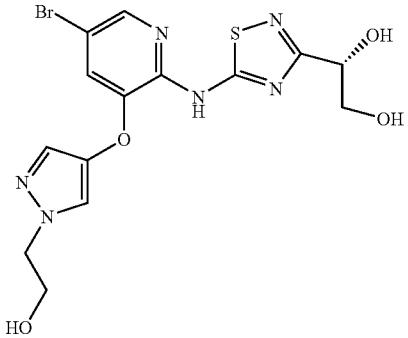

Step A: $POCl_3$ (12.9 ml, 141.2 mmol) was added to DMF (10.9 ml, 141.2 mmol) at 0° C. The reaction was immediately warmed to ambient temperature and stirred for 30 minutes. ((2,2-diethoxyethoxy)methyl)benzene (10.6 g, 47.1 mmol) was added as a solution in 80 mL of chloroform. The solution was stirred at 75° C. for 3.5 hours. The solution was cooled, poured over ice water, and neutralized with $Na_2CO_3$. The residue was extracted with chloroform and the organic layer was dried with $Na_2SO_4$ and concentrated. The residue was re-dissolved in MeOH (450 mL). NaOMe (25% in MeOH, 58 ml, 253 mmol) was added followed by 2-hydrazinylethanol (10.6 g, 139 mmol). The reaction stirred overnight at ambient temperature. The material was concentrated in vacuo followed by dilution with saturated $NH_4Cl$ solution. The material was extracted with EtOAc, dried ($Mg_2SO_4$), and concentrated. Flash chromatography gave 2-(4-(benzyloxy)-1H-pyrazol-1-yl)ethanol (1.81 g, 13% yield).

Step B: 2-(4-(benzyloxy)-1H-pyrazol-1-yl)ethanol (1.81 g, 8.3 mmol) was dissolved in THF (15 mL) under nitrogen. Pd/C (0.22 g, 0.21 mmol) was added and the solution was placed under vacuum and charged with a hydrogen balloon. The mixture stirred at ambient temperature overnight under this hydrogen atmosphere. The solution was filtered through GF/F paper and concentrated to give 1-(2-hydroxyethyl)-1H-pyrazol-4-ol (1.8 g, quantitative).

Step C: (S)-1-(5-(5-bromo-3-(1-(2-hydroxyethyl)-1H-pyrazol-4-yloxy)pyridin-2-ylamino)-1,2,4-thiadiazol-3-yl)ethane-1,2-diol (APCI POS 443, 445 M+H) was synthesized following the procedure in Example 1 substituting 1-(2-hydroxyethyl)-1H-pyrazol-4-ol for 2-methylpyridin-3-ol in Step D.

The following compounds were also prepared according to the above-described methods.

| Example | Structure | Name | M + H |
|---|---|---|---|
| 13 | 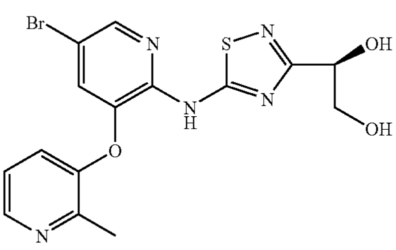 | (R)-1-(2-(5-bromo-3-(2-methylpyridin-3-yloxy)pyridin-2-ylamino)thiazo-4-yl)ethane-1,2-diol | 424 |

-continued

| Example | Structure | Name | M + H |
|---|---|---|---|
| 14 | 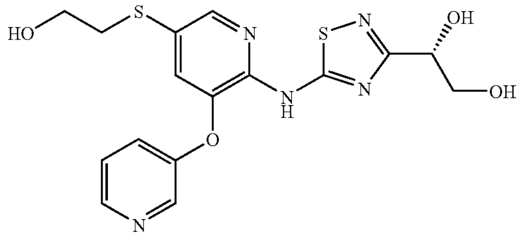 | (S)-1-(5-(5-(2-hydroxyethylthio)-3-(pyridin-3-yloxy)pyridin-2-ylamino)-1,2,4-thiadiazol-3-yl)ethane-1,2-diol | 408 |
| 15 | 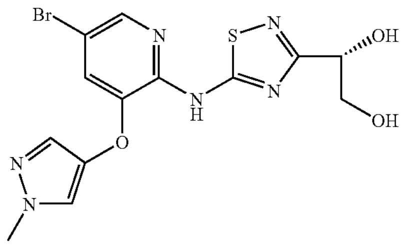 | (S)-1-(5-(5-bromo-3-(1-methyl-1H-pyrazol-4-yloxy)pyridin-2-ylamino)-1,2,4-thiadiazol-3-yl)ethane-1,2-diol | 413, 415 |
| 16 | 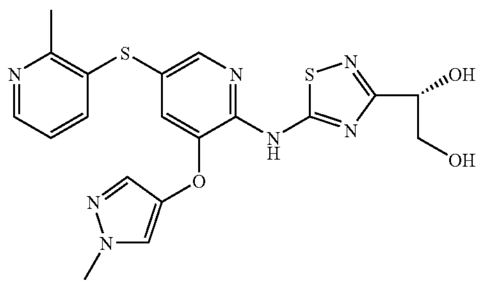 | (S)-1-(5-(3-(1-methyl-1H-pyrazol-4-yloxy)-5-(2-methylpyridin-3-ylthio)pyridin-2-ylamino)-1,2,4-thiadiazol-3-yl)ethane-1,2-diol | 458 |
| 17 | 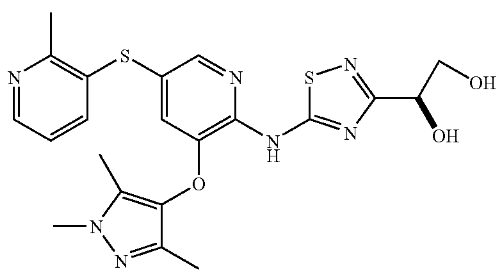 | (S)-1-(5-(5-(2-methylpyridin-3-ylthio)-3-(1,3,5-trimethyl-1H-pyrazol-4-yloxy)pyridin-2-ylamino)-1,2,4-thiadiazol-3-yl)ethane-1,2-diol | 486 |

The present invention further contemplates the preparation of the following compounds of formula I.

| Example | Structure | | |
|---|---|---|---|
| 18<br>18A | 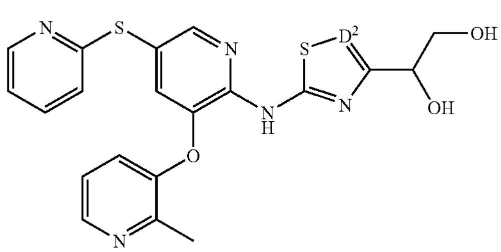 | $D^2$ = CH<br>$D^2$ = N | |

-continued
| Example | Structure | |
|---|---|---|
| 19 19A | 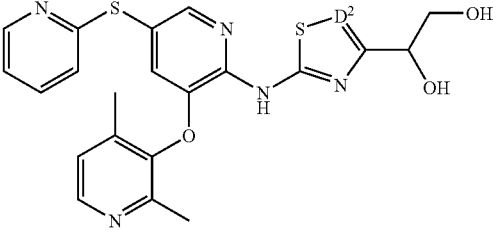 | $D^2$ = CH $D^2$ = N |
| 20 20A | 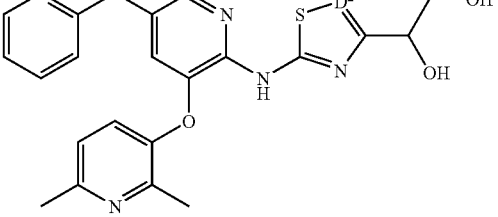 | $D^2$ = CH $D^2$ = N |
| 21 21A | 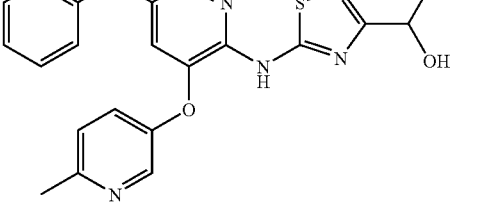 | $D^2$ = CH $D^2$ = N |
| 22 22A | 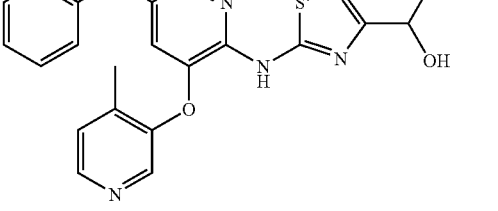 | $D^2$ = CH $D^2$ = N |
| 23 23A | 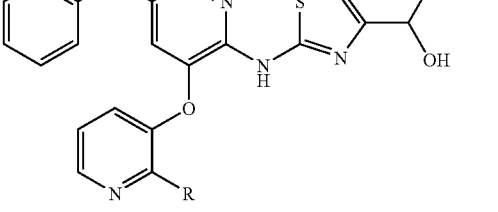 | $D^2$ = CH R = Et, iPr, $CH_2OH$, $CH_2CH_2OH$, or $CF_3$ $D^2$ = N R = Et, iPr, $CH_2OH$, $CH_2CH_2OH$, or $CF_3$ |
| 24 24A | 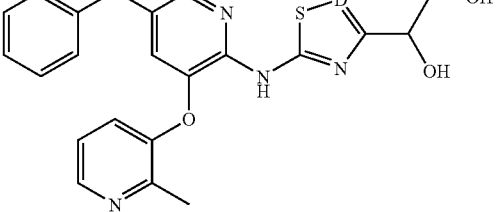 | $D^2$ = CH $D^2$ = N |

-continued
| Example | Structure | |
|---|---|---|
| 25 25A | 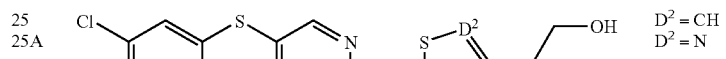 | $D^2 = CH$ $D^2 = N$ |
| 26 26A | 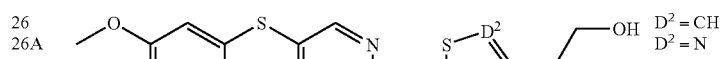 | $D^2 = CH$ $D^2 = N$ |
| 27 27A |  | $D^2 = CH$ $D^2 = N$ |
| 28 28A |  | $D^2 = CH$ $D^2 = N$ |
| 29 29A |  | $D^2 = CH$ $D^2 = N$ |
| 30 30A |  | $D^2 = CH$ $D^2 = N$ |

-continued
| Example | Structure | |
|---|---|---|
| 31<br>31A | 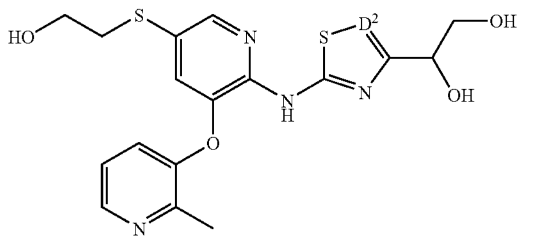 | $D^2$ = CH<br>$D^2$ = N |
| 32<br>32A | 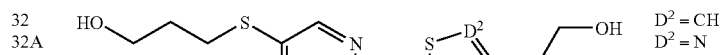 | $D^2$ = CH<br>$D^2$ = N |
| 33<br>33A | 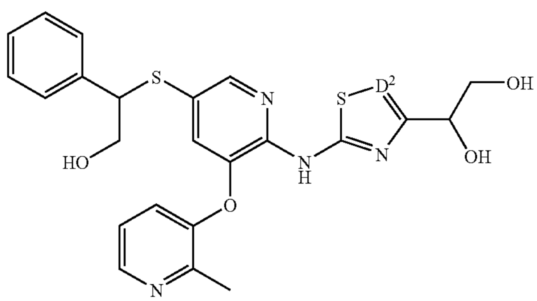 | $D^2$ = CH<br>$D^2$ = N |
| 34<br>34A | 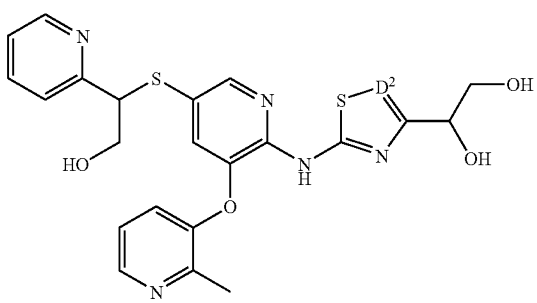 | $D^2$ = CH<br>$D^2$ = N |
| 35<br>35A | 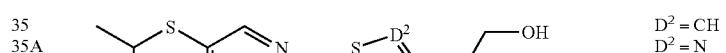 | $D^2$ = CH<br>$D^2$ = N |
| 36<br>36A | 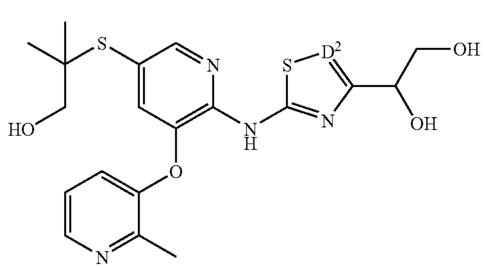 | $D^2$ = CH<br>$D^2$ = N |

| Example | Structure | |
|---|---|---|
| 37<br>37A | 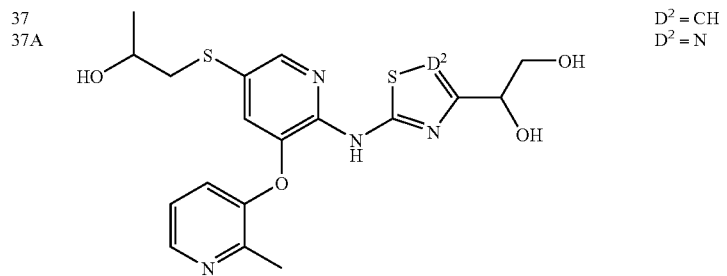 | $D^2$ = CH<br>$D^2$ = N |
| 38<br>38A | 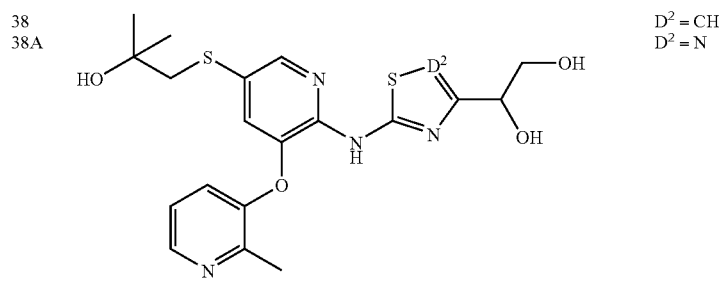 | $D^2$ = CH<br>$D^2$ = N |
| 39<br>39A | 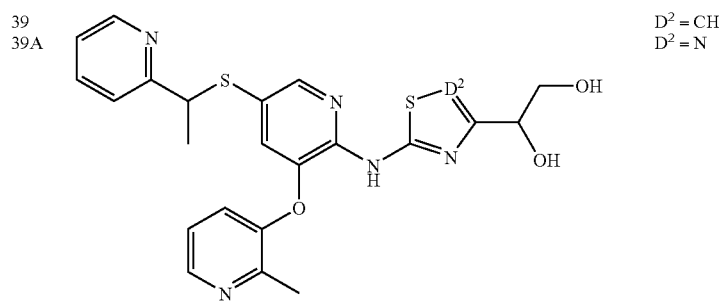 | $D^2$ = CH<br>$D^2$ = N |
| 40<br>40A | 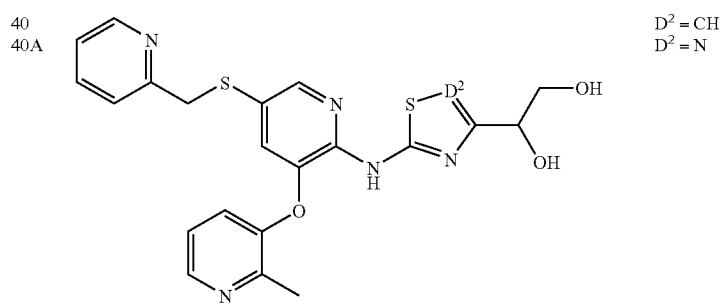 | $D^2$ = CH<br>$D^2$ = N |
| 41<br>41A | 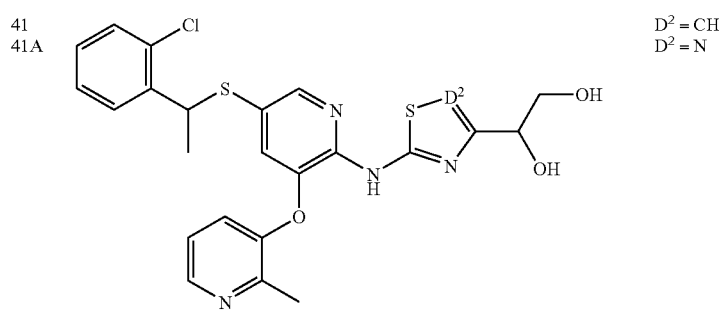 | $D^2$ = CH<br>$D^2$ = N |

-continued
| Example | Structure | |
|---|---|---|
| 42 42A | 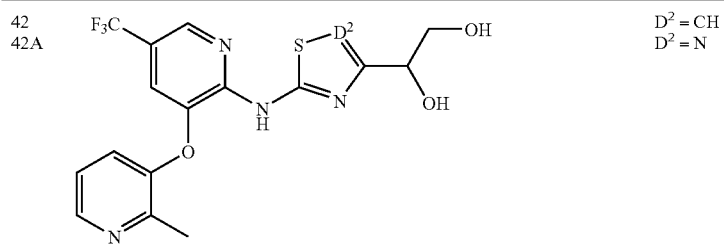 | D² = CH D² = N |
| 43 43A | 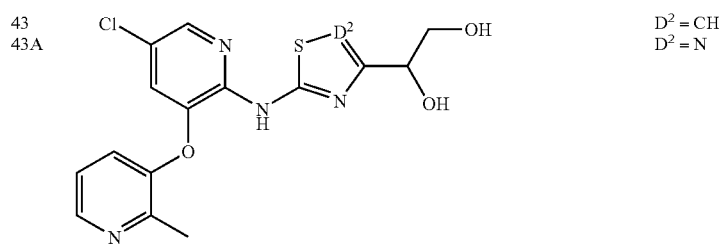 | D² = CH D² = N |
| 44 44A | 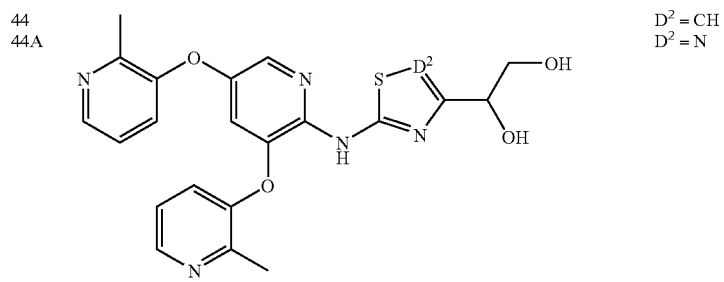 | D² = CH D² = N |
| 45 45A | 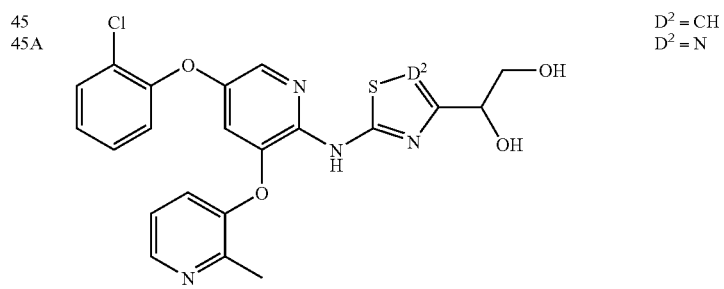 | D² = CH D² = N |
| 46 46A | 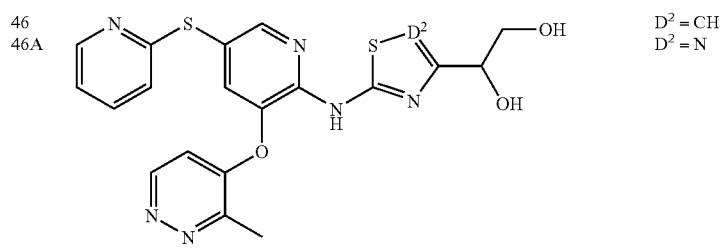 | D² = CH D² = N |
| 47 47A | 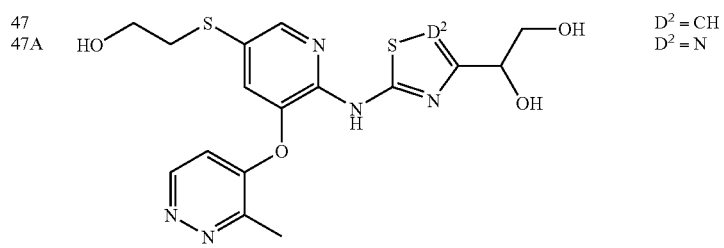 | D² = CH D² = N |

| Example | Structure | |
|---|---|---|
| 48<br>48A | 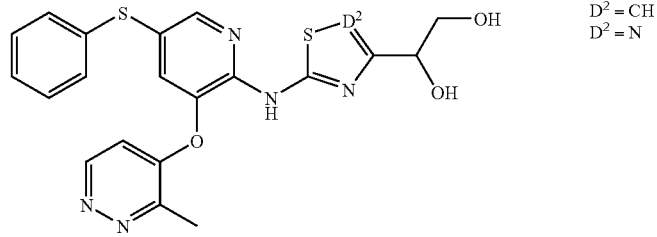 | $D^2 = CH$<br>$D^2 = N$ |
| 49<br>49A | 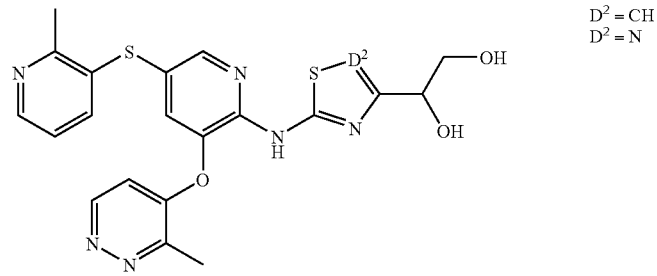 | $D^2 = CH$<br>$D^2 = N$ |
| 50<br>50A | 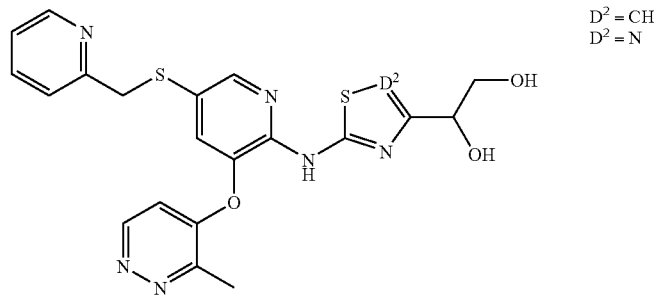 | $D^2 = CH$<br>$D^2 = N$ |
| 51<br>51A | 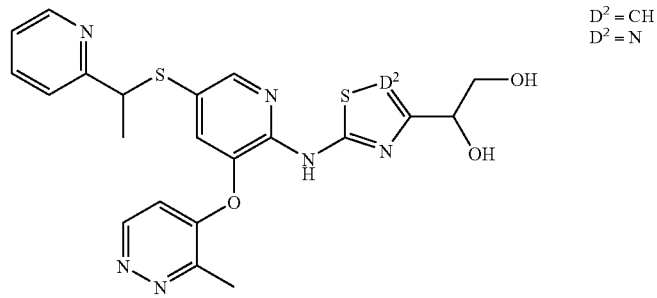 | $D^2 = CH$<br>$D^2 = N$ |
| 52<br>52A | 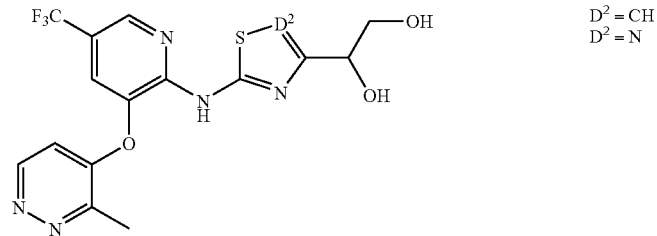 | $D^2 = CH$<br>$D^2 = N$ |

-continued
| Example | Structure | |
|---|---|---|
| 53 53A | 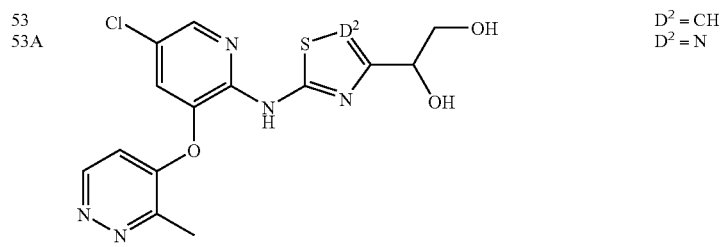 | D² = CH D² = N |
| 54 54A | 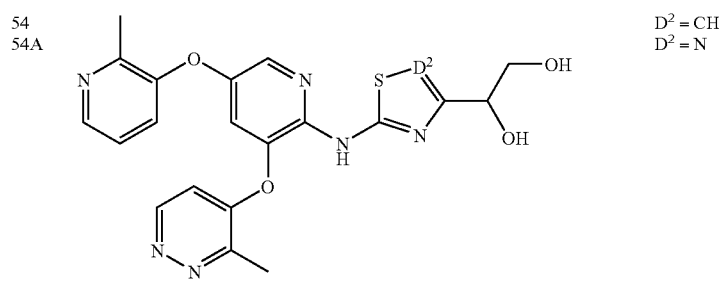 | D² = CH D² = N |
| 55 55A | 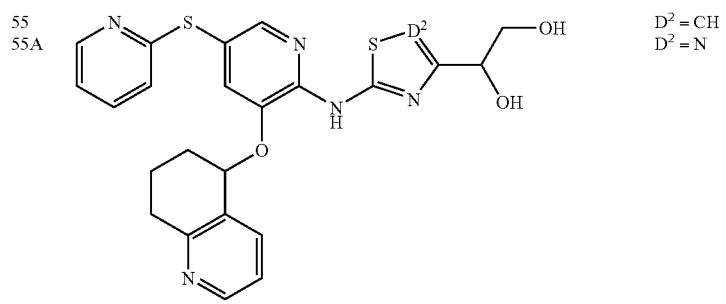 | D² = CH D² = N |
| 56 56A | 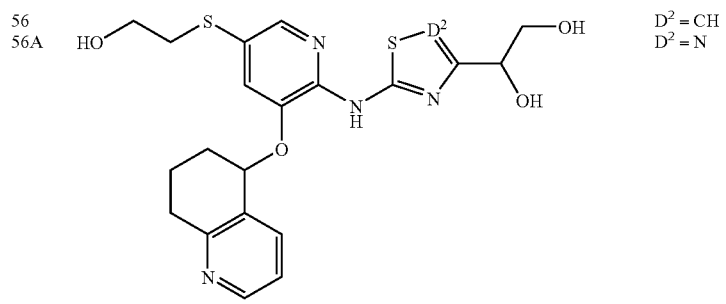 | D² = CH D² = N |
| 57 57A | 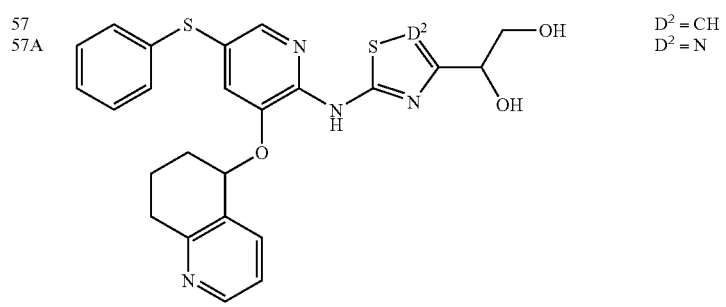 | D² = CH D² = N |

| Example | Structure | |
|---|---|---|
| 58<br>58A | 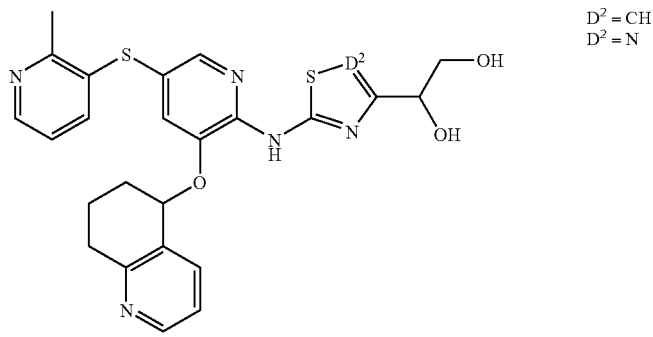 | D² = CH<br>D² = N |
| 59<br>59A | 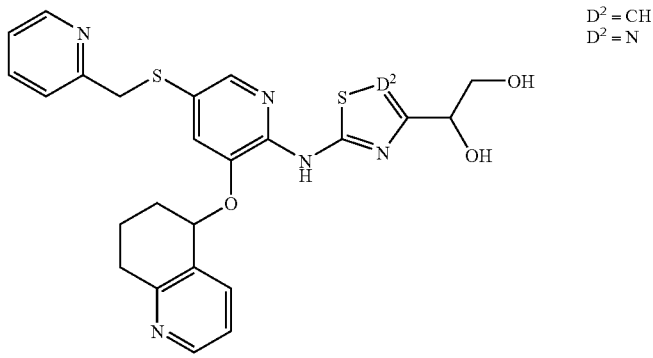 | D² = CH<br>D² = N |
| 60<br>60A | 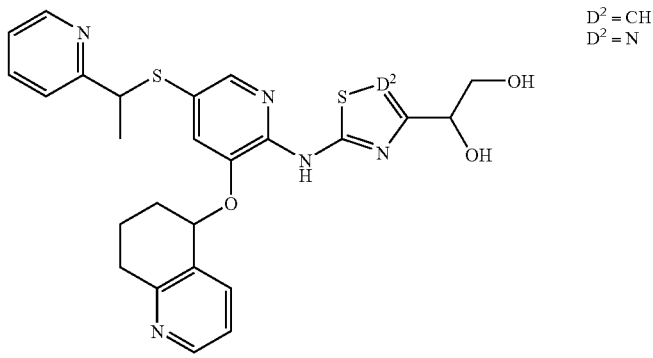 | D² = CH<br>D² = N |
| 61<br>61A | 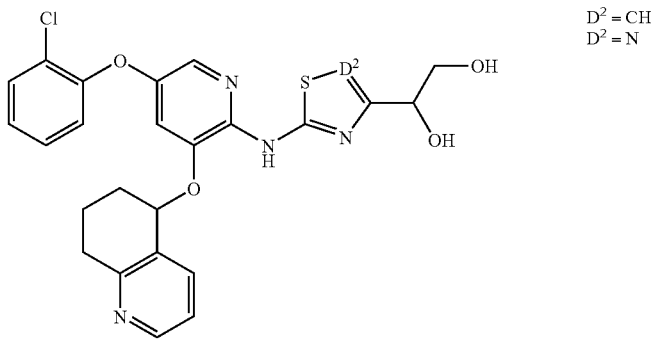 | D² = CH<br>D² = N |

-continued

| Example | Structure | |
|---|---|---|
| 62 | 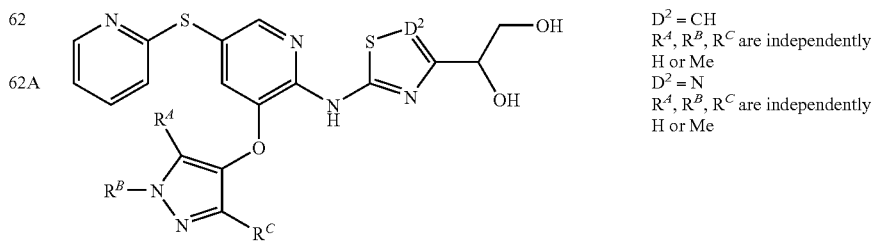 | $D^2$ = CH<br>$R^A$, $R^B$, $R^C$ are independently H or Me |
| 62A | | $D^2$ = N<br>$R^A$, $R^B$, $R^C$ are independently H or Me |
| 63 | 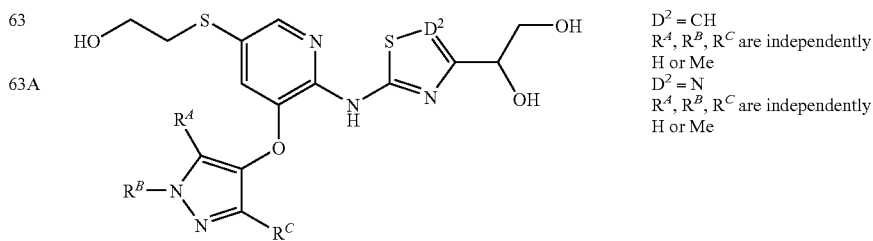 | $D^2$ = CH<br>$R^A$, $R^B$, $R^C$ are independently H or Me |
| 63A | | $D^2$ = N<br>$R^A$, $R^B$, $R^C$ are independently H or Me |
| 64 | 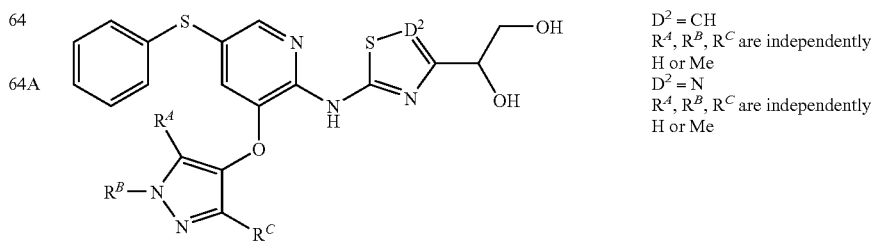 | $D^2$ = CH<br>$R^A$, $R^B$, $R^C$ are independently H or Me |
| 64A | | $D^2$ = N<br>$R^A$, $R^B$, $R^C$ are independently H or Me |
| 65 | 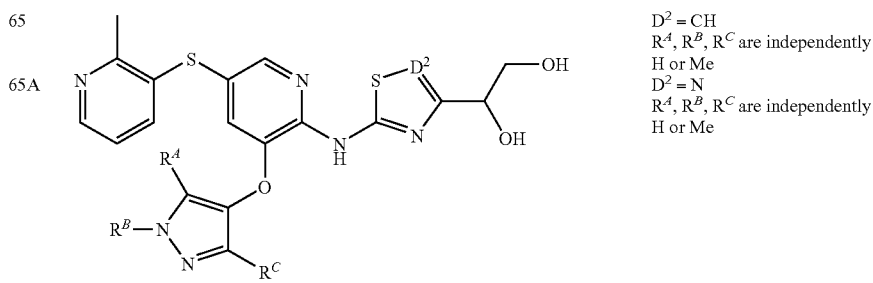 | $D^2$ = CH<br>$R^A$, $R^B$, $R^C$ are independently H or Me |
| 65A | | $D^2$ = N<br>$R^A$, $R^B$, $R^C$ are independently H or Me |
| 66 | 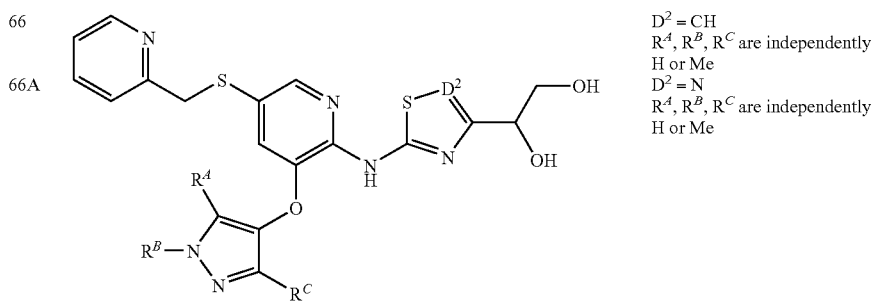 | $D^2$ = CH<br>$R^A$, $R^B$, $R^C$ are independently H or Me |
| 66A | | $D^2$ = N<br>$R^A$, $R^B$, $R^C$ are independently H or Me |

-continued

| Example | Structure | |
|---|---|---|
| 67 67A | (structure) | $D^2$ = CH<br>$R^A$, $R^B$, $R^C$ are independently H or Me<br>$D^2$ = N<br>$R^A$, $R^B$, $R^C$ are independently H or Me |
| 68 68A | (structure) | $D^2$ = CH<br>$R^A$, $R^B$, $R^C$ are independently H or Me<br>$D^2$ = N<br>$R^A$, $R^B$, $R^C$ are independently H or Me |
| 69 69A | (structure) | $D^2$ = CH<br>$R^A$, $R^B$, $R^C$ are independently H or Me<br>$D^2$ = N<br>$R^A$, $R^B$, $R^C$ are independently H or Me |
| 70 70A | (structure) | $D^2$ = CH<br>$D^2$ = N |
| 71 71A | (structure) | $D^2$ = CH<br>$D^2$ = N |
| 72 72A | (structure) | $D^2$ = CH<br>$D^2$ = N |

| Example | Structure | |
|---|---|---|
| 73 73A | 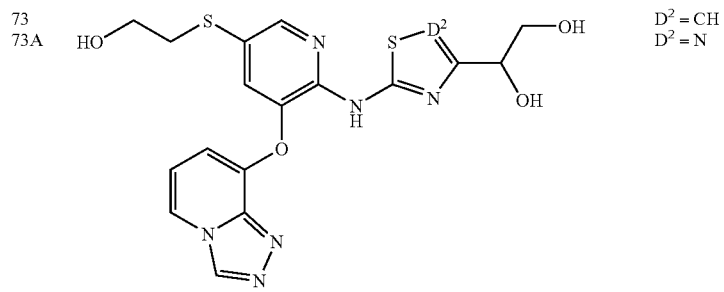 | D² = CH D² = N |
| 74 74A | 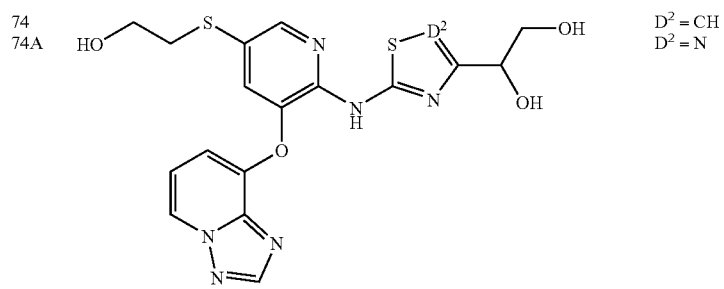 | D² = CH D² = N |
| 75 75A | 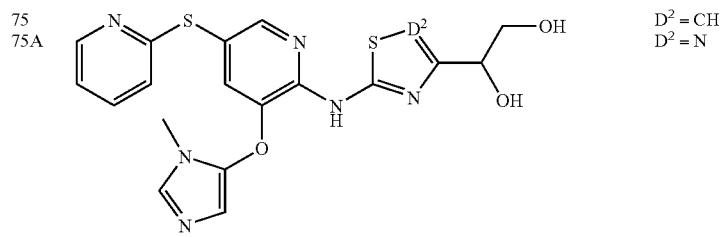 | D² = CH D² = N |
| 76 76A | 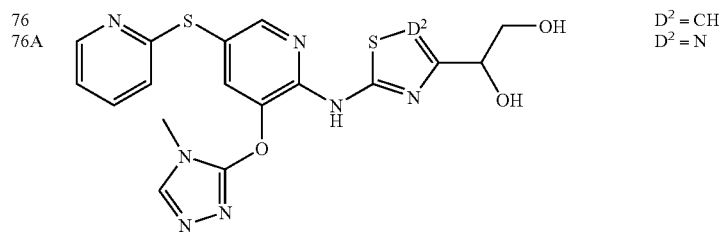 | D² = CH D² = N |
| 77 77A | 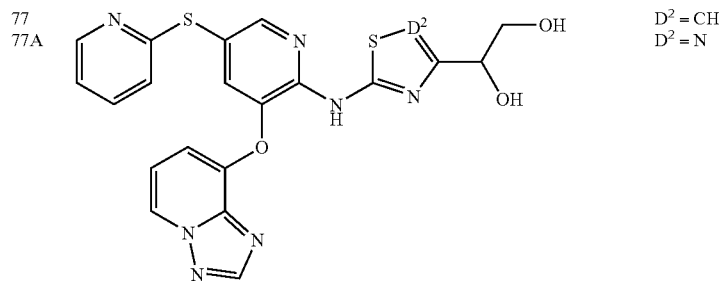 | D² = CH D² = N |

-continued
| Example | Structure | |
|---|---|---|
| 78 78A | 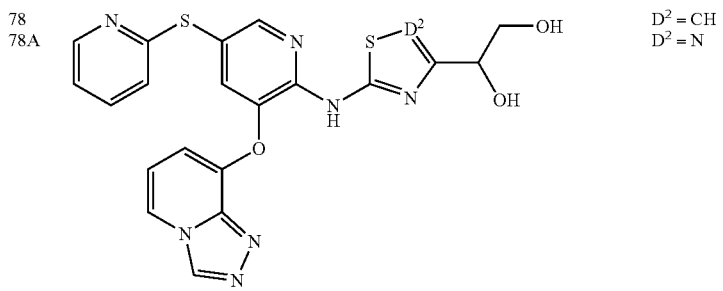 | D² = CH D² = N |
| 79 79A | 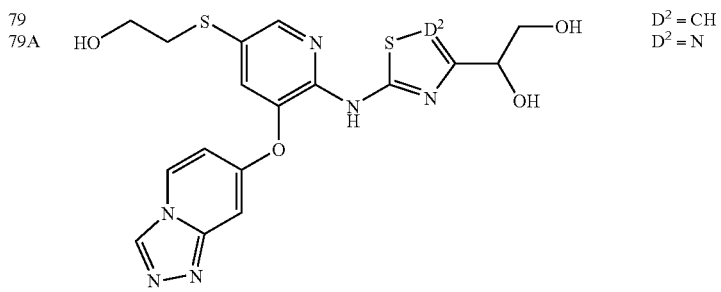 | D² = CH D² = N |
| 80 80A | 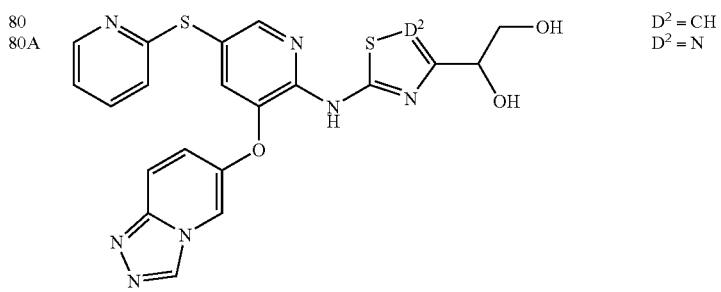 | D² = CH D² = N |
| 81 81A | 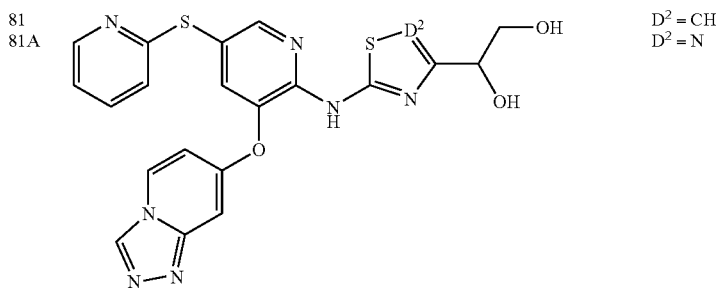 | D² = CH D² = N |
| 82 82A | 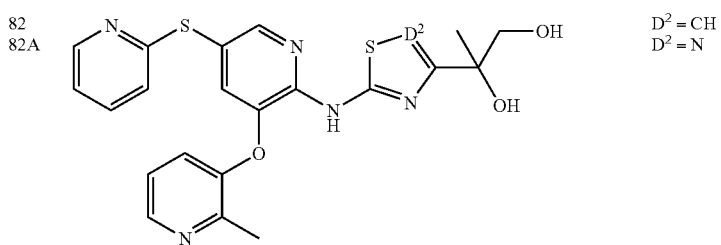 | D² = CH D² = N |

-continued

| Example | Structure | |
|---|---|---|
| 83 83A | (structure) | $D^2$ = CH $D^2$ = N |
| 84 84A | (structure) | $D^2$ = CH $D^2$ = N |
| 85 85A | (structure) | $D^2$ = CH $D^2$ = N |
| 86 86A | (structure) | $D^2$ = CH $D^2$ = N |
| 87 87A | (structure) | $D^2$ = CH $D^2$ = N |
| 88 88A | (structure) | $D^2$ = CH R = S-pyrid-2-yl, CF$_3$, S-2-methylpyrid-3-yl $D^2$ = N R = S-pyrid-2-yl, CF$_3$, S-2-methylpyrid-3-yl |

| Example | Structure | |
|---|---|---|
| 89<br>89A | 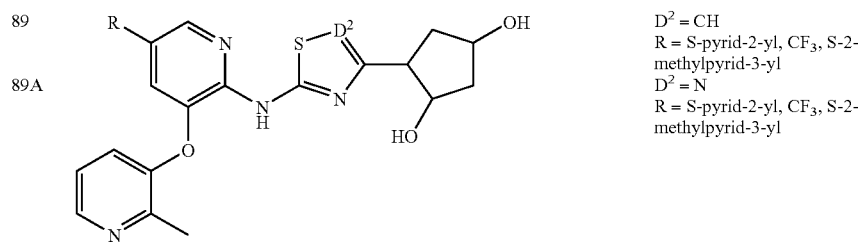 | $D^2 = CH$<br>R = S-pyrid-2-yl, $CF_3$, S-2-methylpyrid-3-yl<br>$D^2 = N$<br>R = S-pyrid-2-yl, $CF_3$, S-2-methylpyrid-3-yl |
| 90<br>90A | 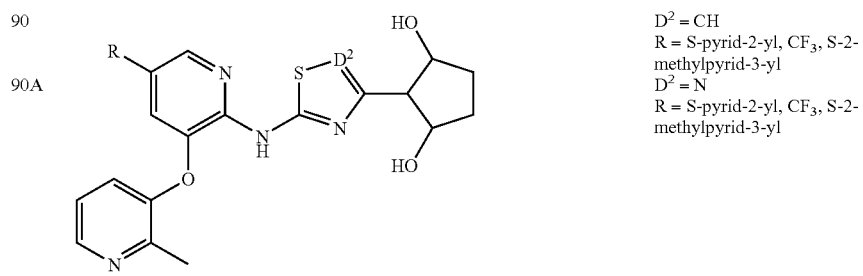 | $D^2 = CH$<br>R = S-pyrid-2-yl, $CF_3$, S-2-methylpyrid-3-yl<br>$D^2 = N$<br>R = S-pyrid-2-yl, $CF_3$, S-2-methylpyrid-3-yl |
| 91<br>91A | 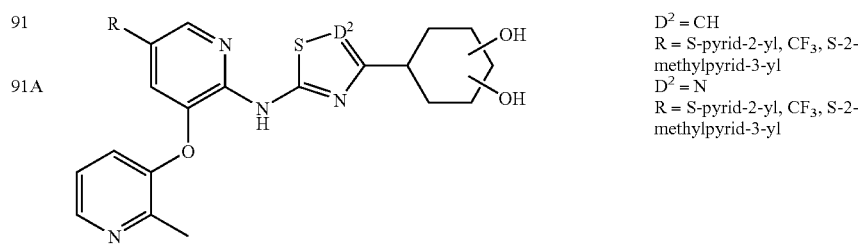 | $D^2 = CH$<br>R = S-pyrid-2-yl, $CF_3$, S-2-methylpyrid-3-yl<br>$D^2 = N$<br>R = S-pyrid-2-yl, $CF_3$, S-2-methylpyrid-3-yl |
| 92<br>92A | 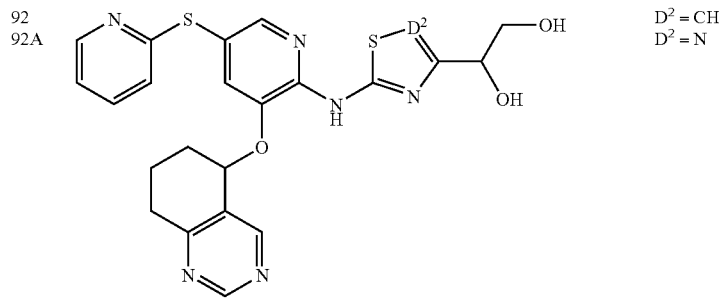 | $D^2 = CH$<br>$D^2 = N$ |
| 93<br>93A | 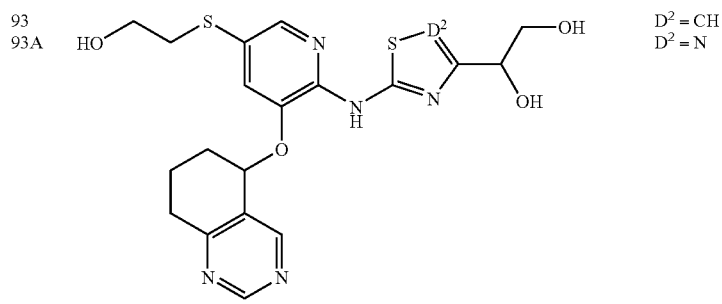 | $D^2 = CH$<br>$D^2 = N$ |

| Example | Structure | |
|---|---|---|
| 94 94A | 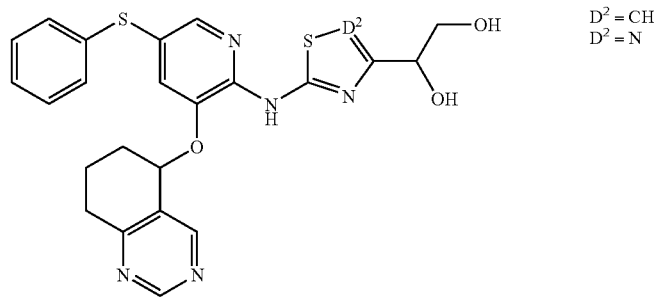 | $D^2$ = CH $D^2$ = N |
| 95 95A | 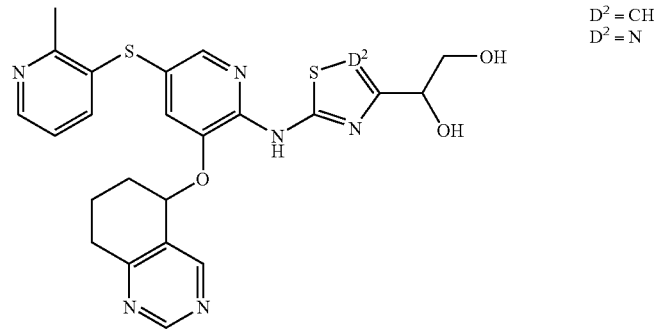 | $D^2$ = CH $D^2$ = N |
| 96 96A | 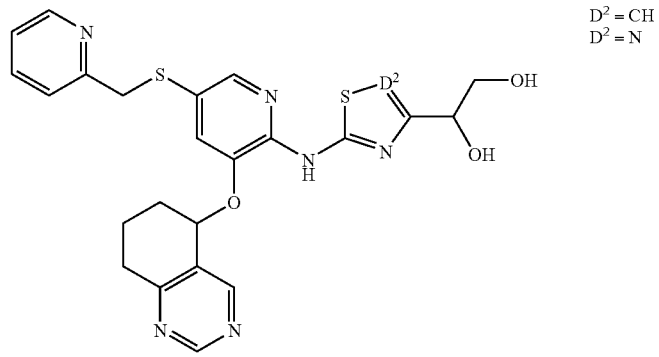 | $D^2$ = CH $D^2$ = N |
| 97 97A | 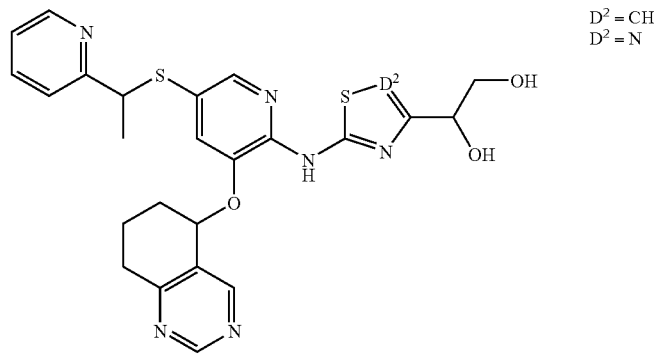 | $D^2$ = CH $D^2$ = N |

| Example | Structure | | |
|---|---|---|---|
| 98 98A | 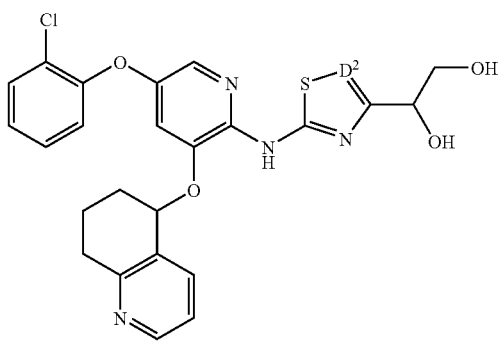 | $D^2$ = CH $D^2$ = N | |
| 99 99A | 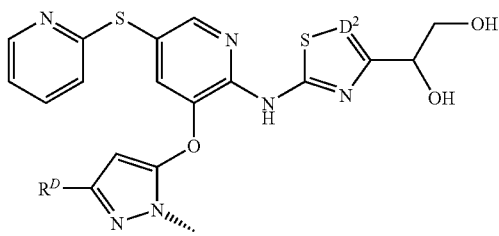 | $D^2$ = CH $R^D$ = H, Me, or CF$_3$ $D^2$ = N $R^D$ = H, Me, or CF$_3$ | |
| 100 100A | 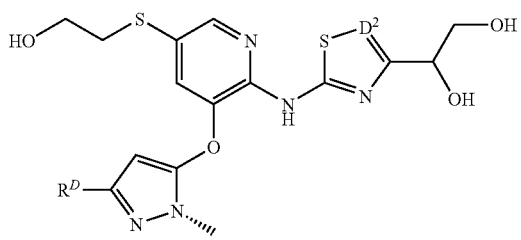 | $D^2$ = CH $R^D$ is H, CF$_3$ or (1-6C alkyl) $D^2$ = N $R^D$ is H, CF$_3$ or (1-6C alkyl) | |
| 101 101A | 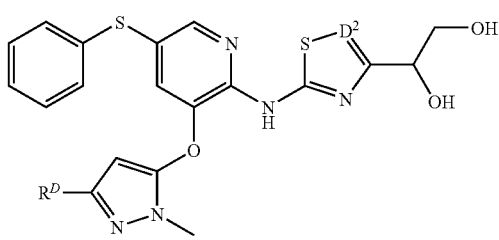 | $D^2$ = CH $R^D$ is H, CF$_3$ or (1-6C alkyl) $D^2$ = N $R^D$ is H, CF$_3$ or (1-6C alkyl) | |
| 102 102A | 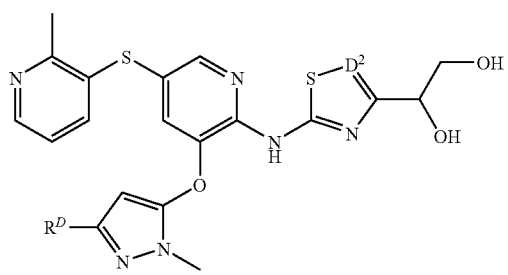 | $D^2$ = CH $R^D$ is H, CF$_3$ or (1-6C alkyl) $D^2$ = N $R^D$ is H, CF$_3$ or (1-6C alkyl) | |

-continued
| Example | Structure | |
|---|---|---|
| 103 103A | 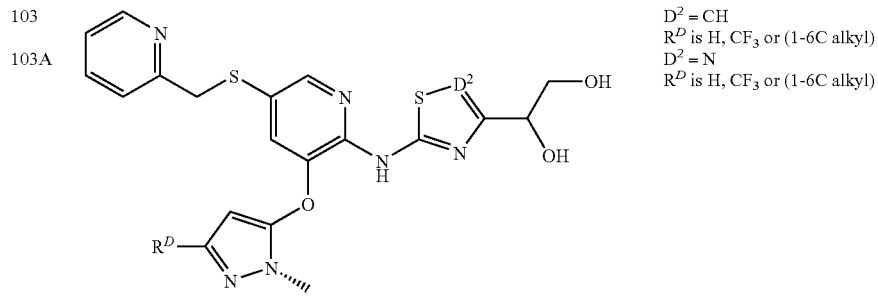 | $D^2$ = CH<br>$R^D$ is H, $CF_3$ or (1-6C alkyl)<br>$D^2$ = N<br>$R^D$ is H, $CF_3$ or (1-6C alkyl) |
| 104 104A | 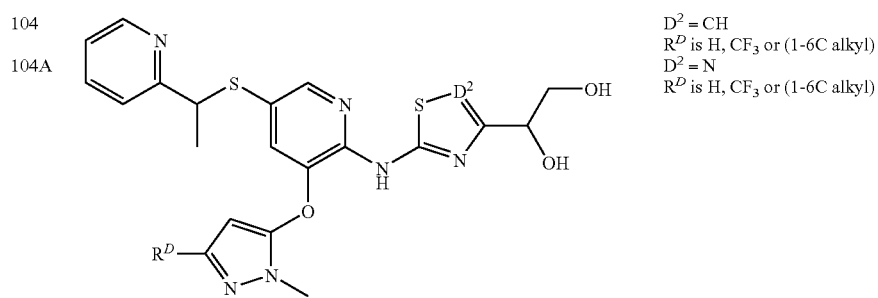 | $D^2$ = CH<br>$R^D$ is H, $CF_3$ or (1-6C alkyl)<br>$D^2$ = N<br>$R^D$ is H, $CF_3$ or (1-6C alkyl) |
| 105 105A | 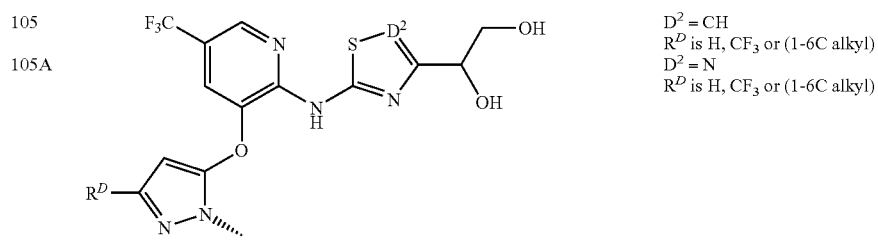 | $D^2$ = CH<br>$R^D$ is H, $CF_3$ or (1-6C alkyl)<br>$D^2$ = N<br>$R^D$ is H, $CF_3$ or (1-6C alkyl) |
| 106 106A | 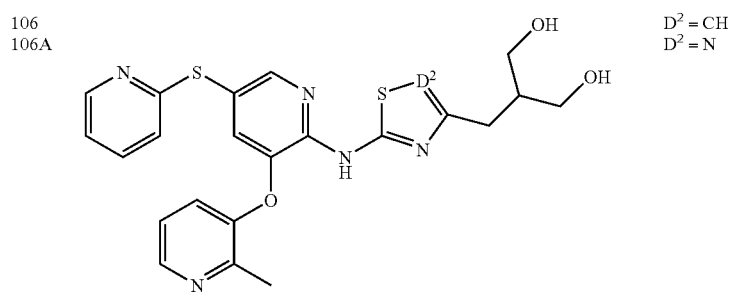 | $D^2$ = CH<br>$D^2$ = N |
| 107 107A | 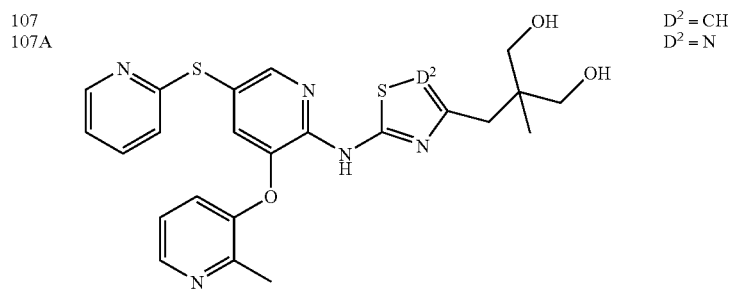 | $D^2$ = CH<br>$D^2$ = N |

-continued
| Example | Structure | |
|---|---|---|
| 108 108A | 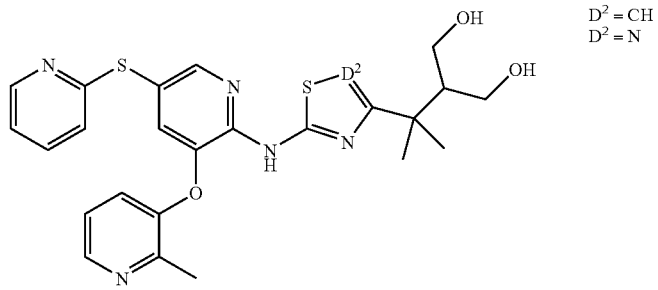 | $D^2$ = CH $D^2$ = N |
| 109 109A | 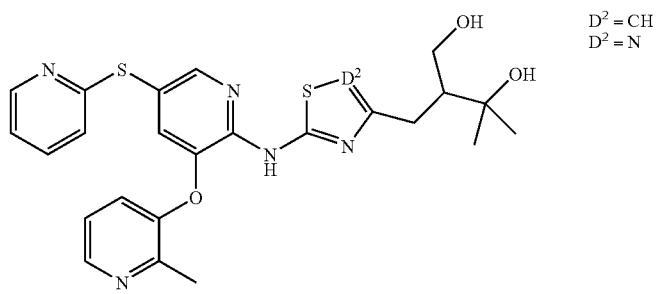 | $D^2$ = CH $D^2$ = N |
| 110 110A | 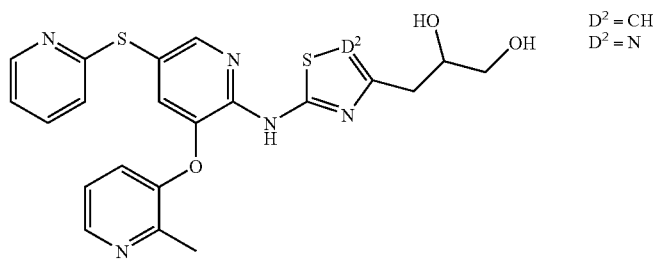 | $D^2$ = CH $D^2$ = N |
| 111 111A | 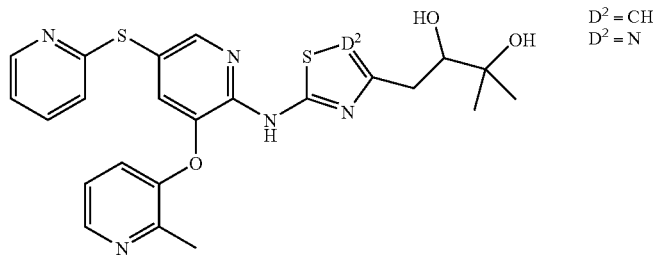 | $D^2$ = CH $D^2$ = N |
| 112 112A | 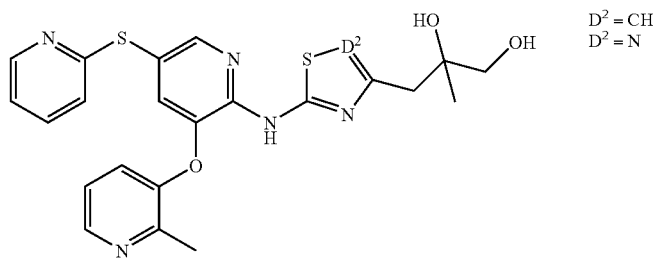 | $D^2$ = CH $D^2$ = N |

-continued
| Example | Structure | |
|---|---|---|
| 113 113A | 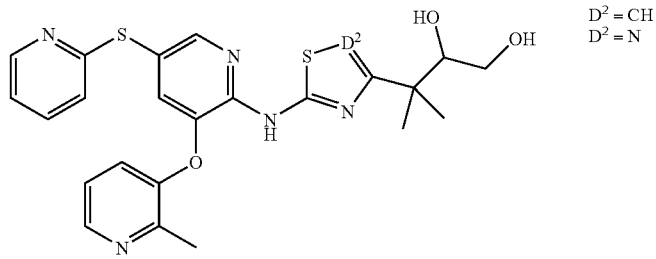 | $D^2$ = CH $D^2$ = N |
| 114 114A | 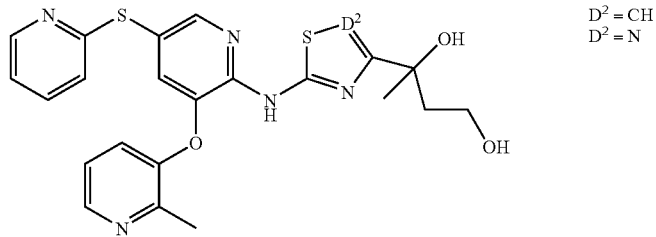 | $D^2$ = CH $D^2$ = N |
| 115 115A | 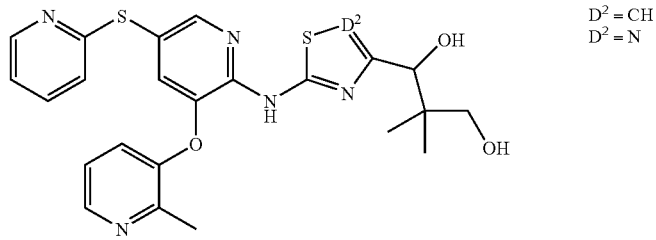 | $D^2$ = CH $D^2$ = N |
| 116 116A | 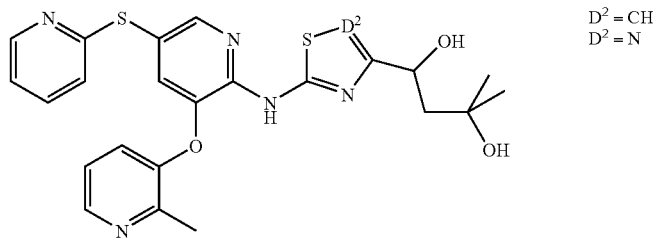 | $D^2$ = CH $D^2$ = N |
| 117 117A 117B 117C | 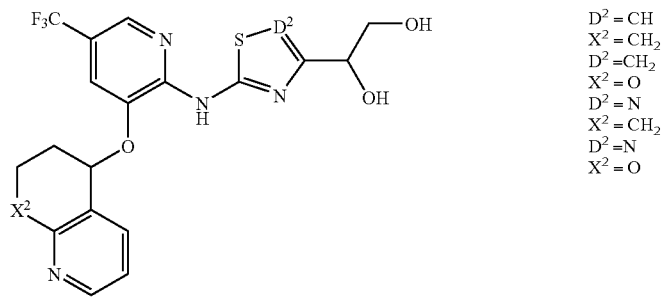 | $D^2$ = CH $X^2$ = $CH_2$ $D^2$ = $CH_2$ $X^2$ = O $D^2$ = N $X^2$ = $CH_2$ $D^2$ = N $X^2$ = O |
| 118 118A 118B 118C | 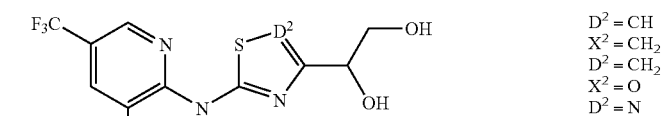 | $D^2$ = CH $X^2$ = $CH_2$ $D^2$ = $CH_2$ $X^2$ = O $D^2$ = N $X^2$ = $CH_2$ $D^2$ = N $X^2$ = O |

-continued

| Example | Structure | |
|---|---|---|
| 119 119A 119B 119C | (structure: 5-CF₃-pyridin-2-yl-amino linked to 1,3,4-thiadiazole with CH(OH)CH₂OH; 3-O-linked tetrahydronaphthyridine with X²) | D² = CH X² = CH₂ D² = CH X² = O D² = N X² = CH₂ D² = N X² = O |
| 120 120A 120B 120C | (structure as above with different fused bicyclic orientation) | D² = CH X² = CH₂ D² = CH X² = O D² = N X² = CH₂ D² = N X² = O |
| 121 121A 121B 121C | (structure with 5-membered fused ring pyridine) | D² = CH X² = CH₂ D² = CH X² = O D² = N X² = CH₂ D² = N X² = O |
| 122 122A 122B 122C | (structure with 5-membered fused ring pyridine variant) | D² = CH X² = CH₂ D² = CH X² = O D² = N X² = CH₂ D² = N X² = O |
| 123 123A 123B 123C | (structure with 5-membered fused ring pyridine variant) | D² = CH X² = CH₂ D² = CH X² = O D² = N X² = CH₂ D² = N X² = O |

| Example | Structure | |
|---|---|---|
| 124 | (F₃C-pyridine-NH-thiadiazole(D²)-CH(OH)-CH₂OH, with O-linked X²-containing bicyclic pyridine) | D² = CH, X² = CH₂ |
| 124A | | D² = CH₂ (sic), X² = O |
| 124B | | D² = N, X² = CH₂ |
| 124C | | D² = N, X² = O |
| 125 | (F₃C-pyridine-NH-thiadiazole(D²)-CH(OH)-CH₂OH, with O-linked tetrahydroquinazoline) | D² = CH |
| 125A | | D² = N |
| 126 | (F₃C-pyridine-NH-thiadiazole(D²)-CH(OH)-CH₂OH, with O-linked tetrahydroquinazoline isomer) | D² = CH |
| 126A | | D² = N |
| 127 | (F₃C-pyridine-NH-thiadiazole(D²)-CH(OH)-CH₂OH, with O-linked cyclopenta-pyrimidine) | D² = CH |
| 127A | | D² = N |
| 128 | (F₃C-pyridine-NH-thiadiazole(D²)-CH(OH)-CH₂OH, with O-linked cyclopenta-pyrimidine isomer) | D² = CH |
| 128A | | D² = N |

| Example | Structure | |
|---|---|---|
| 129<br>129A | 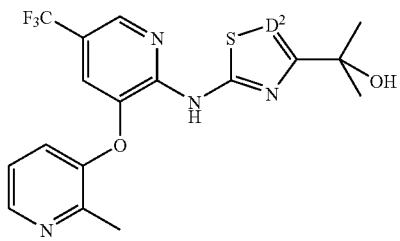 | D² = CH<br>D² = N |
| 130<br>130A | 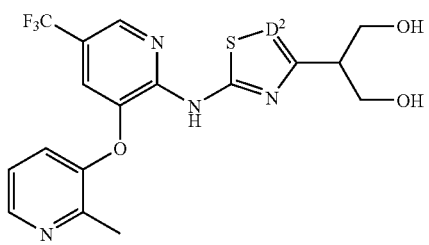 | D² = CH<br>D² = N |
| 131<br>131A | 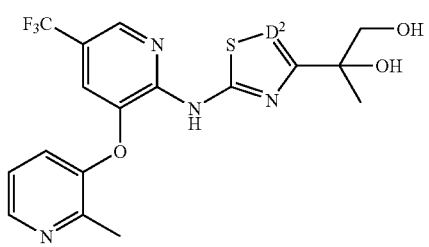 | D² = CH<br>D² = N |
| 132<br>132A | 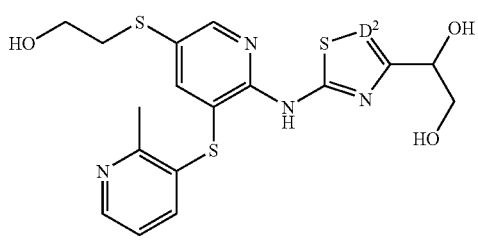 | D² = CH<br>D² = N |
| 133<br>133A | 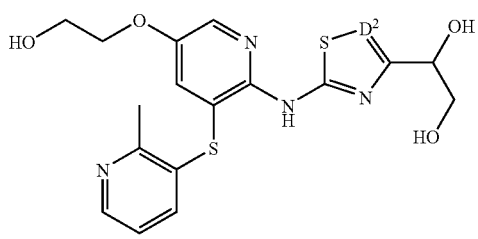 | D² = CH<br>D² = N |

Example 134

(S)-1-(5-(3-(2-methylpyridin-3-yloxy)-5-(pyridin-2-ylthio)pyridin-2-ylamino)-1,2,4-thiadiazol-3-yl)ethane-1,2-diol hydrochloride

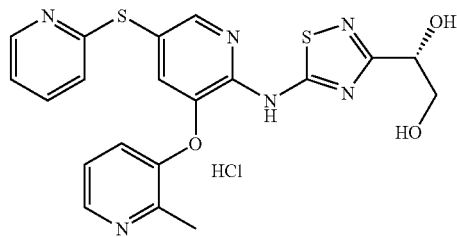

Step A: To 600 mL of DMF in a 4 neck 3000 mL round bottom flask equipped with an overhead stir mechanism under nitrogen was added 2-methylpyridin-3-ol (71.8 g, 658 mmol) and the reaction cooled to 2° C. 60% sodium hydride (26.3 g, 658 mmol) was added at such as rate that the internal temperature did not exceed 10° C. over a period of 30 minutes. The reaction was stirred while warming to ambient temperature for 1 hours. To the reaction was added 5-bromo-3-nitropicolinonitrile (150 g, 658 mmol) in a solution of 400 mL of DMF in two portions and the reaction held at ambient temperature for 1.5 hours. To the reaction at ambient temperature was added pyridine-2-thiol (73.1 g, 658 mmol) as a solid in portions and the reaction was stirred for 15 minutes to dissolve the material. The reaction was cooled to 3° C. and sodium hydride (26.3 g, 658 mmol) again was added in portions such that the internal temp did not go above 10° C. (35 minute addition time). The reaction was removed from the ice bath and warmed to ambient temperature while stirring for 12 hours. The reaction was diluted with 4 volumes (8 L) of brine. The mixture was stirred for 30 minutes, at which point solid formed. The solid was filtered off and filtrate extracted with MTBE (10 L total). The MTBE phase was concentrated in vacuo. The solid was combined with concentrated material and dissolved in ethyl acetate (3 L). The EtOAc was washed with brine (4×1 L), dried over $MgSO_4$, filtered and concentrated in vacuo. The solid that formed was ground into a powder and dried in vacuo for 4 hours. The material was taken up in 30 mL of MTBE/10 g of product and the reaction was stirred for 30 minutes. The solid was filtered and dried in vacuo (2 hours). The solids were combined and dried for 3 hours in vacuo to yield 3-(2-methylpyridin-3-yloxy)-5-(pyridin-2-ylthio)picolinonitrile (181 g, 85%)

Step B: To concentrated $H_2SO_4$ (90 mL) cooled in an ice bath was added 3-(2-methylpyridin-3-yloxy)-5-(pyridin-2-ylthio)picolinonitrile (43 g, 130 mmol) in portions such that the internal temp did not exceed 50° C. but did not go below 25° C. After complete addition, the mixture was stirred in the ice bath until the reaction started to cool, at which point the reaction was removed from the ice bath and the mixture was heated to 50° C. The reaction was cooled to ambient temperature and slowly added to ice water over 3 minutes (about 1400 mL of 30% ice in water). The mixture was further cooled in an ice bath to 5° C. and neutralized to pH ~10 with 4M NaOH (about 800 mL) while keeping the internal temperature below 20° C., at which point a solid formed. The mixture was stirred for 20 minutes. The mixture was filtered and washed with MTBE (5×150 mL), hexanes (×100 mL), and dried at under vacuum to afford 3-(2-methylpyridin-3-yloxy)-5-(pyridin-2-ylthio)picolinamide (43 g, 96%).

Step C: To a 3-neck 2 L round bottom flask was added 2M aqueous sodium hydroxide (343 ml, 686 mmol) and the solution was cooled in an ice bath. Bromine (12 ml, 257 mmol) was added and the mixture was stirred for 30 minutes while the ice bath was removed. 3-(2-Methylpyridin-3-yloxy)-5-(pyridin-2-ylthio)picolinamide (58 g, 171 mmol) was added as a slurry in about 600 mL of dioxane in 1 portion. After 30 minutes, concentrated HCl was added in 1 mL portions to a pH ~1. The reaction was stirred for 15 minutes and 4N NaOH was added to the solution to pH ~10. The aqueous mixture was extracted with EtOAc (3×750 mL), washed with water (2×250 mL) and brine (300 mL), dried over $MgSO_4$, filtered and concentrated. The material was dried in vacuo at 50° C. at which point a red solid formed. The solid was triturated with $CH_2Cl_2$ (about 40 mL of $CH_2Cl_2$ to 5 g of material) and the solid filtered. The solid was washed with $CH_2Cl_2$ and dried under vacuum at 50° C. The filtrate was concentrated in vacuo and material purified over silica gel (3% MeOH/$CH_2Cl_2$) to afford a red solid. The two crops were combined to afford 3-(2-methylpyridin-3-yloxy)-5-(pyridin-2-ylthio)pyridin-2-amine (24 g, 45%).

Step D: To 1000 mL of DI water was added hydroxyl amine hydrochloride (51.0 g, 734 mmol) and the mixture was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) was added in 1 portion in 800 mL of THF. The reaction was stirred for 4 hours and poured into a 4 L separatory funnel and the layers separated. The aqueous layer was extracted twice with MTBE (about 3000 mL total). The combined organic layers were washed with water (700 mL) and brine (300 mL), dried over $MgSO_4$, and concentrated in vacuo to afford (S)-1,4-dioxaspiro[4.5]decane-2-carbaldehyde oxime (135 g, 99%) as a clear oil.

Step E: To a 4-neck 2 L round bottom flask was added (S)-1,4-dioxaspiro[4.5]decane-2-carbaldehyde oxime (135.1 g, 729.4 mmol) and 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours, then diluted with 2 L of MTBE and washed with 1 L of water. The water was extracted with 500 mL of MTBE. The combined organic layers were washed with water (5×800 mL) and brine (300 mL), dried over $MgSO_4$ and concentrated in vacuo to afford added (R)-N-hydroxy-1,4-dioxaspiro[4.5]decane-2-carbimidoyl chloride (158 g, 98%) as a green viscous oil.

Step F: In a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) added in 10 mL portions over 10 minutes. N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids washed with MTBE (about 3 L). The filtrate was concentrated and the residue was purified over silica gel (7:1 to 3:1 Hexanes/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step G: To 700 mL of acetonitrile was added sodium isothiocyanate (12.5 g, 155 mmol), pyridine (25.2 ml, 309 mmol) and (R)-N-(methylsulfonyloxy)-1,4-dioxaspiro[4.5]decane-2-carbimidoyl chloride (38.4 g, 129 mmol) and the reaction heated to 60° C. for 15 minutes (white solid formed). To the mixture was added 3-(2-methylpyridin-3-yloxy)-5-(pyridin-2-ylthio)pyridin-2-amine (32 g, 103 mmol) as a solid and the reaction was stirred for 14 hours at 60° C. The reaction was cooled and concentrated in vacuo. The residue was partitioned between EtOAc and 1N NaOH. The aqueous mixture (basic, about 700 ML) was extracted twice with EtOAc (3000 mL total volume). The combined organic layers were washed with 1 N NaOH (300 mL) and brine (300 mL), dried over MgSO$_4$ and concentrated in vacuo. The residue was purified by chromatography on about 1 kg of silica gel using 1:1 EtOAc/CH$_2$Cl$_2$ with 1% MeOH as eluent to afford (S)-N-(3-(2-methylpyridin-3-yloxy)-5-(pyridin-2-ylthio)pyridin-2-yl)-3-(1,4-dioxaspiro[4.5]decan-2-yl)-1,2,4-thiadiazol-5-amine (38.7 g, 72.4 mmol, 70.2% yield).

Step H: In 1 L of absolute ethanol was added (S)-N-(3-(2-methylpyridin-3-yloxy)-5-(pyridin-2-ylthio)pyridin-2-yl)-3-(1,4-dioxaspiro[4.5]decan-2-yl-1,2,4-thiadiazol-5-amine (41 g, 76.7 mmol) and the reaction was heated to 80° C. 41 mL of aqueous HCl (11.6 mL of concentrated HCl diluted in water) was added. After 2 hours, the resultant solid material was hot filtered, washed with ethanol (200 mL) and dried in vacuo to yield crude product as a solid which contained about 2% starting material. The solids were suspended in EtOH (1 L) and heated to 80° C. followed by 41 mL of aqueous HCl (11.6 mL of concentrated HCl diluted in water). After 3.5 hours the resultant solid material was hot filtered, washed with ethanol (200 mL) and dried in vacuo and to afford (S)-1-(5-(3-(2-methylpyridin-3-yloxy)-5-(pyridin-2-ylthio) pyridin-2-ylamino)-1,2,4-thiadiazol-3-yl)ethane-1,2-diol hydrochloride (35 g, 85%). Mass Spectrum (apci) m/z=455.2 (M+H—HCl).

Example 135

(S)-1-(5-(3-(2,6-dimethylpyridin-3-yloxy)-5-(pyridin-2-ylthio)pyridin-2-ylamino)-1,2,4-thiadiazol-3-yl)ethane-1,2-diol hydrochloride

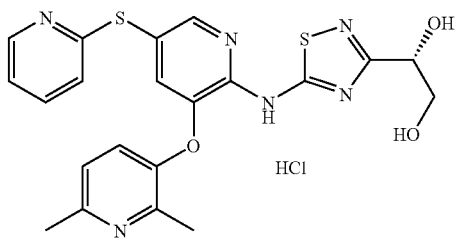

Step A: To a 0° C. solution of 2,6-dimethylpyridin-3-ol (10 g, 81.2 mmol) in DMF (50 ml) was added sodium hydride (60% dispersion in oil, 3.4 g, 85 mmol). After 15 minutes, 5-bromo-3-nitropicolinonitrile (18.5 g, 81 mmol) was added and the mixture was allowed to warm slowly to ambient temperature. The reaction mixture was slowly added to 500 mL of rapidly stirring water. A light red solid formed and then the material formed a gum. The gum was extracted into ethyl acetate, and the organics washed with brine, dried over MgSO$_4$ and concentrated in vacuo to afford 5-bromo-3-(2,6-dimethylpyridin-3-yloxy)picolinonitrile (25 g, 82 mmol, 101% yield).

To 5-bromo-3-(2,6-dimethylpyridin-3-yloxy)picolinonitrile (25 g, 82 mmol) was added concentrated sulfuric acid (25 ml) and the mixture stirred at ambient temperature over night. The mixture was poured onto ice (500 ml) and the aqueous mixture neutralized using 50% NaOH. A solid formed at pH 7. The solid was collected and dried in vacuo to afford 3-(2,6-dimethylpyridin-3-yloxy)-5-bromopicolinamide (24.2 g, 92%).

To a 0° C. solution of NaOH (150 mL, 2M) was added bromine (14.4 g, 90 mmol), followed by 3-(2,6-dimethylpyridin-3-yloxy) 5-bromopicolinamide (24 g, 75 mmol) dissolved in dioxanes (300 ml). The reaction was stirred at ambient temperature for 1 hour and then at 80° C. for 1 hour. The reaction was cooled to ambient temperature and acidified to pH 1 with concentrated HCl. The mixture was stirred at ambient temperature for 1 hour and basified to pH 10 using 2M NaOH. The aqueous layer was extracted into ethyl acetate. The combined organic layers were washed with brine, dried over MgSO$_4$ and concentrated in vacuo to afford 5-bromo-3-(2,6-dimethylpyridin-3-yloxy)pyridin-2-amine (20.5 g, 92%).

Step D: A 250 mL flask was charged with 5-bromo-3-(2,6-dimethylpyridin-3-yloxy)pyridin-2-amine (5.00 g, 17.66 mmol) and THF (100 mL) and purged with nitrogen. The solution was cooled to −78° C., methyl lithium (1.6 M in hexanes, 12.7 mL, 20.4 mmol) was added and the reaction was stirred for 5 minutes. Butyl lithium (2.5 M in Hexanes, 8.1 mL, 20.4 mmol) was added and the reaction was stirred for 10 minutes at −78° C. (solids formed). 2-(2-(Pyridin-3-yl)disulfanyl)pyridine (4.49 g, 20.4 mmol) was added and the reaction was warmed to ambient temperature and stirred for 18 hours. The reaction was poured into aqueous NH$_4$Cl, extracted with EtOAc, washed with brine, dried over MgSO$_4$ and concentrated in vacuo. The residue was purified over silica gel (5% MeOH in CH$_2$Cl$_2$) to afford 3-(2,6-dimethylpyridin-3-yloxy)-5-(pyridin-2-ylthio)pyridin-2-amine (3.5 g, 63%).

Step E: In 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) was added in 1 portion in 800 mL of THF. The reaction was stirred for 4 hours and poured into a 4 L separatory funnel and the layers separated. The aqueous layer was extracted twice with MTBE (about 3000 mL total). The combined organic layers were washed with water (700 mL) and brine (300 mL), dried over MgSO$_4$ and concentrated in vacuo to afford (S)-1,4-dioxaspiro[4.5]decane-2-carbaldehyde oxime (135 g, 99%) as a clear viscous oil.

Step F: To a 4-neck 2 L round bottom flask was added (S)-1,4-dioxaspiro[4.5]decane-2-carbaldehyde oxime (135.1 g, 729.4 mmol) and dissolved in 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours, then diluted with 2 L of MTBE and washed with 1 L of water. The water was extracted with 500 mL of MTBE. The combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step G: In a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) was added through an addition funnel over 12 minutes. The reaction was filtered and the solids washed with MTBE (about 3 L). The filtrate was concentrated and the residue was purified over silica gel (7:1 to 3:1 Hex/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro [4.5]decane-2-carbimidoyl chloride (158 g, 531 mmol, 73.8% yield) as a white solid.

Step H: To a solution of sodium isothiocyanate (0.24 g, 3.0 mmol) in acetonitrile (30 mL) was added pyridine (0.51 g, 6.5 mmol) followed by (R)-N-(methylsulfonyloxy)-1,4-dioxaspiro[4.5]decane-2-carbimidoyl chloride (0.77 g, 2.6 mmol) and the reaction was stirred at 60° C. for 20 minutes, followed by addition of 3-(2,6-dimethylpyridin-3-yloxy)-5-(pyridin-2-ylthio)pyridin-2-ylamine (0.70 g, 2.2 mmol) and the reaction was stirred overnight at 60° C. The reaction was concentrated in vacuo and the residue partitioned between EtOAc and 2 M NaOH. The combined organic layers were washed with brine, dried over $MgSO_4$ and concentrated in vacuo. The material was purified over silica gel (30% EtOAc in $CH_2Cl_2$) to afford (S)-N-(3-(2,6-dimethylpyridin-3-yloxy)-5-(pyridin-2-ylthio)pyridin-2-yl)-3-(1,4-dioxaspiro[4.5]decan-2-yl-1,2,4-thiadiazol-5-amine (0.50 g, 0.91 mmol, 42% yield).

Step I: To a solution of (S)-N-(3-(2,6-dimethylpyridin-3-yloxy)-5-(pyridin-2-ylthio)pyridin-2-yl)-3-(1,4-dioxaspiro [4.5]decan-2-yl)-1,2,4-thiadiazol-5-amine (0.70 g, 1.3 mmol) in ethanol (20 mL) was added concentrated HCl (2.4 ml) and the reaction was heated to 80° C. for 2 hours. The reaction was concentrated and the material triturated with EtOH. The solid was further purified by reverse phase HPLC to yield pure product. The product was taken up in ethanol and HCl (2M in ether) was added. The mixture was stirred for 2 hours and concentrated in vacuo and dried in vacuo to yield the product as the HCl salt (73.2 mg, 12%). Mass Spectrum (apci) m/z=469.2 (M+H—HCl).

Example 136

(S)-1-(5-(5-(cyclopropylmethylthio)-3-(2-methylpyridin-3-yloxy)pyridin-2-ylamino)-1,2,4-thiadiazol-3-yl)ethane-1,2-diol hydrochloride

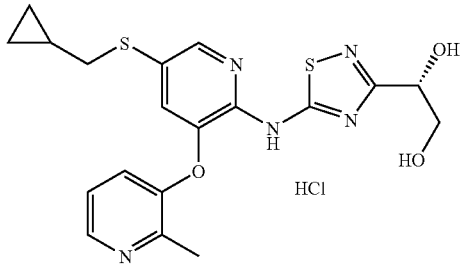

Step A: To a solution of 2-methylpyridin-3-ol (11.8 g, 108 mmol) in DMF at 0° C. was added sodium hydride (60% dispersion in oil, 4.32 g, 108 mmol) in small portions and the reaction was warmed to ambient temperature. To this mixture was added 5-bromo-3-nitropicolinonitrile (24.6 g, 108 mmol) and the reaction was stirred overnight at ambient temperature. The reaction was poured into water (1000 mL) and the aqueous layer extracted with EtOAc. The combined organic layers were washed with water (3×) and brine, dried over $MgSO_4$ and concentrated in vacuo to yield 5-bromo-3-(2-methylpyridin-3-yloxy)picolinonitrile (15 g, 48%).

Step B: To 5-bromo-3-(2-methylpyridin-3-yloxy)picolinonitrile (15 g, 52 mmol) was added concentrated $H_2SO_4$ (30 mL) and the slurry was left to stir overnight, at which point the material was fully dissolved. The reaction was poured into 0° C. water in small portions. While maintaining the temp below 20° C., the aqueous layer was basified by the addition of NaOH pellets, to a pH of ~5, at which point a solid formed. The solid was filtered and the remaining aqueous layer was extracted with EtOAc. The organic layers, combined with the solid, were washed with brine, dried over $MgSO_4$ and concentrated in vacuo to yield 5-bromo-3-(2-methylpyridin-3-yloxy)picolinamide (11 g, 69%).

Step C: To a solution of NaOH (2M, 90 mL, 182 mmol) at 0° C. was added bromine (8.71 g, 54 mmol) and the reaction was stirred at 0° C. for 30 minutes. To this mixture was added 5-bromo-3-(2-methylpyridin-3-yloxy)picolinamide (11.2 g, 36.3 mmol) in dioxanes (100 mL) and the reaction was stirred at ambient temperature for 1 hour followed by heating to 80° C. for 1 hour. The reaction was cooled to ambient temperature and acidified to pH 1 using concentrated HCl. The reaction was basified and a solid precipitated. The solid was filtered and dried in vacuo to yield 5-bromo-3-(2-methylpyridin-3-yloxy)pyridin-2-amine (4.1 g, 41%).

Step D: In 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added to the reaction and (R)-1, 4-dioxaspiro[4.5]decane-2-carbaldehyde (125 g, 734 mmol) in 800 mL of THF was added in 1 portion. The reaction was stirred for 4 hours, then poured into a 4 L separatory funnel. The layers separated and the aqueous layer was extracted twice with MTBE (about 3000 mL total). The combined organic layers were washed with water (700 mL) and brine (300 mL), dried over $MgSO_4$, and concentrated in vacuo to afford (S)-1,4-dioxaspiro[4.5]decane-2-carbaldehyde oxime (135 g, 99%) as a clear viscous oil.

Step E: To a 4-neck 2 L round bottom flask was added (S)-1,4-dioxaspiro[4.5]decane-2-carbaldehyde oxime (135.1 g, 729.4 mmol) dissolved in 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours. The reaction was diluted with 2 L of MTBE and washed with 1 L of water. The water was extracted with 500 mL of MTBE. The combined organic layers were washed with water (5×800 mL) and brine (300 mL), dried over $MgSO_4$ and concentrated in vacuo to afford added (R)-N-hydroxy-1,4-dioxaspiro[4.5] decane-2-carbimidoyl chloride (158 g, 98%) as a green viscous oil.

Step F: In a 4 neck flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) added in 10 mL portions over 10 minutes. Next, N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids washed with MTBE (about 3 L). The filtrate was concentrated and the residue was purified over silica gel (3 kg silica, 7:1 to 3:1 Hex/EtOAc) to afford an oil that slowly solidified under vacuum. The solids were ground using a mortar and pestle and washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step G: In 100 mL of acetonitrile was added sodium thioisocyanate (1.5 g, 20 mmol), pyridine (3.5 g, 44 mmol), followed by (R)-N-(methylsulfonyloxy)-1,4-dioxaspiro[4.5] decane-2-carbimidoyl chloride (5.2 g, 18 mmol) and the reaction was heated to 60° C. for 30 minutes. 5-Bromo-3-(2-methylpyridin-3-yloxy)pyridin-2-amine (4.1 g, 15 mmol)

was added and the reaction was heated overnight at 60° C. The reaction was concentrated to one fourth the volume and the residue partitioned between EtOAc and water made basic with 1N NaOH. The organic layer was separated and the aqueous layer extracted with EtOAc. The combined organic layers were washed with brine, dried over MgSO$_4$ and concentrated in vacuo. The material was purified on silica gel (25% EtOAc in CH$_2$Cl$_2$) to afford (S)-N-(5-bromo-3-(2-methylpyridin-3-yloxy)pyridin-2-yl)-3-(1,4-dioxaspiro[4.5]decan-2-yl)-1,2,4-thiadiazol-5-amine (5.4 g, 73%).

Step H: To a solution of (S)-N-(5-bromo-3-(2-methylpyridin-3-yloxy)pyridin-2-yl)-3-(1,4-dioxaspiro[4.5]decan-2-yl)-1,2,4-thiadiazol-5-amine (3.1 g, 6.14 mmol) in dioxanes (30 mL) continuously purged with nitrogen was added Xanphos (0.177 g, 0.303 mmol), Pd$_2$dba$_3$ (0.14 g, 0.153 mmol), methyl 3-mercaptopropanoate (0.73 g, 6.14 mmol) and N,N-diisopropylethylamine (1.17 mL, 6.45 mmol) and the reaction heated overnight at 80° C. The reaction was concentrated in vacuo and the residue purified over silica gel (5% MeOH/CH$_2$Cl$_2$) to afford (S)-methyl 3-(6-(3-(1,4-dioxaspiro[4.5]decan-2-yl)-1,2,4-thiadiazol-5-ylamino)-5-(2-methylpyridin-3-yloxy)pyridin-3-ylthio)propanoate (2.3 g, 68%).

Step I: To a solution of (S)-methyl 3-(6-(3-(1,4-dioxaspiro[4.5]decan-2-yl)-1,2,4-thiadiazol-5-ylamino)-5-(2-methylpyridin-3-yloxy)pyridin-3-ylthio)propanoate (0.428 g, 0.787 mmol) in THF (20 mL) was added potassium 2-methylpropan-2-olate (1M in THF, 2.36 ml, 2.36 mmol) and the reaction was stirred at ambient temperature for 5 minutes. (Bromomethyl)cyclopropane (0.106 g, 0.787 mmol) was added followed by DMF (5 mL) and the reaction was stirred for 1 hour at ambient temperature. The reaction was poured into EtOAc (500 mL) and the organic layer was washed with a 1:1 solution of water, 1N NaOH (100 mL total) and brine, dried over MgSO$_4$ and concentrated in vacuo. The residue was purified over silica gel (40% EtOAc/CH$_2$Cl$_2$) to afford (S)-N-(5-(cyclopropylmethylthio)-3-(2-methylpyridin-3-yloxy)pyridin-2-yl)-3-(1,4-dioxaspiro[4.5]decan-2-yl)-1,2,4-thiadiazol-5-amine (0.30 g, 0.586 mmol, 74.5% yield).

Step J: To a solution of (S)-N-(5-(cyclopropylmethylthio)-3-(2-methylpyridin-3-yloxy)pyridin-2-yl)-3-(1,4-dioxaspiro[4.5]decan-2-yl)-1,2,4-thiadiazol-5-amine (0.30 g, 0.586 mmol) in ethanol (20 mL) was added 1 M HCl (0.87 mL) and the reaction heated to 80° C. for 2 hours. The reaction was cooled and concentrated in vacuo and the solid triturated with ethanol. The solid was dried in vacuo to afford (S)-1-(5-(5-(cyclopropylmethylthio)-3-(2-methylpyridin-3-yloxy)pyridin-2-ylamino)-1,2,4-thiadiazol-3-yl)ethane-1,2-diol (0.146 g, 0.338 mmol, 57.7% yield) as the mono HCl salt. Mass Spectrum (apci) m/z=432.0 (M+H—HCl).

Example 137

(S)-1-(5-(3-(2-ethylpyridin-3-yloxy)-5-(pyridin-2-ylthio)pyridin-2-ylamino)-1,2,4-thiadiazol-3-yl)ethane-1,2-diol

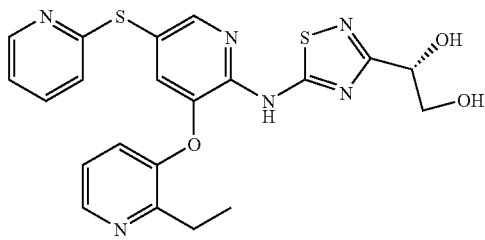

Step A: 2-Bromopyridin-3-yl acetate (10 g, 46 mmol) was dissolved in THF (80 mL) and triethylamine (32 ml, 231 mmol), ethynyltrimethylsilane (19.5 ml, 139 mmol), and CuI (0.44 g, 2.3 mmol) were added. The mixture was degassed with argon for 15 minutes, then PdCl$_2$(PPh$_3$)$_2$ (1.6 g, 2.3 mmol) was added and the mixture was stirred under argon at ambient temperature for 18 hours. The reaction was concentrated in vacuo, dissolved in 25% EtOAc in hexanes, filtered and purified over silica gel (25% ethyl acetate/hexanes) to afford 2-((trimethylsilyl)ethynyl)pyridin-3-yl acetate (9.7 g, 41 mmol).

Step B: To a solution of 2-((trimethylsilyl)ethynyl)pyridin-3-yl acetate (9.5 g, 41 mmol) in THF (200 mL) was added water (25 ml). The reaction was cooled to 0° C. and TBAF (1M, 45 ml, 45 mmol) was added. The mixture warmed to ambient temperature and stirred for 1 hour. Water (100 mL) was added and the volume was reduced by half. The product was extracted into ether (3×100 mL), washed with brine and dried over MgSO$_4$. The solution was concentrated in vacuo to afford 2-ethynylpyridin-3-yl acetate (5.5 g, 34 mmol) as a light brown oil.

Step C: To a solution of 2-ethynylpyridin-3-yl acetate (5.0 g, 31 mmol) in ethanol (50 mL) was added PtO$_2$ (0.50 g, 2.2 mmol). The mixture was degassed with nitrogen and placed under a double-layer balloon of hydrogen. The reaction was stirred at ambient temperature for 30 minutes, then filtered and concentrated in vacuo to give 2-ethylpyridin-3-yl acetate (5.1 g, 31 mmol) which was used in the next step without further purification.

Step D: To a solution of 2-ethylpyridin-3-yl acetate (5.1 g, 31 mmol) in ethanol (50 mL) was added 3M LiOH (50 mL, 150 mmol). The reaction mixture stirred at ambient temperature for 30 minutes. The mixture was concentrated to dryness and purified over silica gel (10% MeOH in CH$_2$Cl$_2$) to afford 2-ethylpyridin-3-ol (2.5 g, 20 mmol).

Step E: To a solution of 2-ethylpyridin-3-ol (2.5 g, 20.3 mmol) in DMF (20 ml) at 0° C. was added sodium hydride (0.512 g, 21.3 mmol). After 15 minutes, 5-bromo-3-nitropicolinonitrile (4.63 g, 20.3 mmol) was added and the mixture was allows to warm slowly to ambient temperature and stirred for 2 hours. Pridine-2-thiol (0.804 g, 7.23 mmol) was added followed by sodium hydride (0.182 g, 7.60 mmol) and the mixture was stirred at ambient temperature overnight. Water (200 ml) was added and the mixture was extracted with diethyl ether (3×100 mL), washed with brine, dried over MgSO$_4$, filtered and concentrated in vacuo. The residue was purified over silica gel (25 to 75% EtOAc in Hexanes) to afford 3-(2-ethylpyridin-3-yloxy)-5-(pyridin-2-ylthio)picolinonitrile (1.4 g, 4.19 mmol).

Step F: 3-(2-Ethylpyridin-3-yloxy)-5-(pyridin-2-ylthio)picolinonitrile (1.4 g, 4.19 mmol) was stirred in concentrated sulfuric acid (10 mL) overnight at ambient temperature. Ice (100 g) was added and the solution was neutralized using 4M NaOH. Ice was added as necessary to maintain the temperature below 20° C. The product was extracted into ethyl acetate, washed with brine, dried over MgSO$_4$, filtered and concentrated to afford 3-(2-ethylpyridin-3-yloxy)-5-(pyridin-2-ylthio)picolinamide (1.5 g, 4.2 mmol).

Step G: A 1M solution of NaOH (10.6 ml, 21.2 mmol) was cooled to 0° C. and bromine (0.38 ml, 7.4 mmol) was added. This mixture stirred at ambient temperature for 30 minutes. Dioxane (15 mL) was added followed by 3-(2-ethylpyridin-3-yloxy)-5-(pyridin-2-ylthio)picolinamide (1.50 g, 4.25 mmol). The mixture stirred at ambient temperature for 30 minutes. Concentrated HCl was added until the solution was pH 1 and the mixture stirred for 5 minutes. The reaction was made basic with 1M NaOH and the product was extracted into ethyl acetate (3×100 mL). The combined organic layers were washed with brine and dried over MgSO$_4$. The solution was concentrated and purified over silica gel (50 to 100% EtOAc in Hexanes) to afford 3-(2-ethylpyridin-3-yloxy)-5-(pyridin-2-ylthio)pyridin-2-amine (0.620 g, 1.91 mmol).

Step H: In 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) was added in 1 portion in 800 mL of THF. The reaction was stirred for 4 hours, then poured into a 4 L separatory funnel and the layers separated. The aqueous layer was extracted twice with MTBE (about 3000 mL total). The combined organic layers were washed with water (700 mL) and brine (300 mL), dried over MgSO$_4$ and concentrated in vacuo to afford (S)-1,4-dioxaspiro[4.5]decane-2-carbaldehyde oxime (135 g, 99%) as a clear viscous oil.

Step I: To a 4-neck 2 L round bottom flask was added (S)-1,4-dioxaspiro[4.5]decane-2-carbaldehyde oxime (135.1 g, 729.4 mmol) and 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours. The reaction was diluted with 2 L of MTBE and washed with 1 L of water. The water was extracted with 500 mL of MTBE, and the combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step J: To a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) added in 10 mL portions over 10 minutes. Next, N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids washed with MTBE (about 3 L). The filtrate was concentrated and the residue was purified by chromatography (3 kg silica, 7:1 to 3:1 Hex/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step K: (R)-N-(methylsulfonyloxy)-1,4-dioxaspiro[4.5]decane-2-carbimidoyl chloride (0.854 g, 2.87 mmol), pyridine (0.618 ml, 7.64 mmol), and sodium thiocyanate (0.310 g, 3.82 mmol) were dissolved in acetonitrile (10 mL). The solution was heated to 60° C. for 30 minutes. 3-(2-ethylpyridin-3-yloxy)-5-(pyridin-2-ylthio)pyridin-2-amine (0.620 g, 1.91 mmol) was added and the reaction was heated at 60° C. overnight. The solution was quenched with saturated aqueous NaHCO$_3$ solution, extracted with EtOAc (3×100 mL), washed with brine, dried over MgSO$_4$, and concentrated. The material was purified over silica gel (25 to 100% ethyl acetate in hexanes) to afford (S)-N-(3-(2-ethylpyridin-3-yloxy)-5-(pyridin-2-ylthio)pyridin-2-yl)-3-(1,4-dioxaspiro[4.5]decan-2-yl)-1,2,4-thiadiazol-5-amine (0.600 g, 1.09 mmol).

Step L: (S)-N-(3-(2-ethylpyridin-3-yloxy)-5-(pyridin-2-ylthio)pyridin-2-yl)-3-(1,4-dioxaspiro[4.5]decan-2-yl)-1,2,4-thiadiazol-5-amine (0.600 g, 1.09 mmol) was dissolved in ethanol (25 ml) and water (600 mg) and concentrated HCl (600 mg) were added. The mixture was heated to reflux for 2 hours, concentrated in vacuo, dissolved and concentrated with EtOH (2×50 mL). The material was triturated from acetonitrile to afford (S)-1-(5-(3-(2-ethylpyridin-3-yloxy)-5-(pyridin-2-ylthio)pyridin-2-ylamino)-1,2,4-thiadiazol-3-yl) ethane-1,2-diol (0.420 g, 0.90 mmol, 82%) as a solid. Mass Spectrum (apci) m/z=469.1 (M+H—HCl).

Example 138

(S)-1-(5-(5-(3-methoxypropylthio)-3-(2-methylpyridin-3-yloxy)pyridin-2-ylamino)-1,2,4-thiadiazol-3-yl)ethane-1,2-diol hydrochloride

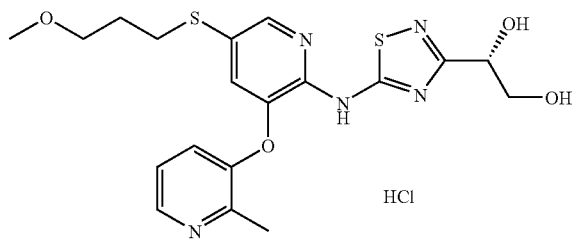

Step A: To a solution of 2-methylpyridin-3-ol (11.8 g, 108 mmol) in DMF at 0° C. was added sodium hydride (60% dispersion in oil, 4.32 g, 108 mmol) in small portions and the reaction warmed to ambient temperature. To this mixture was added 5-bromo-3-nitropicolinonitrile (24.6 g, 108 mmol) and the reaction was stirred overnight at ambient temperature. The reaction was poured into water (1000 mL) and the aqueous layer extracted with EtOAc. The combined organic layers were washed with water and brine, dried over MgSO$_4$ and concentrated in vacuo to yield 5-bromo-3-(2-methylpyridin-3-yloxy)picolinonitrile (15 g, 48%).

Step B: To 5-bromo-3-(2-methylpyridin-3-yloxy)picolinonitrile (15 g, 52 mmol) was added concentrated H$_2$SO$_4$ (30 mL) and the slurry was stirred overnight, at which point the material was fully dissolved. The reaction was poured into 0° C. water in small portions. While maintaining the temp below 20° C., the aqueous layer was basified to about a pH of 5 by the addition of NaOH pellets, at which point a solid formed. The solid was filtered, and the remaining aqueous layer was extracted with EtOAc. The organics layers, combined with the solid, were washed with brine, dried over MgSO$_4$ and concentrated in vacuo to yield 5-bromo-3-(2-methylpyridin-3-yloxy)picolinamide (11 g, 69%).

Step C: To a solution of NaOH (2M, 90 mL, 182 mmol) at 0° C. was added bromine (8.71 g, 54 mmol) and the reaction was stirred at 0° C. for 30 minutes. To this mixture was added 5-bromo-3-(2-methylpyridin-3-yloxy)picolinamide (11.2 g, 36.3 mmol) in dioxanes (100 mL) and the reaction was stirred at ambient temperature for 1 hour followed by heating to 80° C. for 1 hour. The reaction was cooled to ambient temperature and acidified to pH 1 using concentrated HCl. The reaction was basified and a solid precipitated. The solid was filtered and dried in vacuo to yield product 5-bromo-3-(2-methylpyridin-3-yloxy)pyridin-2-amine (4.1 g, 41%).

Step D: In 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) was added in 1 portion in 800 mL of THF. The reaction was stirred for 4 hours and poured into a 4 L separatory funnel and the layers separated. The aqueous layer was extracted twice with MTBE (about 3000 mL total). The combined organic layers were washed with water (700 mL) and brine (300 mL), dried over MgSO₄, and concentrated in vacuo to afford (S)-1,4-dioxaspiro[4.5]decane-2-carbaldehyde oxime (135 g, 99%) as a clear viscous oil.

Step E: To a 4-neck 2 L round bottom flask was added (S)-1,4-dioxaspiro[4.5]decane-2-carbaldehyde oxime (135.1 g, 729.4 mmol) dissolved in 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours, then diluted with 2 L of MTBE and washed with 1 L of water. The water was extracted with 500 mL of MTBE. The combined organic layers were washed with water (5×800 mL) and brine (300 mL), dried over MgSO₄ and concentrated in vacuo to afford added (R)-N-hydroxy-1,4-dioxaspiro[4.5]decane-2-carbimidoyl chloride (158 g, 98%) as a green viscous oil.

Step F: In a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) added in 10 mL portions over 10 minutes. Next, N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids washed with MTBE (about 3 L). The filtrate was concentrated and the residue was purified over silica gel (3 kg silica, 7:1 to 3:1 Hexane/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step G: In 100 mL of acetonitrile was added sodium thioisocyanate (1.5 g, 20 mmol), pyridine (3.5 g, 44 mmol), followed by (R)-N-(methylsulfonyloxy)-1,4-dioxaspiro[4.5]decane-2-carbimidoyl chloride (5.2 g, 18 mmol) and the reaction was heated to 60° C. for 30 minutes. 5-Bromo-3-(2-methylpyridin-3-yloxy)pyridin-2-amine (4.1 g, 15 mmol) was added and the reaction was heated overnight at 60° C. The reaction was concentrated to about one quarter volume, the residue was partitioned between EtOAc and the water layer was made basic with 1N NaOH. The organic layer was separated and the aqueous layer extracted with EtOAc. The combined organic layers were washed with brine, dried over MgSO₄ and concentrated in vacuo. The material was purified on silica gel (25% EtOAc in CH₂Cl₂) to afford (S)-N-(5-bromo-3-(2-methylpyridin-3-yloxy)pyridin-2-yl)-3-(1,4-dioxaspiro[4.5]decan-2-yl)-1,2,4-thiadiazol-5-amine (5.4 g, 73%).

Step H: To a solution of (S)-N-(5-bromo-3-(2-methylpyridin-3-yloxy)pyridin-2-yl)-3-(1,4-dioxaspiro[4.5]decan-2-yl)-1,2,4-thiadiazol-5-amine (3.1 g, 6.14 mmol) in dioxanes (30 mL) continuously purged with nitrogen was added Xanphos (0.177 g, 0.303 mmol), Pd₂dba₃ (0.14 g, 0.15 mmol), methyl 3-mercaptopropanoate (0.73 g, 6.14 mmol) and N,N-diisopropylethylamine (1.17 mL, 6.45 mmol) and the reaction was heated overnight at 80° C. The reaction was concentrated in vacuo and the residue purified over silica gel (5% MeOH/CH₂Cl₂) to afford (S)-methyl 3-(6-(3-(1,4-dioxaspiro[4.5]decan-2-yl)-1,2,4-thiadiazol-5-ylamino)-5-(2-methylpyridin-3-yloxy)pyridin-3-ylthio)propanoate (2.3 g, 68%).

Step I: (S)-Methyl 3-(6-(3-(1,4-dioxaspiro[4.5]decan-2-yl)-1,2,4-thiadiazol-5-ylamino)-5-(2-methylpyridin-3-yloxy)pyridin-3-ylthio)propanoate (105 mg, 0.19 mmol) was dissolved in THF (5 ml) and KOtBu (65 mg, 0.58 mmol) was added. The mixture was agitated for 30 minutes and 1-bromo-3-methoxypropane (37 mg, 0.24 mmol) was added. The mixture was agitated for 1 hour, diluted with ethyl acetate, washed with sodium bicarbonate solution and brine, dried over sodium sulfate, filtered and evaporated. The residue was purified over silica gel (60-75% ethyl acetate/hexanes) to afford (S)-N-(5-(3-methoxypropylthio)-3-(2-methylpyridin-3-yloxy)pyridin-2-yl)-3-(1,4-dioxaspiro[4.5]decan-2-yl)-1,2,4-thiadiazol-5-amine (85 mg, 83% yield) as glassy colorless solid.

Step J: (S)-N-(5-(3-methoxypropylthio)-3-(2-methylpyridin-3-yloxy)pyridin-2-yl)-3-(1,4-dioxaspiro[4.5]decan-2-yl)-1,2,4-thiadiazol-5-amine (85 mg, 0.16 mmol) was dissolved in ethanol (5 ml) and 1M HCl (0.5 ml) was added. The mixture was heated to 70° C. and agitated 3 hours. Upon cooling, the reaction was diluted with ethyl acetate, basified with sodium carbonate solution and washed with water and brine, dried (MgSO₄), filtered and evaporated. The resulting solid was dissolved in small amount of dichloromethane and treated with 1M HCl in ether. After evaporation, (S)-1-(5-(5-(3-methoxypropylthio)-3-(2-methylpyridin-3-yloxy)pyridin-2-ylamino)-1,2,4-thiadiazol-3-yl)ethane-1,2-diol hydrochloride (65 mg, 90% yield) was obtained as white solid. Mass Spectrum (apci) m/z=450.1 (M+H—HCl).

Example 139

(S)-1-(5-(3-(1-Ethyl-1H-pyrazol-5-yloxy)-5-(pyridin-2-ylthio)pyridin-2-ylamino)-1,2,4-thiadiazol-3-yl)ethane-1,2-diol hydrochloride

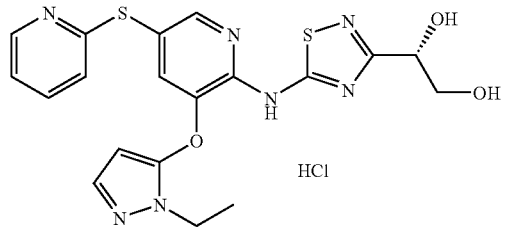

Step A: In 1 L glass beaker, ethylhydrazine oxalate (51.4 g, 342 mmol) was combined with water (300 ml). To the resulting slurry was added a 50% w/v NaOH solution (75.5 g) to adjust the pH to 9.5 (by pH-meter). The mixture was heated to 40° C. and methyl trans-3-methoxyacrylate (24.5 ml, 228 mmol) was added dropwise over 1 hour. The pH was adjusted periodically to 9.0-9.5 range by addition of 50% w/v NaOH solution. After the completion of addition, the mixture was agitated for additional 3 hours at 40° C. and the pH was adjusted occasionally to about 9.0-9.5. The mixture was cooled to 5° C. and filtered. The filtrate was evaporated to about 150 ml, cooled to 5° C. and filtered again. The filtrate was acidified to pH 3-4 with 6M HCl (45 ml) and extracted 8 times with 3:1 mixture of chloroform/isopropanol. The combined extracts were dried (MgSO₄), filtered and evaporated. The crude product was purified over silica gel (20% MeOH/EtOAc) to afford 1-ethyl-1H-pyrazol-5-ol (18.3 g, 71% yield) as a yellow solid.

Step B: 5-Bromo-3-nitropicolinonitrile (24.0 g, 105 mmol), 1-ethyl-1H-pyrazol-5-ol (13.0 g, 116 mmol), and sodium carbonate (11.2 g, 105 mmol) were combined with acetonitrile (400 ml). The mixture was heated to reflux for 20 hours, then cooled to ambient temperature, filtered and evaporated. The residue was dissolved in ethyl acetate (800 ml) and washed with water (3×200 ml) and brine, dried (MgSO$_4$), filtered and evaporated. The crude material was purified over silica gel (15:35:50, then 20:30:50 ethyl acetate/chloroform/hexane) to afford 5-bromo-3-(1-ethyl-1H-pyrazol-5-yloxy)picolinonitrile (16.4 g, 53% yield) as a white solid.

Step C: 5-Bromo-3-(1-ethyl-1H-pyrazol-5-yloxy)picolinonitrile (16.1 g, 55 mmol) and cesium carbonate (17.9 g, 55 mmol) were combined with DMF (160 ml) and pyridin-2-thiol (6.1 g, 55 mmol) dissolved in DMF (40 ml) was added dropwise over 30 minutes. The mixture was agitated for 1 hour, quenched with saturated ammonium chloride solution and extracted with ethyl acetate. The combined organic extracts were washed with water and brine, dried (MgSO$_4$), filtered and evaporated. The residue was purified over silica gel (20-35% ethyl acetate/hexanes) to afford 3-(1-ethyl-1H-pyrazol-5-yloxy)-5-(pyridin-2-ylthio)picolinonitrile (16.6 g, 93% yield) as a white solid.

Step D: 3-(1-Ethyl-1H-pyrazol-5-yloxy)-5-(pyridin-2-ylthio)picolinonitrile (16.6 g, 51.33 mmol) was cooled to −10° C. and concentrated HCl (120 ml, 1440 mmol) cooled to the same temperature was added slowly. The mixture was agitated in the cooling bath until the solids were mostly dissolved (30 minutes). The bath was removed and the mixture was agitated for 24 hours. The mixture was then cooled to −10° C. and a mixture of ice (150 g) and 50% w/v NaOH (120 ml) was added slowly, keeping the temperature below 20° C., to adjust the pH to about 12-13. The mixture was then extracted twice with dichloromethane and the combined organic extracts were washed with sodium bicarbonate solution, dried (MgSO$_4$), filtered and evaporated to afford 3-(1-ethyl-1H-pyrazol-5-yloxy)-5-(pyridin-2-ylthio)picolinamide (16.5 g, 94% yield) as thick amber oil which later solidified.

Step E: A 3 M solution of KOH (15.99 ml, 47.98 mmol) was chilled in a 0° C. bath, bromine (0.5120 ml, 9.996 mmol) was added in one portion and the mixture was stirred 15 minutes. A solution of 3-(1-ethyl-1H-pyrazol-5-yloxy)-5-(pyridin-2-ylthio)picolinamide (1.365 g, 3.998 mmol) dissolved in dioxane (10 ml) was added, and the resulting mixture was stirred overnight at ambient temperature. The majority of the dioxane was removed in vacuo and the resulting aqueous mixture was extracted with EtOAc. The organic extract was washed with water, dried over Na$_2$SO$_4$, filtered and concentrated to afford crude 3-(1-ethyl-1H-pyrazol-5-yloxy)-5-(pyridin-2-ylthio)pyridin-2-amine (1.12 g, 3.574 mmol, 89.39% yield) (82% Product and 18% starting material by LC.). The crude product was carried directly onto the next step without further purification.

Step F: In 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) was added in 1 portion in 800 mL of THF. The reaction was stirred for 4 hours and poured into a 4 L separatory funnel and the layers separated. The aqueous layer was extracted twice with MTBE (about 3000 mL total). The combined organic layers were washed with water (700 mL) and brine (300 mL), dried over MgSO$_4$, and concentrated in vacuo to afford (S)-1,4-dioxaspiro[4.5]decane-2-carbaldehyde oxime (135 g, 99%) as a clear viscous oil.

Step G: To a 4-neck 2 L round bottom flask was added (S)-1,4-dioxaspiro[4.5]decane-2-carbaldehyde oxime (135.1 g, 729.4 mmol) dissolved in 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours, then diluted with 2 L of MTBE and washed with 1 L of water. The water was extracted with 500 mL of MTBE. The combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step H: In a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) added in 10 mL portions over 10 minutes. Next, N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids washed with MTBE (about 3 L). The filtrate was concentrated and the residue was purified by chromatography (3 kg silica, 7:1 to 3:1 Hexane/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step I: To 75 mL of EtOAc was added sodium isothiocyanate (0.579 g, 7.15 mmol), pyridine (0.874 ml, 10.7 mmol) and (R)-N-(methylsulfonyloxy)-1,4-dioxaspiro[4.5]decane-2-carbimidoyl chloride (2.13 g, 7.15 mmol) and the reaction was heated to 50° C. for 30 minutes. The reaction mixture was added to 3-(1-ethyl-1H-pyrazol-5-yloxy)-5-(pyridin-2-ylthio)pyridin-2-amine (1.12 g, 3.57 mmol) and the reaction was stirred for 65 hours at 75° C. The reaction was cooled and diluted with 50 ml EtOAc and 75 ml 1N NaOH. The aqueous layer was extracted with EtOAc. The organic layer was dried over Na$_2$SO$_4$, filtered and concentrated. The residue was purified over silica gel (75% EtOAc/Hexanes) to afford (S)-N-(3-(1-ethyl-1H-pyrazol-5-yloxy)-5-(pyridin-2-ylthio)pyridin-2-yl)-3-(1,4-dioxaspiro[4.5]decan-2-yl)-1,2,4-thiadiazol-5-amine (1.24 g, 2.31 mmol, 64.5% yield) as a tan solid.

Step J: To a mixture of (S)-N-(3-(1-ethyl-1H-pyrazol-5-yloxy)-5-(pyridin-2-ylthio)pyridin-2-yl)-3-(1,4-dioxaspiro[4.5]decan-2-yl)-1,2,4-thiadiazol-5-amine (1.24 g, 2.31 mmol) in EtOH (25 ml) and H$_2$O (1.09 ml, 2.31 mmol) was added concentrate HCl (0.480 ml, 5.77 mmol) and the reaction was heated at reflux for 8 hours. The reaction was allowed to cool to ambient temperature and stirred overnight. The mixture was concentrated to a residue that was dissolved in EtOAc and saturated aqueous NaHCO$_3$. The combined organic layers were washed with water, dried over Na$_2$SO$_4$, filtered and concentrated. The residue was purified over silica gel (3% MeOH/CH$_2$Cl$_2$) to afford (S)-1-(5-(3-(1-ethyl-1H-pyrazol-5-yloxy)-5-(pyridin-2-ylthio)pyridin-2-ylamino)-1,2,4-thiadiazol-3-yl)ethane-1,2-diol as cream solids. The solids were dissolved in CH$_2$Cl$_2$ (25 ml) and 1N HCl in Et$_2$O (20 ml) was added. The mixture was concentrated to dryness and dried in the vacuum oven to afford (S)-1-(5-(3-(1-ethyl-1H-pyrazol-5-yloxy)-5-(pyridin-2-ylthio)pyridin-2-ylamino)-1,2,4-thiadiazol-3-yl)ethane-1,2-diol hydrochloride (0.569 g, 49.9% yield) as an off-white solid. Mass spectrum (apci) m/z=458.1 (M+H—HCl).

Example 140

(S)-1-(5-(3-(1-ethyl-1H-pyrazol-5-yloxy)-5-(pyridin-2-ylthio)pyridin-2-ylamino)-1,2,4-thiadiazol-3-yl)-2-methylpropane-1,2-diol

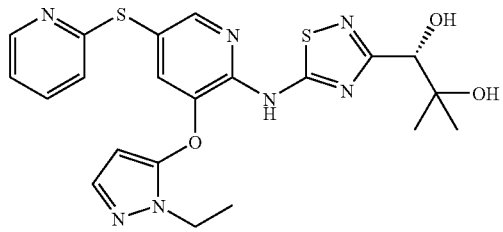

Step A: In 1 L glass beaker, ethylhydrazine oxalate (51.4 g, 342 mmol) was combined with water (300 ml). To the resulting slurry, 50% w/v NaOH solution was added (75.5 g) to adjust the pH to 9.5 (by pH-meter). The mixture was heated to p40° C. and methyl trans-3-methoxyacrylate (24.5 ml, 228 mmol) was added dropwise over 1 hours. The pH was adjusted periodically to about 9.0-9.5 by the addition of a 50% w/v NaOH solution. After the completion of addition, the mixture was agitated for additional 3 hours at 40° C. and the pH was adjusted occasionally to about 9.0-9.5. The mixture was cooled to 5° C. and filtered. The filtrate was evaporated to about 150 ml, cooled to 5° C. and filtered. The filtrate was acidified to pH 3-4 with 6M HCl (45 ml) and extracted 8 times with a 3:1 mixture of chloroform/isopropanol. The combined extracts were dried (MgSO$_4$), filtered and concentrated. The crude product was purified over silica gel (20% MeOH/EtOAc) to afford 1-ethyl-1H-pyrazol-5-ol (18.3 g, 71% yield) as a yellow solid.

Step B: 5-Bromo-3-nitropicolinonitrile (24.0 g, 105 mmol), 1-ethyl-1H-5-ol (13.0 g, 116 mmol), and sodium carbonate (11.2 g, 105 mmol) were combined with acetonitrile (400 ml). The mixture was heated to reflux for 20 hours. The mixture was then cooled to ambient temperature, filtered and evaporated. The residue was dissolved in ethyl acetate (800 ml) and washed with water (3×200 ml) and brine, dried (MgSO$_4$), filtered and evaporated. The crude material was purified over silica gel (15:35:50, then 20:30:50 ethyl acetate/chloroform/hexane) to afford 5-bromo-3-(1-ethyl-1H-pyrazol-5-yloxy)picolinonitrile (16.4 g, 53% yield) as a white solid.

Step C: 5-Bromo-3-(1-ethyl-1H-pyrazol-5-yloxy)picolinonitrile (16.1 g, 55 mmol) and cesium carbonate (17.9 g, 55 mmol) were combined with DMF (160 ml) and pyridine-2-thiol (6.1 g, 55 mmol) dissolved in DMF (40 ml) was added dropwise over 30 minutes. The mixture was then agitated for 1 hour, quenched with saturated ammonium chloride solution and extracted with ethyl acetate. The combined organic extracts were washed with water and brine, dried (MgSO$_4$), filtered and evaporated. The residue was purified over silica gel (20-35% ethyl acetate/hexanes) to afford 3-(1-ethyl-1H-pyrazol-5-yloxy)-5-(pyridin-2-ylthio)picolinonitrile (16.6 g, 93% yield) as a white solid.

Step D: Preparation of 3-(1-ethyl-1H-pyrazol-5-yloxy)-5-(pyridin-2-ylthio)picolinamide: 3-(1-Ethyl-1H-pyrazol-5-yloxy)-5-(pyridin-2-ylthio)picolinonitrile (16.6 g, 51.33 mmol) was cooled to −10° C. and concentrated HCl (120 ml, 1440 mmol) cooled to the same temperature was added slowly. The mixture was agitated in the cooling bath until solids mostly dissolved (30 minutes). The bath was removed and the mixture was agitated for 24 hours. It was then cooled to −10° C. and a mixture of ice (150 g) and 50% w/v NaOH (120 ml) was added slowly, keeping the temperature below 20° C., to adjust the pH to 12-13. The mixture was extracted twice with dichloromethane and the combined organic extracts were washed with sodium bicarbonate solution, dried (MgSO$_4$), filtered and evaporated to afford 3-(1-ethyl-1H-pyrazol-5-yloxy)-5-(pyridin-2-ylthio)picolinamide (16.5 g, 94% yield) as thick amber oil which later solidified.

Step E: A 3 M solution of KOH (15.99 ml, 47.98 mmol) was chilled in a 0° C. bath, bromine (0.5120 ml, 9.996 mmol) was added in one portion and the mixture was stirred 15 minutes. A solution of 3-(1-ethyl-1H-pyrazol-5-yloxy)-5-(pyridin-2-ylthio)picolinamide (1.365 g, 3.998 mmol) dissolved in dioxane (10 ml) was added. The resulting mixture was then stirred overnight at ambient temperature. The dioxane was mostly removed in vacuo and the resulting aqueous mixture was extracted with EtOAc and the organics washed with water, dried over Na$_2$SO$_4$, filtered and concentrated to afford crude 3-(1-ethyl-1H-pyrazol-5-yloxy)-5-(pyridin-2-ylthio)pyridin-2-amine (1.12 g, 3.574 mmol, 89.39% yield) (82% product and 18% starting material by LC.) The crude product was carried directly into next reaction without further purification.

Step F: (R)-2,2,5,5-Tetramethyl-1,3-dioxolane-4-carbaldehyde (16 g, 101 mmol) (Burger, A. Synthesis 1989, (2) 93-97) was dissolved in 1:1 methanol:water (250 mL), and hydroxylamine hydrochloride (7.0 g, 101 mmol) and Na$_2$CO$_3$ (5.4 g, 51 mmol) were added and the reaction was stirred at ambient temperature for 2 hours. The methanol was partially removed in vacuo and the aqueous layer was extracted with CH$_2$Cl$_2$, dried, filtered, and concentrated to afford (S)-2,2,5,5-tetramethyl-1,3-dioxolane-4-carbaldehyde oxime (13 g, 75 mmol, 74% yield) as an amber oil.

Step G: (S)-2,2,5,5-Tetramethyl-1,3-dioxolane-4-carbaldehyde oxime (13 g, 75.1 mmol) was dissolved in DMF (200 mL) and cooled in an ice bath. 1-Chloropyrrolidine-2,5-dione (10.0 g, 75.1 mmol) was added and the reaction was stirred overnight while slowly warming to ambient temperature. The pale yellow solution was poured into water (1.5 L) and extracted with EtOAc. The organic layers were washed with water and brine, dried, filtered and concentrated. The residue was purified over silica gel (40% EtOAc in hexanes) to afford (R)-N-hydroxy-2,2,5,5-tetramethyl-1,3-dioxolane-4-carbimidoyl chloride (12.4 g, 59.7 mmol, 79.6% yield).

Step H: (R)-N-hydroxy-2,2,5,5-tetramethyl-1,3-dioxolane-4-carbimidoyl chloride (12.4 g, 59.7 mmol) was dissolved in Et$_2$O (200 mL) and cooled in an ice bath. Methanesulfonyl chloride (4.6 ml, 59.7 mmol) was added. Triethylamine (8.3 ml, 59.7 mmol) was added slowly and the reaction was stirred in an ice bath for 30 minutes. The reaction was filtered and concentrated. The residue was purified over silica gel (100% CH$_2$Cl$_2$) to afford (R)-2,2,5,5-tetramethyl-N-(methylsulfonyloxy)-1,3-dioxolane-4-carbimidoyl chloride (11.3 g, 39.55 mmol, 66.22% yield) as a white solid.

Step I: To 30 mL of EtOAc was added sodium isothiocyanate (0.0970 g, 1.20 mmol), pyridine (0.195 ml, 2.39 mmol) and (R)-2,2,5,5-tetramethyl-N-(methylsulfonyloxy)-1,3-dioxolane-4-carbimidoyl chloride (0.342 g, 1.20 mmol). The reaction was heated to 60° C. The reaction was cooled and diluted with 50 ml EtOAc and 50 ml 1N NaOH. The aqueous layer was extracted with EtOAc. The combined organic layers were dried over Na$_2$SO$_4$, filtered and concentrated in-vacuo. The residue was purified over silica gel (50% EtOAc/Hexanes) to afford (S)-N-(3-(1-ethyl-1H-pyrazol-5-yloxy)-5-(pyridin-2-ylthio)pyridin-2-yl)-3-(2,2,5,5-tetramethyl-1,3-dioxolan-4-yl)-1,2,4-thiadiazol-5-amine (0.134 g, 0.255 mmol, 32.0% yield).

Step J: To a mixture of (S)-N-(3-(1-ethyl-1H-pyrazol-5-yloxy)-5-(pyridin-2-ylthio)pyridin-2-yl)-3-(2,2,5,5-tetramethyl-1,3-dioxolan-4-yl)-1,2,4-thiadiazol-5-amine (0.134 g, 0.255 mmol) in EtOH (5 ml) and water (0.227 ml, 0.255 mmol) was added concentrated HCl (0.0531 ml, 0.637 mmol) and the reaction heated at reflux for 5 hours. The reaction was concentrated to a residue that was partitioned between EtOAc and saturated aqueous NaHCO$_3$ solution. The combined organic layers were dried over Na$_2$SO$_4$, filtered and concentrated to give (S)-1-(5-(3-(1-ethyl-1H-pyrazol-5-yloxy)-5-(pyridin-2-ylthio)pyridin-2-ylamino)-1,2,4-thiadiazol-3-yl)-2-methylpropane-1,2-diol (0.115 g, 92.9% yield) as a white solid. Mass Spectrum (apci) m/z=468.1 (M+H—H$_2$O).

Example 141

(S)-1-(5-(5-(3-methylpyridin-2-ylthio)-3-(2-methylpyridin-3-yloxy)pyridin-2-ylamino)-1,2,4-thiadiazol-3-yl)ethane-1,2-diol hydrochloride

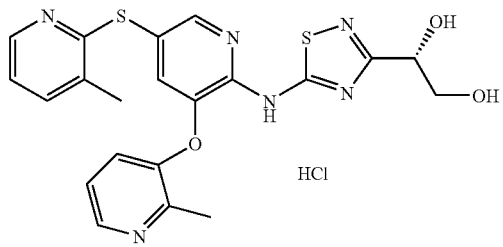

Step A: Thiourea (22.1 g, 291 mmol) was added to a solution of 2-bromo-3-methylpyridine (25.0 g, 145 mmol) in ethanol (500 mL) and refluxed overnight. The reaction was cooled to ambient temperature, and a 25% aqueous solution of sodium hydroxide (2.33 ml, 14.5 mmol) was added. The reaction was heated at reflux for an hour and cooled. A waxy solid formed. The reaction mixture was partitioned between ethyl acetate (600 mL) and water (1 L), and the aqueous layer was extracted with ethyl acetate. The combined organic layers were washed with brine, dried, and concentrated. The solids were triturated with ether (150 mL) for an hour and filtered to afford 3-methylpyridine-2-thiol (5.69 g, 45.5 mmol, 31.3% yield) as a yellow powder.

Step B: To a solution of 2-methylpyridin-3-ol (11.8 g, 108 mmol) in DMF at 0° C. was added sodium hydride (60% dispersion in oil, 4.32 g, 108 mmol) in small portions and the reaction was warmed to ambient temperature. To this mixture was added 5-bromo-3-nitropicolinonitrile (24.6 g, 108 mmol) and the reaction was stirred overnight at ambient temperature. The reaction was poured into water (1000 mL) and the aqueous layer extracted with EtOAc. The combined organic layers were washed with water and brine, dried over MgSO$_4$ and concentrated in vacuo to yield 5-bromo-3-(2-methylpyridin-3-yloxy)picolinonitrile (15 g, 48%).

Step C: 3-Methylpyridine-2(1H)-thione (0.906 g, 7.24 mmol) and 5-bromo-3-(2-methylpyridin-3-yloxy)picolinonitrile (2.00 g, 6.89 mmol) were dissolved in DMF (12 mL) and the mixture was cooled to 0° C. Sodium hydride (95%; 0.183 g, 7.24 mmol) was slowly added and the reaction was warmed to ambient temperature and stirred overnight. The reaction mixture was poured into water (100 mL), stirred for 30 minutes, then filtered to afford a solid which was purified over silica gel (2:3 hexanes:ethyl acetate). Concentration of the second UV active fraction to elute afforded 5-(3-methylpyridin-2-ylthio)-3-(2-methylpyridin-3-yloxy)picolinonitrile (1.40 g, 4.19 mmol, 60.7% yield) as a pale yellow/off white powder/crystals.

Step D: Concentrated sulfuric acid (8 mL) was added to 5-(3-methylpyridin-2-ylthio)-3-(2-methylpyridin-3-yloxy)picolinonitrile (1.40 g, 4.19 mmol). The reaction was stirred over the weekend, then poured onto ice (100 g), cooled in an ice bath and made basic to pH 10 with 50% NaOH. The reaction mixture was extracted with ethyl acetate, washed with brine, dried (MgSO$_4$), and concentrated to afford 5-(3-methylpyridin-2-ylthio)-3-(2-methylpyridin-3-yloxy)picolinamide (1.40 g, 3.97 mmol, 94.9% yield) as a colorless oil which became a white crystalline solid overnight under vacuo.

Step E: To a solution of 2N sodium hydroxide (8.94 ml, 17.9 mmol) at 0° C. was added bromine (0.825 g, 5.16 mmol) in one portion. The reaction was stirred for 15 minutes and a solution of 5-(3-methylpyridin-2-ylthio)-3-(2-methylpyridin-3-yloxy)picolinamide (1.40 g, 3.97 mmol) in dioxane (30 mL) was added. The reaction was stirred at ambient temperature for one hour, and then at 80° C. for an additional hour. The reaction was cooled, then stirred overnight at ambient temperature. Concentrated HCl was added to adjust the reaction mixture to about pH 2, and the mixture was stirred about 20 minutes until carbon dioxide formation stopped. The mixture was partitioned between 2N NaOH and ethyl acetate. The organic layer was washed with water and brine, dried, and concentrated. The residue was triturated with 1:5 dichloromethane (60 mL), filtered, washed with hexanes, and dried to afford 5-(3-methylpyridin-2-ylthio)-3-(2-methylpyridin-3-yloxy)pyridin-2-amine (0.920 g, 2.84 mmol, 71.4% yield) as a light yellow powder.

Step F: To 1000 mL of DI water was added hydroxyl amine hydrochloride (51.0 g, 734 mmol) and the mixture was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) in 800 mL of THF was added in 1 portion. The reaction was stirred for 4 hours and poured into a 4 L separatory funnel and the layers were separated. The aqueous layer was extracted twice with MTBE (about 3000 mL total). The combined organic layers were washed with water (700 mL) and brine (300 mL), dried over MgSO$_4$, and concentrated in vacuo to afford (S)-1,4-dioxaspiro[4.5]decane-2-carbaldehyde oxime (135 g, 99%) as a clear viscous oil.

Step G: To a 4-neck 2 L round bottom flask was added (S)-1,4-dioxaspiro[4.5]decane-2-carbaldehyde oxime (135.1 g, 729.4 mmol) dissolved in 750 mL of DMF. The reaction was placed in a water bath and 1-chloropyridine-2,5-dione (97.40 g, 729.4 mmol) was added in portions over 2 minutes. The reaction was stirred in a water bath for 3 hours, then diluted with 2 L of MTBE and washed with 1 L of water. The water was extracted with 500 mL of MTBE. The combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step H: To a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) as added in 10 mL portions over 10 minutes. N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids were washed with MTBE (about 3 L). The filtrate was concentrated and the residue was purified over silica gel (7:1 to 3:1 Hexanes/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step I: To acetonitrile (50 mL) was added sodium isothiocyanate (0.1749 g, 2.158 mmol), pyridine (0.3740 ml, 4.624 mmol), followed by (R)-N-(methylsulfonyloxy)-1,4-dioxaspiro[4.5]decane-2-carbimidoyl chloride (0.5507 g, 1.850 mmol), and the resulting mixture was heated to 60° C. for 30 minutes. 5-(3-Methylpyridin-2-ylthio)-3-(2-methylpyridin-3-yloxy)pyridin-2-amine (0.500 g, 1.541 mmol) was added and the reaction was stirred overnight at 60° C. The reaction was concentrated in vacuo and the residue was partitioned between ethyl acetate and 1N NaOH. The organic layer was separated and the aqueous layer was extracted with ethyl acetate. The combined organic layers were washed with brine, dried (MgSO₄) and concentrated. The residue was dried over silica gel (100% ethyl acetate). Concentration of the major UV active fraction with an Rf of 0.5 afforded (S)-N-(5-(3-methylpyridin-2-ylthio)-3-(2-methylpyridin-3-yloxy)pyridin-2-yl)-3-(1,4-dioxaspiro[4.5]decan-2-yl)-1,2,4-thiadiazol-5-amine (0.565 g, 1.030 mmol, 66.8% yield) as an off white powder/crystals.

Step J: To a solution of (S)-N-(5-(3-methylpyridin-2-ylthio)-3-(2-methylpyridin-3-yloxy)pyridin-2-yl)-3-(1,4-dioxaspiro[4.5]decan-2-yl)-1,2,4-thiadiazol-5-amine (0.565 g, 1.03 mmol) in ethanol (25 mL) was added an aqueous solution of 6N HCl (2 mL). The reaction was heated at 80° C. for 2 hours, cooled to ambient temperature, stirred for 30 minutes, then cooled at 0° C. for an hour. The reaction was filtered, washed with cold ethanol, hexanes, and dried to afford (S)-1-(5-(5-(3-methylpyridin-2-ylthio)-3-(2-methylpyridin-3-yloxy)pyridin-2-ylamino)-1,2,4-thiadiazol-3-yl)ethane-1,2-diol hydrochloride (0.450 g, 0.891 mmol, 86.5% yield) as white crystals. Mass Spectrum (apci) m/z=469.1 (M+H—HCl).

Example 142

(S)-1-(5-(3-(2,4-dimethylpyridin-3-yloxy)-5-(pyridin-2-ylthio)pyridin-2-ylamino-1,2,4-thiadiazol-3-yl)ethane-1,2-diol hydrochloride

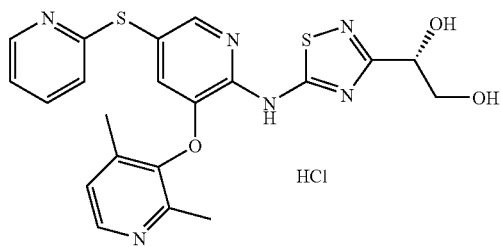

Step A: A flask was charged with 2,4-dimethylpyridin-3-ol (9.0 g, 73.1 mmol) and DMF (80 mL) was added. Sodium hydride (2.03 g, 80.4 mmol) was added and the reaction was stirred for 15 minutes. 5-Bromo-3-nitropicolinonitrile (16.7 g, 73.1 mmol) was added and the reaction was stirred for 25 minutes. The reaction mixture was poured into 600 mL saturated NH₄Cl and 600 mL water and then filtered, washed with water and a small amount of hexanes, and dried over high vacuum to provide 5-bromo-3-(2,4-dimethylpyridin-3-yloxy)picolinonitrile (20.5 g, 67.4 mmol, 92.2% yield) as a light tan solid.

Step B: Pyridin-2(1H)-thione (0.768 g, 6.90 mmol) and 5-bromo-3-(2,4-dimethylpyridin-3-yloxy)picolinonitrile (2.00 g, 6.58 mmol) were added to DMF (12 mL) and cooled to 0° C. 95% Sodium hydride (0.174 g, 6.90 mmol) was slowly added and the reaction was warmed to ambient temperature and stirred overnight. The reaction mixture was poured into water (100 mL) and stirred for 30 minutes. A cloudy milky solution that was not filterable resulted. The reaction was extracted twice with ethyl acetate. The combined organic layers were washed twice with water and brine, dried, and concentrated. The residue was purified over silica gel (2:3 to 0:1 hexane:ethyl acetate) to afford 3-(2,4-dimethylpyridin-3-yloxy)-5-(pyridin-2-ylthio)picolinonitrile (2.03 g, 6.07 mmol, 92.3% yield) as a white powder.

Step C: Concentrated sulfuric acid (8 mL) was added to 3-(2,4-dimethylpyridin-3-yloxy)-5-(pyridin-2-ylthio)picolinonitrile (2.03 g, 6.07 mmol). The reaction was stirred overnight, then poured onto ice (100 g), cooled in an ice batch and made basic to pH 10 with 50% NaOH. The reaction was extracted with ethyl acetate, washed with brine, dried (MgSO₄), and concentrated to afford 3-(2,4-dimethylpyridin-3-yloxy)-5-(pyridin-2-ylthio)picolinoamide (2.02 g, 5.73 mmol, 94.4% yield) as a white solid.

Step D: To a solution of 2N sodium hydroxide (12.9 ml, 25.8 mmol) at 0° C. was added bromine (1.19 g, 7.45 mmol) in one portion. The reaction was stirred 15 minutes, then a solution of 3-(2,4-dimethylpyridin-3-yloxy)-5-(pyridin-2-ylthio)picolinamide (2.02 g, 5.73 mmol) in dioxane (30 mL) was added. The reaction was stirred at ambient temperature for one hour, at 80° C. for an additional hour, then overnight at ambient temperature. Concentrated hydrochloric was added to adjust the mixture to about pH 2. The reaction was stirred for 20 minutes until CO₂ formation subsided and the reaction was homogenous. The reaction was partitioned between 2N NaOH and ethyl acetate. The organic layer was washed with water and brine, dried, and concentrated to afford 3-(2,4-dimethylpyridin-3-yloxy)-5-(pyridin-2-ylthio)pyridin-2-amine (1.90 g, 4.92 mmol, 85.8% yield).

Step E: In 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) was added in 1 portion in 800 mL of THF. The reaction was stirred for 4 hours and poured into a 4 L separatory funnel and the layers separated. The aqueous layer was extracted twice with MTBE (about 3000 mL total). The combined organic layers were washed with water (700 mL) and brine (300 mL), dried over MgSO₄, and concentrated in vacuo to afford (S)-1,4-dioxaspiro[4.5]decane-2-carbaldehyde oxime (135 g, 99%) as a clear viscous oil.

Step F: to a 4-neck 2 L round bottom flask was added (S)-1,4-dioxaspiro[4.5]decane-2-carbaldehyde oxime (135.1 g, 729.4 mmol) and 750 mL of DMF. The reaction was placed in a water bath and 1-chloropyrrolidine-2,5-dione (97.40 g, 729.4 mmol) as added in portions over 2 minutes. The reaction was stirred in the water bath for 3 hours, then diluted with 2 L of MTBE and washed with 1 L of water. The water was extracted with 500 mL of MTBE. The combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step G: To a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) was added in 10 mL portions over 10 minutes. N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids were washed with MTBE (about 3 L). The filtrate was concentrated and the residue was purified over silica gel (7:1 to 3:1 Hexanes/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step H: To acetonitrile (50 mL) was added sodium isothiocyanate (0.1469 g, 1.813 mmol), pyridine (0.3141 ml, 3.884 mmol), followed by (R)-N-(methylsulfonyloxy)-1,4-dioxaspiro[4.5]decane-2-carbimidoyl chloride (0.4626 g, 1.554 mmol) and the resulting mixture was heated to 60° C. for 30 minutes. 3-(2,4-Dimethylpyridin-3-yloxy)-5-(pyridin-2-ylthio)pyridin-2-amine (0.500 g, 1.295 mmol) was added and the reaction was stirred overnight at 60° C. The reaction was concentrated in vacuo and the residue was partitioned between ethyl acetate and 1N NaOH. The organic layer was separated and the aqueous layer was extracted with ethyl acetate. The combined organic layers were washed with brine, dried (MgSO$_4$) and concentrated. The residue was purified over silica gel (100% ethyl acetate). Concentration of the major UV component with an Rf of 0.5 afforded (S)-N-(3-(2,4-dimethylpyridin-3-yloxy)-5-(pyridin-2-ylthio)pyridin-2-yl)-3-(1,4-dioxaspiro[4.5]decan-2-yl)-1,2,4-thiadiazol-5-amine (0.360 g, 0.6561 mmol, 50.7% yield) as a light yellow powder.

Step I: To a solution of (S)-N-(3-(2,4-dimethylpyridin-3-yloxy)-5-(pyridin-2-ylthio)pyridin-2-yl-3-(1,4-dioxaspiro[4.5]decan-2-yl)-1,2,4-thiadiazol-5-amine (0.360 g, 0.656 mmol) in ethanol (25 mL) was added an aqueous 6N solution of HCl (2 mL). The reaction was heated at 80° C. for 2 hours, then cooled to ambient temperature, stirred for 30 minutes, then cooled to 0° C. Ether (25 mL) was slowly added to initiate precipitation/crystallization. The reaction was stirred 30 minutes, then filtered. The solids were washed with ether several times, then hexanes, and dried overnight under vacuum at 50° C. to afford (S)-1-(5-(3-(2,4-dimethylpyridin-3-yloxy)-5-(pyridin-2-ylthio)pyridin-2-ylamino)-1,2,4-thiadiazol-3-yl)ethane-1,2-diol hydrochloride (0.205 g, 0.406 mmol, 61.9% yield) as a light yellow powder/fine crystals. Mass Spectrum (apci) m/z=469.2 (M+H—HCl).

Example 143

(S)-2-methyl-1-(5-(3-(2-methylpyridin-3-yloxy)-5-(pyridin-2-ylthio)pyridin-2-ylamino)-1,2,4-thiadiazol-3-yl)propane-1,2-diol hydrochloride

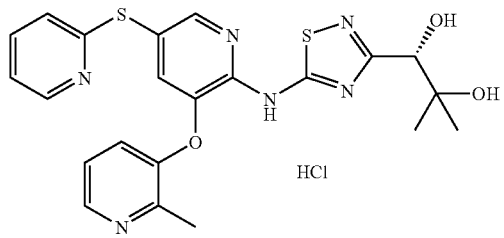

Step A: To 600 mL of DMF in a 4 neck 3000 mL round bottom flask equipped with an overhead stir mechanism under nitrogen was added 2-methylpyridin-3-ol (71.8 g, 658 mmol), and the reaction was cooled to 2° C. 60% sodium hydride (26.3 g, 658 mmol) was added over 30 minutes while maintaining the internal temperature below 10° C. The reaction was stirred while warming to ambient temperature for 1 hour. To the reaction was added 5-bromo-3-nitropicolinonitrile (150 g, 658 mmol) in a solution of 400 mL of DMF in two portions and the reaction held at ambient temperature for 1.5 hours. Pyridine-2-thiol (73.1 g, 658 mmol) was added as a solid in portions at ambient temperature and the reaction was stirred for 15 minutes to dissolve the material. The reaction was cooled to 3° C. and sodium hydride (26.3 g, 658 mmol) again was added in portions over about 35 minutes while maintaining the reaction temperature below 10° C. The reaction was removed from the ice bath and warmed to ambient temperature while stirring for 12 hours. The reaction was diluted with 4 volumes (8 L) of brine and stirred for 30 minutes, at which point solid formed. The solid was removed by filtration and the filtrate was extracted with MTBE (10 L total). The MTBE phase was concentrated in vacuo. The solid was combined with concentrated material and dissolved in ethyl acetate (3 L). The EtOAc was washed with brine, dried over MgSO$_4$, filtered and concentrated in vacuo. The solid that formed was ground into a powder and dried in vacuo for 4 hours. The material was taken up in 30 mL of MTBE/10 g of product and the reaction was stirred for 30 minutes. The solid was filtered and dried in vacuo (2 hours). The mother liquor was concentrated and triturated again with MTBE (same dilution rate). The solids were combined and dried for 3 hours in vacuo to yield 3-(2-methylpyridin-3-yloxy)-5-(pyridin-2-ylthio)picolinonitrile (181 g, 85%)

Step B: To concentrated H$_2$SO$_4$ (90 mL) cooled with an ice bath was added 3-(2-methylpyridin-3-yloxy)-5-(pyridin-2-ylthio)picolinonitrile (43 g, 130 mmol) in portions such that the internal temperature did not exceed 50° C. but did not go below 25° C. After complete addition, the mixture was stirred in the ice bath until the reaction started to cool, at which point the reaction was removed from the ice bath and the mixture was heated to 50° C. The reaction was cooled to ambient temperature and slowly added to ice water over 3 minutes (about 1400 mL of 30% ice in water). The mixture was further cooled in an ice bath to 5° C. The mixture was neutralized to pH ~10 with 4M NaOH (about 800 mL) such that the internal temperature did not exceed 20° C., at which point a solid formed. The mixture was stirred for 20 minutes, then filtered and washed with MTBE (5×150 mL), hexanes (5×100 mL), and dried at under vacuum to afford 3-(2-methylpyridin-3-yloxy)-5-(pyridin-2-ylthio)picolinamide (43 g, 96%).

Step C: To a 3-neck 2 L round bottom flask was added 2M aqueous sodium hydroxide (343 ml, 686 mmol) and the solution was cooled in an ice bath. Bromine (12 ml, 257 mmol) was added the reaction was stirred for 30 minutes while the ice bath was removed. 3-(2-Methylpyridin-3-yloxy)-5-(pyridin-2-ylthio)picolinamide (58 g, 171 mmol) was added as a slurry in about 600 mL of dioxanes in 1 portion. After 30 minutes, concentrated HCl was added in 1 mL portions to about pH 1. The reaction was stirred for 15 minutes and 4N NaOH was added to the solution to about pH 10. The aqueous mixture was extracted with EtOAc (3×750 mL), washed with water (2×250 mL) and brine (300 mL), dried over MgSO$_4$, filtered and concentrated. The material was dried in vacuo at 50° C. at which point a red solid formed. The solid was triturated with CH$_2$Cl$_2$ (about 40 mL of CH$_2$Cl$_2$ to 5 g of material) and the solid filtered. The solid was washed with CH$_2$Cl$_2$ and dried under vacuum at 50° C. The filtrate was concentrated in vacuo and material purified over silica gel (3% MeOH/CH$_2$Cl$_2$) to afford a red solid. The two crops were combined to afford 3-(2-methylpyridin-3-yloxy)-5-(pyridin-2-ylthio)pyridin-2-amine (24 g, 45%).

Step D: (R)-2,2,5,5-Tetramethyl-1,3-dioxolane-4-carbaldehyde (16 g, 101 mmol) [Burger, A. Synthesis 1989, (2) 93-97] was dissolved in 1:1 methanol:water (250 mL) and hydroxylamine hydrochloride (7.0 g, 101 mmol), and Na$_2$CO$_3$ (5.4 g, 51 mmol) was added. The reaction was stirred at ambient temperature for 2 hours. The methanol was partially removed in vacuo and the aqueous layer was extracted with CH$_2$Cl$_2$, dried, filtered and concentrated to afford (S)-2,2,5,5-tetramethyl-1,3-dioxolane-4-carbaldehyde oxime (13 g, 75 mmol, 74% yield) as an amber oil.

Step E: (S)-2,2,5,5-tetramethyl-1,3-dioxolane-4-carbaldehyde oxime (13 g, 75.1 mmol) was dissolved in DMF (200 mL) and cooled in an ice bath. 1-Chloropyrrolidine-2,5-dione (10.0 g, 75.1 mmol) was added and the reaction was stirred overnight while slowly warming to ambient temperature. The pale yellow solution was poured into water (1.5 L) and extracted with EtOAc. The organic layers were washed with water and brine, dried, filtered and concentrated. The residue was purified over silica gel (40% EtOAc in hexanes) to afford (R)-N-hydroxy-2,2,5,5-tetramethyl-1,3-dioxolane-4-carbimidoyl chloride (12.4 g, 59.7 mmol, 79.6% yield).

Step F: (R)-N-hydroxy-2,2,5,5-tetramethyl-1,3-dioxolane-4-carbimidoyl chloride (12.4 g, 59.7 mmol) was dissolved in Et$_2$O (200 mL) and cooled in an ice bath. Methanesulfonyl chloride (4.6 ml, 59.7 mmol) was added. Triethylamine (8.3 ml, 59.7 mmol) was added slowly and the reaction was stirred in an ice bath for 30 minutes. The reaction was filtered and concentrated. The residue was purified over silica gel (100% CH$_2$Cl$_2$) to afford (R)-2,2,5,5-tetramethyl-N-(methylsulfonyloxy)-1,3-dioxolane-4-carbimidoyl chloride (11.3 g, 39.55 mmol, 66.22% yield) as a white solid.

Step G: (R)-2,2,5,5-Tetramethyl-N-(methylsulfonyloxy)-1,3-dioxolane-4-carbimidoyl chloride (138 mg, 0.483 mmol) was dissolved in CH$_3$CN (3 mL). NaNCS (39.2 mg, 0.483 mmol) and pyridine (104 µL, 1.29 mmol) were added, and the reaction was heated to 45° C. for 45 minutes. 3-(2-Methylpyridin-3-yloxy)-5-(pyridin-2-ylthio)pyridin-2-amine (100 mg, 0.322 mmol) was added, and the reaction was heated to 65° C. overnight. The reaction was partitioned between EtOAc and water, dried, filtered and concentrated. The residue was purified over silica gel (80% EtOAc in hexanes) to afford (S)-N-(3-(2-methylpyridin-3-yloxy)-5-(pyridin-2-ylthio)pyridin-2-yl)-3-(2,2,5,5-tetramethyl-1,3-dioxolan-4-yl)-1,2,4-thiadiazol-5-amine (145 mg, 0.277 mmol, 86.1% yield).

Step H: (S)-N-(3-(2-methylpyridin-3-yloxy)-5-(pyridin-2-ylthio)pyridin-2-yl)-3-(2,2,5,5-tetramethyl-1,3-dioxolan-4-yl)-1,2,4-thiadiazol-5-amine (145 mg, 0.2774 mmol) was dissolved in EtOH (5 mL), and 6M HCl (0.3 mL) was added. The reaction was stirred at ambient temperature for 2 hours and then at 70° C. for 2 hours. The reaction was cooled to ambient temperature and partitioned between CH$_2$Cl$_2$ and saturated aqueous sodium bicarbonate. The organic layer was dried, filtered, concentrated and purified over silica gel (10% methanol in EtOAc) to afford (S)-2-methyl-1-(5-(3-(2-methylpyridin-3-yloxy)-5-(pyridin-2-ylthio)pyridin-2-ylamino)-1,2,4-thiadiazol-3-yl)propane-1,2-diol hydrochloride (111.7 mg, 0.215 mmol, 77.6% yield) as a pale yellow solid after HCl salt formation. Mass Spectrum (apci) m/z=465.2 (M+H—HCl).

Example 144

(S)-1-(5-(5-(2-methoxyethylthio)-3-(2-methylpyridin-3-yloxy)pyridin-2-ylamino)-1,2,4-thiadiazol-3-yl)ethane-1,2-diol hydrochloride

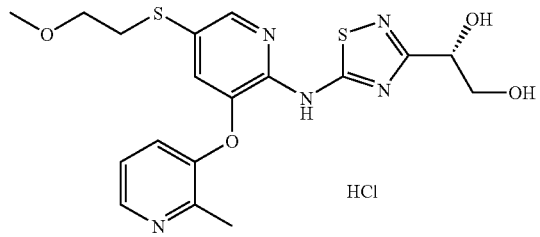

Step A: To a solution of 2-methylpyridin-3-ol (11.8 g, 108 mmol) in DMF at 0° C. was added sodium hydride (60% dispersion in oil, 4.32 g, 108 mmol) in small portions and the reaction was warmed to ambient temperature. 5-Bromo-3-nitropicolinonitrile (24.6 g, 108 mmol) was added and the reaction was stirred overnight at ambient temperature. The reaction was poured into water (1000 mL) and the aqueous layer extracted with EtOAc. The combined organic layers were washed with water and brine, dried over MgSO$_4$ and concentrated in vacuo to yield 5-bromo-3-(2-methylpyridin-3-yloxy)picolinonitrile (15 g, 48%).

Step B: To 5-bromo-3-(2-methylpyridin-3-yloxy)picolinonitrile (15 g, 52 mmol) was added concentrated H$_2$SO$_4$ (30 mL) and the slurry was stirred overnight, at which point the material was fully dissolved. The reaction was poured into 0° C. water in small portions. While maintaining the temp below 20° C., the aqueous layer was basified by the addition of NaOH pellets, to a pH of about 5, at which point a solid formed. The solid was filtered, and the remaining aqueous layer was extracted with EtOAc. The organic layers, combined with the solid, were washed with brine, dried over MgSO$_4$ and concentrated in vacuo to yield 5-bromo-3-(2-methylpyridin-3-yloxy)picolinamide (11 g, 69%).

Step C: To a solution of NaOH (2M, 90 mL, 182 mmol) at 0° C. was added bromine (8.71 g, 54 mmol) and the reaction was stirred at 0° C. for 30 minutes. 5-Bromo-3-(2-methylpyridin-3-yloxy)picolinamide (11.2 g, 36.3 mmol) in dioxanes (100 mL) was added and the reaction was stirred at ambient temperature for 1 hour followed by heating at 80° C. for 1 hour. The reaction was cooled to ambient temperature and acidified to pH 1 using concentrated HCl. The reaction was basified and a solid precipitated. The solid was filtered and dried in vacuo to yield product 5-bromo-3-(2-methylpyridin-3-yloxy)pyridin-2-amine (4.1 g, 41%).

Step D: In 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added to the reaction and (R)-1,4-dioxaspiro[4.5]decane-2-carbaldehyde (125 g, 734 mmol) was added in 1 portion in 800 mL of THF. The reaction was stirred for 4 hours and poured into a 4 L separatory funnel and the layers separated. The aqueous layer was extracted twice with MTBE (3000 mL total). The combined organic layers were washed with water (700 mL) and brine (300 mL), dried over MgSO$_4$ and concentrated in vacuo to afford (S)-1,4-dioxaspiro[4.5]decane-2-carbaldehyde oxime (135 g, 99%) as a clear viscous oil.

Step E: To a 4-neck 2 L round bottom flask was added (S)-1,4-dioxaspiro[4.5]decane-2-carbaldehyde oxime (135.1 g, 729.4 mmol) and dissolved in 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours, then diluted with 2 L of MTBE and washed with 1 L of water. The aqueous layer was extracted with 500 mL of MTBE. The combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step F: In a 4 neck 5 L flask was added (R)-N-hydroxy-1,4-dioxaspiro[4.5]decane-2-carbimidoyl chloride (158 g, 719 mmol) in 2.5 L of THF. The material was cooled to 3° C. and methanesulfonyl chloride (56.1 ml, 719 mmol) added in 10 mL portions over 10 minutes. N-ethyl-N-iospropylpropan-2-amine (126 ml, 719 mmol) was added through an addition funnel over 12 minutes. The reaction was stirred in an ice bath for 30 minutes and then at ambient temperature for 1 hour. The reaction was filtered and the solids washed with MTBE (3 L). The filtrate was concentrated and the residue was purified over silica gel (3 kg silica, 7:1 to 3:1 Hexane/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step G: In 100 mL of acetonitrile was added sodium thioisocyanate (1.5 g, 20 mmol), pyridine (3.5 g, 44 mmol), followed by (R)-N-(methylsulfonyloxy)-1,4-dioxaspiro[4.5]decane-2-carbimidoyl chloride (5.2 g, 18 mmol) and the reaction heated to 60° C. for 30 minutes. 5-Bromo-3-(2-methylpyridin-3-yloxy)pyridin-2-amine (4.1 g, 15 mmol) was added and the reaction was heated overnight at 60° C. The reaction was concentrated to one quarter volume and the residue was partitioned between EtOAc and water made basic with 1N NaOH. The combined organic layers were separated and the aqueous layer extracted with EtOAc. The combined organic layers were washed with brine, dried over MgSO$_4$ and concentrated in vacuo. The material was purified on silica gel (25% EtOAc in CH$_2$Cl$_2$) to afford (S)-N-(5-bromo-3-(2-methylpyridin-3-yloxy)pyridin-2-yl)-3-(1,4-dioxaspiro[4.5]decan-2-yl)-1,2,4-thiadiazol-5-amine (5.4 g, 73%).

Step H: To a solution of (S)-N-(5-bromo-3-(2-methylpyridin-3-yloxy)pyridin-2-yl)-3-(1,4-dioxaspiro[4.5]decan-2-yl)-1,2,4-thiadiazol-5-amine (3.1 g, 6.14 mmol) in dioxanes (30 mL) continuously purged with nitrogen was added Xanphos (0.177 g, 0.303 mmol), Pd$_2$dba$_3$ (0.14 g, 0.153 mmol), methyl 3-mercaptopropanoate (0.73 g, 6.14 mmol) and N,N-diisopropylethylamine (1.17 mL, 6.45 mmol) and the reaction was heated overnight at 80° C. The reaction was concentrated in vacuo and the residue purified over silica gel (5% MeOH/CH$_2$Cl$_2$) to afford (S)-methyl 3-(6-(3-(1,4-dioxaspiro[4.5]decan-2-yl)-1,2,4-thiadiazol-5-ylamino)-5-(2-methylpyridin-3-yloxy)pyridin-3-ylthio)propanoate (2.3 g, 68%).

Step I: (S)-Methyl 3-(6-(3-(1,4-dioxaspiro[4.5]decan-2-yl)-1,2,4-thiadiazol-5-ylamino)-5-(2-methylpyridin-3-yloxy)pyridin-3-ylthio)propanoate (2.0 g, 3.68 mmol) was dissolved in THF (20 mL) and nitrogen was bubbled through the solution for 5 minutes. Potassium 2-methylpropan-2-olate (1M in THF, 11.0 ml, 11.0 mmol) was added and the reaction was stirred at ambient temperature for 1 minute. 1-Bromo-2-methoxyethane (0.518 ml, 5.52 mmol) was added and the reaction was stirred at ambient temperature for 20 minutes. The reaction was partitioned between EtOAc and aqueous NH$_4$Cl, dried, filtered and concentrated. The residue was purified over silica gel (100% EtOAc) to afford (S)-N-(5-(2-methoxyethylthio)-3-(2-methylpyridin-3-yloxy)pyridin-2-yl)-3-(1,4-dioxaspiro[4.5]decan-2-yl)-1,2,4-thiadiazol-5-amine (1.9 g, 3.68 mmol, 100% yield).

Step J: (S)-N-(5-(2-methoxyethylthio)-3-(2-methylpyridin-3-yloxy)pyridin-2-yl)-3-(1,4-dioxaspiro[4.5]decan-2-yl)-1,2,4-thiadiazol-5-amine (1.9 g, 3.68 mmol) was dissolved in EtOH (50 mL) and 6M HCl (3 mL) added and heated to 60° C. for 1.5 hours. The reaction was cooled to ambient temperature and partitioned between CH$_2$Cl$_2$ and saturated aqueous sodium bicarbonate, extracted with CH$_2$Cl$_2$, dried, filtered and concentrated. The residue was purified over silica gel (0 to 10% methanol in EtOAc) to afford (S)-1-(5-(5-(2-methoxyethylthio)-3-(2-methylpyridin-3-yloxy)pyridin-2-ylamino)-1,2,4-thiadiazol-3-yl)ethane-1,2-diol hydrochloride (1.13 g, 2.39 mmol, 65.0% yield) as a white solid after HCl salt formation. Mass Spectrum (apci) m/z=436.1 (M+H—HCl).

Example 145

(1S,2S)-1-(5-(3-(2-ethylpyridin-3-yloxy)-5-(pyridin-2-ylthio)pyridin-2-ylamino)-1,2,4-thiadiazol-3-yl)-3-methoxypropane-1,2-diol hydrochloride

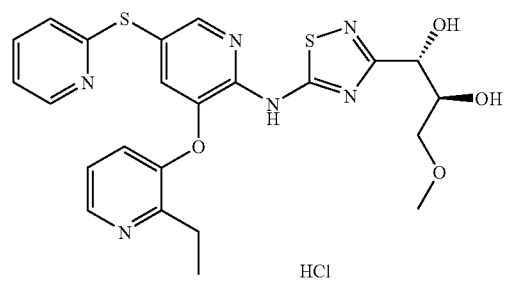

Step A: 2-Bromopyridin-3-yl acetate (10 g, 46 mmol) was dissolved in THF (80 mL) and triethylamine (32 ml, 231 mmol), ethynyltrimethylsilane (19.5 ml, 139 mmol), and CuI (0.44 g, 2.3 mmol) were added. The mixture was degassed with argon for 15 minutes. PdCl$_2$(PPh$_3$)$_2$ (1.6 g, 2.3 mmol) was added and the mixture stirred under argon at ambient temperature for 18 hours. The reaction was concentrated in vacuo, dissolved in 25% EtOAc in hexanes, filtered and purified over silica gel (25% ethyl acetate/hexanes) to afford 2-((trimethylsilyl)ethynyl)pyridin-3-yl acetate (9.7 g, 41 mmol).

Step B: To a solution of 2-((trimethylsilyl)ethynyl)pyridin-3-yl acetate (9.5 g, 41 mmol) in THF (200 mL) was added water (25 ml). The reaction was cooled to 0° C. and TBAF (1M, 45 ml, 45 mmol) was added. The mixture warmed to ambient temperature and stirred for 1 hour. Water (100 mL) was added and the volume was reduced by half. The product was extracted into ether (3×100 mL), washed with brine and dried over $MgSO_4$. The solution was concentrated in vacuo to afford 2-ethynylpyridin-3-yl acetate (5.5 g, 34 mmol) as a light brown oil.

Step C: To a solution of 2-ethynylpyridin-3-yl acetate (5.0 g, 31 mmol) in ethanol (50 mL) was added $PtO_2$ (0.50 g, 2.2 mmol). The mixture was degassed with nitrogen and placed under a double-layer balloon of hydrogen. The reaction was stirred at ambient temperature for 30 minutes. The mixture was filtered and concentrated in vacuo to give 2-ethylpyridin-3-yl acetate (5.1 g, 31 mmol) that was used without further purification.

Step D: To a solution of 2-ethylpyridin-3-yl acetate (5.1 g, 31 mmol) in ethanol (50 mL) was added 3M LiOH (50 mL, 150 mmol). The reaction mixture stirred at ambient temperature for 30 minutes. The mixture was concentrated to dryness and purified over silica gel (10% MeOH in $CH_2Cl_2$) to afford 2-ethylpyridin-3-ol (2.5 g, 20 mmol).

Step E: 2-Ethylpyridin-3-ol (27.5 g, 223 mmol) was dissolved in DMF (900 mL) and cooled in an ice bath. 60% Sodium hydride (8.93 g, 223 mmol) was added portionwise and stirred in an ice bath for 30 minutes. 5-Bromo-3-nitropicolinonitrile (50.9 g, 223 mmol) was added in one portion and the reaction was stirred in an ice bath for 1 hour. Pyridine-2(1H)-thione (24.8 g, 223 mmol) was added, followed by 60% sodium hydride (8.93 g, 223 mmol) and reaction was stirred in an ice bath slowly warming to ambient temperature overnight. The reaction was concentrated in vacuo to about 300 mL and poured into 3 L water with vigorous stirring. The mixture was extracted with EtOAc, washed with water and brine, dried over sodium sulfate, filtered and concentrated to afford 3-(2-ethylpyridin-3-yloxy)-5-(pyridin-2-ylthio)picolinonitrile (81 g, 242 mmol, 108% yield) as a dark oil.

Step F: 3-(2-Ethylpyridin-3-yloxy)-5-(pyridin-2-ylthio)picolinonitrile (80 g, 239 mmol) was cooled in an ice/acetone bath. 12M Hydrogen chloride (598 ml, 7177 mmol) was chilled in an ice/acetone bath and then added slowly to the oil in the flask. After agitating for 40 minutes all the starting material dissolved and the bath was removed and the mixture was stirred at ambient temperature over the weekend. The reaction was cooled in an ice bath and 6N NaOH (1200 mL) was added slowly while keeping the temperature below 20° C. to a final pH of about 9. The aqueous mixture was extracted with $CH_2Cl_2$, washed with water and brine, dried over sodium sulfate, filtered and concentrated to afford 3-(2-ethylpyridin-3-yloxy)-5-(pyridin-2-ylthio)picolinamide (71 g, 201 mmol, 84% yield) as a dark green foam.

Step G: 3-(2-Ethylpyridin-3-yloxy)-5-(pyridin-2-ylthio)picolinamide (71 g, 201 mmol) was dissolved in MeOH (1 L). 1-Bromopyrrolidine-2,5-dione (46.6 g, 262 mmol) was added and the reaction was stirred at ambient temperature for 5 minutes and then cooled in an ice bath. Sodium hydroxide (41.9 g, 1048 mmol) dissolved in water (200 mL) was added slowly and the reaction was stirred at ambient temperature for 1 hour, refluxed for 8 hours and then cooled to ambient temperature overnight. The reaction was diluted with 2.5 L water and 0.5 L $NH_4Cl$ and stirred for 30 minutes. The precipitate was filtered and dried to afford 3-(2-ethylpyridin-3-yloxy)-5-(pyridin-2-ylthio)pyridin-2-amine (52.6 g, 162 mmol, 80.5% yield) as a tan solid.

Step H: (2R,3R)-diethyl 2,3-dihydroxysuccinate (82.99 ml, 485.0 mmol) was dissolved in Toluene (400 mL) and cyclohexanone (55.29 ml, 533.5 mmol) and Amberlyst 15 ion-exchange resin (2.0 g) were added and the reaction refluxed under dean stark trap for 12 hours. The reaction was cooled to ambient temperature, filtered and concentrated. The residue was distilled at 0.5 mM Hg and the 125-140° C. fraction was collected to afford (2R,3R)-diethyl 1,4-dioxaspiro[4.5]decane-2,3-dicarboxylate (91.3 g, 66% yield).

Step I: (2R,3R)-diethyl 1,4-dioxaspiro[4.5]decane-2,3-dicarboxylate (91.3 g, 319 mmol) was dissolved in THF (1.5 L) and cooled in ice bath. 2M LAH (120 ml, 239 mmol) was added slowly and the reaction stirred at 0° C. Small aliquots were taken and $^1$H NMR analyzed for completion of reaction. Sodium sulfate decahydrate was added slowly, and allowed to stir at ambient temperature for 1 hour. The reaction was filtered through celite and concentrated to afford batch 1 (45.3 g). The celite was stirred in EtOAc for 30 min and filtered again to afford batch 2 (9.8 g). The celite was stirred again in $CH_2Cl_2$/MeOH for 30 min and filtered again to afford batch 3 (1.6 g). The three batches were combined to afford (2S,3S)-1,4-dioxaspiro[4.5]decane-2,3-diyldimethanol (56.7 g, 88% yield).

Step J: (2S,3S)-1,4-dioxaspiro[4.5]decane-2,3-diyldimethanol (65 g, 321.4 mmol) was dissolved in DMF (500 mL) and cooled in an ice bath. 60% Sodium hydride (15.43 g, 385.7 mmol) was added slowly and the reaction was stirred for 30 minutes in an ice bath then warmed to ambient temperature for 2 hours. Iodomethane (20.05 ml, 321.4 mmol) was added and the reaction was stirred at ambient temperature overnight. The majority of the DMF was removed on a rotary evaporator, and the residue was partitioned between aqueous $NH_4Cl$ and EtOAc. The organic layer was washed with brine, dried over sodium sulfate, filtered and concentrated. The residue was purified over 1 Kg of $SiO_2$ (20 to 40% EtOAc in hexanes) to afford ((2S,3S)-3-(methoxymethyl)-1,4-dioxaspiro[4.5]decan-2-yl)methanol (31.3 g, 144.7 mmol, 45.03% yield) as an oil.

Step K: A solution of methylsulfinylmethane (20.6 ml, 289 mmol) in $CH_2Cl_2$ (260 mL) at −60° C., was added dropwise to a 2M solution of oxalyl dichloride (15.2 ml, 174 mmol) in $CH_2Cl_2$ (80 mL). The mixture was stirred for 20 minutes and then a solution of ((2S,3S)-3-(methoxymethyl)-1,4-dioxaspiro[4.5]decan-2-yl)methanol (31.3 g, 145 mmol) in $CH_2Cl_2$ (80 mL) was added dropwise. The mixture was stirred for 10 minutes and then triethylamine (101 ml, 724 mmol) was slowly added. The reaction mixture was warmed to ambient temperature and water was added. When the mixture became clear, it was extracted with $CH_2Cl_2$, dried over sodium sulfate, filtered and concentrated to afford crude (2R,3S)-3-(methoxymethyl)-1,4-dioxaspiro[4.5]decane-2-carbaldehyde (34.3 g, 96.2% yield, 87% pure) which was taken on to next reaction without further purification.

Step L: Crude (2R,3S)-3-(methoxymethyl)-1,4-dioxaspiro[4.5]decane-2-carbaldehyde (31 g, 145 mmol) was dissolved in 1:1 methanol:water (600 mL), and hydroxylamine hydrochloride (10.1 g, 145 mmol) and $Na_2CO_3$ (7.67 g, 72.3 mmol) were added. The reaction was stirred at ambient temperature for 3 hours. The methanol was removed under reduced pressure and the remaining material was extracted with $CH_2Cl_2$, dried over sodium sulfate, filtered and concentrated to afford 3-(methoxymethyl)-1,4-dioxaspiro[4.5]decane-2-carbaldehyde oxime (33.6 g, 147 mmol, 101% yield) which was taken forward without purification.

Step M: 3-(Methoxymethyl)-1,4-dioxaspiro[4.5]decane-2-carbaldehyde oxime (33.2 g, 145 mmol) was dissolved in DMF (600 mL) and cooled in an ice bath. 1-Chloropyrrolidine-2,5-dione (19.3 g, 145 mmol) was added and the reaction allowed to slowly warm to ambient temperature overnight. Most of the DMF was removed under reduced pressure and the remaining material was partitioned between water and EtOAc. The organic layer was washed with water and brine, dried over sodium sulfate, filtered and concentrated to afford (2R,3S)-N-hydroxy-3-(methoxymethyl)-1,4-dioxaspiro[4.5]decane-2-carbimidoyl chloride (35.6 g, 135 mmol, 93.2% yield) which was taken forward without further purification.

Step N: (2R,3S)-N-hydroxy-3-(methoxymethyl)-1,4-dioxaspiro[4.5]decane-2-carbimidoyl chloride (35.6 g, 135.0 mmol) was dissolved in Et$_2$O (600 mL) and cooled in an ice bath. Methanesulfonyl chloride (10.49 ml, 135.0 mmol) was added, followed by dropwise addition of triethylamine (18.82 ml, 135.0 mmol). The reaction was stirred for 30 minutes and then filtered and concentrated. The residue was purified on 1 Kg SiO$_2$ (1 to 5% EtOAc in CH$_2$Cl$_2$) to afford (2R,3S)-3-(methoxymethyl)-N-(methylsulfonyloxy)-1,4-dioxaspiro[4.5]decane-2-carbimidoyl chloride (22.6 g, 66.12 mmol, 48.98% yield).

Step O: (2R,3S)-3-(Methoxymethyl)-N-(methylsulfonyloxy)-1,4-dioxaspiro[4.5]decane-2-carbimidoyl chloride (2.29 g, 6.70 mmol) was dissolved in EtOAc (40 mL), and NaNCS (0.544 g, 6.70 mmol) and pyridine (1.44 ml, 17.9 mmol) were added and the reaction was heated to 45° C. for 45 minutes. 3-(2-Ethylpyridin-3-yloxy)-5-(pyridin-2-ylthio)pyridin-2-amine (1.45 g, 4.47 mmol) was added and the reaction was heated to 70° C. overnight. (2R,3S)-3-(methoxymethyl)-N-(methylsulfonyloxy)-1,4-dioxaspiro[4.5]decane-2-carbimidoyl chloride (1.15 g, 3.3 mmol) was dissolved in EtOAc (20 mL). NaNCS (0.270 g, 3.3 mmol) and pyridine (0.7 ml, 9.0 mmol) were added and the reaction was heated to 45° C. for 45 minutes. This solution was added to the initial reaction and heated to 70° C. overnight. The reaction was cooled and partitioned between EtOAc and water, dried over sodium sulfate, filtered and concentrated. The residue was purified over silica gel (80% EtOAc in Hexane) to afford N-(3-(2-ethylpyridin-3-yloxy)-5-(pyridin-2-ylthio)pyridin-2-yl)-3-((2S,3S)-3-(methoxymethyl)-1,4-dioxaspiro[4.5]decan-2-yl)-1,2,4-thiadiazol-5-amine (1.6 g, 2.70 mmol, 60.4% yield).

Step P: N-(3-(2-ethylpyridin-3-yloxy)-5-(pyridin-2-ylthio)pyridin-2-yl)-3-((2S,3S)-3-(methoxymethyl)-1,4-dioxaspiro[4.5]decan-2-yl)-1,2,4-thiadiazol-5-amine (1.6 g, 2.70 mmol) was dissolved in EtOH (30 mL) and 4N HCl (1 mL) added and heated to 50° C. overnight. Additional 4N HCl was added (1 mL) and heated for 4 hours. The reaction was cooled to ambient temperature, partitioned between CH$_2$Cl$_2$ and saturated aqueous sodium bicarbonate, extracted with CH$_2$Cl$_2$, dried over sodium sulfate, filtered and concentrated. The residue was purified over silica gel (10% methanol in EtOAc) to afford (1S,2S)-1-(5-(3-(2-ethylpyridin-3-yloxy)-5-(pyridin-2-ylthio)pyridin-2-ylamino)-1,2,4-thiadiazol-3-yl)-3-methoxypropane-1,2-diol hydrochloride (0.957 g, 1.74 mmol, 64.6% yield) as a tan solid after HCl salt formation. Mass Spectrum (apci) m/z=513.1 (M+H—HCl).

Example 146

(S)-2-methyl-1-(5-(5-(pyridin-2-ylthio)-3-(1,3,5-trimethyl-1H-pyrazol-4-yloxy)pyridin-2-ylamino)-1,2,4-thiadiazol-3-yl)propane-1,2-diol hydrochloride

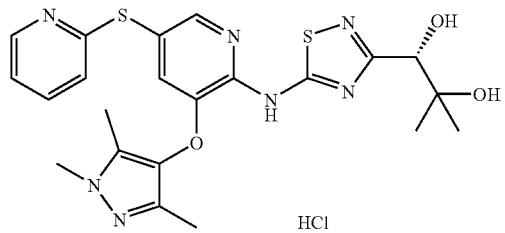

Step A: A flask was charged with powdered potassium hydroxide (21.89 g, 390.2 mmol), benzoic acid (47.65 g, 390.2 mmol), and DMF (500 mL) was added. The mixture was heated at 50° C. for 1 hour. 3-Chloropentane-2,4-dione (52.5 g, 390.2 mmol) was added and the reaction was stirred at 50° C. overnight. The reaction was cooled to ambient temperature, diluted in water (1.5 L) and extracted with ether (3×500 mL). The combined organic layers were washed with water, saturated NH$_4$Cl and brine. The organic layer was dried over sodium sulfate and concentrated in vacuo to afford 2,4-dioxopentan-3-yl benzoate (82.59 g, 96.12% yield) as a yellow oil.

Step B: A flask was charged with 2,4-dioxopentan-3-yl benzoate (82.59 g, 375.0 mmol) and ethanol (1.5 L) was added. Methylhydrazine (39.90 ml, 750.1 mmol) in ethanol (150 mL) was added, and the reaction was stirred at ambient temperature for 2 hours, then concentrated in vacuo to afford 1,3,5-trimethyl-1H-pyrazol-4-yl benzoate (80 g, 92.6% yield).

Step C: A flask was charged with 1,3,5-trimethyl-1H-pyrazol-4-yl benzoate (80 g, 347 mmol), and added 500 mL ethanol. 3M NaOH (174 ml, 521 mmol) was added and the reaction was stirred at ambient temperature for 2 hours. The ethanol was removed in vacuo and the aqueous layer was extracted with dichloromethane, ethyl acetate and dichloromethane:isopropyl alcohol (4:1). The combined organic layers were dried over sodium sulfate, filtered and concentrated in vacuo to afford 1,3,5-trimethyl-1H-pyrazol-4-ol (34 g, 78% yield) as white solid.

Step D: A flask was charged with 1,3,5-trimethyl-1H-pyrazol-4-ol (10.46 g, 82.89 mmol), and DMF:dioxane (9:1) (700 mL). The reaction mixture was cooled to 0° C. and 60% sodium hydride (3.315 g, 82.89 mmol) was added portionwise. The reaction mixture was added. The reaction was stirred at ambient temperature for 3 hours, then poured slowly into 600 mL water and stirred for 10 minutes. The resultant solids were filtered and dried to afford 5-bromo-3-(1,3,5-trimethyl-1H-pyrazol-4-yloxy)picolinonitrile (23.70 g, 97.74% yield) as very lightly tan (white) solid.

Step E: A flask was charged with 5-bromo-3-(1,3,5-trimethyl-1H-pyrazol-4-yloxy)picolinonitrile (27.77 g, 90.41 mmol), pyridine-2-thiol (10.55 g, 94.93 mmol), and DMF (300 mL). The reaction was cooled to 0° C. and 95% sodium hydride (2.741 g, 108.5 mmol) was added portionwise. The reaction was stirred at ambient temperature overnight, then carefully diluted with water (2 L) and extracted with ethyl acetate. The organic layer was washed with brine (4×500 mL), dried over sodium sulfate and concentrated to afford 5-(pyridin-2-ylthio)-3-(1,3,5-trimethyl-1H-pyrazol-4-yloxy)picolinonitrile (29.50 g, 87.43 mmol, 96.70% yield) as yellow solid.

Step F: A flask was charged with 5-(pyridin-2-ylthio)-3-(1,3,5-trimethyl-1H-pyrazol-4-yloxy)picolinonitrile (35.19 g, 88.1 mmol), and sulfuric acid (227.3 g, 2317 mmol) and stirred at ambient temperature overnight. Water (100 mL) was added very slowly to the reaction which was cooled in an ice bath, and then 150 g of ice was added. NaOH (40%) was slowly added until pH was adjusted to about 12. The mixture was extracted ethyl acetate (750 mL×2), and dichloromethane (500 mL). The combined organic layers were dried over sodium sulfate, filtered and concentrated in vacuo to afford 5-(pyridin-2-ylthio)-3-(1,3,5-trimethyl-1H-pyrazol-4-yloxy)picolinamide (27.69 g, 77.9 mmol, 89% yield).

Step G: A flask was charged with potassium hydroxide (78.8 ml, 236 mmol), bromine (4.04 ml, 78.8 mmol) was added and the reaction was stirred at ambient temperature for 15 minutes. 5-(Pyridin-2-ylthio)-3-(1,3,5-trimethyl-1H-pyrazol-4-yloxy)picolinamide (14 g, 39.4 mmol) in dioxane (280 mL) was added and the reaction was stirred at ambient temperature overnight. Water (300 mL) was added and the reaction was extracted with ethyl acetate. The organic layer was dried over sodium sulfate, filtered and concentrated. The residue was purified over silica gel (50 to 100% ethyl acetate in hexanes) to afford 5-(pyridin-2-ylthio)-3-(1,3,5-trimethyl-1H-pyrazol-4-yloxy)pyridin-2-amine (4.64 g, 14.18 mmol, 36% yield) as yellow solid.

Step H: (R)-2,2,5,5-Tetramethyl-1,3-dioxolane-4-carbaldehyde (16 g, 101 mmol) [Burger, A. Synthesis 1989, (2) 93-97] was dissolved in 1:1 methanol:water (250 mL). Hydroxylamine hydrochloride (7.0 g, 101 mmol) and $Na_2CO_3$ (5.4 g, 51 mmol) were added and the reaction was stirred at ambient temperature for 2 hours. The methanol was partially removed in vacuo and the aqueous layer was extracted with $CH_2Cl_2$ dried, filtered and concentrated to afford (S)-2,2,5,5-tetramethyl-1,3-dioxolane-4-carbaldehyde oxime (13 g, 75 mmol, 74% yield) as an amber oil.

Step I: (S)-2,2,5,5-tetramethyl-1,3-dioxolane-4-carbaldehyde oxime (13 g, 75.1 mmol) was dissolved in DMF (200 mL) and cooled in an ice bath. 1-Chloropyrrolidine-2,5-dione (10.0 g, 75.1 mmol) was added and the reaction was stirred overnight, slowly warming to ambient temperature. The pale yellow solution was poured into water (1.5 L) and extracted with EtOAc. The combined organic layers were washed with water and brine, dried, filtered and concentrated. The residue was purified over silica gel (40% EtOAc in hexanes) to afford (R)-N-hydroxy-2,2,5,5-tetramethyl-1,3-dioxolane-4-carbimidoyl chloride (12.4 g, 59.7 mmol, 79.6% yield).

Step J: (R)-N-hydroxy-2,2,5,5-tetramethyl-1,3-dioxolane-4-carbimidoyl chloride (12.4 g, 59.7 mmol) was dissolved in $Et_2O$ (200 mL) and cooled in an ice bath. Methanesulfonyl chloride (4.6 ml, 59.7 mmol) was added. Triethylamine (8.3 ml, 59.7 mmol) was added slowly and the reaction was stirred in an ice bath for 30 minutes. The reaction was filtered and concentrate. The residue was purified over silica gel (100% $CH_2Cl_2$) to afford (R)-2,2,5,5-tetramethyl-N-(methylsulfonyloxy)-1,3-dioxolane-4-carbimidoyl chloride (11.3 g, 39.55 mmol, 66.22% yield) as a white solid.

Step K: A flask was charged with (R)-2,2,5,5-tetramethyl-N-(methylsulfonyloxy)-1,3-dioxolane-4-carbimidoyl chloride (0.371 g, 1.30 mmol), sodium thiocyanate (0.0929 g, 1.15 mmol), pyridine (0.278 g, 0.764 mmol) was added and the reaction was heated to 40° C. for 30 minutes. 5-(Pyridin-2-ylthio)-3-(1,3,5-trimethyl-1H-pyrazol-4-yloxy)pyridin-2-amine (0.250 g, 0.764 mmol) was added and the reaction was stirred at 70° C. overnight. Water was added and the reaction was extracted with ethyl acetate. The organic layer was dried over sodium sulfate, filtered and concentrated. The residue was purified over silica gel (50 to 100% ethyl acetate in hexanes) to afford (S)-N-(5-(pyridin-2-ylthio)-3-(1,3,5-trimethyl-1H-pyrazol-4-yloxy)pyridin-2-yl)-3-(2,2,5,5-tetramethyl-1,3-dioxolan-4-yl)-1,2,4-thiadiazol-5-amine (0.233 g, 56.5% yield) as yellow solid.

Step L: A flask was charged with (S)-N-(5-pyridin-2-ylthio)-3-(1,3,5-trimethyl-1H-pyrazol-4-yloxy)pyridin-2-yl)-3-(2,2,5,5-tetramethyl-1,3-dioxolan-4-yl)-1,2,4-thiadiazol-5-amine (0.233 g, 0.432 mmol), ethanol (10 mL), and 3M HCl (0.288 ml, 0.863 mmol). The reaction was heated to 75° C. for 1 hour and then concentrated in vacuo. Ether was added to the residue and the mixture was stirred for 2 minutes to precipitate the product. The mixture was decanted and the resulting solids were dried in vacuo to afford (S)-2-methyl-1-(5-(5-(pyridin-2-ylthio)-3-(1,3,5-trimethyl-1H-pyrazol-4-yloxy)pyridin-2-ylamino)-1,2,4-thiadiazol-3-yl)propane-1,2-diol hydrochloride (0.248 g, 0.387 mmol, 89.6% yield) as yellow solid. Mass Spectrum (apci) m/z=500.1 (M+H—HCl).

Example 147

(S)-1-(5-(5-(pyridin-2-ylthio)-3-(1,3,5-trimethyl-1H-pyrazol-4-yloxy)pyridin-2-ylamino)-1,2,4-thiadiazol-3-yl)ethane-1,2-diol hydrochloride

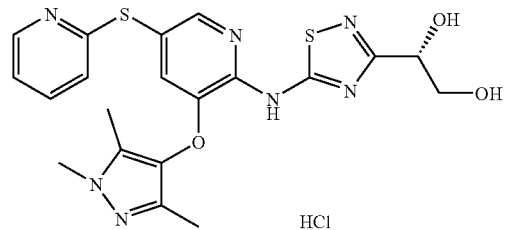

Step A: A flask was charged with powdered potassium hydroxide (21.89 g, 390.2 mmol), benzoic acid (47.65 g, 390.2 mmol), and DMF (500 mL). The mixture was heated at 50° C. for 1 hour. 3-Chloropentane-2,4-dione (52.5 g, 390.2 mmol) was added and the reaction was stirred at 50° C. overnight. The reaction was cooled to ambient temperature, diluted in water (1.5 L) and extracted with ether (3×500 mL). The combined organic layers were washed with water, saturated $NH_4Cl$ and brine. The organic layer was dried over sodium sulfate and concentrated in vacuo to afford 2,4-dioxopentan-3-yl benzoate (82.59 g, 96.12% yield) as yellow oil.

Step B: A flask was charged with 2,4-dioxopentan-3-yl benzoate (82.59 g, 375.0 mmol) and ethanol (1.5 L) was added. To this solution was added methylhydrazine (39.90 ml, 750.1 mmol) in ethanol (150 mL). The reaction was stirred at ambient temperature for 2 hours and concentrated in vacuo to afford 1,3,5-trimethyl-1H-pyrazol-4-yl benzoate (80 g, 92.6% yield).

Step C: A flask was charged with 1,3,5-trimethyl-1H-pyrazol-4-yl benzoate (80 g, 347 mmol), and 500 mL ethanol was added. 3M NaOH (174 ml, 521 mmol) was added and the reaction was stirred at ambient temperature for 2 hours. The ethanol was removed in vacuo and the aqueous layer was extracted with dichloromethane, ethyl acetate and dichloromethane:isopropyl alcohol (4:1). The combined organic layers were dried over sodium sulfate, filtered and concentrated in vacuo to afford 1,3,5-trimethyl-1H-pyrazol-4-ol (34 g, 78% yield) as white solid.

Step D: A flask was charged with 1,3,5-trimethyl-1H-pyrazol-4-ol (10.46 g, 82.89 mmol), and added DMF:dioxane (9:1) (700 mL). The reaction mixture was cooled to 0° C. and 60% sodium hydride (3.315 g, 82.89 mmol) was added portionwise and the reaction was stirred for 15 minutes. 5-Bromo-3-nitropicolinonitrile (18 g, 78.95 mmol) was added and the reaction was stirred at ambient temperature for 3 hours. The reaction was poured slowly into 600 mL water and stirred for 10 minutes. The resultant solids were filtered and dried to afford 5-bromo-3-(1,3,5-trimethyl-1H-pyrazol-4-yloxy)picolinonitrile (23.70 g, 97.74% yield) as very lightly tan (white) solid.

Step E: A flask was charged with 5-bromo-3-(1,3,5-trimethyl-1H-pyrazol-4-yloxy)picolinonitrile (27.77 g, 90.41 mmol), pyridine-2-thiol (10.55 g, 94.93 mmol), and DMF (300 mL). The reaction was cooled to 0° C. and 95% sodium hydride (2.741 g, 108.5 mmol) was added portionwise. The reaction was stirred at ambient temperature overnight, then carefully diluted with water (2 L) and extracted with ethyl acetate. The organic layer was washed with brine (4×500 mL), dried over sodium sulfate and concentrated to afford 5-(pyridin-2-ylthio)-3-(1,3,5-trimethyl-1H-pyrazol-4-yloxy)picolinonitrile (29.50 g, 87.43 mmol, 96.70% yield) as yellow solid.

Step F: A flask was charged with 5-(pyridin-2-ylthio)-3-(1,3,5-trimethyl-1H-pyrazol-4-yloxy)picolinonitrile (35.19 g, 88.1 mmol), and sulfuric acid (227.3 g, 2317 mmol) and stirred at ambient temperature overnight. Water (100 mL) was slowly added to the reaction which was cooled in an ice bath, then ice (150 g) was added. 40% NaOH was slowly added until the pH was about 12. The mixture was extracted ethyl acetate (750 mL×2), and dichloromethane (500 mL). The organic layers were dried over sodium sulfate and concentrated in vacuo to afford 5-(pyridin-2-ylthio)-3-(1,3,5-trimethyl-1H-pyrazol-4-yloxy)picolinamide (27.69 g, 77.9 mmol, 89% yield).

Step G: A flask was charged with potassium hydroxide (78.8 ml, 236 mmol), and bromine (4.04 ml, 78.8 mmol), and the mixture was stirred at ambient temperature for 15 minutes. 5-(Pyridin-2-ylthio)-3-(1,3,5-trimethyl-1H-pyrazol-4-yloxy)picolinamide (14 g, 39.4 mmol) in dioxane (280 mL) was added and the reaction was stirred at ambient temperature overnight. Water (300 mL) was added and the mixture was extracted with ethyl acetate. The organic layer was dried over sodium sulfate, filtered and concentrated. The residue was purified over silica gel (50 to 100% ethyl acetate in hexanes) to afford 5-(pyridin-2-ylthio)-3-(1,3,5-trimethyl-1H-pyrazol-4-yloxy)pyridin-2-amine (4.64 g, 14.18 mmol, 36% yield) as yellow solid.

Step H: To 1000 mL of DI water was added hydroxyl amine hydrochloride (51.0 g, 734 mmol) and the reaction was stirred for 5 minutes. Sodium carbonate (38.1 g, 360 mmol) was added in 3 large portions and the reaction was stirred for 15 minutes. THF (700 mL) was added, followed by (R)-1,4-dioxaspiro[4.5]decane-2-carbaldehyde (125 g, 734 mmol) in 800 mL of THF. The reaction was stirred for 4 hours, then poured into a 4 L separatory funnel. The layers were separated and the aqueous layer was extracted twice with MTBE (about 3000 mL total). The combined organic layers were washed with water (700 mL) and brine (300 mL), dried over MgSO$_4$ and concentrated in vacuo to afford (S)-1,4-dioxaspiro[4.5]decane-2-carbaldehyde oxime (135 g, 99%) as a clear viscous oil.

Step I: To a 4-neck 2 L round bottom flask was added (S)-1,4-dioxaspiro[4.5]decane-2-carbaldehyde oxime (135.1 g, 729.4 mmol) and dissolved in 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours. The reaction was diluted with 2 L of MTBE and washed with 1 L of water. The water was extracted with 500 mL of MTBE. The combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step J: to a 4 neck 5 L flask was added (R)-N-hydroxy-1,4-dioxaspiro[4.5]decane-2-carbimidoyl chloride (158 g, 719 mmol) in 2.5 L of THF. The mixture was cooled to 3° C., and methanesulfonyl chloride (56.1 ml, 719 mmol) was added in 10 mL portions over 10 minutes. N-ethyl-N-isopropylpropan-2-amine (126 ml, 719 mmol) was added through an addition funnel over 12 minutes. The reaction was stirred in the ice bath for 30 minutes and then at ambient temperature for 1 hour. The reaction was filtered and the solids washed with MTBE (about 3 L). The filtrate was concentrated and the residue was purified by chromatography (3 kg silica, 7:1 to 3:1 Hex/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step K: A flask was charged with (R)-N-(methylsulfonyloxy)-1,4-dioxaspiro[4.5]decane-2-carbimidoyl chloride (2.32 g, 7.79 mmol), sodium thiocyanate (0.557 g, 6.87 mmol), pyridine (1.67 ml, 20.6 mmol), and acetonitrile (100 mL). The reaction was heated to 40° C. for 30 minutes, then 5-(pyridin-2-ylthio)-3-(1,3,5-trimethyl-1H-pyrazol-4-yloxy)pyridin-2-amine (1.5 g, 4.58 mmol) was added and the reaction was heated to 70° C. overnight. Water was added and the reaction was extracted with ethyl acetate and dichloromethane. The combined organic layers were dried over sodium sulfate, filtered and concentrated in vacuo. The residue was purified over silica gel (50-100% ethyl acetate in hexanes) to afford (S)-N-(5-(pyridin-2-ylthio)-3-(1,3,5-trimethyl-1H-pyrazol-4-yloxy)pyridin-2-yl)-3-(1,4-dioxaspiro[4.5]decan-2-yl)-1,2,4-thiadiazol-5-amine (1.38 g, 2.50 mmol, 54.6% yield) as yellow solid.

Step L: A flask was charged with (S)-N-(5-(pyridin-2-ylthio)-3-(1,3,5-trimethyl-1H-pyrazol-4-yloxy)pyridin-2-yl)-3-(1,4-dioxaspiro[4.5]decan-2-yl)-1,2,4-thiadiazol-5-amine (1.38 g, 2.50 mmol), ethanol (50 mL), and 3M HCl (1.67 ml, 5.00 mmol) and heated to 75° C. for 1 hour. The reaction was cooled to ambient temperature, and saturated aqueous sodium bicarbonate was added slowly. The mixture was extracted with ethyl acetate and dichloromethane. The combined organic layers were dried over sodium sulfate, filtered and concentrated in vacuo. The residue was purified over silica gel (50 to 100% ethyl acetate in hexanes followed 5% methanol in ethyl acetate). The product was dissolved in 10% methanol in dichloromethane and 5 mL 2M HCl in ether was added. The solution was concentrated and dried in a vacuum oven to afford (S)-1-(5-(5-(pyridin-2-ylthio)-3-(1,3,5-trimethyl-1H-pyrazol-4-yloxy)pyridin-2-ylamino)-1,2,4-thiadiazol-3-yl)ethane-1,2-diol hydrochloride (0.958 g, 1.65 mmol, 65.9% yield) as yellow solid. Mass Spectrum (apci) m/z=472.1 (M+H—HCl).

Example 148

(S)-1-(5-(5-(2-methoxyethylthio)-3-(1,3,5-trimethyl-1H-pyrazol-4-yloxy)pyridin-2-ylamino)-1,2,4-thiadiazol-3-yl)ethane-1,2-diol hydrochloride

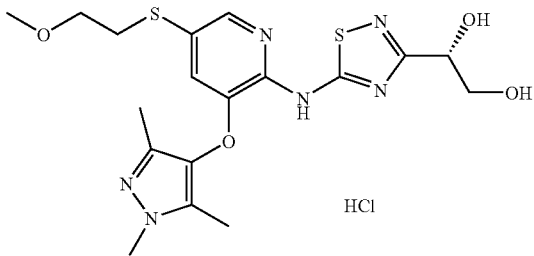

Step A: A flask was charged with powdered potassium hydroxide (21.89 g, 390.2 mmol), benzoic acid (47.65 g, 390.2 mmol), and DMF (500 mL) was added. The mixture was heated at 50° C. for 1 hour. 3-Chloropentane-2,4-dione (52.5 g, 390.2 mmol) and the reaction was stirred at 50° C. overnight. The reaction was cooled to ambient temperature, diluted in water (1.5 L) and extracted with ether (3×500 mL). The combined organic layers were washed with water, saturated NH$_4$Cl and brine. The organic layer was dried over sodium sulfate and concentrated in vacuo to afford 2,4-dioxopentan-3-yl benzoate (82.59 g, 96.12% yield) as yellow oil.

Step B: A flask was charged with 2,4-dioxopentan-3-yl benzoate (82.59 g, 375.0 mmol) and ethanol (1.5 L). To this solution was added methylhydrazine (39.90 ml, 750.1 mmol) in ethanol (150 mL). The reaction was stirred at ambient temperature for 2 hours and concentrated in vacuo to afford 1,3,5-trimethyl-1H-pyrazol-4-yl benzoate (80 g, 92.6% yield).

Step C: A flask was charged with 1,3,5-trimethyl-1H-pyrazol-4-yl benzoate (80 g, 347 mmol), and 500 mL ethanol. To the above mixture was added 3M NaOH (174 ml, 521 mmol) and stirred at ambient temperature for 2 hours. The ethanol was removed in vacuo and the aqueous layer was extracted with dichloromethane, ethyl acetate and dichloromethane: isopropyl alcohol (4:1). The combined organic layers were dried over sodium sulfate, filtered and concentrated in vacuo to afford 1,3,5-trimethyl-1H-pyrazol-4-ol (34 g, 78% yield) as white solid.

Step D: A flask was charged with 1,3,5-trimethyl-1H-pyrazol-4-ol (10.46 g, 82.89 mmol), and DMF:dioxane (9:1) (700 mL). The reaction mixture was cooled to 0° C. and 60% sodium hydride (3.315 g, 82.89 mmol) was added portionwise. The reaction mixture was stirred for 15 minutes, then 5-bromo-3-nitropicolinonitrile (18 g, 78.95 mmol) was added and the reaction was stirred at ambient temperature for 3 hours. The reaction was poured slowly into 600 mL water and stirred for 10 minutes. The resultant solids were filtered and dried to afford 5-bromo-3-(1,3,5-trimethyl-1H-pyrazol-4-yloxy)picolinonitrile (23.70 g, 97.74% yield) as very lightly tan (white) solid.

Step E: A flask was charged with 5-bromo-3-(1,3,5-trimethyl-1H-pyrazol-4-yloxy)picolinonitrile (7.0 g, 23 mmol) and H$_2$SO$_4$ (56 g, 570 mmol) and the reaction was stirred at ambient temperature overnight. The reaction was cooled in an ice bath and water (100 mL) was carefully added. 40% NaOH solution was slowly added till the pH was about 12. The mixture was extracted with ethyl acetate and dichloromethane, and the combined organic layers were dried over sodium sulfate, filtered and concentrated in vacuo to afford 5-bromo-3-(1,3,5-trimethyl-1H-pyrazol-4-yloxy)picolinamide (7.4 g, 23 mmol, 100% yield) as light yellow solid.

Step F: A flask was charged with 3M KOH (45.5 ml, 137 mmol) and bromine (1.98 ml, 38.7 mmol) and the reaction was stirred for 5 minutes at ambient temperature. 5-Bromo-3-(1,3,5-trimethyl-1H-pyrazol-4-yloxy)picolinamide (7.4 g, 22.8 mmol) in dioxane (150 mL) was added and the reaction was stirred at ambient temperature for 6 hours. Water was added and the reaction was extracted with ethyl acetate. The combined organic layers were dried over sodium sulfate, filtered and concentrated in vacuo. The residue was purified over silica gel (50 to 100% ethyl acetate in hexanes) to afford 5-bromo-3-(1,3,5-trimethyl-1H-pyrazol-4-yloxy)pyridin-2-amine (3.8 g, 12.8 mmol, 56.2% yield) as yellow solid.

Step G: To 1000 mL of DI water was added hydroxyl amine hydrochloride (51.0 g, 734 mmol) and the mixture was stirred for 5 minutes. Sodium carbonate (38.1 g, 360 mmol) was added in 3 large portions and the reaction was stirred for 15 minutes. THF (700 mL) was added, followed by (R)-1,4-dioxaspiro[4.5]decane-2-carbaldehyde (125 g, 734 mmol) in 800 mL of THF. The reaction was stirred for 4 hours. The layers separated and the aqueous layer was extracted twice with MTBE (about 3000 mL total). The combined organic layers were washed with water (700 ml) and brine (300 mL), dried over MgSO$_4$, and concentrated in vacuo to afford (S)-1,4-dioxaspiro[4.5]decane-2-carbaldehyde oxime (135 g, 99%) as a clear viscous oil.

Step H: To a 4-neck 2 L round bottom flask was added (S)-1,4-dioxaspiro[4.5]decane-2-carbaldehyde oxime (135.1 g, 729.4 mmol) and 750 mL of DMF. The reaction was placed in a water bath and 1-chloropyrrolidine-2,5-dione (97.40 g, 729.4 mmol) was added in portions over 2 minutes. The reaction was stirred in the water bath for 3 hours, then diluted with 2 L of MTBE and washed with 1 L of water. The aqueous layer was extracted with 500 mL of MTBE. The combined organic layers were washed with water (5×800 mL) and brine (300 mL), dried over MgSO$_4$ and concentrated in vacuo to afford added (R)-N-hydroxy-1,4-dioxaspiro[4.5]decane-2-carbimidoyl chloride (158 g, 98%) as a green viscous oil.

Step I: To a 4 neck 5 L flask was added (R)-N-hydroxy-1,4-dioxaspiro[4.5]decane-2-carbimidoyl chloride (158 g, 719 mmol) in 2.5 L of THF. The mixture was cooled to 3° C. and methanesulfonyl chloride (56.1 ml, 719 mmol) added in 10 mL portions over 10 minutes. N-ethyl-N-isopropylpropan-2-amine (126 ml, 719 mmol) was added through an addition funnel over 12 minutes. The reaction was stirred in an ice bath for 30 minutes and then at ambient temperature for 1 hour. The reaction was filtered and the solids were washed with MTBE (about 3 L). The filtrate was concentrated and the residue was purified by chromatography (3 kg silica, 7:1 to 3:1 Hexane/EtOAc) to afford an oil that slowly solidified under vacuum. The solids were ground using a mortar and pestle, washed with hexanes (about 1000 mL) and dried to afford (R)-N-(methylsulfonyloxy)-1,4-dioxaspiro[4.5]decane-2-carbimidoyl chloride (158 g, 531 mmol, 73.8% yield) as a white solid.

Step J: A flask was charged with (R)-N-(methylsulfonyloxy)-1,4-dioxaspiro[4.5]decane-2-carbimidoyl chloride (1.53 g. 5.15 mmol), pyridine (1.25 ml, 15.4 mmol), sodium thiocyanate (0.417 g, 5.15 mmol) and acetonitrile (15 mL). The solution was heated to 40° C. for 40 minutes. 5-Bromo-3-(1,3,5-trimethyl-1H-pyrazol-4-yloxy)pyridin-2-amine (1.02 g, 3.43 mmol) was added and the reaction was heated to 70° C. overnight. The reaction was cooled to ambient temperature, partitioned between EtOAc and water, dried over sodium sulfate, filtered and concentrated. The residue was purified over silica gel (10% MeOH/EtOAc) to afford (S)-N-

(5-bromo-3-(1,3,5-trimethyl-1H-pyrazol-4-yloxy)pyridin-2-yl)-3-(1,4-dioxaspiro[4.5]decan-2-yl)-1,2,4-thiadiazol-5-amine (1.66 g, 3.18 mmol, 92.7% yield) as a yellow solid.

Step K: A sealed tube was charged with (S)-N-(5-bromo-3-(1,3,5-trimethyl-1H-pyrazol-4-yloxy)pyridin-2-yl)-3-(1,4-dioxaspiro[4.5]decan-2-yl)-1,2,4-thiadiazol-5-amine (0.550 g, 1.055 mmol), Pd₂(dba)₃ (0.06065 g, 0.1055 mmol), K₃PO₄ (0.5821 g, 2.742 mmol), Xantphos (0.1221 g, 0.2110 mmol), and degassed toluene (5 mL). Nitrogen was bubbled through the solution for 5 minutes. Methyl 3-mercaptopropanoate (0.1752 ml, 1.582 mmol) was added and the reaction was heated to 100° C. overnight. The reaction was cooled to ambient temperature, water was added and the reaction was extracted with ethyl acetate. The organic layer was dried over sodium sulfate, filtered and concentrated in vacuo. The residue was purified over silica gel (50 to 100% ethyl acetate in hexanes) to afford (S)-methyl 3-(6-(3-(1,4-dioxaspiro[4.5]decan-2-yl)-1,2,4-thiadiazol-5-ylamino)-5-(1,3,5-trimethyl-1H-pyrazol-4-yloxy)pyridin-3-ylthio)propanoate (0.276 g, 0.4923 mmol, 46.67% yield) as yellow oil.

Step L: To a solution of (S)-methyl 3-(6-(3-(1,4-dioxaspiro[4.5]decan-2-yl)-1,2,4-thiadiazol-5-ylamino)-5-(1,3,5-trimethyl-1H-pyrazol-4-yloxy)pyridin-3-ylthio)propanoate (0.420 g, 0.749 mmol) in THF (10 mL) was added potassium 2-methylpropan-2-olate (2.36 ml, 2.36 mmol) and the reaction was stirred at ambient temperature for 5 minutes. 1-Bromo-2-methoxyethane (0.132 g, 0.899 mmol) (as a solution in 2 mL THF) and DMF (1 mL) were added and the reaction was stirred for 20 minutes at ambient temperature. The solution was quenched with water, extracted with CH₂Cl₂, dried over sodium sulfate, filtered and concentrated. The residue was purified over silica gel (100% EtOAc) to afford (S)-N-(5-(2-methoxyethylthio)-3-(1,3,5-trimethyl-1H-pyrazol-4-yloxy)pyridin-2-yl)-3-(1,4-dioxaspiro[4.5]decan-2-yl)-1,2,4-thiadiazol-5-amine (0.200 g, 50.1% yield).

Step M: A flask was charged with (S)-N-(5-(2-methoxyethylthio)-3-(1,3,5-trimethyl-1H-pyrazol-4-yloxy)pyridin-2-yl)-3-(1,4-dioxaspiro[4.5]decan-2-yl)-1,2,4-thiadiazol-5-amine (0.200 g, 0.375 mmol), 3M HCl (0.751 ml, 0.751 mmol), and ethanol (5 mL). The reaction was heated to 80° C. for 1 hour and then cooled to ambient temperature. The reaction was concentrated in vacuo and purified using reverse phase chromatography (5 to 95% acetonitrile in water) to afford (S)-1-(5-(5-(2-methoxyethylthio)-3-(1,3,5-trimethyl-1H-pyrazol-4-yloxy)pyridin-2-ylamino)-1,2,4-thiadiazol-3-yl)ethane-1,2-diol hydrochloride (0.165 g, 0.298 mmol, 79.4% yield) as white solid after HCl salt formation. Mass Spectrum (apci) m/z=453.1 (M+H—HCl).

Example 149

(R)-1-(5-(3-(2-methylpyridin-3-yloxy)-5-(pyridin-2-ylthio)pyridin-2-ylamino)-1,2,4-thiadiazol-3-yl)ethane-1,2-diol

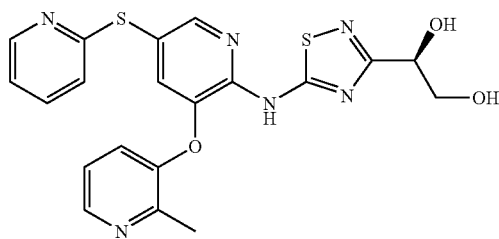

Step A: To a solution of (S)-1-(2,2-dimethyl-1,3-dioxolan-4-yl)ethanone (10.5 g, 72.8 mmol) in 150 (mL) THF: 60 mL was added hydroxylamine hydrochloride (5.06 g, 72.8 mmol), and the reaction was stirred for 20 minutes. Na₂CO₃ (3.78 g, 35.7 mmol) was added and the reaction was stirred overnight. The reaction was extracted with ethyl acetate, washed with water and brine, dried over MgSO₄, filtered and concentrated to afford (R)-2,2-dimethyl-1,3-dioxolane-4-carbaldehyde oxime (10.3 g, 71.0 mmol, 97.4% yield).

Step B: To a solution of (R)-2,2-dimethyl-1,3-dioxolane-4-carbaldehyde oxime (10.3 g, 71.0 mmol) in 40 mL DMF was added 1-chloropyrrolidine-2,5-dione (10.4 g, 78.1 mmol) and the reaction was stirred overnight at ambient temperature. The reaction mixture was poured into ether (1400 mL) and water (500 mL). The ether layer was extracted with water (5×500 mL), dried over MgSO₄, filtered and concentrated to (S)-N-hydroxy-2,2-dimethyl-1,3-dioxolane-4-carbimidoyl chloride (10.0 g, 55.7 mmol, 78.5% yield) as white solid.

Step C: A solution of (S)-N-hydroxy-2,2-dimethyl-1,3-dioxolane-4-carbimidoyl chloride (9.88 g, 55.01 mmol) in THF (200 mL) at 0° C. was added methanesulfonyl chloride (4.703 ml, 60.51 mmol), followed by N,N-diisopropylethylamine (10.54 ml, 60.51 mmol) and the reaction was stirred for 1 hour at ambient temperature, filtered and concentrated in vacuo. The residue was purified over silica gel (25 to 100% ethyl acetate in hexanes) to afford (S)-2,2-dimethyl-N-(methylsulfonyloxy)-1,3-dioxolane-4-carbimidoyl chloride (12.28 g, 47.65 mmol, 86.63% yield) as colorless oil.

Step D: To 600 mL of DMF in a 4 neck 3000 mL round bottom flask equipped with an overhead stir mechanism under nitrogen was added 2-methylpyridin-3-ol (71.8 g, 658 mmol) and the mixture was cooled to 2° C. 60% Sodium hydride (26.3 g, 658 mmol) was added over 30 minutes while maintaining the internal temperature below 10° C. The reaction was stirred while warming to ambient temperature for 1 hour. 5-Bromo-3-nitropicolinonitrile (150 g, 658 mmol) in a solution of 400 mL of DMF was added in two portions and the reaction was held at ambient temperature for 1.5 hours. Pyridine-2-thiol (73.1 g, 658 mmol) was added as a solid in portions and the reaction was stirred for 15 minutes to dissolved the material, then cooled to 3° C. Sodium hydride (26.3 g, 658 mmol) was added in portions over 35 minutes while maintaining the internal temperature below 10° C. The reaction was removed from the ice bath and warmed to ambient temperature while stirring for 12 hours. The reaction was diluted with 4 volumes (8 L) of brine and stirred for 30 minutes, at which point solid formed. The solid was filtered off and filtrate extracted with MTBE (10 L total). The MTBE phase was concentrated in vacuo. The solid was combined with concentrated material and dissolved in ethyl acetate (3 L). The organic layer was washed with brine (4×1 L), dried over MgSO₄, filtered and concentrated in vacuo. The solid that formed was ground into a powder and dried in vacuo for 4 hours. The powder was taken up in 30 mL of MTBE/10 g of product and the mixture was stirred for 30 minutes. The solid was filtered and dried in vacuo (2 hours). The mother liquor was concentrated and triturated with MTBE (same diluted rate). The solids were combined and dried for 3 hours in vacuo to yield 3-(2-methylpyridin-3-yloxy)-5-(pyridin-2-ylthio)picolinonitrile (181 g, 85%).

149

Step E: To concentrated H₂SO₄ (90 mL) cooled with an ice bath was added 3-2-methylpyridin-3-yloxy)-5-(pyridin-2-ylthio)picolinonitrile (43 g, 130 mmol) in portions such that the internal temp did not exceed 50° C. but did not go below 25° C. After complete addition, the mixture was stirred in the ice bath until the reaction started to cool, at which point the reaction was removed from the ice bath and the mixture was heated to 50° C. The reaction was cooled to ambient temperature and the mixture added to ice water slowly over 3 minutes (about 1400 mL of 30% ice in water). The mixture was further cooled in an ice bath to 5° C. The mixture was neutralized to about pH with 4M NaOH (about 800 mL) while maintaining the internal temperature below 20° C., at which point a solid formed. The mixture was stirred for 20 minutes. The mixture was filtered and washed with MTBE (5×150 mL), hexanes (5×100 mL), and dried at under vacuum to afford 3-(2-methylpyridin-3-yloxy)-5-(pyridin-2-ylthio)picolinamide (43 g, 96%).

Step F: To a solution of NaOH (2M, 90 mL, 182 mmol) at 0° C. was added bromine (8.71 g, 54 mmol) and the reaction was stirred at 0° C. for 30 minutes. 5-Bromo-3-(2-methylpyridin-3-yloxy)picolinamide (11.2 g, 36.3 mmol) in dioxanes (100 mL) was added and the reaction was stirred at ambient temperature for 1 hour, followed by heating to 80° C. for 1 hour. The reaction was cooled to ambient temperature and acidified to pH 1 using concentrated HCl. The reaction was basified and a solid precipitated. The solid was filtered and dried in vacuo to yield 5-bromo-3-(2-methylpyridin-3-yloxy)pyridin-2-amine (4.1 g, 41%).

Step G: A flask was charged with (S)-2,2-dimethyl-N-(methylsulfonyloxy)-1,3-dioxolane-4-carbimidoyl chloride (4.5 g, 18 mmol), sodium thiocyanate (1.3 g, 15 mmol), pyridine (3.8 ml, 46 mmol), and ethyl acetate (200 mL). The reaction was stirred and heated at 40° C. for 45 minutes. 3-(2-Methylpyridin-3-yloxy)-5-(pyridin-2-ylthio)pyridin-2-amine (3.2 g, 10 mmol) was added and the reaction was stirred at 70° C. overnight. Water was added and the reaction was extracted with ethyl acetate, dried over sodium sulfate, filtered and concentrated. The residue was purified over silica gel (25 to 100% ethyl acetate in hexanes) to afford (R)-3-(2,2-dimethyl-1,3-dioxolan-4-yl)-N-(3-(2-methylpyridin-3-yloxy)-5-(pyridin-2-ylthio)pyridin-2-yl)-1,2,4-thiadiazol-5-amine (3.8 g, 7.7 mmol, 75% yield).

Step H: A flask was charged with (R)-3-(2,2-dimethyl-1,3-dioxolan-4-yl)-N-(3-(2-methylpyridin-3-yloxy)-5-(pyridin-2-ylthio)pyridin-2-yl)-1,2,4-thiadiazol-5-amine (3.8 g, 7.683 mmol) and added ethanol (40 mL). 3M HCl (5.122 ml, 15.37 mmol) was added, and the reaction was heated to 70° C. for 1 hour, then cooled to ambient temperature. The ethanol removed in vacuo and saturated sodium bicarbonate solution was added. The aqueous layer was extracted with ethyl acetate. The majority of product crashed out of the aqueous layer and collected by filtration. The solids and residue from organic layer were purified over silica gel (10-15% methanol in ethyl acetate) to afford (R)-1-(5-(3-(2-methylpyridin-3-yloxy)-5-(pyridin-2-ylthio)pyridin-2-ylamino)-1,2,4-thiadiazol-4-yl)ethane-1,2-diol (2.877 g, 6.330 mmol, 82.38% yield) as yellow solid. Mass Spectrum (apci) m/z=455.1 (M+H).

150

Example 150

(S)-2-(5-(3-(2-methylpyridin-3-yloxy)-5-(pyridin-2-ylthio)pyridin-2-ylamino)-1,2,4-thiadiazol-3-yl)propane-1,2-diol hydrochloride

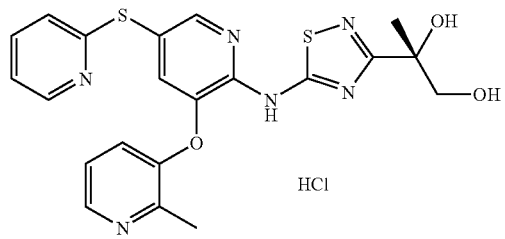

Step A: To 600 mL of DMF in a 4 neck 3000 mL round bottom flask equipped with an overhead stir mechanism under nitrogen was added 2-methylpyridin-3-ol (71.8 g, 658 mmol) and the reaction was cooled to 2° C. Sodium hydride (60%; 26.3 g, 658 mmol) was added over a period of 30 minutes at a rate such that the internal temperature did not exceed 10° C. The reaction was stirred while warming to ambient temperature for 1 hour. 5-Bromo-3-nitropicolinonitrile (150 g, 658 mmol) in a solution of 400 mL of DMF was added in two portions and the reaction was held at ambient temperature for 1.5 hour. To the reaction at ambient temperature was added pyridine-2-thiol (73.1 g, 658 mmol) as a solid in portions and the reaction was stirred for 15 minutes to dissolve the material. The reaction was cooled to 3° C. and sodium hydride (26.3 g, 658 mmol) was added in portions over 35 minutes at a rate such that the internal temperature did not go above 10° C. The reaction was removed from the ice bath and warmed to ambient temperature while stirring for 12 hour. The reaction was diluted with 4 volumes (8 L) of brine and stirred for 30 minutes, at which point solid formed. The solid was filtered off and the filtrate was extracted with MTBE (10 L total). The MTBE phase was concentrated in vacuo. The solid was combined with concentrated material and dissolved in ethyl acetate (3 L). The EtOAc was washed with brine (4×1 L), dried over MgSO₄, filtered and concentrated in vacuo. The solid that formed was ground into a powder and dried in vacuo for 4 hours. The powder was taken up in 30 mL of MTBE/10 g of product and the mixture was stirred for 30 minutes. The solid was filtered and dried in vacuo (2 hours). The mother liquor was concentrated and triturated with MTBE (same dilution rate). The solids were combined and dried for 3 hours in vacuo to yield 3-(2-methylpyridin-3-yloxy)-5-(pyridin-2-ylthio)picolinonitrile (181 g, 85%)

Step B: To concentrated H₂SO₄ (90 mL) cooled with an ice bath was added 3-(2-methylpyridin-3-yloxy)-5-(pyridin-2-ylthio)picolinonitrile (43 g, 130 mmol) in portions such that the internal temperature did not exceed 50° C. but did not go below 25° C. After complete addition, the mixture was stirred in the ice bath until the reaction started to cool, at which point the reaction was removed from the ice bath and the mixture was heated to 50° C. The reaction was cooled to ambient temperature and then added to ice water slowly over 3 minutes (about 1400 mL of 30% ice in water). The mixture was further cooled in an ice bath to 5° C. and neutralized to about pH 10 with 4M NaOH (about 800 mL) while maintaining the internal temperature below 20° C., at which point a solid formed. The mixture was stirred for 20 minutes, then filtered and washed with MTBE (5×150 mL) and hexanes (5×100 mL), and dried at under vacuum to afford (3-(2-methylpyridin-3-yloxy)-5-(pyridin-2-ylthio)picolinamide (43 g, 96%).

Step C: To a 3-neck 2 L round bottom flask was added 2M aqueous sodium hydroxide (343 ml, 686 mmol) and the solution was cooled in an ice bath. Bromine (12 ml, 257 mmol) was added and the reaction was stirred for 30 minutes while the ice bath was removed. 3-(2-Methylpyridin-3-yloxy)-5-(pyridin-2-ylthio)picolinamide (58 g, 171 mmol) was added as a slurry in about 600 mL of dioxanes in 1 portion. After 30 minutes, concentrated HCl was added in 1 mL portions to adjust the mixture to about pH 1. The reaction was stirred for 15 minutes and 4N NaOH was added to the solution to about pH 10. The aqueous mixture was extracted with EtOAc (3×750 mL), washed with water (2×250 mL) and brine (300 mL), dried over $MgSO_4$, filtered and concentrated. The material was dried in vacuo at 50° C. at which point a red solid formed. The solid was triturated with $CH_2Cl_2$ and dried under vacuum at 50° C. The filtrate was concentrated in vacuo and material purified over silica gel (3% $MeOH/CH_2Cl_2$) to afford a red solid. The two crops were combined to afford 3-(2-methylpyridin-3-yloxy)-5-(pyridin-2-ylthio)pyridin-2-amine (24 g, 45%).

Step D: O,N-dimethylhydroxylamine hydrochloride (74.6 g, 765 mmol) was dissolved in THF (1 L) and pyridine (123 ml, 1531 mmol) was added and stirred for 30 minutes. Methacryloyl chloride (37.4 ml, 383 mmol) was added slowly and stirred overnight. The solids were filtered and concentrated. The residue was partitioned between water and $CH_2Cl_2$, washed with water, dried over sodium sulfate, filtered and concentrated to afford N-methoxy-N-methylmethacrylamide (56.5 g, 335 mmol, 87.5% yield).

Step E: A round bottom flask was charged with t-BuOH (850 mL), water (850 mL), Ad-Mix-α (230 g, 166 mmol) and methanesulfonamide (15.8 g, 166 mmol). The mixture was stirred at ambient temperature until both phases were clear (about 5 minutes) and then cooled to 0° C., after which orange salts precipitated. N-methoxy-N-methylmethacrylamide (21.5 g, 166 mmol) was added and the heterogeneous slurry was stirred vigorously at 0° C. for 2 hours, warmed to ambient temperature and stirred for 24 hours. The reaction was quenched by the slow, portionwise addition of sodium bisulfite (223 g) and stirred for 1 hour. The reaction mixture was extracted with EtOAc (3×300 mL), dried over sodium sulfate, filtered and concentrated to afford (R)-2,3-dihydroxy-N-methoxy-N,2-dimethylpropanamide (32.7 g, 200 mmol, 120% yield) as a yellow oil.

Step F: (R)-2,3-dihydroxy-N-methoxy-N,2-dimethylpropanamide (32 g, 196 mmol) was dissolved in 2,2-dimethoxypropane (241 ml, 1961 mmol) and 4-methylbenzenesulfonic acid hydrate (3.73 g, 19.6 mmol) was added and stirred at ambient temperature overnight. The reaction was partitioned between saturated aqueous sodium bicarbonate and $CH_2Cl_2$, extracted with $CH_2Cl_2$, dried over sodium sulfate, filtered and concentrated to afford (R)-N-methoxy-N,2,2,4-tetramethyl-tetramethyl-1,3-dioxolane-4-carboxamide (22.9 g, 113 mmol, 57.5% yield).

Step G: (R)-N-methoxy-N,2,2,4-tetramethyl-1,3-dioxolane-4-carboxamide (22.9 g, 113 mmol) was dissolved in THF (500 mL) and cooled to −78° C. 1M LAH (124 ml, 124 mmol) was added slowly through an addition funnel over about 30 minutes. The reaction was stirred for another 30 minutes, a saturated aqueous $NH_4Cl$ was added (125 mL) and the reaction was allowed to warm to ambient temperature. After filtration, the slurry mixture was washed several times with EtOAc, and concentrated to afford crude (R)-2,2,4-trimethyl-1,3-dioxolane-4-carbaldehyde (10 g, 69.4 mmol, 61.6% yield) which was taken on to next reaction without further purification.

Step H: (R)-2,2,4-Trimethyl-1,3-dioxolane-4-carbaldehyde (6.9 g, 48 mmol) was dissolved in 1:1 methanol water (100 mL), and hydroxylamine hydrochloride (3.3 g, 48 mmol) and $Na_2CO_3$ (2.5 g, 24 mmol) were added. The reaction was stirred at ambient temperature overnight. The methanol was removed in vacuo and the remaining material was extracted with $CH_2Cl_2$, dried over sodium sulfate, filtered and concentrated to afford (S)-2,2,4-trimethyl-1,3-dioxolane-4-carbaldehyde oxime (5.7 g, 36 mmol, 75% yield).

Step I: (S)-2,2,4-Trimethyl-1,3-dioxolane-4-carbaldehyde oxime (5.7 g, 36 mmol) was dissolved in DMF (120 mL) and 1-chloropyrrolidine-2,5-dione (4.8 g, 36 mmol) was added. The reaction was stirred at ambient temperature overnight, and then poured in water (600 mL) with stirring. After 15 minutes the cloudy suspension was extracted with EtOAc, washed with water and brine, dried over sodium sulfate, filtered and concentrated to afford (R)-N-hydroxy-2,2,4-trimethyl-1,3-dioxolane-4-carbimidoyl chloride (6.4 g, 33 mmol, 92% yield).

Step J: (R)-N-hydroxy-2,2,4-trimethyl-1,3-dioxolane-4-carbimidoyl chloride (6.4 g, 33.1 mmol) was dissolved in $Et_2O$ (150 mL) and methanesulfonyl chloride (2.21 ml, 28.4 mmol) was added. Triethylamine (3.96 ml, 28.4 mmol) was added dropwise and the reaction stirred at ambient temperature for 1 hour. The resulting solids were filtered and the filtrate was concentrated. The residue was purified over silica gel (100% $CH_2Cl_2$) to afford (R)-2,2,4-trimethyl-N-(methylsulfonyloxy)-1,3-dioxolane-4-carbimidoyl chloride (5.8 g, 21.3 mmol, 64.6% yield) as an amber oil.

Step K: (R)-2,2,4-trimethyl-N-(methylsulfonyloxy)-1,3-dioxolane-4-carbimidoyl chloride (350 mg, 1.29 mmol) was dissolved in $CH_3CN$ (6 mL). NaNCS (104 mg, 1.29 mmol) and pyridine (260 μl, 3.22 mmol) were added and the reaction was heated to 45° C. for 45 minutes. 3-(2-Methylpyridin-3-yloxy)-5-(pyridin-2-ylthio)pyridin-2-amine (200 mg, 0.644 mmol) was added and the reaction was heated to 70° C. for 24 hours. The reaction was poured into water and extracted with EtOAc, dried over sodium sulfate, filtered and concentrated. The residue was purified over silica gel (80% EtOAc in hexanes) to afford (S)-N-(3-(2-methylpyridin-3-yloxy)-5-(pyridin-2-ylthio)pyridin-2-yl)-3-(2,2,4-trimethyl-1,3-dioxolan-4-yl)-1,2,4-thiadiazol-5-amine (55 mg, 0.108 mmol, 16.8% yield).

Step L: (S)-N-(3-(2-methylpyridin-3-yloxy)-5-(pyridin-2-ylthio)pyridin-2-yl)-3-(2,2,4-trimethyl-1,3-dioxolan-4-yl)-1,2,4-thiadiazol-5-amine (55 mg, 0.108 mmol) was dissolved in EtOH (3 mL). 1M HCl (0.3 mL) was added and the mixture was stirred at ambient temperature for 24 hours. Additional 1M HCl (0.3 mL) was added and the mixture was stirred overnight. The mixture was partitioned between saturated aqueous sodium bicarbonate and $CH_2Cl_2$, dried over sodium sulfate, filtered and concentrated. The residue was purified over silica gel (15% methanol in EtOAc) to afford (S)-2-(5-(3-(2-methylpyridin-3-yloxy)-5-(pyridin-2-ylthio)pyridin-2-ylamino)-1,2,4-thiadiazol-3-yl)propane-1,2-diol hydrochloride (34.9 mg, 0.0691 mmol, 63.9% yield) as a white solid after HCl salt formation. Mass Spectrum (apci) m/Z=451.1 (M+H—$H_2O$—HCl) (100) and 469.1 (M+H—HCl) (30).

Example 151

(R)-2-(5-(3-(2-methylpyridin-3-yloxy)-5-(pyridin-2-ylthio)pyridin-2-ylamino-1,2,4-thiadiazol-3-yl)propane-1,2-diol hydrochloride

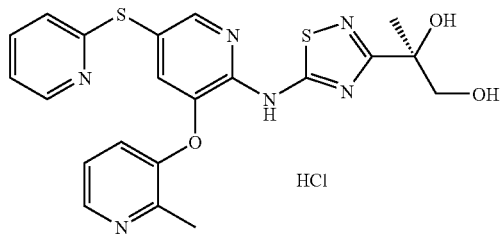

Step A: To 600 mL of DMF in a 4 neck 3000 mL round bottom flask equipped with an overhead stir mechanism under nitrogen was added 2-methylpyridin-3-ol (71.8 g, 658 mmol) and the reaction was cooled to 2° C. Sodium hydride (60%; 26.3 g, 658 mmol) was added over a period of 30 minutes at a rate such that the internal temperature did not exceed 10° C. the reaction was stirred while warming to ambient temperature for 1 hour. 5-Bromo-3-nitropicolinonitrile (150 g, 658 mmol) in a solution of 400 mL of DMF was added in two portions and the reaction held at ambient temperature for 1.5 hour. To the reaction at ambient temperature was added pyridine-2-thiol (73.1 g, 658 mmol) as a solid in portions and the reaction was stirred for 15 minutes to dissolve the material. The reaction was cooled to 3° C. and sodium hydride (26.3 g, 658 mmol) again was added in portions over 35 minutes such that the internal temperature did not go above 10° C. The reaction was removed from the ice bath and warmed to ambient temperature while stirring for 12 hours. The reaction was diluted with 4 volumes (8 L) of brine and stirred for 30 minutes, at which point solid formed. The solid was filtered off and the filtrate was extracted with MTBE (10 L total). The MTBE phase was concentrated in vacuo. The solid was combined with concentrated material and dissolved in ethyl acetate (3 L). The EtOAc was washed with brine (4×1 L), dried over $MgSO_4$, filtered and concentrated in vacuo. The solid that formed was ground into a powder and dried in vacuo for 4 hours. The material was taken up in 30 mL of MTBE/10 g of product and the reaction was stirred for 30 minutes. The solid was filtered and dried in vacuo (2 hours). The mother liquor was concentrated and triturated with MTBE (same dilution rate). The solids were combined and dried for 3 hours in vacuo to yield 3-(2-methylpyridin-3-yloxy)-5-(pyridin-2-ylthio)picolinonitrile (181 g, 85%).

Step B: To concentrated $H_2SO_4$ (90 mL) cooled with an ice bath was added 3-(2-methylpyridin-3-yloxy)-5-(pyridin-2-ylthio)picolinonitrile (43 g, 130 mmol) in portions such that the internal temperature did not exceed 50° C. but did not go below 25° C. After complete addition, the mixture was stirred in the ice bath until the reaction started to cool, at which point the reaction was removed from the ice bath and the mixture was heated to 50° C. The reaction was cooled to ambient temperature and added to ice water slowly over 3 minutes (about 1400 mL of 30% ice in water). The mixture was further cooled in an ice bath to 5° C. and neutralized to about pH 10 with 4M NaOH (about 800 mL) at a rate such that the internal temperature did not exceed 20° C., at which point a solid formed. The mixture was stirred for 20 minutes, then filtered and washed with MTBE (5×150 mL), hexanes (5×100 mL), and dried at under vacuum to afford 3-(2-methylpyridin-3-yloxy)-5-(pyridin-2-ylthio)picolinamide (43 g, 96%).

Step C: To a 3-neck 2 L round bottom flask was added 2M aqueous sodium hydroxide (343 ml, 686 mmol) and the solution was cooled in an ice bath. Bromine (12 ml, 257 mmol) was added and the reaction was stirred for 30 minutes while the ice bath was removed. 3-(2-Methylpyridin-3-yloxy)-5-(pyridin-2-ylthio)picolinamide (58 g, 171 mmol) was added as a slurry in about 600 mL of dioxanes in 1 portion. After 30 minutes, concentrated HCl was added in 1 mL portions to about pH 1. The reaction was stirred for 15 minutes and 4N NaOH was added to the solution to pH ~10. The aqueous mixture was extracted with EtOAc (3×750 mL), washed with water (2×250 mL) and brine (300 mL), dried over $MgSO_4$, filtered and concentrated. The material was dried in vacuo at 50° C. at which point a red solid formed. The solid was triturated with $CH_2Cl_2$ (about 40 mL of $CH_2Cl_2$ to 5 g of material) and the solid filtered. The solid was washed with $CH_2Cl_2$ and dried under vacuum at 50° C. the filtrate was concentrated in vacuo and the residue was purified over silica gel (3% MeOH/$CH_2Cl_2$) to afford a red solid. The two crops were combined to afford 3-(2-methylpyridin-3-yloxy)-5-(pyridin-2-ylthio)pyridin-2-amine (24 g, 45%).

Step D: O,N-dimethylhydroxylamine hydrochloride (74.6 g, 765 mmol) was dissolved in THF (1 L) and pyridine (123 ml, 1531 mmol) was added and stirred for 30 min. Methacryloyl chloride (37.4 ml, 383 mmol) was added slowly and stirred overnight. The solids were filtered and concentrated. The residue was partitioned between water and $CH_2Cl_2$, washed with water, dried over sodium sulfate, filtered and concentrated to afford N-methoxy-N-methylmethacrylamide (56.5 g, 335 mmol, 87.5% yield).

Step E: A round bottom flask was charged with $^3$BuOH (850 mL), water (850 mL), Ad-Mix-β (230 g, 166 mmol) and methanesulfonamide (15.8 g, 166 mmol). The mixture was stirred at ambient temperature until both phases were clear (about 5 minutes) and then cooled to 0° C., after which orange salts precipitated. N-methoxy-N-methylmethacrylamide (21.5 g, 166 mmol) was added and the heterogeneous slurry was stirred vigorously at 0° C. for 2 hours and warmed to ambient temperature and stirred for 24 hours. The reaction was quenched by the slow, portionwise addition of sodium bisulfite (223 g) and stirred for 1 hour. The reaction mixture was extracted with EtOAc (3×300 mL), dried over sodium sulfate, filtered and concentrated to afford (S)-2,3-dihydroxy-N-methoxy-N,2-dimethylpropanamide (32 g, 196 mmol, 118% yield) as a yellow oil.

Step F: (S)-2,3-dihydroxy-N-methoxy-N,2-dimethylpropanamide (32 g, 196 mmol) was dissolved in 2,2-dimethoxypropane (241 ml, 1961 mmol, 4-methylbenzenesulfonic acid hydrate (3.73 g, 19.6 mmol) was added, and the reaction was stirred at ambient temperature overnight. The reaction was partitioned between $CH_2Cl_2$ and saturated aqueous sodium bicarbonate, extracted with $CH_2Cl_2$, dried over sodium sulfate, filtered and concentrated. The residue was purified on silica plug (1.5 L, eluting with 25% EtOAc in hexanes) to afford (S)-N-methoxy-N,2,2,4-tetramethyl-1,3-dioxolane-4-carboxamide (23.1 g, 114 mmol, 58.0% yield).

Step G: (S)-N-methoxy-N,2,2,4-tetramethyl-1,3-dioxolane-4-carboxamide (23.1 g, 114 mmol) was dissolved in THF (600 mL) and cooled to −78° C. DIBAL-H (1M in toluene, 125 ml, 125 mmol) was added slowly through an addition funnel over about 15 minutes. The reaction was stirred for an additional 30 minutes at −78° C. and then quenched with saturated aqueous $NH_4Cl$. The mixture was partitioned between EtOAc and water. The two layers were filtered through a silica plug and separated. The organic layer was dried over sodium sulfate, filtered and concentrated to afford (S)-2,2,4-trimethyl-1,3-dioxolane-4-carbaldehyde (16.4 g, 114 mmol, 100% yield).

Step H: (S)-2,2,4-trimethyl-1,3-dioxolane-4-carbaldehyde (5.8 g, 40 mmol) was dissolved in 1:1 methanol water (100 mL) and hydroxylamine hydrochloride (2.8 g, 40 mmol) and $Na_2CO_3$ (2.1 g, 20 mmol). The reaction was stirred at ambient temperature overnight, then concentrated in vacuo. The aqueous layer was extracted with $CH_2Cl_2$, and the organic layer was dried over sodium sulfate, filtered and concentrated to afford (R)-2,2,4-trimethyl-1,3-dioxolane-4-carbaldehyde oxime (4.8 g, 30 mmol, 75% yield).

Step I: (R)-2,2,4-Trimethyl-1,3-dioxolane-4-carbaldehyde oxime (4.8 g, 30 mmol) was dissolved in DMF (100 mL) and 1-chloropyrrolidine-2,5-dione (4.0 g, 30 mmol) was added. The reaction was stirred at ambient temperature overnight, then poured in water (600 mL) with of stirring. After 15 minutes the cloudy suspension was extracted with EtOAc and washed with water and brine. The organic layer was dried over sodium sulfate, filtered and concentrated to afford (S)-N-hydroxy-2,2,4-trimethyl-1,3-dioxolane-4-carbimidoyl chloride (5.5 g, 28 mmol, 94% yield).

Step J: (S)-N-hydroxy-2,2,4-trimethyl-1,3-dioxolane-4-carbimidoyl chloride (5.5 g, 28.4 mmol) was dissolved in $Et_2O$ (150 mL) and methanesulfonyl chloride (2.21 ml, 28.4 mmol) was added. Triethylamine (3.96 ml, 28.4 mmol) was added dropwise and the reaction was stirred at ambient temperature for 1 hour. The resulting solids were filtered and the filtrate concentrated. The residue was purified over silica gel (100% $CH_2Cl_2$) to afford (S)-2,2,4-trimethyl-N-(methylsulfonyloxy)-1,3-dioxolane-4-carbimidoyl chloride (4.7 g, 17.3 mmol, 60.9% yield) as an amber oil.

Step K: (S)-2,2,4-Trimethyl-N-(methylsulfonyloxy)-1,3-dioxolane-4-carbimidoyl chloride (438 mg, 1.61 mmol) was dissolved in $CH_3CN$ (6 mL) and NaNCS (131 mg, 1.61 mmol) and pyridine (311 µL, 3.87 mmol) were added and the reaction was heated to 45° C. for 45 minutes. 3-(2-Methylpyridin-3-yloxy)-5-(pyridin-2-ylthio)pyridin-2-amine (200 mg, 0.644 mmol) was added and the reaction was heated to 70° C. for 24 hours. The reaction was poured into water and extracted with EtOAc, dried over sodium sulfate, filtered and concentrated. The residue was purified over silica gel (80% EtOAc in hexanes) to afford (R)-N-(3-(2-methylpyridin-3-yloxy)-5-(pyridin-2-ylthio)pyridin-2-yl)-3-(2,2,4-trimethyl-1,3-dioxolan-4-yl)-1,2,4-thiadiazol-5-amine (65 mg, 0.128 mmol, 19.8% yield).

Step L: (R)-N-(3-(2-methylpyridin-3-yloxy)-5-(pyridin-2-ylthio)pyridin-2-yl)-3-(2,2,4-trimethyl-1,3-dioxolan-4-yl)-1,2,4-thiadiazol-5-amine (65 mg, 0.128 mmol) was dissolved in EtOH (3 mL) and 1M HCl (0.3 mL) was added. The mixture was stirred at ambient temperature for 24 hours. Additional 1M HCl (0.3 mL) was added and the mixture was stirred overnight. The mixture was partitioned between saturated aqueous sodium bicarbonate and $CH_2Cl_2$, and the organic layer was dried over sodium sulfate, filtered and concentrated. The residue was purified over silica gel (15% methanol in EtOAc) to afford (R)-2-(5-(3-(2-methylpyridin-3-yloxy)-5-(pyridin-2-ylthio)pyridin-2-ylamino)-1,2,4-thiadiazol-3-yl)propane-1,2-diol hydrochloride (42.6 mg, 0.0844 mmol, 66.0% yield) as a white solid after HCl salt formation. Mass Spectrum (apci) m/z=469.1 (M+H—HCl).

Example A

In Vitro Glucokinase Assays

The in vitro efficacy of glucokinase activators of the present invention was assessed in two separate assays: an $EC_{50}$ assay to evaluate the potency of each compound at a fixed, physiologically relevant concentration of glucose, and a glucose $S_{0.5}$ assay at a fixed, near saturating (if possible) concentration of compound to evaluate its effect on the $V_m$ and $S_{0.5}$ for glucose. For each of these assays, glucokinase activity was estimated by monitoring the increase in absorbance at 340 nm in a coupled assay system containing NAD+ and glucose 6-phosphate dehydrogenase. Assays were conducted at 30° C. using a thermostatically controlled absorbance plate reader (Spectramax 340PC, Molecular Devices Corp.) and clear, 96-well, flat bottom polystyrene plates (Costar 3695, Corning). Each 50-µL assay mixture contained 10 mM K+MOPS, pH 7.2, 2 mM $MgCl_2$, 50 mM KCl, 0.01% Triton X-100, 2% DMSO, 1 mM DTT, 1 mM ATP, 1 mM NAD+, 5 U/mL glucose 6-phosphate dehydrogenase, approximately 5 or 0.2 nM human glucokinase and (depending on the assay) varying concentrations of glucose and test compound. The absorbance at 340 nm was monitored kinetically over a period of 5 minutes (10 s/cycle), and rate were estimated from the slopes of linear fits to the raw data.

Glucokinase $EC_{50}$ Assay:

For this assay, the glucose concentration was fixed at 5 mM, while the control or test compound was varied over a 10-point, 3-fold dilution series and typically ranged from a high dose of 50 µM to a low dose of approximately 2.5 nM. In certain assays, the plasma protein binding potential of each of the test compounds was assessed by the inclusion of 4% human serum albumin (HSA) in the assay buffer and comparing the estimated $EC_{50}$ value with that determined in the absence of HSA.

In each case (with or without HAS), a standard, four-parameter logistic model (Equation 1) was fit to the raw data (rate versus concentration of compound):

$$y = A + \frac{B - A}{1 + \left[\frac{C}{x}\right]^D} \quad (1)$$

where x is the concentration of compound, y is the estimated rate, A and B are the lower and upper asymptotes, respectively, C is the $EC_{50}$ and D is the Hill slope. The $EC_{50}$ is defined as the midpoint or inflection point between the upper and lower asymptotes.

The compounds exemplified herein have been found to have an $EC_{50}$ in the range of 6 and 50,000 nM in the above described assay. Certain compounds exemplified herein have been found to have an $EC_{50}$ in the range of 2 and 5000 nM. Certain compound exemplified herein were found to have an $EC_{50}$ in the range of 10-400 when the assay was performed without HSA. Certain compound exemplified herein were found to have an $EC_{50}$ in the range of 30-1000 when the assay was performed with 4% HSA.

Glucose $S_{0.5}$ Assay:

For this assay, the concentration of control or test compound was fixed at or near a saturating concentration, if possible, typically 50 µM, while the glucose concentration was varied over a 10-point, 2-fold dilution series ranging from 80 to approximately 0.16 mM. The same four-parameter logistic model used for the $EC_{50}$ assay (Equation 1) was employed to estimate the relevant kinetic parameters. In this assay, the definitions for the variables and parameters are similar except that x represents the concentration of glucose, B is the rate at saturating glucose ($V_m$), C is the $S_{0.5}$ for glucose (the concentration of glucose at $V_m/2$) and D is the Hill Coefficient.

Certain compounds exemplified herein have been found to have an $S_{0.5}$ of between 0.3 and 5 mM in the above described assay. Certain compounds exemplified herein have been found to have an $S_{0.5}$ of between 0.30 and 1.5 mM.

Example B

Mouse PK Study

Oral pharmacokinetics of each of the compounds shown in Table 1 ("test compound") were determined as follows.
Materials Test compound was formulated in PEG400:ethanol:saline (40:20:40, by volume) for IV administration and in 30% Captisol in water for both IV and PO administration in CD-1 mice. Labetalol was used as an internal standard for the LC-MS/MS assay of the CD-1 mouse samples.

Adult male CD-1 mice were obtained from Charles River Laboratories in Portage, Mich. At the time of study-start, each CD-1 mouse weighed approximately 30 grams and was between the ages of 7-9 weeks. All CD-1 mice were acclimated to the Array BioPharma Inc. vivarium for at least 5 days prior to administration of an IV dose by way of a tail vein injection (5 mL/kg) or a PO dose by oral gavage (10 mL/kg).

Animals were euthanized by $CO_2$ inhalation and blood samples were collected by cardiac puncture into syringes containing a 1.5% EDTA solution in water (w/v; pH was titrated to 7.4 with 5 N NaOH; the final ratio of blood to EDTA was approximately 1:9) as the anticoagulant. Plasma was harvested from blood samples by centrifugation and stored at −20° C. until analysis. The following time points were collected for the IV arm: 0.017, 0.083, 0.25, 0.5, 1, 2, 4, 8, 12 and 24 hours post dose. The following time points were collected for the PO arm: 0.25, 0.50, 1, 4, 8, and 24 hours post dose.
Methods Protein was precipitated from 20 µL of mouse plasma with the addition of 200 µL of 0.1% acetic acid in acetonitrile. A single 12-point calibration curve was prepared by first serially diluting (3-fold) a 40-µg/mL stock solution of the test compound in acetonitrile. Naïve CD-1 mouse plasma (20 µL) was then added to each standard solution (200 µL). A stock solution of the internal standard (Labetalol; 180 µL of 0.1 µg/mL in acetonitrile) was subsequently added to each standard and sample solution, for a total volume of 400 µL. Samples were vortex-mixed for 5 minutes and spun in an Allegra X-12R centrifuge (Beckman Coulter, Fullerton, Calif.) for 15 minutes at approximately 1,500×g at 4° C. A 100-µL aliquot of each supernatant was transferred via a 550 µL Personal Pipettor (Apricot Designs, Monrovia, Calif.) to 96-well plates and diluted 1:1 with HPLC grade water. The resulting plates were sealed with plate mats and analyzed by LC-MS/MS.

The LC-MS/MS system was comprised of an HTC-PAL autosampler (Leap Technologies, Inc., Carrboro, N.C.), an HP1100 HPLC (Agilent Technologies Inc., Santa Clear, Calif.), and an API4000 triple quadrupole mass spectrometer (Applied Biosystems, Foster City, Calif.). Chromatographic retention of the analyte and internal standard was achieved using a Betasil Phenyl-Hexyl column (2.1×30 mm, 3 µm particle size, Thermo Scientific) in conjunction with gradient conditions using mobile phases A (aqueous 0.1% formic acid and 1% IPA) and B (0.1% formic acid in acetonitrile). The total run time, including re-equilibration time, for a single injection was 3.5 minutes. Mass spectrometric detection of the analytes was accomplished using ESI+ ionization mode. Ion current was optimized during infusion of a stock solution of the test compound. Analyte responses were measured by multiple reaction monitoring (MRM) of transitions unique to each compound.
Calculations Data were acquired and processed using the Applied Biosystems Analyst software (version 1.4.2). Calibration was achieved by plotting the peak area ratios of analyte to internal standard as a function of the nominal concentrations of standard samples. A calibration model was generated by quadratic regression of the calibration curve with a weighting factor of 1/x. The model was used to calculate the concentrations in all samples. The lower limit of quantitation (LLOQ) for this analysis was in the single-digit µg/mL range (either 2.03 or 6.10 µg/mL).

Pharmacokinetic parameters were calculated by established non-compartmental methods using an in-house Excel® (Microsoft Corporation, Redmond, Wash.) macro, PK Toolbox version 2.0. Plasma concentrations of test compound from replicate animals (n=3) for each time-point were averaged. The average concentrations versus time were modeled to determine PK parameters. Standard deviations of plasma concentrations were determined only when more than two replicates were available for comparison (i.e., values greater than the LLOQ). The area under the plasma concentration versus time curve (AUC) was determined using linear trapezoidal integration. The portion of the AUC from the last measurable concentration to infinity was estimated from the equation, $C_t/k_{el}$, where $C_t$ represents the last measurable concentration and $k_{el}$ is the elimination rate constant. The latter was determined from the concentration versus time curve by linear regression of user-selected data points at the terminal phase of the semi-logarithmic plot. Use sum of the AUC values before and after extrapolation from the last time point is reported as the $AUC_{inf}$ value. Oral bioavailability was calculated by taking the ratio of the average dose-normalized $AUC_{inf}$ values for IV and PO administration.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound selected from:
  (S)-1-(5-(3-(2-methylpyridin-3-yloxy)-5-(pyridin-2-ylthio)pyridin-2-ylamino)-1,2,4-thiadiazol-3-yl)ethane-1,2-diol;
  (S)-2-methyl-1-(5-(3-(2-methylpyridin-3-yloxy)-5-(pyridin-2-ylthio)pyridin-2-ylamino)-1,2,4-thiadiazol-3-yl)propane-1,2-diol;
  (S)-2-(5-(3-(2-methylpyridin-3-yloxy)-5-(pyridin-2-ylthio)pyridin-2-ylamino)-1,2,4-thiadiazol-3-yl)propane-1,2-diol;
  (R)-2-(5-(3-(2-methylpyridin-3-yloxy)-5-(pyridin-2-ylthio)pyridin-2-ylamino)-1,2,4-thiadiazol-3-yl)propane-1,2-diol;
  (S)-1-(5-(5-(cyclopropylmethylthio)-3-(2-methylpyridin-3-yloxy)pyridin-2-ylamino)-1,2,4-thiadiazol-3-yl)ethane-1,2-diol;
  (S)-1-(5-(3-(1-Ethyl-1H-pyrazol-5-yloxy)-5-(pyridin-2-ylthio)pyridin-2-ylamino)-1,2,4-thiadiazol-3-yl)ethane-1,2-diol;

(S)-1-(5-(3-(1-ethyl-1H-pyrazol-5-yloxy)-5-(pyridin-2-ylthio)pyridin-2-ylamino)-1,2,4-thiadiazol-3-yl)-2-methylpropane-1,2-diol;

(S)-2-methyl-1-(5-(5-(pyridin-2-ylthio)-3-(1,3,5-trimethyl-1H-pyrazol-4-yloxy)pyridin-2-ylamino)-1,2,4-thiadiazol-3-yl)propane-1,2-diol;

or pharmaceutically acceptable salts thereof.

2. A compound selected from (S)-1-(5-(3-(2-methylpyridin-3-yloxy)-5-(pyridin-2-ylthio)pyridin-2-ylamino)-1,2,4-thiadiazol-3-yl) ethane-1,2-diol, or a pharmaceutically acceptable salt thereof.

3. A compound selected from (S)-2-methyl-1-(5-(5-(pyridin-2-ylthio)-3-(1,3,5-trimethyl-1H-pyrazol-4-yloxy)pyridin-2-ylamino)-1,2,4-thiadiazol-3-yl)propane-1,2-diol, or a pharmaceutically acceptable salt thereof.

4. A pharmaceutical composition, which comprises a compound of claim 1, or a pharmaceutically acceptable salt thereof, and a pharmaceutically acceptable diluent or carrier.

5. The pharmaceutical composition of claim 4 wherein the compound is (S)-1-(5-(3-(2-methylpyridin-3-yloxy)-5-(pyridin-2-ylthio)pyridin-2-ylamino)-1,2,4-thiadiazol-3-yl) ethane-1,2-diol, or a pharmaceutically acceptable salt thereof.

6. The pharmaceutical composition of claim 4 wherein the compound is (S)-2-methyl-1-(5-(5-(pyridin-2-ylthio)-3-(1,3,5-trimethyl-1H-pyrazol-4-yloxy)pyridin-2-ylamino)-1,2,4-thiadiazol-3-yl)propane-1,2-diol, or a pharmaceutically acceptable salt thereof.

7. A method of treating non-insulin-dependent diabetes comprising administering to a mammal a therapeutically effective amount of a compound of claim 1, or a pharmaceutically acceptable salt thereof.

8. The method of claim 7 wherein the compound is (S)-1-(5-(3-(2-methylpyridin-3-yloxy)-5-(pyridin-2-ylthio)pyridin-2-ylamino)-1,2,4-thiadiazol-3-yl)ethane-1,2-diol, or a pharmaceutically acceptable salt thereof.

9. The method of claim 7 wherein the compound is (S)-2-methyl-1-(S-(5-(pyridin-2-ylthio)-3-(1,3,5-trimethyl-1H-pyrazol-4-yloxy)pyridin-2-ylamino)-1,2,4-thiadiazol-3-yl) propane-1,2-diol, or a pharmaceutically acceptable salt thereof.

* * * * *